United States Patent
D'Alessio et al.

(10) Patent No.: US 11,999,786 B2
(45) Date of Patent: Jun. 4, 2024

(54) ANTI-CD48 ANTIBODIES, ANTIBODY DRUG CONJUGATES, AND USES THEREOF

(71) Applicant: Novartis AG, Basel (CH)

(72) Inventors: Joseph Anthony D'Alessio, Boston, MA (US); Claudia Judith Klinter, Basel-stadt (CH); Cornelia Anne Mundt, Lorrach (DE); Richard Vaughan Newcombe, Acton, MA (US); Tamás Schweighoffer, Riehen (CH); Katharina Winkelbach, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 17/534,126

(22) Filed: Nov. 23, 2021

(65) Prior Publication Data
US 2022/0162308 A1    May 26, 2022

Related U.S. Application Data

(60) Provisional application No. 63/117,817, filed on Nov. 24, 2020.

(51) Int. Cl.
*C07K 16/28* (2006.01)
*A61K 45/06* (2006.01)
*A61K 47/68* (2017.01)

(52) U.S. Cl.
CPC .......... *C07K 16/2803* (2013.01); *A61K 45/06* (2013.01); *A61K 47/6803* (2017.08); *A61K 47/6851* (2017.08); *C07K 2317/565* (2013.01); *C07K 2317/92* (2013.01)

(58) Field of Classification Search
CPC combination set(s) only.
See application file for complete search history.

(56) References Cited

FOREIGN PATENT DOCUMENTS

| EP | 2418222 A1 | 2/2012 | |
|---|---|---|---|
| WO | 2005081711 A2 | 9/2005 | |
| WO | 2012047567 A1 | 4/2012 | |
| WO | 2016149535 A1 | 9/2016 | |
| WO | WO-2016203432 A1 * | 12/2016 | ............. A61K 38/07 |
| WO | 2019244082 A2 | 12/2019 | |
| WO | 2020035027 A1 | 2/2020 | |
| WO | WO-2020053742 A2 * | 3/2020 | ............. A61P 31/20 |

OTHER PUBLICATIONS

Lewis et al., SGN-CD48A: a Novel Humanized Anti-CD48 Antibody-Drug Conjugate for the Treatment of Multiple Myeloma, blood, Dec. 2, 2016, 4470, 128 (22).

* cited by examiner

*Primary Examiner* — Adam Weidner
*Assistant Examiner* — Laura Ann Essex
(74) *Attorney, Agent, or Firm* — Jana E. Harris

(57) ABSTRACT

Disclosed herein are antibodies, antigen binding fragments thereof, and antibody drug conjugates thereof that bind human CD48. Also disclosed are pharmaceutical compositions comprising the antibodies, antigen binding fragments thereof, and antibody drug conjugates thereof; and methods of making and using such pharmaceutical compositions for treating cancer in a patient in need of treatment.

41 Claims, 15 Drawing Sheets
Specification includes a Sequence Listing.

NY920 WT binding with huCD48

Exp#1: ka (1/Ms) = 2.57E+05, kd (1/s) = 7.21E-04, KD (M) = 2.81E-09

Exp#2: ka (1/Ms) = 2.24E+05, kd (1/s) = 6.98E-04, KD (M) = 3.11E-09

NY920 DAPA binding with huCD48

Exp#1: ka (1/Ms) = 2.74E+05, kd (1/s) = 7.26E-04, KD (M) = 2.65E-09

Exp#2: ka (1/Ms) = 2.06E+05, kd (1/s) = 3.43E-04, KD (M) = 1.67E-09

NY938 DAPA binding with huCD48

Exp#1: ka (1/Ms) = 3.52E+05, kd (1/s) = 1.04E-04, KD (M) = 2.96E-10

Exp#2: ka (1/Ms) = 4.56E+05, kd (1/s) = 1.15E-04, KD (M) = 2.52E-10

NY920 WT binding with cynoCD48

Exp#1: ka (1/Ms) = 3.25E+05, kd (1/s) = 4.47E-03, KD (M) = 1.38E-08

Exp#2: ka (1/Ms) = 3.11E+05, kd (1/s) = 4.01E-03, KD (M) = 1.29E-08

NY920 DAPA binding with cynoCD48

Exp#1: ka (1/Ms) = 3.19E+05, kd (1/s) = 4.25E-03, KD (M) = 1.34E-08

Exp#2: ka (1/Ms) = 3.01E+05, kd (1/s) = 3.92E-03, KD (M) = 1.30E-08

Exp#1: ka (1/Ms) = 2.71E+05, kd (1/s) = 2.89E-04, KD (M) = 1.07E-09

Exp#2: ka (1/Ms) = 4.09E+05, kd (1/s) = 3.16E-04, KD (M) = 7.74E-10

ANTI-CD48 ANTIBODIES, ANTIBODY DRUG CONJUGATES, AND USES THEREOF

CROSS-REFERENCE TO RELATED APPLICATION

This application claims the benefit of the following U.S. Provisional Application No. 63/117,817, filed Nov. 24, 2020, the entire contents of which are incorporated herein by reference.

FIELD OF THE INVENTION

The present disclosure is directed to anti-CD48 antibodies and antigen binding fragments thereof, antibody drug conjugates thereof, and their uses for treating cancer in a patient in need thereof.

SEQUENCE LISTING

The instant application contains a Sequence Listing, which has been submitted electronically in ASCII format and is hereby incorporated by reference in its entirety. Said ASCII copy, created on Nov. 18, 2021, is named PAT058966_SL.txt and is 79,220 bytes in size.

BACKGROUND OF THE INVENTION

CD48 (also known as BLAST-1 and SLAMF2) is an adhesion and costimulatory molecule involved in a wide variety of innate and adaptive immune responses, ranging from granulocyte activity and allergy to T cell activation and autoimmunity (McArdel et al. (2016) Clin Immunol 164: 10-20). In normal hematologic tissues, CD48 helps to regulate the activation and differentiation of lymphocytes, dendritic, and endothelial cells. In oncology it has been well established that CD48 is significantly upregulated at both the RNA and protein level in a range of B-cell malignancies including in a high proportion of multiple myeloma patients, a subset of diffuse large B-cell lymphoma patients, as well as smaller indications with significant unmet medical need.

CD48 is an attractive target for antibody drug conjugates due to its absence in normal non-hematopoietic tissues, expression restricted to mature lymphocytes and monocytes, and significant upregulation in a range of hematological malignancies. Antibodies and antibody drug conjugates targeting CD48 have previously demonstrated anti-tumor activity in preclinical models of hematological cancers. Prior therapeutic efforts have shown that CD48 has the potential to rapidly internalize upon antibody engagement and traffic to the lysosome as well as to be rapidly repopulated on the surface of tumor cells following internalization. There remains a need for additional therapeutic compounds that target CD48.

SUMMARY OF THE INVENTION

Disclosed herein are antibodies, or antigen binding fragments thereof, that bind human CD48. In one embodiment, the anti-CD48 antibody, or antigen binding fragment thereof, comprises three heavy chain CDRs and three light chain CDRs selected from:
(i) heavy chain CDR1 (HCDR1) consisting of SEQ ID NO:1, heavy chain CDR2 (HCDR2) consisting of SEQ ID NO:2, heavy chain CDR3 (HCDR3) consisting of SEQ ID NO:3; light chain CDR1 (LCDR1) consisting of SEQ ID NO:16, light chain CDR2 (LCDR2) consisting of SEQ ID NO:17, and light chain CDR3 (LCDR3) consisting of SEQ ID NO:18;
(ii) heavy chain CDR1 (HCDR1) consisting of SEQ ID NO:4, heavy chain CDR2 (HCDR2) consisting of SEQ ID NO:2, heavy chain CDR3 (HCDR3) consisting of SEQ ID NO:3; light chain CDR1 (LCDR1) consisting of SEQ ID NO:16, light chain CDR2 (LCDR2) consisting of SEQ ID NO:17, and light chain CDR3 (LCDR3) consisting of SEQ ID NO:18;
(iii) heavy chain CDR1 (HCDR1) consisting of SEQ ID NO:5, heavy chain CDR2 (HCDR2) consisting of SEQ ID NO:6, heavy chain CDR3 (HCDR3) consisting of SEQ ID NO:3; light chain CDR1 (LCDR1) consisting of SEQ ID NO:19, light chain CDR2 (LCDR2) consisting of SEQ ID NO:20, and light chain CDR3 (LCDR3) consisting of SEQ ID NO:21;
(iv) heavy chain CDR1 (HCDR1) consisting of SEQ ID NO:7, heavy chain CDR2 (HCDR2) consisting of SEQ ID NO:8, heavy chain CDR3 (HCDR3) consisting of SEQ ID NO:9; light chain CDR1 (LCDR1) consisting of SEQ ID NO:22, light chain CDR2 (LCDR2) consisting of SEQ ID NO:20, and light chain CDR3 (LCDR3) consisting of SEQ ID NO:18;
(v) heavy chain CDR1 (HCDR1) consisting of SEQ ID NO:27, heavy chain CDR2 (HCDR2) consisting of SEQ ID NO:28, heavy chain CDR3 (HCDR3) consisting of SEQ ID NO:29; light chain CDR1 (LCDR1) consisting of SEQ ID NO:42, light chain CDR2 (LCDR2) consisting of SEQ ID NO:43, and light chain CDR3 (LCDR3) consisting of SEQ ID NO:44;
(vi) heavy chain CDR1 (HCDR1) consisting of SEQ ID NO:30, heavy chain CDR2 (HCDR2) consisting of SEQ ID NO:28, heavy chain CDR3 (HCDR3) consisting of SEQ ID NO:29; light chain CDR1 (LCDR1) consisting of SEQ ID NO:42, light chain CDR2 (LCDR2) consisting of SEQ ID NO:43, and light chain CDR3 (LCDR3) consisting of SEQ ID NO:44;
(vii) heavy chain CDR1 (HCDR1) consisting of SEQ ID NO:31, heavy chain CDR2 (HCDR2) consisting of SEQ ID NO:32, heavy chain CDR3 (HCDR3) consisting of SEQ ID NO:29; light chain CDR1 (LCDR1) consisting of SEQ ID NO:45, light chain CDR2 (LCDR2) consisting of SEQ ID NO:46, and light chain CDR3 (LCDR3) consisting of SEQ ID NO:47; or
(viii) heavy chain CDR1 (HCDR1) consisting of SEQ ID NO:33, heavy chain CDR2 (HCDR2) consisting of SEQ ID NO:34, heavy chain CDR3 (HCDR3) consisting of SEQ ID NO:35; light chain CDR1 (LCDR1) consisting of SEQ ID NO:48, light chain CDR2 (LCDR2) consisting of SEQ ID NO:46, and light chain CDR3 (LCDR3) consisting of SEQ ID NO:44. In another embodiment, the anti-CD48 antibody or antigen binding fragment thereof comprises:
(i) a heavy chain variable region comprising the amino acid sequence of SEQ ID NO:10, and a light chain variable region comprising the amino acid sequence of SEQ ID NO:23; or
(ii) a heavy chain variable region comprising the amino acid sequence of SEQ ID NO:36, and a light chain variable region comprising the amino acid sequence of SEQ ID NO:49.

In another embodiment, the anti-CD48 antibody comprises:
(a) the heavy chain amino acid sequence of SEQ ID NO:12 and the light chain amino acid sequence of SEQ ID NO:25;

(b) the heavy chain amino acid sequence of SEQ ID NO:14 and the light chain amino acid sequence of SEQ ID NO:25;

(c) The heavy chain amino acid sequence of SEQ ID NO:63 and the light chain amino acid sequence of SEQ ID NO:25;

(e) the heavy chain amino acid sequence of SEQ ID NO:38 and the light chain amino acid sequence of SEQ ID NO:51;

(f) the heavy chain amino acid sequence of SEQ ID NO:40 and the light chain amino acid sequence of SEQ ID NO:51; or (g) The heavy chain amino acid sequence of SEQ ID NO:65 and the light chain amino acid sequence of SEQ ID NO:51.

In yet another embodiment, the anti-CD48 antibody or antigen binding fragment thereof comprises a Fab fragment, a Fab' fragment, a F(ab')$_2$ fragment, a single chain Fv (scFv), a disulfide-linked Fv (sdFv), a Fd fragment, a Fv fragment, a dAb fragment, a single domain antibody, a maxibody, a minibody, a nanobody, an intrabody, a diabody, a half antibody, a one-arm antibody, a monoclonal antibody, a bispecific antibody, a bispecific T-cell engage antibody, a multispecific antibody, a chimeric antigen receptor T-cell, or a radioimmunconjugate.

Also disclosed are nucleic acids that encode the antibodies or antigen binding fragments thereof as disclosed herein. In one embodiment, the nucleic acid comprises a sequence encoding a variable heavy chain (VH) or variable light chain (VL) of the antibodies selected from SEQ ID NO:11, SEQ ID NO:37, SEQ ID NO:24, or SEQ ID NO:50. In other embodiments, the nucleic acids disclosed herein encode heavy chain and light chain sequences of the antibodies and comprise sequences selected from SEQ ID NOs:13, 15, 39, 41, 75, 77, 26, or 52.

Also disclosed are vectors comprising any of the nucleic acids as provided herein, cell lines comprising any of the vectors as provided herein, and methods of making the antibodies or antigen binding fragments thereof as provided herein using the nucleic acids, vectors, and cell lines. In one embodiment, the method of making the anti-CD48 antibody or antigen binding fragment thereof comprises growing any of the cell lines as provided herein under suitable conditions to express the antibody or antigen-binding fragment thereof, then purifying and isolating the antibody or antigen-binding fragment thereof.

In another embodiment, the present application also discloses antibody drug conjugates of Formula (I):

A-(L$_B$-(D)$_n$)$_y$  (I);

wherein:

A is an antibody, or antibody antigen binding fragment thereof, that specifically binds to human CD48 as disclosed herein;

L$_B$ is a linker;

D is a cytotoxic agent;

n is an integer from 1 to 10, and y is an integer from 1 to 10, wherein the Linker-Drug moiety (L$_B$-(D)$_n$) is covalently attached to the antibody, or antigen binding fragment thereof, (A). In some embodiments, n is 1, 2, 3, 4, 5, 6, 7 or 8. In some embodiments, y is 1, 2, 3 or 4. In one embodiment, L$_B$ is independently selected from a cleavable linker or a non-cleavable linker. In some embodiments, each L$_B$ is a cleavable linker. In other embodiments, each L$_B$ is a non-cleavable linker.

In some embodiments, the drug moiety is an Eg5 inhibitor, a V-ATPase inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alkylating agent, a DNA intercalator, a DNA minor groove binder, an RNA polymerase inhibitor, an amanitin, a spliceosome inhibitor, a topoisomerase inhibitor, a DHFR inhibitor, or a pro-apoptotic agent, but excluding BCL-2 inhibitors, MCL-1 inhibitors, and BCL-XL inhibitors. In some embodiments, the drug moiety is an auristatin.

In one embodiment, the drug moiety D is a cytotoxic agent selected from a compound of Formula (A):

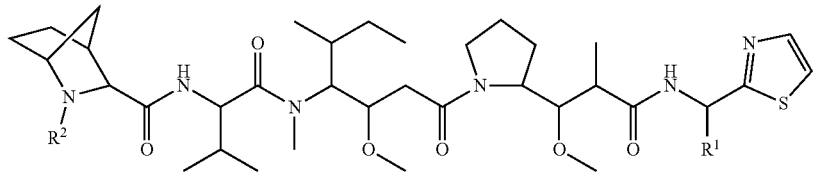

Formula (A)

wherein:

R$^1$ is

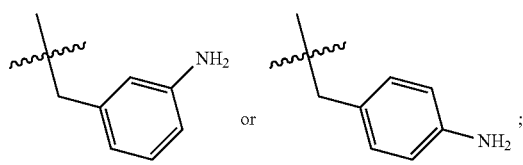 [SMILES: *Cc1cccc(N)c1 ; *Cc1ccc(N)cc1]

R$^2$ is H, C$_1$-C$_6$alkyl, —C(=O)R$^3$, —(CH$_2$)$_m$OH, —C(=O)(CH$_2$)$_m$OH, —C(=O)((CH$_2$)$_m$O)$_n$R$^4$, —((CH$_2$)$_m$O)$_n$R$^4$ or C$_1$-C$_6$alkyl which is optionally substituted with —CN, —C(=O)NH$_2$ or 1 to 5 hydroxyl;

each R$^3$ is independently selected from C$_1$-C$_6$alkyl and C$_1$-C$_6$alkyl which is optionally substituted with 1 to 5 hydroxyl;

and each R$^4$ is independently selected from H and C$_1$-C$_6$alkyl.

or D is a cytotoxic agent selected from a compound of Formula (B):

Formula (B)

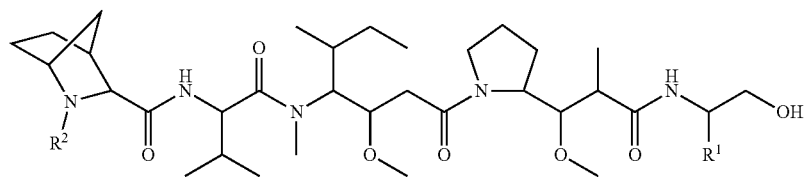

wherein:
R¹ is

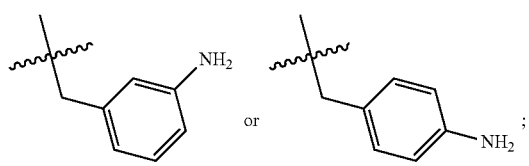 [SMILES: *Cc1cccc(N)c1 ; *Cc1ccc(N)cc1]

R² is H, C₁-C₆alkyl, —C(=O)R³, —(CH₂)ₘOH, —C(=O)(CH₂)ₘOH, —C(=O)((CH₂)ₘO)ₙR⁴, —((CH₂)ₘO)ₙR⁴ or C₁-C₆alkyl which is optionally substituted with —CN, —C(=O)NH₂ or 1 to 5 hydroxyl;
each R³ is independently selected from C₁-C₆alkyl and C₁-C₆alkyl which is optionally substituted with 1 to 5 hydroxyl;
and each R⁴ is independently selected from H and C₁-C₆alkyl.
Also disclosed herein is an antibody drug conjugate comprising the structure of Formula (E):

$(CH_2)_m$—, —$X_3C(=O)(CH_2)_m$—, —$X_3C(=O)(CH_2)_mNHC(=O)((CH_2)_mO)_p(CH_2)_m$—, —$X_3C(=O)(CH_2)_mNHC(=O)(CH_2)_m$—, —$X_3C(=O)(CH_2)_m$—, —$X_1C(=O)((CH_2)_mO)_p(CH_2)_mX_4(CH_2)_m$—, —$X_1C(=O)(CH_2)_mX_4(CH_2)_m$—, —$X_2X_1C(=O)((CH_2)_mO)_p(CH_2)_mX_4(CH_2)_m$— or —$X_2X_1C(=O)(CH_2)_mX_4(CH_2)_m$—, where  indicates the point of attachment to R¹⁴;
X₁ is

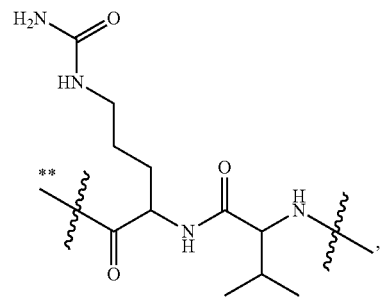

Formula (E)

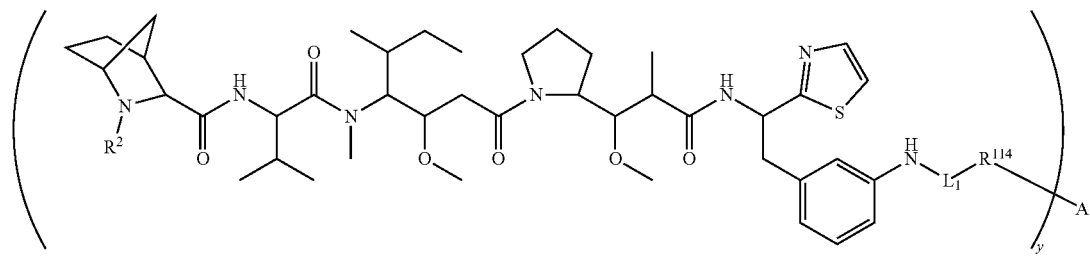

wherein:
A represents an antibody or antigen binding fragment thereof that specifically binds to human CD48 as disclosed herein;
y is an integer from 1 to 10;
R² is H, C₁-C₆alkyl, —C(=O)R³, —(CH₂)ₘOH, —C(=O)(CH₂)ₘOH, —C(=O)((CH₂)ₘO)ₙR⁴, —((CH₂)ₘO)ₙR⁴ or C₁-C₆alkyl which is optionally substituted with —CN, —C(=O)NH₂ or 1 to 5 hydroxy;
each R³ is independently selected from C₁-C₆alkyl and C₁-C₆alkyl which is optionally substituted with 1 to 5 hydroxyl;
each R⁴ is independently selected from H and C₁-C₆alkyl;
L₁ is —$X_1C(=O)((CH_2)_mO)_p(CH_2)_m$—, —$X_1C(=O)(CH_2)_m$—, —$X_2X_1C(=O)((CH_2)_mO)_p(CH_2)_m$—, —$X_2X_1C(=O)(CH_2)_m$—, —$X_3C(=O)((CH_2)_mO)_p$ -continued

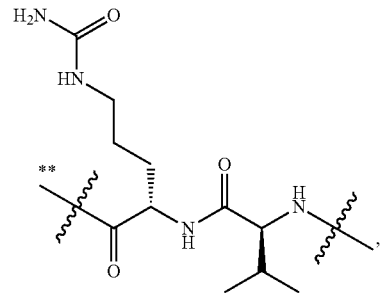

-continued
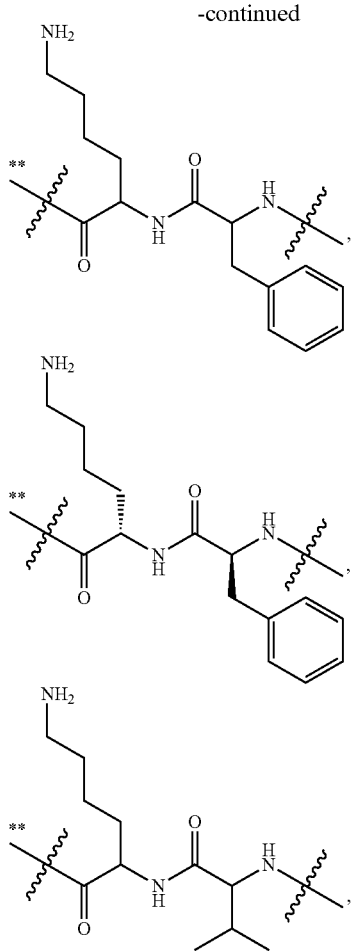
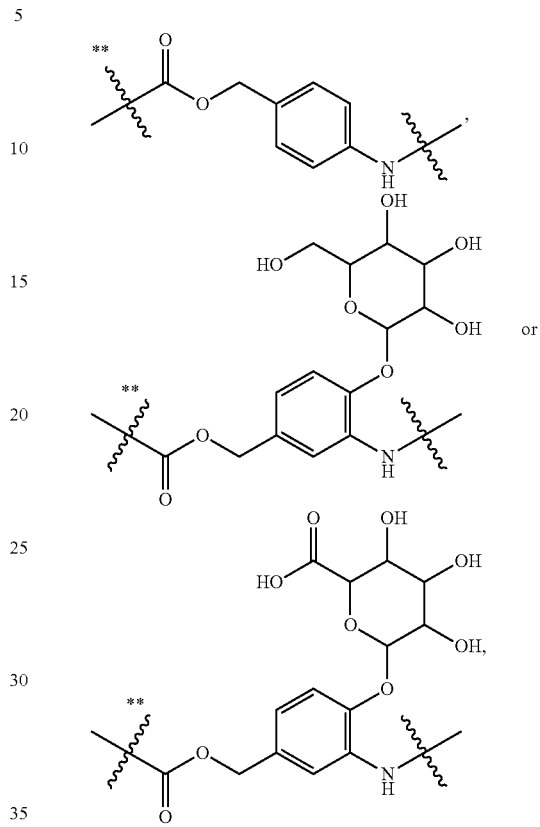
where ** indicates the point of attachment to the —NH— or to $X_2$;
$X_2$ is
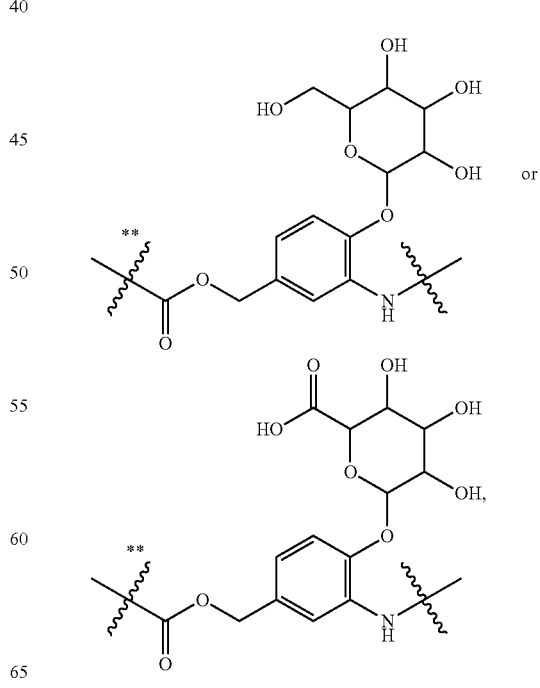
where ** indicates the point of attachment to the —NH—;
$X_3$ is
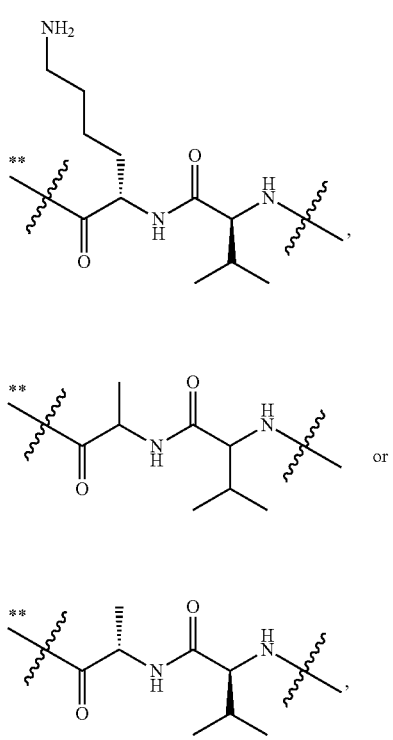

where ** indicates the point of attachment to the —NH—;
$X_4$ is
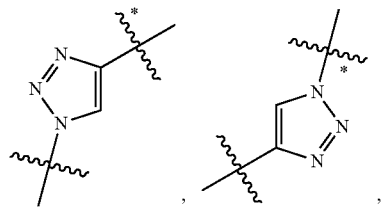,
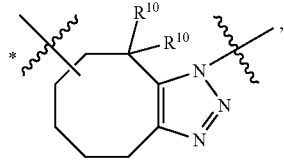,
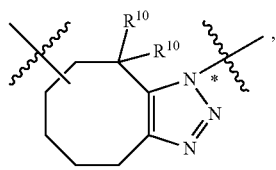,
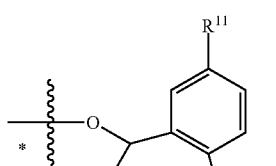,
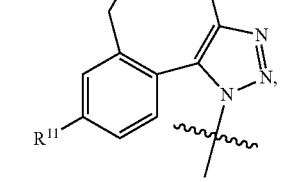,
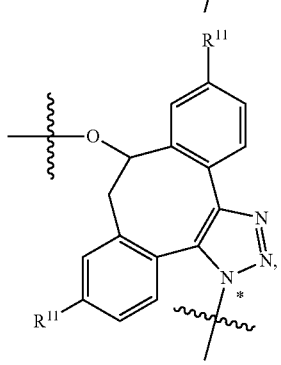,
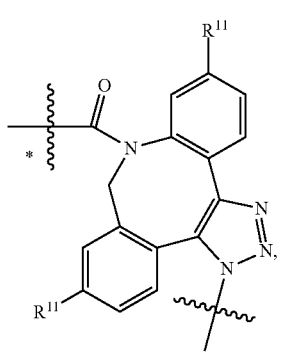,
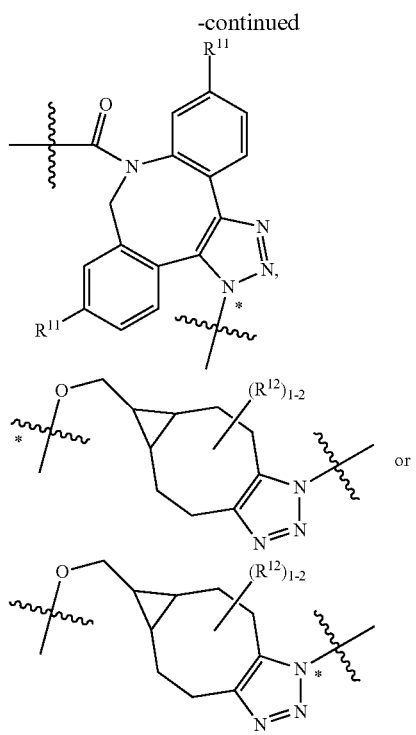,
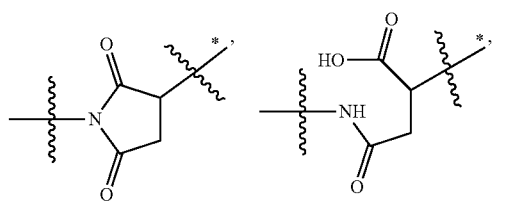 or
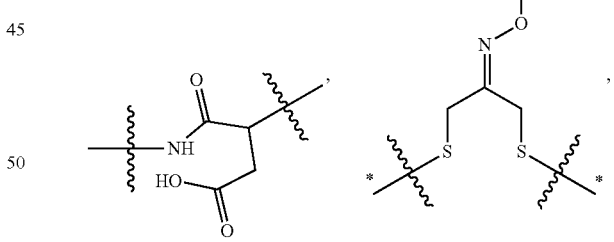
where the * indicates the point of attachment is toward $R^{114}$;
$R^{114}$ is
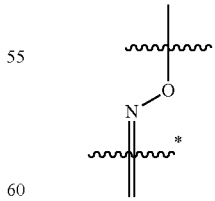,
—$NR^6C(=O)CH_2$—*, —$NHC(=O)CH_2$—*,
—$S(=O)_2CH_2CH_2$—*, —$(CH_2)_2S(=O)_2CH_2CH_2$—*,
—$NR^6S(=O)_2CH_2CH_2$—*, —$NR^6C(=O)CH_2CH_2$—*,
—NH—, —C(=O)—, —NHC(=O)—*,
—$CH_2NHCH_2CH_2$—*, —$NHCH_2CH_2$—*, —S—,

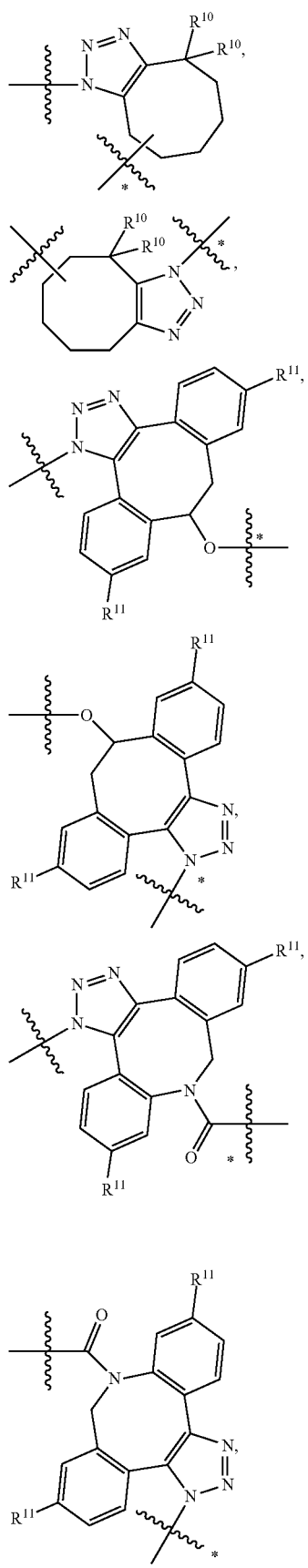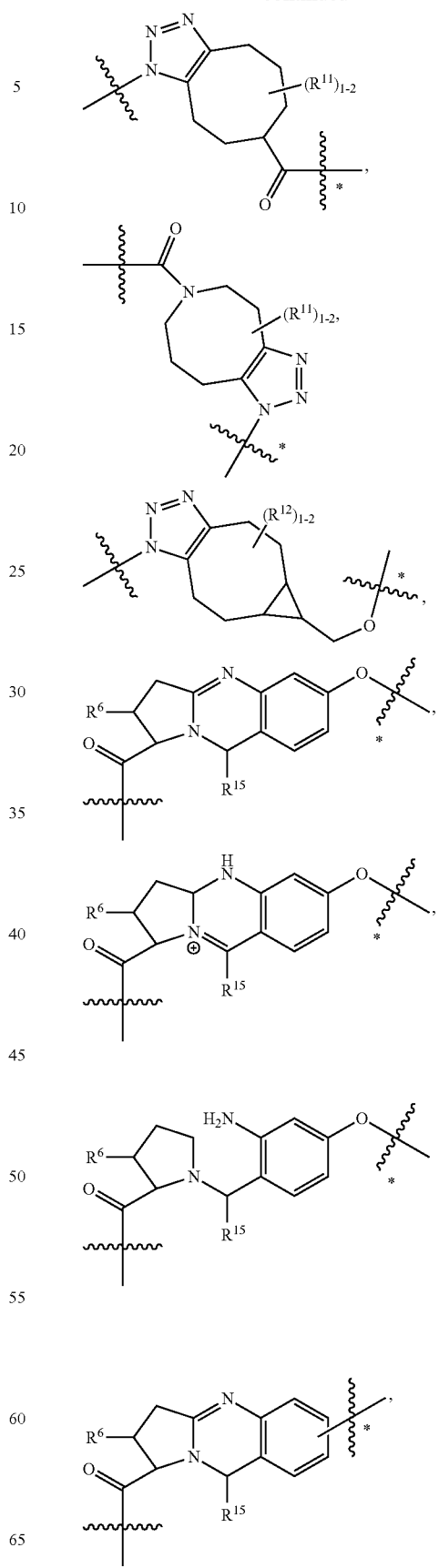

13

-continued

14

-continued

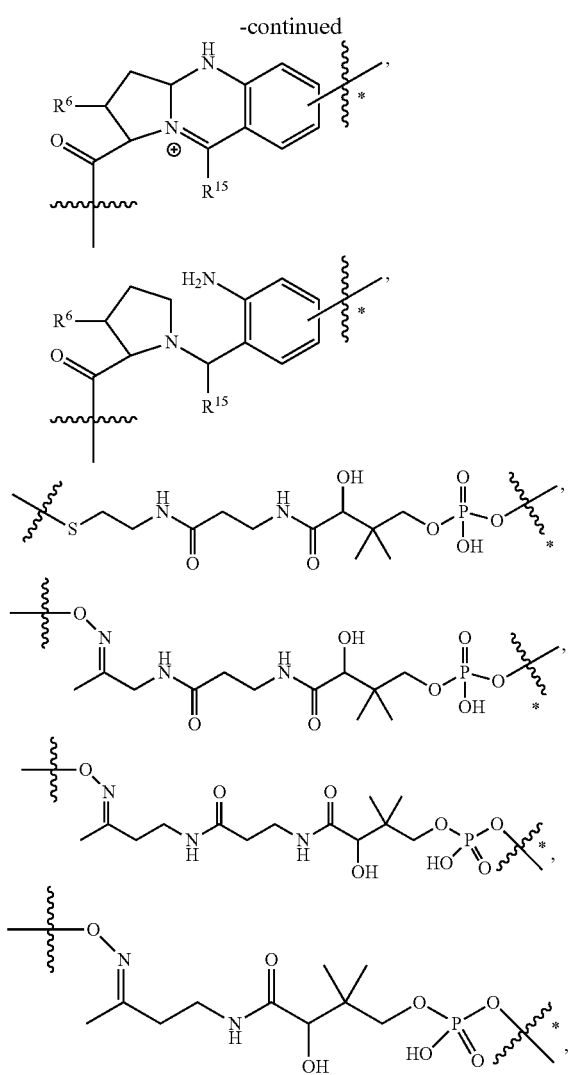

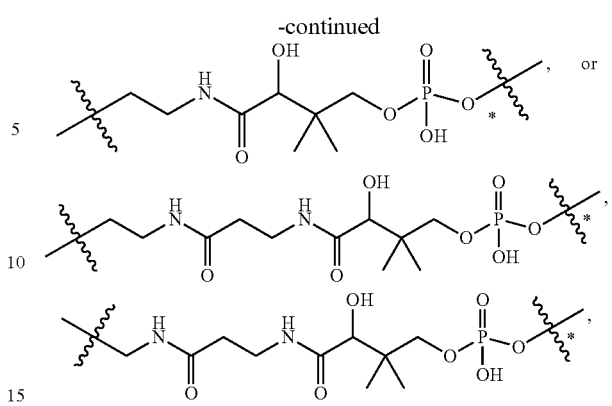

where the * indicates the point of attachment to A;

each $R^6$ is independently selected from H and $C_1$-$C_6$alkyl;

each $R^{10}$ is independently selected from H, $C_1$-$C_6$alkyl, F, Cl, and —OH;

each $R^{11}$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;

each $R^{12}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each $R^{15}$ is independently selected from H, —$CH_3$ and phenyl;

each m is independently selected from 1, 2, 3, 4, 5, 6, 7, 8, 9 and 10, and each p is independently selected from 1, 2, 3, 4, 5, 6, 7, 8, 9, 10, 11, 12, 13 and 14.

In some embodiments, the antibody drug conjugate of is selected from

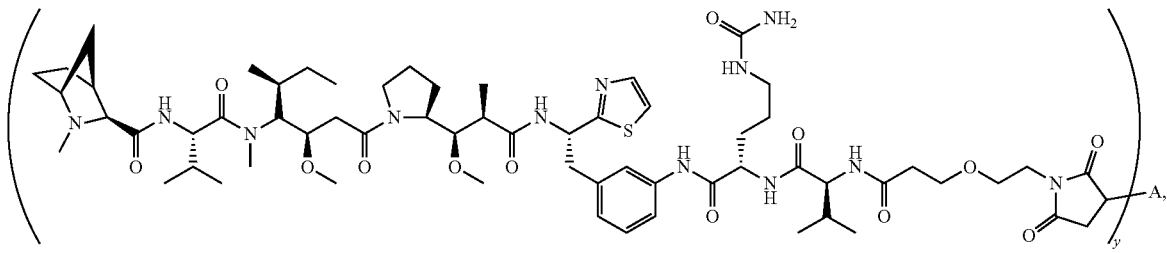

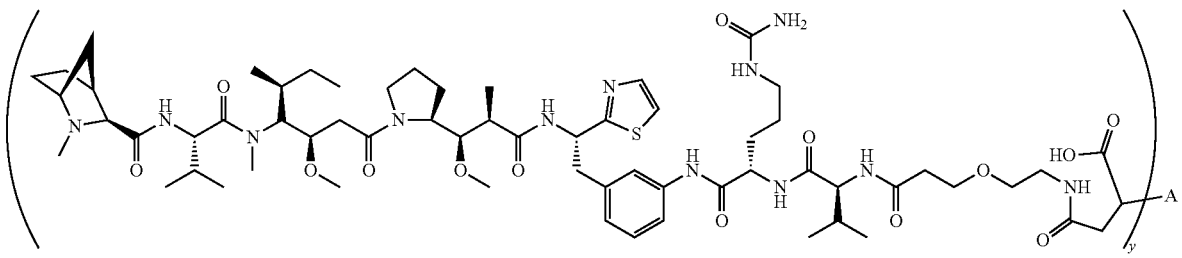

-continued

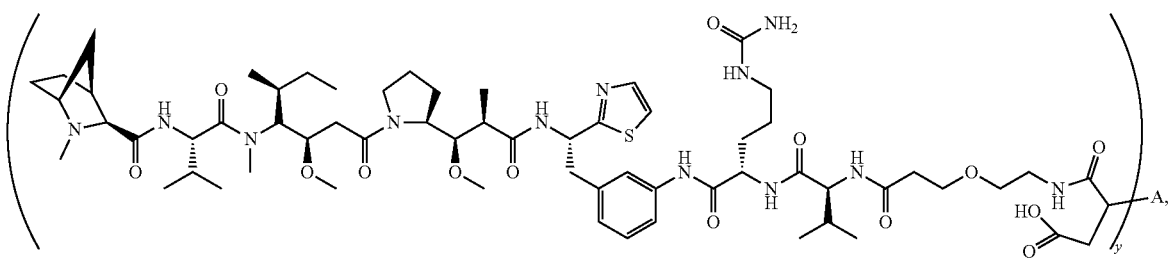

15 wherein:
A represents an antibody or antigen binding fragment thereof that specifically binds to human CD48 as disclosed herein, and
y is an integer from 1 to 10.

In some embodiments, the antibody drug conjugate comprises the structure of Formula (G):

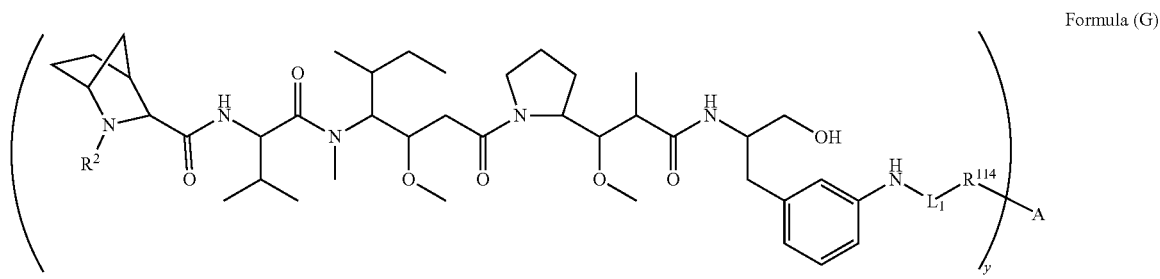

Formula (G)

wherein:
A represents an antibody or antigen binding fragment thereof that specifically binds to human CD48 as disclosed herein;
y is an integer from 1 to 10;
$R^2$ is H, $C_1$-$C_6$alkyl, —C(=O)$R^3$, —(CH$_2$)$_m$OH, —C(=O)(CH$_2$)$_m$OH, —C(=O)((CH$_2$)$_m$O)$_n$$R^4$, —((CH$_2$)$_m$O)$_n$$R^4$ or $C_1$-$C_6$alkyl which is optionally substituted with —CN, —C(=O)NH$_2$ or 1 to 5 hydroxy;
each $R^3$ is independently selected from $C_1$-$C_6$alkyl and $C_1$-$C_6$alkyl which is optionally substituted with 1 to 5 hydroxyl;
each $R^4$ is independently selected from H and $C_1$-$C_6$alkyl;
$L_1$ is —$X_1$C(=O)((CH$_2$)$_m$O)$_p$(CH$_2$)$_m$—, —$X_1$C(=O)(CH$_2$)$_m$—, —$X_2$$X_1$C(=O)((CH$_2$)$_m$O)$_p$(CH$_2$)$_m$—, —$X_2$$X_1$C(=O)(CH$_2$)$_m$—, —$X_3$C(=O)((CH$_2$)$_m$O)$_p$(CH$_2$)$_m$—, —$X_3$C(=O)(CH$_2$)$_m$—, —$X_3$C(=O)(CH$_2$)$_m$NHC(=O)((CH$_2$)$_m$O)$_p$(CH$_2$)$_m$—, —$X_3$C(=O)(CH$_2$)$_m$NHC(=O)(CH$_2$)$_m$—, —$X_3$C(=O)(CH$_2$)$_m$—, —$X_1$C(=O)((CH$_2$)$_m$O)$_p$(CH$_2$)$_m$$X_4$(CH$_2$)$_m$—, —$X_1$C(=O)(CH$_2$)$_m$$X_4$(CH$_2$)$_m$—, —$X_2$$X_1$C(=O)((CH$_2$)$_m$O)$_p$(CH$_2$)$_m$$X_4$(CH$_2$)$_m$— or —$X_2$$X_1$C(=O)(CH$_2$)$_m$$X_4$(CH$_2$)$_m$—, where  indicates the point of attachment to $R^{114}$;

$X_1$ is

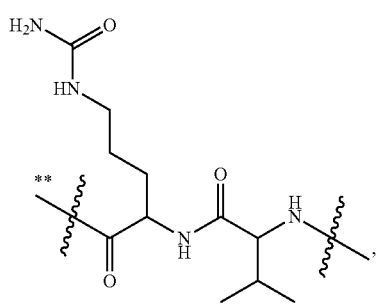

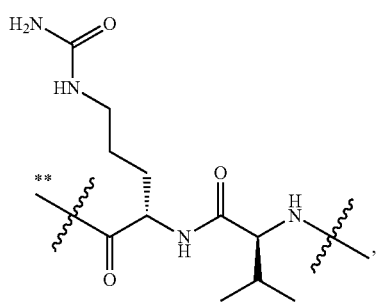

-continued

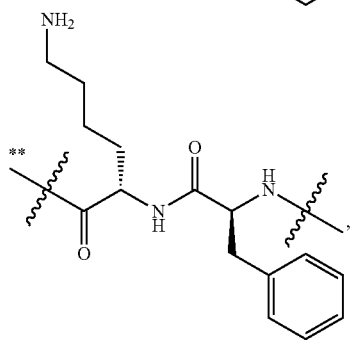
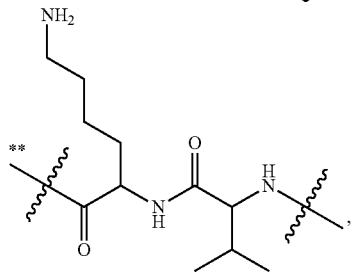
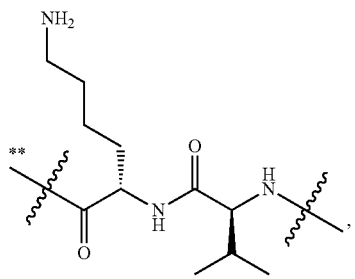
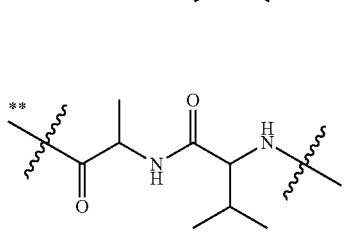
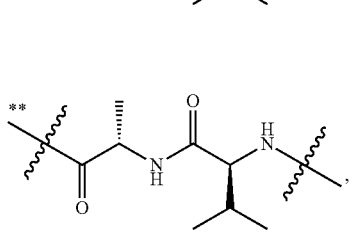
where ** indicates the point of attachment to the —NH— or to $X_2$;
$X_2$ is
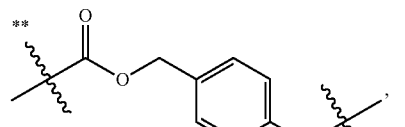
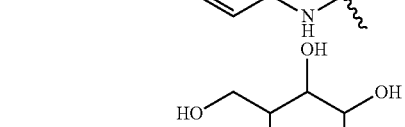
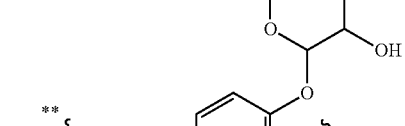
where ** indicates the point of attachment to the —NH—;
$X_3$ is
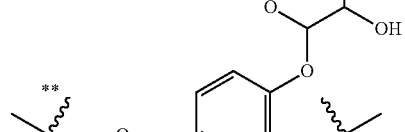
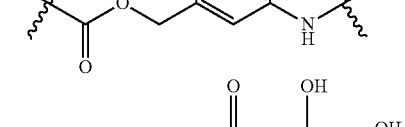
where ** indicates the point of attachment to the —NH—;

$X_4$ is
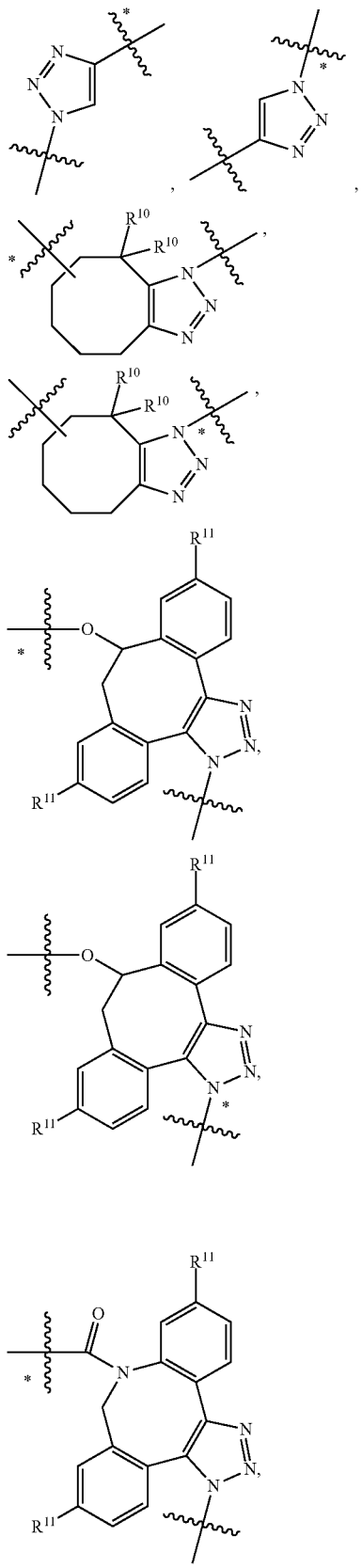
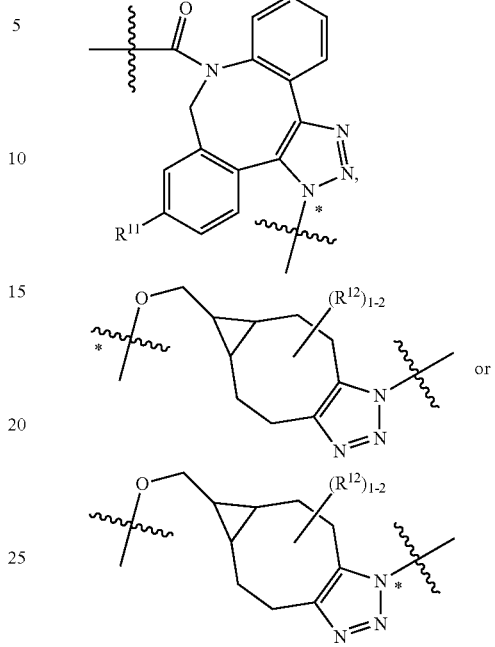
where the * indicates the point of attachment is toward $R^{114}$;
$R^{114}$ is
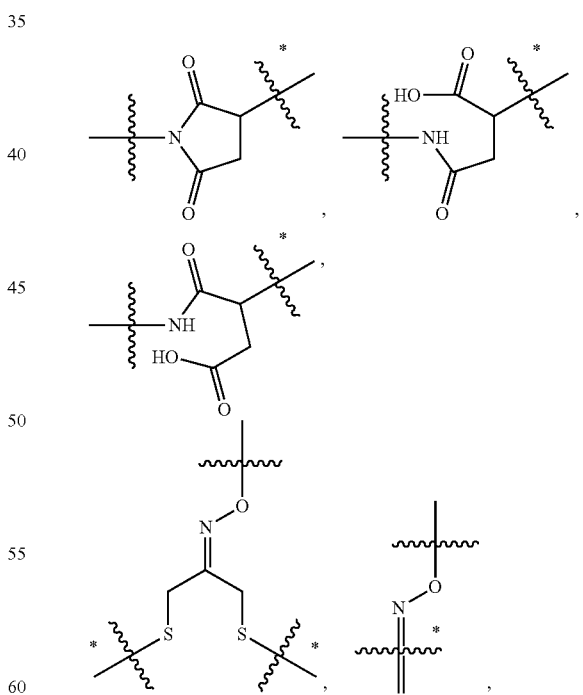
—NR$^6$C(=O)CH$_2$—*, —NHC(=O)CH$_2$—*,
—S(=O)$_2$CH$_2$CH$_2$—*, —(CH$_2$)$_2$S(=O)$_2$CH$_2$CH$_2$—*,
—NR$^6$S(=O)$_2$CH$_2$CH$_2$—*, —NR$^6$C(=O)CH$_2$CH$_2$—*,
—NH—, —C(=O)—, —NHC(=O)—*,
—CH$_2$NHCH$_2$CH$_2$—*, —NHCH$_2$CH$_2$—*, —S—,

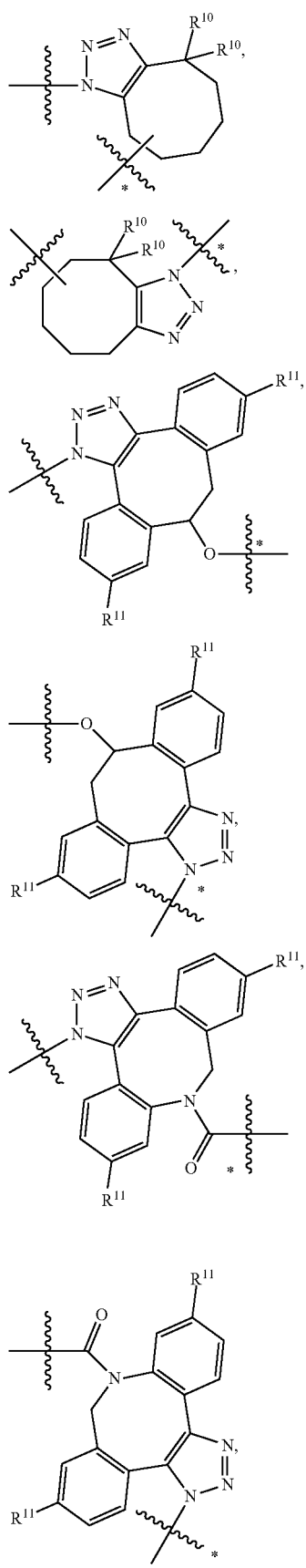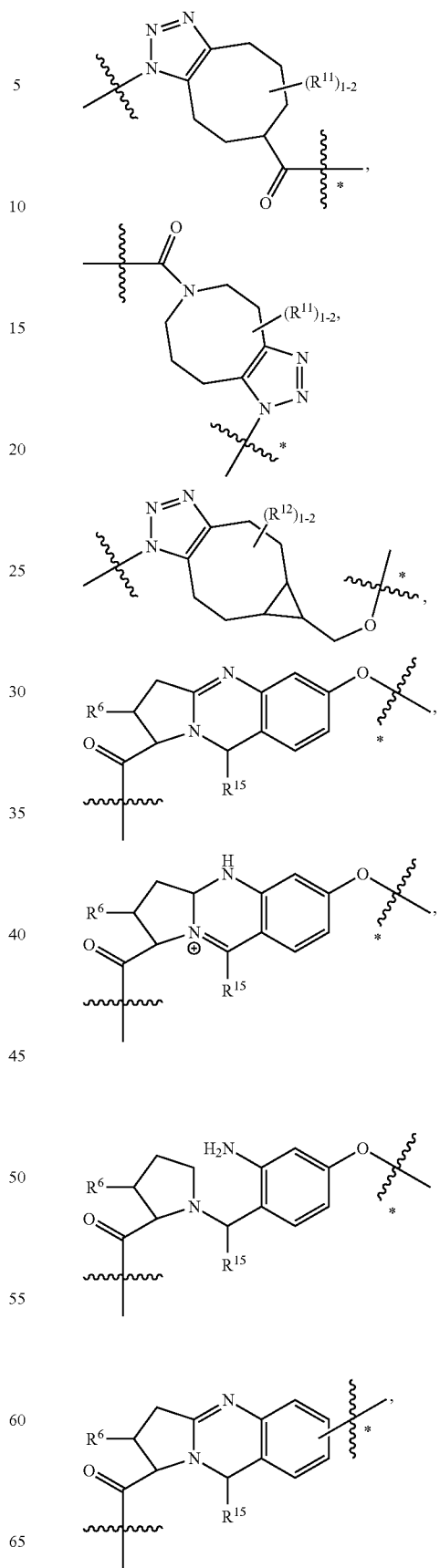

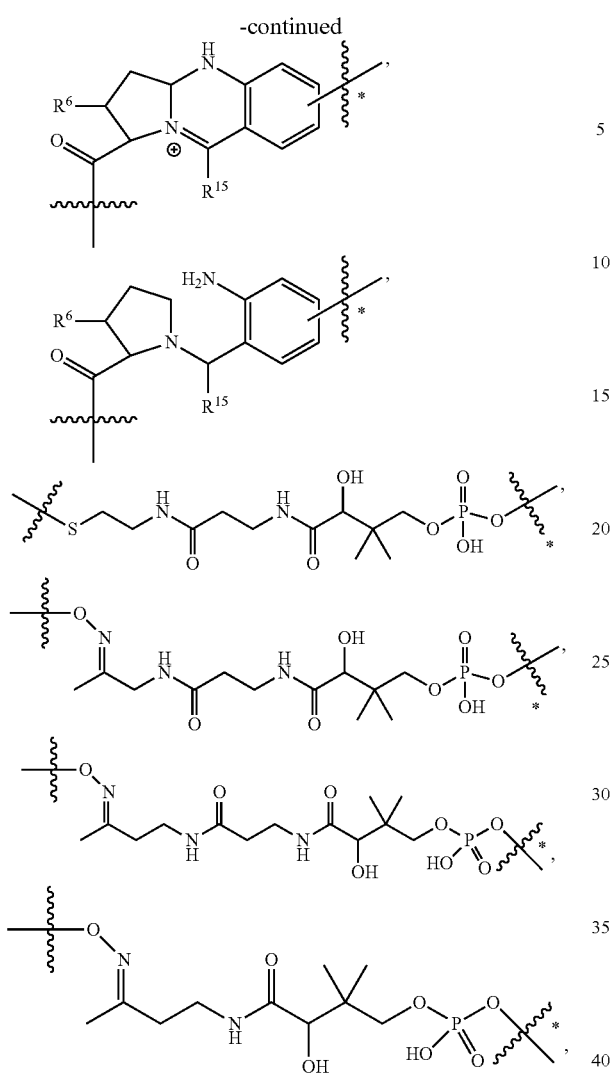
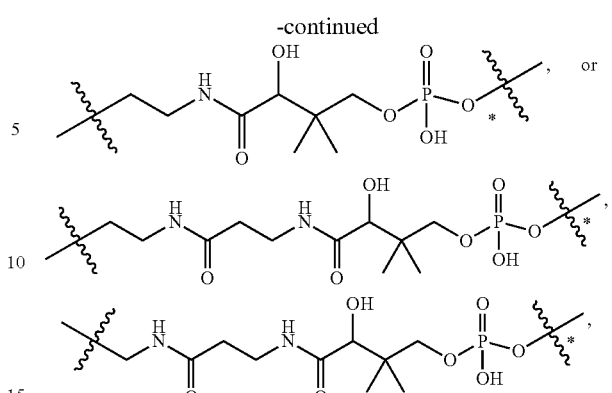

where the indicates the point of attachment to A;

each $R^6$ is independently selected from H and $C_1$-$C_6$alkyl;

each $R^{10}$ is independently selected from H, $C_1$-$C_6$alkyl, F, Cl, and —OH;

each $R^{11}$ is independently selected from H, $C_1$-$C_6$alkyl, F, Cl, —NH$_2$, —OCH$_3$, —OCH$_2$CH$_3$, —N(CH$_3$)$_2$, —ON, —NO$_2$ and —OH;

each $R^{12}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each $R^{15}$ is independently selected from H, —OH$_3$ and phenyl;

each m is independently selected from 1, 2, 3, 4, 5, 6, 7, 8, 9 and 10, and each p is independently selected from 1, 2, 3, 4, 5, 6, 7, 8, 9, 10, 11, 12, 13 and 14.

In some embodiments, the antibody drug conjugate is selected from

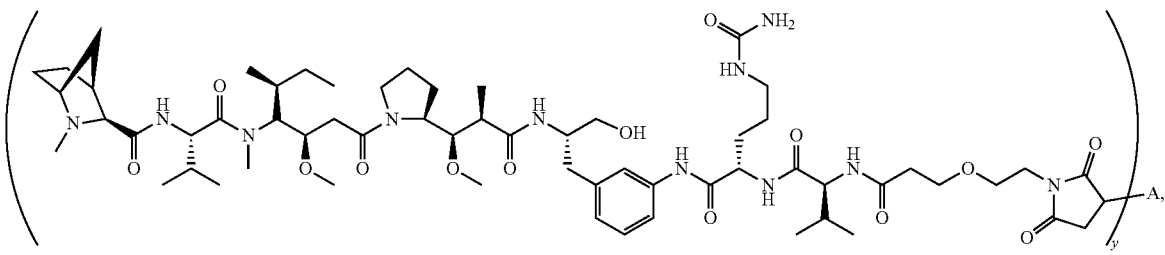

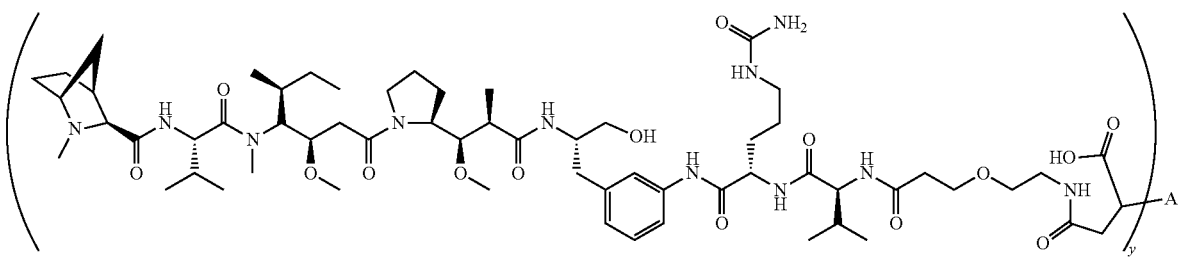

and
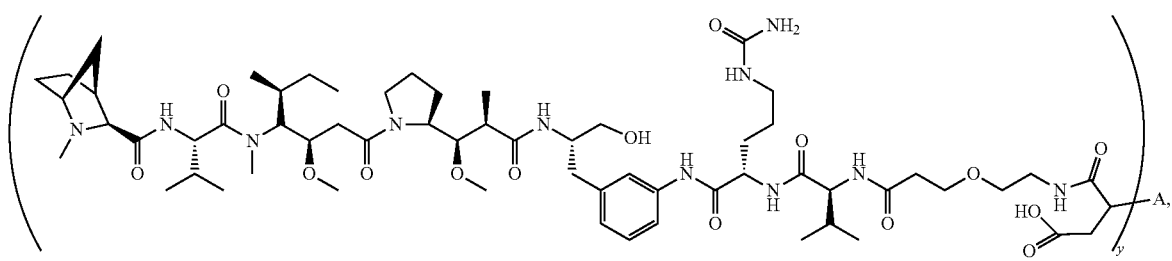
wherein:
A represents an antibody or antigen binding fragment thereof that specifically binds to human CD48 as disclosed herein, and
y is an integer from 1 to 10.
In another embodiment, the antibody drug conjugated is selected from
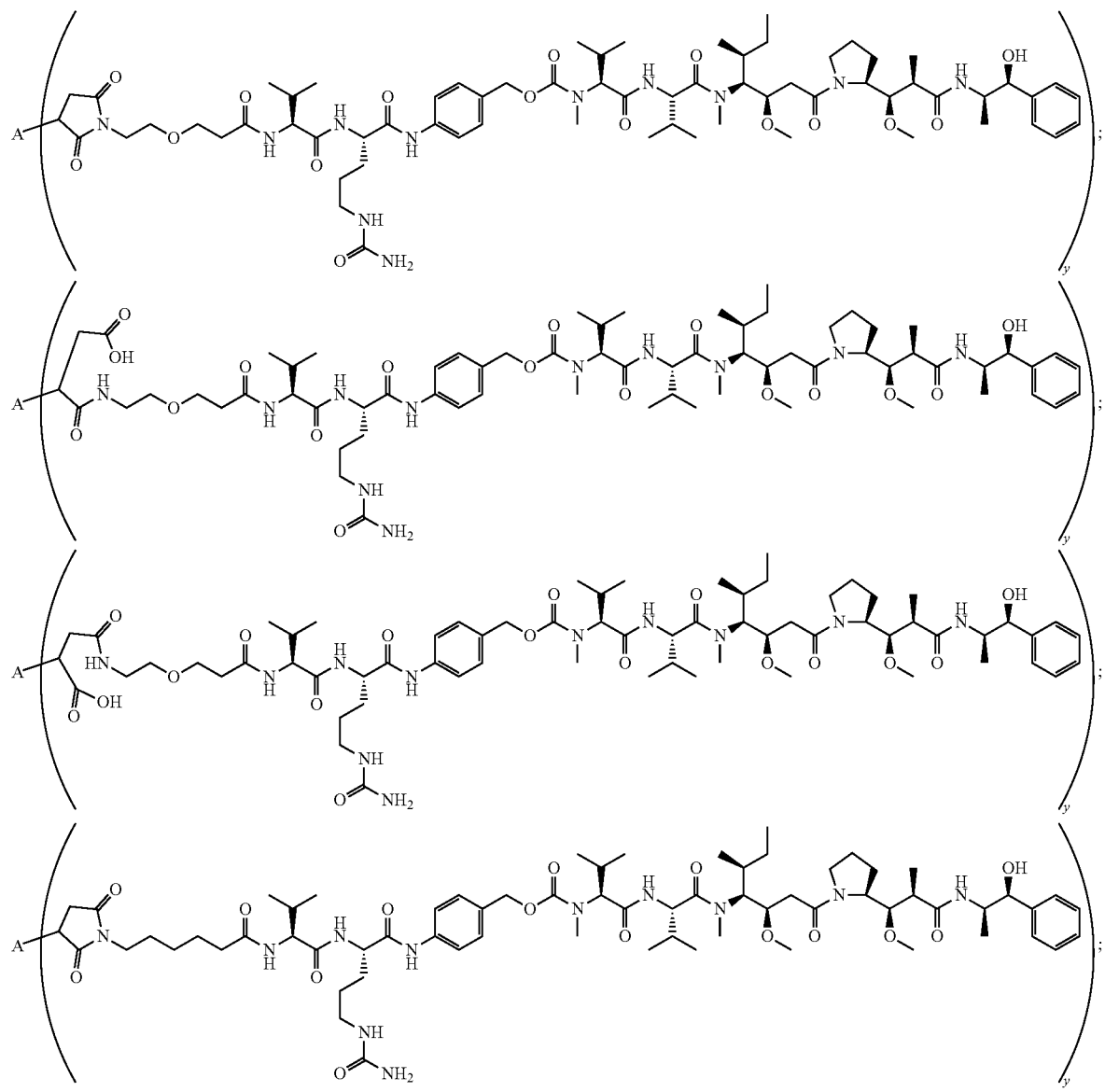

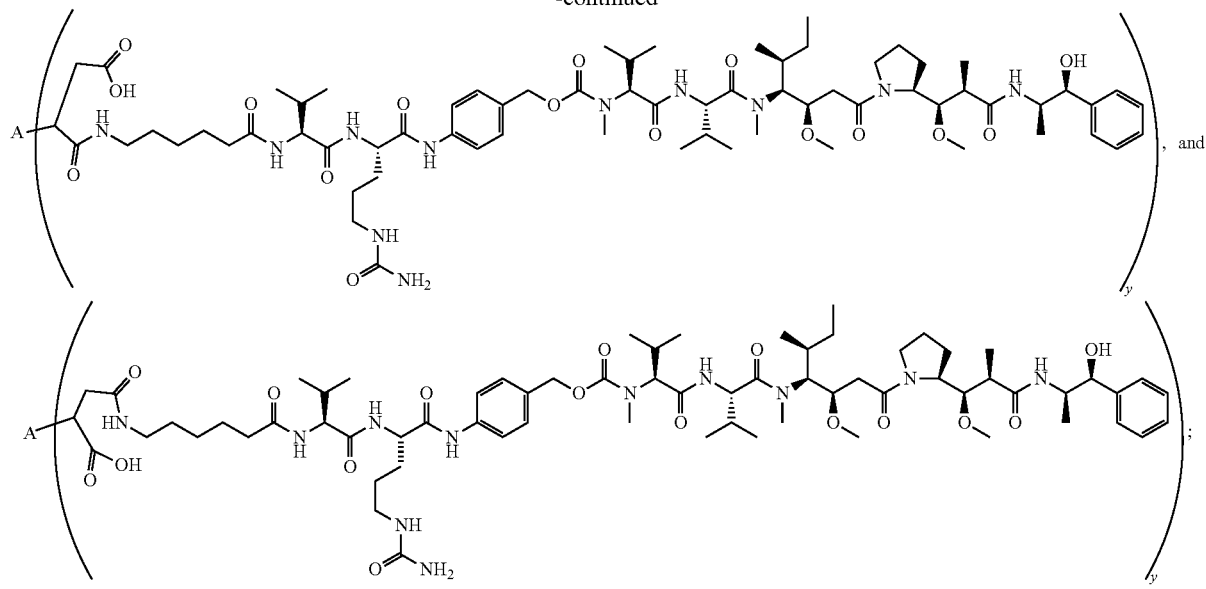

-continued wherein:
A represents an antibody or antigen binding fragment thereof that specifically binds to human CD48 as disclosed herein, and
y is an integer from 1 to 10.

Also disclosed herein are pharmaceutical compositions comprising any of the anti-CD48 antibodies, or antigen binding fragments thereof, or the antibody drug conjugates as disclosed herein, and a pharmaceutically acceptable carrier. In some embodiments, the pharmaceutical composition comprises one or more additional therapeutic agents. In some embodiments, the pharmaceutical composition is a lyophilisate.

The present application also discloses methods of treating cancer in a subject, methods of reducing or inhibiting the growth of a tumor in a subject, or methods of reducing or slowing the expansion of a cancer cell population in a subject, comprising administering to the subject a therapeutically effective amount of any of the anti-CD48 antibodies, or antigen binding fragments thereof, the antibody-drug conjugates, or the pharmaceutical compositions as disclosed herein. In some embodiments, the method reduces or inhibits the growth of the tumor by at least about 10%, at least about 20%, at least about 30%, at least about 40%, at least about 50%, at least about 60%, at least about 70%, at least about 80%, at least about 90%, at least about 95%, or at least about 99%. In other embodiments, the method reduces the cancer cell population or slows the expansion of the cancer cell population by at least about 10%, at least about 20%, at least about 30%, at least about 40%, at least about 50%, at least about 60%, at least about 70%, at least about 80%, at least about 90%, at least about 95%, or at least about 99%. In some embodiments, the cancer, tumor, or cancer cell population expresses CD48. In some embodiments, the cancer is a tumor or a hematological cancer, preferably, the cancer is a breast cancer, multiple myeloma, B-cell lymphoma, plasma cell myeloma, leukemia, lymphoma, gastric cancer, acute myeloid leukemia, bladder cancer, brain cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, prostate cancer, small cell lung cancer, or spleen cancer.

Also disclosed herein are antibodies that compete with any of the antibodies disclosed herein, including NY920 or NY938, for binding to human CD48. In some embodiments, the antibodies bind to the same or overlapping epitope of human CD48 as NY920 or NY938. In one embodiment, the antibodies bind to one or more amino acids within residues 54-64 or 105-121 of human CD48 (SEQ ID NO:53). In other embodiments, the antibody binds to one or more amino acids selected from residues 54, 58, 60, 61, 62, 64, 105, 107, 119, 111, 114, 115, 117, 119, or 121 of human CD48 (SEQ ID NO:53). In some embodiments, the antibody contacts the one or more amino acids within 4.0 Å.

The present disclosure also provides diagnostic agents comprising any of the anti-CD48 antibodies or antigen binding fragments thereof, or the antibody drug conjugates as disclosed herein. In some embodiments, the anti-CD48 antibody or antigen binding fragment thereof, or the antibody drug conjugate, is labeled or conjugated with a radiolabel, a fluorophore, a chromophore, an imaging agent, or a metal ion. Also disclosed are methods of detecting human CD48 in a tissue or cell comprising contacting the diagnostic agent to the tissue or cell and detecting binding of the diagnostic agent to the tissue or cell.

BRIEF DESCRIPTION OF THE DRAWINGS

FIG. 1 depicts binding curves of three (3) anti-CD48 antibodies to various constructs of the extracellular domain of human CD48 protein. Construct #2248 carries mutated residues at amino acids 50-55 (ENYKQ (SEQ ID NO: 78)-modified into GSSKQ (SEQ ID NO: 79)). Construct #2249 carries mutated residues at amino acids 70-74 (DSRK (SEQ ID NO: 80)-modified into AAGK (SEQ ID NO: 81)). Construct #2250 carries mutated residues at amino acids 103-105 (KKTGNE (SEQ ID NO: 82) modified into KKDASG (SEQ ID NO: 83)). FIG. 1C is a graph depicting binding of humanized anti-CD48A (also known as MEM102) to the constructs. The graphs indicate that NOV3731 and NY920 do not bind to the same CD48 extracellular domain constructs as CD48a.

DETAILED DESCRIPTION

Figure 1A:
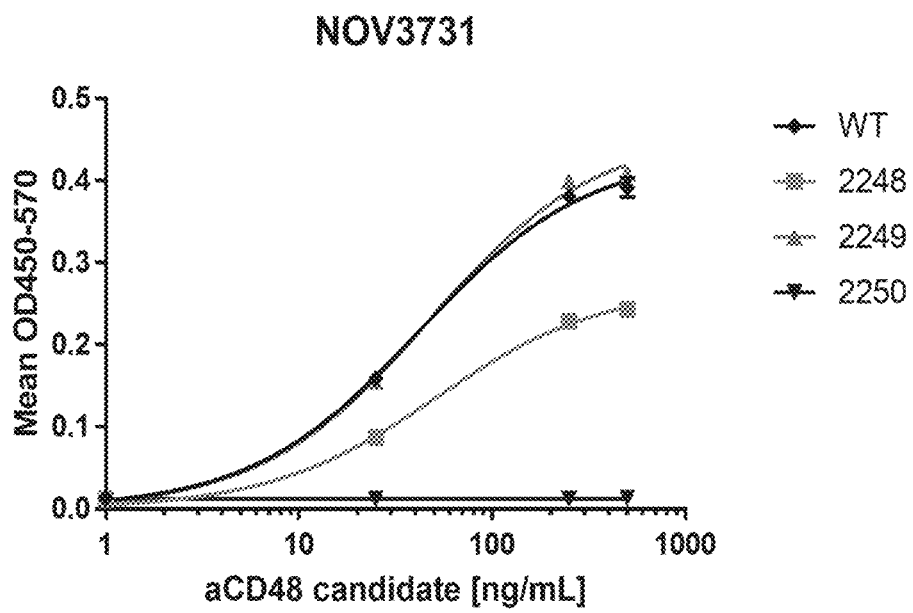
FIG. 1A is a graph depicting binding of anti-CD48 antibody NOV3731 (parental antibody of NY920) to the constructs.

The present disclosure provides antibodies and antigen binding fragments thereof that specifically bind to CD48. In some embodiments, the CD48 antibody or antigen binding fragment thereof is part of an antibody drug conjugate, wherein an antibody or antibody fragment that specifically binds to human CD48 is linked to a drug moiety (e.g., a cytotoxic agent, a targeted inhibitor, an immunomodulatory compound, but excluding BH3 mimetic inhibitors), optionally through a linker. Those antibody drug conjugates can selectively deliver a drug moiety to cells expressing CD48, e.g., B lymphoblasts, thereby treating those cells in a patient, e.g. a B-cell lymphoma patient. The present disclosure further provides pharmaceutical compositions comprising the antibody or antigen binding fragments disclosed herein, antibody drug conjugates thereof, and methods of making and using such pharmaceutical compositions for treating patients in need thereof.

Definitions

Unless stated otherwise, the following terms and phrases as used herein are intended to have the following meanings:

As used herein, the singular forms "a," "an," and "the" include plural forms unless the context clearly dictates otherwise. The terms "comprising", "having", "being of" as in "being of a chemical formula", "including", and "containing" are to be construed as open terms (i.e., meaning "including but not limited to") unless otherwise noted. Additionally whenever "comprising" or another open-ended term is used in an embodiment, it is to be understood that the same embodiment can be more narrowly claimed using the intermediate term "consisting essentially of" or the closed term "consisting of".

The term "about" or "approximately," when used in the context of numerical values and ranges, refers to values or ranges that approximate or are close to the recited values or ranges such that the embodiment may perform as intended, as is apparent to the skilled person from the teachings contained herein. In some embodiments, about means plus or minus 20%, 15%, 10%, 5%, 1%, 0.5%, or 0.1% of a numerical amount. In one embodiment, the term "about" refers to a range of values which are 10% more or less than the specified value. In another embodiment, the term "about" refers to a range of values which are 5% more or less than the specified value. In another embodiment, the term "about" refers to a range of values which are 1% more or less than the specified value.

The term "alkyl" refers to a monovalent saturated hydrocarbon chain having the specified number of carbon atoms. For example, $C_1$-$C_6$alkyl refers to an alkyl group having from 1 to 6 carbon atoms. Alkyl groups may be straight or branched. Representative branched alkyl groups have one, two, or three branches. Examples of alkyl groups include, but are not limited to, methyl, ethyl, propyl (n-propyl and isopropyl), butyl (n-butyl, isobutyl, sec-butyl, and t-butyl), pentyl (n-pentyl, isopentyl, and neopentyl), and hexyl.

The term "antibody," as used herein, refers to a protein, or polypeptide sequence derived from an immunoglobulin molecule that specifically binds to an antigen. Antibodies can be polyclonal or monoclonal, multiple or single chain, or intact immunoglobulins, and may be derived from natural sources or from recombinant sources. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. An antibody can be a monoclonal antibody, human antibody, humanized antibody, camelid antibody, or chimeric antibody. The antibodies can be of any isotype (e.g., IgG, IgE, IgM, IgD, IgA and IgY), class (e.g., IgG1, IgG2, IgG3, IgG4, IgA1 and IgA2) or subclass.

"Complementarity-determining domains" or "complementary-determining regions" ("CDRs") interchangeably refer to the hypervariable regions of VL and VH. The CDRs are the target protein-binding site of the antibody chains that harbors specificity for such target protein. There are three CDRs (CDR1-3, numbered sequentially from the N-terminus) in each human VL or VH, constituting about 15-20% of the variable domains. CDRs can be referred to by their region and order. For example, "VHCDR1" or "HCDR1" both refer to the first CDR of the heavy chain variable region. The CDRs are structurally complementary to the epitope of the target protein and are thus directly responsible for the binding specificity. The remaining stretches of the VL or VH, the so-called framework regions, exhibit less variation in amino acid sequence (Kuby, Immunology, 4th ed., Chapter 4. W.H. Freeman & Co., New York, 2000).

The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme) and ImMunoGenTics (IMGT) numbering (Lefranc, M.-P., The Immunologist, 7, 132-136 (1999); Lefranc, M.-P. et al., Dev. Comp. Immunol., 27, 55-77 (2003) ("IMGT" numbering scheme). For example, for classic formats, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL. Under IMGT the CDR amino acid residues in the VH are numbered approximately 26-35 (CDR1), 51-57 (CDR2) and 93-102 (CDR3), and the CDR amino acid residues in the VL are numbered approximately 27-32 (CDR1), 50-52 (CDR2), and 89-97 (CDR3) (numbering according to "Kabat"). Under IMGT, the CDR regions of an antibody can be determined using the program IMGT/DomainGap Align.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3, and in some cases, CH4) confer important biological properties such as secretion, transplacental mobility, Fc receptor binding, complement binding, FcRn receptor binding, half-life, pharmacokinetics and the like. By convention, the numbering of the constant region domains increases as they become more distal from the antigen binding site or amino-terminus of the antibody. The N-terminus is a variable region and at the C-terminus is a constant region; the $CH_3$ and CL domains actually comprise the carboxy-terminal domains of the heavy and light chain, respectively.

The term "antibody fragment" or "antigen binding fragment", as used herein, refers to one or more portions of an antibody that retain the ability to specifically interact with (e.g., by binding, steric hindrance, stabilizing/destabilizing, spatial distribution) an epitope of an antigen (e.g., CD48). Examples of antibody fragments include, but are not limited to, a Fab fragment, which is a monovalent fragment consisting of the VL, VH, CL and CH1 domains; a Fab' fragment, which is a monovalent fragment consisting of the VL, VH, CL, CH1 domains, and the hinge region; a $F(ab')_2$ fragment, which is a bivalent fragment comprising two Fab fragments linked by a disulfide bridge at the hinge region; a half antibody, which includes a single heavy chain and a single light chain linked by a disulfide bridge; an one-arm antibody, which includes a Fab fragment linked to an Fc region; a CH2 domain-deleted antibody, which includes two Fab fragments linked to the CH3 domain dimers (see Glaser, J Biol Chem. 2005; 280(50):41494-503); a single-chain Fv (scFv); a disulfide-linked Fv (sdFv); a Fd fragment consisting of the VH and CH1 domains; a Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody. For example, a Fab fragment can include amino acid residues 1-222 (EU numbering) of the heavy chain of an antibody; whereas a Fab' fragment can include amino acid residues 1-236 (EU numbering) of the heavy chain of an antibody. The Fab or Fab' fragment of an antibody can be generated recombinantly or by enzymatic digestion of a parent antibody. Recombinantly generated Fab or Fab' may be engineered to introduce amino acids for site-specific conjugation such as cysteines (Junutula, J. R.; et al., Nature biotechnology 2008, 26, 925), pyrroline-carboxy-lysines (Ou, W. et al., Proc Natl Acad Sci USA 2011; 108(26):10437-42) or unnatural amino acids (for example Tian, F. et al., Proc Natl Acad Sci USA 2014, 111, 1766, Axup, J. Y. et al., Proc Natl Acad Sci USA. 2012, 109, 16101. Similarly, mutations or peptide tags can be added to facilitate conjugation through phosphopantetheine transferases (Grunewald, J. et al., Bioconjugate chemistry 2015, 26, 2554), formyl glycine forming enzyme (Drake, P. M. et al., Bioconjugate chemistry 2014, 25, 1331), transglutaminase (Strop, P. et al., *Chemistry & biology* 2013, 20, 161), sortase (Beerli, R. R.; Hell, T.; Merkel, A. S.; Grawunder, U. *PloS one* 2015, 10, e0131177) or other enzymatic conjugation strategies. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antibody fragments or antigen binding fragments can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antibody fragments or antigen binding fragments can be incorporated into single chain molecules comprising a pair of tandem Fv segments (VH-CH1-VH-CH1) which, together with complementary light chain polypeptides, form a pair of antigen binding regions (Zapata et al., Protein Eng. 8:1057-1062, 1995; and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000.

The human antibodies of the present disclosure can include amino acid residues not encoded by human sequences (e.g., mutations introduced by random or site-specific mutagenesis in vitro or by somatic mutation in vivo, or a conservative substitution to promote stability or manufacturing).

The term "recognize" as used herein refers to an antibody or antigen binding fragment thereof that finds and interacts (e.g., binds) with its epitope, whether that epitope is linear or conformational. The term "epitope" refers to a site on an antigen to which an antibody or antigen binding fragment of the disclosure specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 1, 2, 3, 4, 5, 6, 7, 8, 9, 10, 11, 12, 13, 14, 15 or more amino acids in a unique spatial conformation. Methods of determining spatial conformation of epitopes include techniques in the art, for example, x-ray crystallography and 2-dimensional nuclear magnetic resonance (see, e.g., Epitope Mapping Protocols in Methods in Molecular Biology, Vol. 66, G. E. Morris, Ed. (1996)). A "paratope" is the part of the antibody which recognizes the epitope of the antigen.

The phrase "specifically binds" or "selectively binds," when used in the context of describing the interaction between an antigen (e.g., a protein) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one aspect, under designated immunoassay conditions, the antibody or binding agent with a particular binding specificity binds to a particular antigen at least ten (10) times the background and does not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some aspects, antibodies or antibody fragments are selected that cross-react with certain desired molecules.

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other all other known variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementarity determining regions only, framework and complementary determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 91%, 92%, 93%, 94%, 95%, 96%, 97%, 98%, 99%, or 100% sequence identity with the reference variable region nucleic acid or amino acid sequence.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least 10 to 100 times over the background.

The term "equilibrium dissociation constant (KD [M])" refers to the dissociation rate constant (kd [$s^{-1}$]) divided by the association rate constant (ka [$s^{-1}$, $M^{-1}$]). Equilibrium dissociation constants can be measured using any known method in the art. The antibodies of the present disclosure generally will have an equilibrium dissociation constant of less than about $10^{-7}$ or $10^{-8}$ M, for example, less than about $10^{-9}$ M or $10^{-10}$ M, in some aspects, less than about $10^{-11}$ M, $10^{-12}$ M or $10^{-13}$ M.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

As used herein, the phrase "consisting essentially of" refers to the genera or species of active pharmaceutical agents included in a method or composition, as well as any excipients inactive for the intended purpose of the methods or compositions. In some aspects, the phrase "consisting essentially of" expressly excludes the inclusion of one or more additional active agents other than an antibody drug conjugate of the present disclosure. In some aspects, the phrase "consisting essentially of" expressly excludes the inclusion of one or more additional active agents other than an antibody drug conjugate of the present disclosure and a second co-administered agent.

The term "amino acid" refers to naturally occurring, synthetic, and unnatural amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some aspects, the term "conservative sequence modifications" are used to refer to amino acid modifications that do not significantly affect or alter the binding characteristics of the antibody containing the amino acid sequence.

The term "optimized" as used herein refers to a nucleotide sequence that has been altered to encode an amino acid sequence using codons that are preferred in the production cell or organism, generally a eukaryotic cell, for example, a yeast cell, a *Pichia* cell, a fungal cell, a *Trichoderma* cell, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

The terms "percent identical" or "percent identity," in the context of two or more nucleic acids or polypeptide sequences, refers to the extent to which two or more sequences or subsequences that are the same. Two sequences are "identical" if they have the same sequence of amino acids or nucleotides over the region being compared. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 30 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated.

Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, Adv. Appl. Math. 2:482c (1970), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Brent et al., Current Protocols in Molecular Biology, 2003).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, Comput. Appl. Biosci. 4:11-17, (1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, J. Mol. Biol. 48:444-453, (1970) algorithm which has been incorporated into the GAP program in the GCG software package (available on the World Wide Web at gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260: 2605-2608; and Rossolini et al., (1994) Mol. Cell. Probes 8:91-98).

The term "operably linked" in the context of nucleic acids refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "conjugate" or "antibody drug conjugate" as used herein refers to the linkage of an antibody or an antigen binding fragment thereof with another agent, such as a chemotherapeutic agent, a toxin, an immunotherapeutic agent, an imaging probe, and the like. The linkage can be covalent bonds, or non-covalent interactions such as through electrostatic forces. Various linkers, known in the art, can be employed in order to form the conjugate. Additionally, the conjugate can be provided in the form of a fusion protein that may be expressed from a polynucleotide encoding the conjugate. As used herein, "fusion protein" refers to proteins created through the joining of two or more genes or gene fragments, which originally coded for separate proteins (including peptides and polypeptides). Translation of the fusion gene results in a single protein with functional properties derived from each of the original proteins.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "toxin", "cytotoxin" or "cytotoxic agent" as used herein, refers to any agent that is detrimental to the growth and proliferation of cells and may act to reduce, inhibit, or destroy a cell or malignancy.

The term "anti-cancer agent" as used herein refers to any agent that can be used to treat a cell proliferative disorder such as cancer, including but not limited to, cytotoxic agents, chemotherapeutic agents, radiotherapy and radiotherapeutic agents, targeted anti-cancer agents, and immunotherapeutic agents.

The term "drug moiety" or "payload" as used herein refers to a chemical moiety that is conjugated or is suitable for conjugation to an antibody or antigen binding fragment, and can include any therapeutic or diagnostic agent and a metabolite of the antibody drug conjugate disclosed herein that has the desired therapeutic or diagnostic properties, for example, an anti-cancer, anti-inflammatory, anti-infective (e.g., anti-fungal, antibacterial, anti-parasitic, anti-viral), or an anesthetic agent. In certain aspects, a drug moiety is selected from an Eg5 inhibitor, a V-ATPase inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alkylating agent, a DNA intercalator, a DNA minor groove binder, an RNA polymerase inhibitor, an amanitin, a spliceosome inhibitor, a topoisomerase inhibitor, a DHFR inhibitor, and a pro-apoptotic agent.

The term "drug moiety" as used herein excludes BH3 mimetic inhibitors that specifically inhibit MCL-1, BCL-2, or BCLXL, also referred to as MCL-1 inhibitors, BCL-2 inhibitors, and BCLXL inhibitors. The terms "myeloid cell leukemia 1" or "Mcl-1" or "MCL1" as used herein, refer to any native form of human Mcl-1, encompasses full-length human Mcl-1 (e.g., UniProt Reference Sequence: Q07820), as well as any splice variants, allelic variants, and isoforms that retain one or more biologic functions of human Mcl-1. Specific Mcl-1 inhibitors excluded herein are disclosed in PCT application numbers PCT/EP2014/078947, PCT/EP2016/064417, PCT/EP2016/064418, PCT/EP2016/064433, PCT/EP2016/064436, and PCT/EP2016/081688, each of which are incorporated herein by reference in their entireties.

The terms "B-cell lymphoma 2" or "Bcl-2" or "BCL2" as used herein, refer to any native form of human Bcl-2, encompasses full-length human Bcl-2 (e.g. UniProf Reference Sequence P10415-1 or P10415-2), as well as any splice variants, allelic variants, and isoforms that retain one or more biologic functions of human Bcl-2. Specific Bcl-2 inhibitors excluded herein are disclosed in PCT application numbers PCT/FR2013/050136, PCT/FR2014/051888, PCT/FR2014/051887, PCT/FR2014/051884, PCT/FR2014/051885, PCT/EP2014/065764, and PCT/EP2018/079113, each of which are incorporated herein by reference in their entireties.

The terms "B-cell lymphoma-extra large" or "Bcl-xL" or "BCLXL" as used herein, refer to any native form of human Bcl-xL, encompasses full-length human Bcl-xL (e.g. UniProt Reference Sequence: Q07817-1), as well as any splice variants, allelic variants, and isoforms that retain one or more biologic functions of human Bcl-xL. Specific Bcl-xL inhibitors excluded herein are disclosed in PCT application numbers PCT/EP2020/071179 and PCT/EP2020/071181, each of which are incorporated herein by reference in their entireties.

Methods for attaching each of these drug moieties to a linker compatible with the antibodies and methods of the present disclosure are known in the art. See, e.g., Singh et al., (2009) Therapeutic Antibodies: Methods and Protocols, vol. 525, 445-457. In addition, a payload can be a biophysical probe, a fluorophore, a spin label, an infrared probe, an affinity probe, a chelator, a spectroscopic probe, a radioactivprobe, a lipid molecule, a polyethylene glycol, a polymer, a spin label, DNA, RNA, a protein, a peptide, a surface, an antibody, an antibody fragment, a nanoparticle, a quantum dot, a liposome, a PLGA particle, a saccharide or a polysaccharide.

The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor). The term "cancer" includes all types of cancers and cancer metastases, including hematological cancers, solid tumors, sarcomas, carcinomas and other solid and non-solid tumor cancers. Hematological cancers may include B-cell malignancies, cancers of the blood (leukemias), cancers of plasma cells (myelomas, e.g., multiple myeloma), or cancers of the lymph nodes (lymphomas). Exemplary B-cell malignancies include chronic lymphocytic leukemia (CLL), follicular lymphoma, mantle cell lymphoma, and diffuse large B-cell lymphoma. Leukemias may include acute lymphoblastic leukemia (ALL), acute myeloid leukemia (AML), chronic lymphocytic leukemia (CLL), chronic myelogenous leukemia (CML), chronic myelomonocytic leukemia (CMML), acute monocytic leukemia (AMoL), etc. Lymphomas may include Hodgkin's lymphoma, non-Hodgkin's lymphoma, etc. Other hematologic cancers may include myelodysplasia syndrome (MDS). Solid tumors may include carcinomas such as adenocarcinoma, e.g., breast cancer, pancreatic cancer, prostate cancer, colon or colorectal cancer, lung cancer, gastric cancer, cervical cancer, endometrial cancer, ovarian cancer, cholangiocarcinoma, glioma, melanoma, etc. In some embodiments, the cancer is a breast cancer, multiple myeloma, plasma cell myeloma, leukemia, lymphoma, gastric cancer, acute myeloid leukemia, bladder cancer, brain cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, prostate cancer, small cell lung cancer, or spleen cancer.

In some embodiments, the cancer is a hematological cancer, e.g., a leukemia, a lymphoma, or a myeloma. For example, an combination described herein can be used to treat cancers malignancies, and related disorders, including, but not limited to, e.g., an acute leukemia, e.g., B-cell acute lymphoid leukemia (BALL), T-cell acute lymphoid leukemia (TALL), acute myeloid leukemia (AML), acute lymphoid leukemia (ALL); a chronic leukemia, e.g., chronic myelogenous leukemia (CML), chronic lymphocytic leukemia (CLL); an additional hematologic cancer or hematologic condition, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenström macroglobulinemia, myelofibrosis, amyloid light chain amyloidosis, chronic neutrophilic leukemia, essential thrombocythemia, chronic eosinophilic leukemia, chronic myelomonocytic leukemia, Richter Syndrome, mixed phenotype acute leukemia, acute biphenotypic leukemia, and "preleukemia" which are a diverse collection of hematological conditions united by ineffective production (or dysplasia) of myeloid blood cells, and the like.

As used herein, the term "tumor" refers to any mass of tissue that results from excessive cell growth or proliferation, either benign or malignant, including precancerous lesions. In some embodiments, the tumor is a breast cancer, gastric cancer, bladder cancer, brain cancer, cervical cancer, colorectal cancer, esophageal cancer, hepatocellular cancer, melanoma, oral cancer, ovarian cancer, non-small cell lung cancer, prostate cancer, small cell lung cancer, or spleen cancer. In some embodiments, the tumor is a gastric cancer.

The terms "tumor cell" and "cancer cell" may be used interchangeably herein and refer to individual cells or the total population of cells derived from a tumor or cancer, including both non-tumorigenic cells and cancer stem cells. The terms "tumor cell" and "cancer cell" will be modified by the term "non-tumorigenic" when referring solely to those cells lacking the capacity to renew and differentiate to distinguish those cells from cancer stem cells.

The term "CD48" refers to Cluster of Differentiation 48 protein, also known as B-lymphocyte activation marker (BLAST-1) or signaling lymphocytic activation molecule 2 (SLAMF2). In some embodiments, CD48 is a human CD48 isoform. In some embodiments, the human CD48 isoform is isoform 1 (NP_001769.2) having an amino acid sequence of:

```
                                    (SEQ ID NO: 53)
MCSRGWDSCLALELLLLPLSLLVTSIQGHLVHMTV

VSGSNVTLNISESLPENYKQLTWFYTFDQKIVEWD

SRKSKYFESKFKGRVRLDPQSGALYISKVQKEDNS

TYIMRVLKKTGNEQEWKIKLQVLDPVPKPVIKIEK

IEDMDDNCYLKLSCVIPGESVNYTWYGDKRPFPKE

LQNSVLETTLMPHNYSRCYTCQVSNSVSSKNGTVC

LSPPCTLARSFGVEWIASWLVVTVPTILGLLLT.
```

In some embodiments, the human CD48 isoform is isoform 2 (NP_001242959.1) having an amino acid sequence of:

```
                                    (SEQ ID NO: 54)
MCSRGWDSCLALELLLLPLSLLVTSIQGHLVHMTV

VSGSNVTLNISESLPENYKQLTWFYTFDQKIVEWD

SRKSKYFESKFKGRVRLDPQSGALYISKVQKEDNS

TYIMRVLKKTGNEQEWKIKLQVLDPVPKPVIKIEK

IEDMDDNCYLKLSCVIPGESVNYTWYGDKRPFPKE

LQNSVLETTLMPHNYSRCYTCQVSNSVSSKNGTVC

LSPPCTLGKKDPWELRGAQGNWSCFEQRKAGGPIQ

PPCTVWW.
```

As used herein, the term "CD48" is used to refer collectively to all naturally occurring isoforms of CD48 protein, or a variant thereof.

The term "variant" refers to a polypeptide that has a substantially identical amino acid sequence to a reference polypeptide, or is encoded by a substantially identical nucleotide sequence, and is capable of having one or more activities of the reference polypeptide. For example, a variant can have about 85%, 90%, 91%, 92%, 93%, 94%, 95%, 96%, 97%, 98%, 99% or higher sequence identity to a reference polypeptide, while retain one or more activities of the reference polypeptide.

As used herein, the terms "treat", "treating," or "treatment" of any disease or disorder refer in one aspect, to ameliorating the disease or disorder (i.e., slowing or arresting or reducing the development of the disease or at least one of the clinical symptoms thereof). In another aspect, "treat", "treating," or "treatment" refers to alleviating or ameliorating at least one physical parameter including those which may not be discernible by the patient. In yet another aspect, "treat", "treating," or "treatment" refers to modulating the disease or disorder, either physically, (e.g., stabilization of a discernible symptom), physiologically, (e.g., stabilization of a physical parameter), or both. In yet another aspect, "treat", "treating," or "treatment" refers to delaying the onset or development or progression of the disease or disorder. In some embodiments, treatment comprises modulating a disease, disorder, or condition, either physically (e.g., stabilization of a discernible symptom), physiologically (e.g., stabilization of a physical parameter), or both. In some embodiments, treatment comprises administration of a described antibody, antigen binding fragment thereof, ADC thereof, or composition to a subject, e.g., a patient, to obtain a treatment benefit enumerated herein. The treatment can be to cure, heal, alleviate, delay, relieve, alter, remedy, ameliorate, palliate, improve, or affect a disease, disorder, or condition (e.g., a cancer), the symptoms of a disease, disorder, or condition (e.g., a cancer).

The term "therapeutically acceptable amount" or "therapeutically effective dose" interchangeably refers to an amount sufficient to effect the desired result (i.e., a reduction in tumor size, inhibition of tumor growth, prevention of metastasis, inhibition or prevention of viral, bacterial, fungal or parasitic infection). In some aspects, a therapeutically acceptable amount does not induce or cause undesirable side effects. A therapeutically acceptable amount can be determined by first administering a low dose, and then incrementally increasing that dose until the desired effect is achieved. A "therapeutically effective dosage," of the molecules of the present disclosure can prevent the onset of, or result in a decrease in severity of, respectively, disease symptoms, including symptoms associated with cancer.

The term "co-administer" refers to the simultaneous presence of two active agents in the blood of an individual. Active agents that are co-administered can be concurrently or sequentially delivered.

The term 'thiol-maleimide' as used herein refers to a group formed by reaction of a thiol with maleimide, having this general formula:

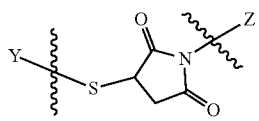

where Y and Z are groups to be connected via the thiol-maleimide linkage and can comprise linker components, antibodies or payloads. The thiol-maleimide may form the following ring opened structures

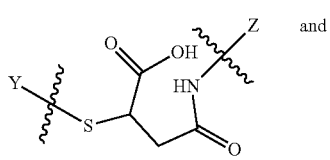

-continued

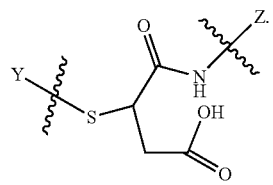

"Cleavable" as used herein refers to a linking group or linker component that connects two moieties by covalent connections, but breaks down to sever the covalent connection between the moieties under physiologically relevant conditions, typically a cleavable linking group is severed in vivo more rapidly in an intracellular environment than when outside a cell, causing release of the payload to preferentially occur inside a targeted cell. Cleavage may be enzymatic or non-enzymatic, but generally releases a payload from an antibody without degrading the antibody. Cleavage may leave some portion of a linking group or linker component attached to the payload, or it may release the payload without any residue of the linking group.

"Non-cleavable" as used herein refers to a linking group or linker component that is not especially susceptible to breaking down under physiological conditions, e.g., it is at least as stable as the antibody or antigen binding fragment portion of the conjugate. Such linking groups are sometimes referred to as 'stable', meaning they are sufficiently resistant to degradation to keep the payload connected to antibody or antigen binding fragment until the antibody or antigen binding fragment is itself at least partially degraded, i.e., the degradation of the antibody or antigen binding fragment precedes cleavage of the linking group in vivo. Degradation of the antibody portion of an ADC having a stable or non-cleavable linking group may leave some or all of the linking group, e.g., one or more amino acid groups from an antibody, attached to the payload or drug moiety that is delivered in vivo.

CD48 Antibodies

Disclosed herein are antibodies or antibody fragments (e.g. antigen binding fragments) that specifically bind to human CD48. Antibodies or antibody fragments (e.g., antigen binding fragments) of the present disclosure include, but are not limited to, the human monoclonal antibodies or antigen binding fragments thereof described herein.

Amino acid sequences of exemplary anti-CD48 antibodies of the present disclosure are set forth in Table 1, Table 2, and Table 3.

As set forth herein, antibodies are named by their designation, e.g. NY920. If modifications are made to the antibodies, they are further designated with that modification. For example if select amino acids in the antibody have been changed to cysteines (e.g. E152C, S375C according to EU numbering of the antibody heavy chain to facilitate conjugation to linker-drug moieties) they are designated as "CysMab"; or if the antibody has been modified with Fc silencing mutations D265A and P329A of the IgG1 constant region according to EU numbering, "DAPA" is added to the antibody name. If the antibody is used in an antibody drug conjugate, they are named using the following format: Antibody designation-linker-payload.

TABLE 1

Amino acid sequences of anti-CD48 mAb CDRs

| Ab Designation | SEQ ID NO | IgG chain | Amino acid sequence |
|---|---|---|---|
| NY920 CysMab | SEQ ID NO: 1 (Combined) | HCDR1 | GFTFSSFAMS |
| | SEQ ID NO: 2 (Combined) | HCDR2 | AISGFGGSTYYADSVKG |
| | SEQ ID NO: 3 (Combined) | HCDR3 | QFWEDQPFYFDY |
| | SEQ ID NO: 4 (Kabat) | HCDR1 | SFAMS |
| | SEQ ID NO: 2 (Kabat) | HCDR2 | AISGFGGSTYYADSVKG |
| | SEQ ID NO: 3 (Kabat) | HCDR3 | QFWEDQPFYFDY |
| | SEQ ID NO: 5 (Chothia) | HCDR1 | GFTFSSF |
| | SEQ ID NO: 6 (Chothia) | HCDR2 | SGFGGS |
| | SEQ ID NO: 3 (Chothia) | HCDR3 | QFWEDQPFYFDY |
| | SEQ ID NO: 7 (IMGT) | HCDR1 | GFTFSSFA |
| | SEQ ID NO: 8 (IMGT) | HCDR2 | ISGFGGST |
| | SEQ ID NO: 9 (IMGT) | HCDR3 | ARQFWEDQPFYFDY |
| | SEQ ID NO: 16 (Combined) | LCDR1 | RASQSISSYLN |
| | SEQ ID NO: 17 (Combined) | LCDR2 | AASSLQS |
| | SEQ ID NO: 18 (Combined) | LCDR3 | QQSYSTPLT |
| | SEQ ID NO: 16 (Kabat) | LCDR1 | RASQSISSYLN |
| | SEQ ID NO: 17 (Kabat) | LCDR2 | AASSLQS |
| | SEQ ID NO: 18 (Kabat) | LCDR3 | QQSYSTPLT |
| | SEQ ID NO: 19 (Chothia) | LCDR1 | SQSISSY |
| | SEQ ID NO: 20 (Chothia) | LCDR2 | AAS |
| | SEQ ID NO: 21 (Chothia) | LCDR3 | SYSTPL |
| | SEQ ID NO: 22 (IMGT) | LCDR1 | QSISSY |
| | SEQ ID NO: 20 (IMGT) | LCDR2 | AAS |
| | SEQ ID NO: 18 (IMGT) | LCDR3 | QQSYSTPLT |
| NY920 CysMab DAPA | SEQ ID NO: 1 (Combined) | HCDR1 | GFTFSSFAMS |
| | SEQ ID NO: 2 (Combined) | HCDR2 | AISGFGGSTYYADSVKG |
| | SEQ ID NO: 3 (Combined) | HCDR3 | QFWEDQPFYFDY |
| | SEQ ID NO: 4 (Kabat) | HCDR1 | SFAMS |
| | SEQ ID NO: 2 (Kabat) | HCDR2 | AISGFGGSTYYADSVKG |
| | SEQ ID NO: 3 (Kabat) | HCDR3 | QFWEDQPFYFDY |
| | SEQ ID NO: 5 (Chothia) | HCDR1 | GFTFSSF |
| | SEQ ID NO: 6 (Chothia) | HCDR2 | SGFGGS |
| | SEQ ID NO: 3 (Chothia) | HCDR3 | QFWEDQPFYFDY |
| | SEQ ID NO: 7 (IMGT) | HCDR1 | GFTFSSFA |
| | SEQ ID NO: 8 (IMGT) | HCDR2 | ISGFGGST |
| | SEQ ID NO: 9 (IMGT) | HCDR3 | ARQFWEDQPFYFDY |
| | SEQ ID NO: 16 (Combined) | LCDR1 | RASQSISSYLN |

TABLE 1-continued

Amino acid sequences of anti-CD48 mAb CDRs

| Ab Designation | SEQ ID NO | IgG chain | Amino acid sequence |
|---|---|---|---|
| | SEQ ID NO: 17 (Combined) | LCDR2 | AASSLQS |
| | SEQ ID NO: 18 (Combined) | LCDR3 | QQSYSTPLT |
| | SEQ ID NO: 16 (Kabat) | LCDR1 | RASQSISSYLN |
| | SEQ ID NO: 17 (Kabat) | LCDR2 | AASSLQS |
| | SEQ ID NO: 18 (Kabat) | LCDR3 | QQSYSTPLT |
| | SEQ ID NO: 19 (Chothia) | LCDR1 | SQSISSY |
| | SEQ ID NO: 20 (Chothia) | LCDR2 | AAS |
| | SEQ ID NO: 21 (Chothia) | LCDR3 | SYSTPL |
| | SEQ ID NO: 22 (IMGT) | LCDR1 | QSISSY |
| | SEQ ID NO: 20 (IMGT) | LCDR2 | AAS |
| | SEQ ID NO: 18 (IMGT) | LCDR3 | QQSYSTPLT |
| NY938 CysMab | SEQ ID NO: 27 (Combined) | HCDR1 | GYTFTEYTMH |
| | SEQ ID NO: 28 (Combined) | HCDR2 | GINPDTGDTSYNQKFTG |
| | SEQ ID NO: 29 (Combined) | HCDR3 | AQFWTTPRFAY |
| | SEQ ID NO: 30 (Kabat) | HCDR1 | EYTMH |
| | SEQ ID NO: 28 (Kabat) | HCDR2 | GINPDTGDTSYNQKFTG |
| | SEQ ID NO: 29 (Kabat) | HCDR3 | AQFWTTPRFAY |
| | SEQ ID NO: 31 (Chothia) | HCDR1 | GYTFTEY |
| | SEQ ID NO: 32 (Chothia) | HCDR2 | NPDTGD |
| | SEQ ID NO: 29 (Chothia) | HCDR3 | AQFWTTPRFAY |
| | SEQ ID NO: 33 (IMGT) | HCDR1 | GYTFTEYT |
| | SEQ ID NO: 34 (IMGT) | HCDR2 | INPDTGDT |
| | SEQ ID NO: 35 (IMGT) | HCDR3 | ARAQFWTTPRFAY |
| | SEQ ID NO: 42 (Combined) | LCDR1 | KASQDVGTAVA |
| | SEQ ID NO: 43 (Combined) | LCDR2 | WASTRHT |
| | SEQ ID NO: 44 (Combined) | LCDR3 | QQYSTYPIT |
| | SEQ ID NO: 42 (Kabat) | LCDR1 | KASQDVGTAVA |
| | SEQ ID NO: 43 (Kabat) | LCDR2 | WASTRHT |
| | SEQ ID NO: 44 (Kabat) | LCDR3 | QQYSTYPIT |
| | SEQ ID NO: 45 (Chothia) | LCDR1 | SQDVGTA |
| | SEQ ID NO: 46 (Chothia) | LCDR2 | WAS |
| | SEQ ID NO: 47 (Chothia) | LCDR3 | YSTYPI |
| | SEQ ID NO: 48 (IMGT) | LCDR1 | QDVGTA |
| | SEQ ID NO: 46 (IMGT) | LCDR2 | WAS |
| | SEQ ID NO: 44 (IMGT) | LCDR3 | QQYSTYPIT |

TABLE 1-continued

Amino acid sequences of anti-CD48 mAb CDRs

| Ab Designation | SEQ ID NO | IgG chain | Amino acid sequence |
|---|---|---|---|
| NY938 CysMab DAPA | SEQ ID NO: 27 (Combined) | HCDR1 | GYTFTEYTMH |
| | SEQ ID NO: 28 (Combined) | HCDR2 | GINPDTGDTSYNQKFTG |
| | SEQ ID NO: 29 (Combined) | HCDR3 | AQFWTTPRFAY |
| | SEQ ID NO: 30 (Kabat) | HCDR1 | EYTMH |
| | SEQ ID NO: 28 (Kabat) | HCDR2 | GINPDTGDTSYNQKFTG |
| | SEQ ID NO: 29 (Kabat) | HCDR3 | AQFWTTPRFAY |
| | SEQ ID NO: 31 (Chothia) | HCDR1 | GYTFTEY |
| | SEQ ID NO: 32 (Chothia) | HCDR2 | NPDTGD |
| | SEQ ID NO: 29 (Chothia) | HCDR3 | AQFWTTPRFAY |
| | SEQ ID NO: 33 (IMGT) | HCDR1 | GYTFTEYT |
| | SEQ ID NO: 34 (IMGT) | HCDR2 | INPDTGDT |
| | SEQ ID NO: 35 (IMGT) | HCDR3 | ARAQFWTTPRFAY |
| | SEQ ID NO: 42 (Combined) | LCDR1 | KASQDVGTAVA |
| | SEQ ID NO: 43 (Combined) | LCDR2 | WASTRHT |
| | SEQ ID NO: 44 (Combined) | LCDR3 | QQYSTYPIT |
| | SEQ ID NO: 42 (Kabat) | LCDR1 | KASQDVGTAVA |
| | SEQ ID NO: 43 (Kabat) | LCDR2 | WASTRHT |
| | SEQ ID NO: 44 (Kabat) | LCDR3 | QQYSTYPIT |
| | SEQ ID NO: 45 (Chothia) | LCDR1 | SQDVGTA |
| | SEQ ID NO: 46 (Chothia) | LCDR2 | WAS |
| | SEQ ID NO: 47 (Chothia) | LCDR3 | YSTYPI |
| | SEQ ID NO: 48 (IMGT) | LCDR1 | QDVGTA |
| | SEQ ID NO: 46 (IMGT) | LCDR2 | WAS |
| | SEQ ID NO: 44 (IMGT) | LCDR3 | QQYSTYPIT |

TABLE 2

Amino acid sequence and nucleic acid sequences of anti-CD48 mAb variable regions

| Ab | SEQ ID NO | IgG chain | Amino acid sequence |
|---|---|---|---|
| NY920 CysMab | SEQ ID NO: 10 | VH | EVQLLESGGGLVQPGGSLRLSCAASGFTFSSFAMSWVRQAPGKGLEWVSAISGFGGSTYYADSVKGRFTISRDNSKNTLYLQMNSLRAEDTAVYYCARQFWEDQPFYFDYWGQGTLVTVSS |
| | SEQ ID NO: 11 | DNA VH | GAAGTGCAGCTGCTGGAGTCCGGGGGTGGACTGGTGCAGCCCGGAGGTTCCCTGCGGTTGTCTTGTGCCGCCTCGGGATTCACCTTCTCGTCCTTCGCGATGAGCTGGGTCCGCCAAGCTCCTGGAAAAGGGCTCGAATGGGTGTCCGCGATCAGCGGATTTGGCGGCTCCACCTACTACGCCGATTCAGTGAAGGGCCGGTTCACCATCTCACGGGACAACAGCAAGAACACGCTGTATCTGCAAATGAACTCCCTGCGCGCTGAGGACACCGCAGTGTACTACTGCGCGAGACAGTTCTGGGAGGACCAGCCGTTCTA |

TABLE 2-continued

Amino acid sequence and nucleic acid sequences of anti-CD48 mAb variable regions

| Ab | SEQ ID NO | IgG chain | Amino acid sequence |
|---|---|---|---|
| | | | CTTCGACTACTGGGGACAGG GGACCCTCGTGACTGTCTCC TCC |
| | SEQ ID NO: 23 | VL | DIQMTQSPSSLSASVGDRVT ITCRASQSISSYLNWYQQKP GKAPKLLIYAASSLQSGVPS RFSGSGSGTDFTLTISSLQP EDFATYYCQQSYSTPLTFGQ GTKVEIK |
| | SEQ ID NO: 24 | DNA VL | GATATTCAGATGACCCAGTC CCCGTCGTCGCTGAGCGCCA GCGTGGGAGACAGAGTGACC ATTACCTGTCGGGCCAGCCA GTCGATCTCCTCCTACCTTA ACTGGTATCAGCAGAAGCCA GGAAAGGCACCGAAACTGCT GATCTACGCCGCGTCCTCCT TGCAATCCGGAGTGCCCTCA AGGTTCTCCGGGTCGGGTTC TGGCACTGACTTTACCCTGA CCATCAGCAGCCTCCAGCCC GAGGACTTCGCCACCTACTA CTGCCAGCAGTCATACTCCA CCCCTCTGACATTCGGCCAA GGGACCAAGGTCGAAATCAA G |
| NY920 CysMab DAPA | SEQ ID NO: 10 | VH | EVQLLESGGGLVQPGGSLRL SCAASGFTFSSFAMSWVRQA PGKGLEWVSAISGFGGSTYY ADSVKGRFTISRDNSKNTLY LQMNSLRAEDTAVYYCARQF WEDQPFYFDYWGQGTLVTVS S |
| | SEQ ID NO: 11 | DNA VH | GAAGTGCAGCTGCTGGAGTC CGGGGGTGGACTGGTGCAGC CCGGAGGTTCCCTGCGGTTG TCTTGTGCCGCCTCGGGATT CACCTTCTCGTCCTTCGCGA TGAGCTGGGTCCGCCAAGCT CCTGGAAAAGGGCTCGAATG GGTGTCCGCGATCAGCGGAT TTGGCGGCTCCACCTACTAC GCCGATTCAGTGAAGGGCCG GTTCACCATCTCACGGGACA ACAGCAAGAACACGCTGTAT CTGCAAATGAACTCCCTGCG CGCTGAGGACACCGCAGTGT ACTACTGCGCGAGACAGTTC TGGGAGGACCAGCCGTTCTA CTTCGACTACTGGGGACAGG GGACCCTCGTGACTGTCTCC TCC |
| | SEQ ID NO: 23 | VL | DIQMTQSPSSLSASVGDRVT ITCRASQSISSYLNWYQQKP GKAPKLLIYAASSLQSGVPS RFSGSGSGTDFTLTISSLQP EDFATYYCQQSYSTPLTFGQ GTKVEIK |
| | SEQ ID NO: 24 | DNA VL | GATATTCAGATGACCCAGTC CCCGTCGTCGCTGAGCGCCA GCGTGGGAGACAGAGTGACC ATTACCTGTCGGGCCAGCCA GTCGATCTCCTCCTACCTTA ACTGGTATCAGCAGAAGCCA GGAAAGGCACCGAAACTGCT GATCTACGCCGCGTCCTCCT TGCAATCCGGAGTGCCCTCA |

TABLE 2-continued

Amino acid sequence and nucleic acid sequences of anti-CD48 mAb variable regions

| Ab | SEQ ID NO | IgG chain | Amino acid sequence |
|---|---|---|---|
| | | | AGGTTCTCCGGGTCGGGTTC TGGCACTGACTTTACCCTGA CCATCAGCAGCCTCCAGCCC GAGGACTTCGCCACCTACTA CTGCCAGCAGTCATACTCCA CCCCTCTGACATTCGGCCAA GGGACCAAGGTCGAAATCAA G |
| NY938 CysMab | SEQ ID NO: 36 | VH | QVQLVQSGAEVKKPGASVKV SCKASGYTFTEYTMHWVRQA PGQGLEWMGGINPDTGDTSY NQKFTGRATLTVDKSTSTAY MELSSLRSEDTAVYYCARAQ FWTTPRFAYWGQGTLVTVSS |
| | SEQ ID NO: 37 | DNA VH | CAAGTGCAGCTCGTGCAGTC CGGAGCGGAAGTGAAAAAGC CCGGAGCCTCAGTGAAAGTG TCCTGCAAAGCCTCGGGGTA CACCTTCACCGAGTACACTA TGCATTGGGTCCGCCAAGCT CCTGGTCAAGGCCTCGAATG GATGGGCGGCATCAATCCCG ACACCGGCGACACCAGCTAT AACCAGAAGTTCACCGGACG CGCCACTCTGACTGTCGATA AGAGCACAAGCACCGCCTAC ATGGAACTGTCGTCCTTGCG GTCCGAGGATACCGCCGTGT ACTACTGCGCGAGAGCGCAG TTTTTGGACTACCCCGCGGTT CGCCTACTGGGGACAGGGCA CTCTCGTGACTGTGTCATCG |
| | SEQ ID NO: 49 | VL | DIQMTQSPSSLSASVGDRVT ITCKASQDVGTAVAWYQQKP GKVPKLLIYWASTRHTGVPS RFSGSGSGTDFTLTISSLQP EDVATYYCQQYSTYPITFGQ GTKLEIK |
| | SEQ ID NO: 50 | DNA VL | GACATCCAAATGACCCAGAG CCCCTTCGAGCCTGTCAGCCT CCGTGGGCGACAGAGTGACC ATTACTTGCAAAGCCAGCCA GGACGTGGGAACTGCAGTCG CCTGGTATCAGCAGAAGCCA GGAAAGGTCCCCAAGCTCCT GATCTACTGGGCTTCCACCC GGCACACTGGCGTGCCGTCA AGGTTTTCGGGATCGGGTTC CGGGACTGATTTCACCCTGA CCATTTCCTCCCTCCAACCC GAGGATGTGGCCACCTACTA CTGCCAGCAGTACTCCACCT ACCCGATCACATTCGGACAG GGCACCAAGCTCGAAATCAA G |
| NY938 CysMab DAPA | SEQ ID NO: 36 | VH | QVQLVQSGAEVKKPGASVKV SCKASGYTFTEYTMHWVRQA PGQGLEWMGGINPDTGDTSY NQKFTGRATLTVDKSTSTAY MELSSLRSEDTAVYYCARAQ FWTTPRFAYWGQGTLVTVSS |
| | SEQ ID NO: 37 | DNA VH | CAAGTGCAGCTCGTGCAGTC CGGAGCGGAAGTGAAAAAGC CCGGAGCCTCAGTGAAAGTG TCCTGCAAAGCCTCGGGGTA CACCTTCACCGAGTACACTA TGCATTGGGTCCGCCAAGCT |

TABLE 2-continued

Amino acid sequence and nucleic acid sequences of anti-CD48 mAb variable regions

| Ab | SEQ ID NO | IgG chain | Amino acid sequence |
|---|---|---|---|
| | | | CCTGGTCAAGGCCTCGAATG GATGGGCGGCATCAATCCCG ACACCGGCGACACCAGCTAT AACCAGAAGTTCACCGGACG CGCCACTCTGACTGTCGATA AGAGCACAAGCACCGCCTAC ATGGAACTGTCGTCCTTGCG GTCCGAGGATACCGCCGTGT ACTACTGCGCGAGAGCGCAG TTTTGGACTACCCCGCGGTT CGCCTACTGGGGACAGGGCA CTCTCGTGACTGTGTCATCG |
| | SEQ ID NO: 49 | VL | DIQMTQSPSSLSASVGDRVT ITCKASQDVGTAVAWYQQKP GKVPKLLIYWASTRHTGVPS RFSGSGSGTDFTLTISSLQP EDVATYYCQQYSTYPITFGQ GTKLEIK |
| | SEQ ID NO: 50 | DNA VL | GACATCCAAATGACCCAGAG CCCTTCGAGCCTGTCAGCCT CCGTGGGCGACAGAGTGACC ATTACTTGCAAAGCCAGCCA GGACGTGGGAACTGCAGTCG CCTGGTATCAGCAGAAGCCA GGAAAGGTCCCCAAGCTCCT GATCTACTGGGCTTCCACCC GGCACACTGGCGTGCCGTCA AGGTTTTCGGGATCGGGTTC CGGGACTGATTTCACCCTGA CCATTTCCTCCCTCCAACCC GAGGATGTGGCCACCTACTA CTGCCAGCAGTACTCCACCT ACCCGATCACATTCGGACAG GGCACCAAGCTCGAAATCAA G |

TABLE 3

Amino acid and nucleic acid sequences of full length mAb IgG chains

| Ab | SEQ ID NO | IgG chain | Amino acid sequence |
|---|---|---|---|
| NY920 CysMab | SEQ ID NO: 12 | Heavy Chain | EVQLLESGGGLVQPGGSLRL SCAASGFTFSSFAMSWVRQA PGKGLEWVSAISGFGGSTYY ADSVKGRFTISRDNSKNTLY LQMNSLRAEDTAVYYCARQF WEDQPFYFDYWGQGTLVTVS SASTKGPSVFPLAPSSKSTS GGTAALGCLVKDYFPCPVTV SWNSGALTSGVHTFPAVLQS SGLYSLSSVVTVPSSSLGTQ TYICNVNHKPSNTKVDKRVE PKSCDKTHTCPPCPAPELLG GPSVFLFPPKPKDTLMISRT PEVTCVVVDVSHEDPEVKFN WYVDGVEVHNAKTKPREEQY NSTYRVVSVLTVLHQDWLNG KEYKCKVSNKALPAPIEKTI SKAKGQPREPQVYTLPPSRE EMTKNQVSLTCLVKGFYPCD IAVEWESNGQPENNYKTTPP VLDSDGSFFLYSKLTVDKSR WQQGNVFSCSVMHEALHNHY TQKSLSLSPGK |
| | SEQ ID NO: 13 | DNA Heavy Chain | GAAGTGCAGCTGCTGGAGTC CGGGGGTGGACTGGTGCAGC CCGGAGGTTCCCTGCGGTTG TCTTGTGCCGCCTCGGGATT CACCTTCTCGTCCTTCGCGA TGAGCTGGGTCCGCCAAGCT CCTGGAAAAGGGCTCGAATG GGTGTCCGCGATCAGCGGAT TTGGCGGCTCCACCTACTAC GCCGATTCAGTGAAGGGCCG GTTCACCATCTCACGGGACA ACAGCAAGAACACGCTGTAT CTGCAAATGAACTCCCTGCG CGCTGAGGACACCGCAGTGT ACTACTGCGCGAGACAGTTC TGGGAGGACCAGCCGTTCTA CTTCGACTACTGGGGACAGG GGACCCTCGTGACTGTCTCC TCCGCCTCCACTAAGGGCCC ATCCGTGTTCCCTCTGGCCC CTTCCAGCAAGTCCACCTCT GGCGGCACCGCCGCTCTGGG CTGCCTGGTCAAGGACTACT TCCCCGTCCCGTGACCGTG TCCTGGAACTCTGGCGCCCT GACCTCCGGCGTGCACACCT TCCCTGCCGTGCTGCAGTCC TCCGGCCTGTACTCCCTGTC CTCCGTCGTGACCGTGCCCT CCAGCTCTCTGGGCACCCAG ACCTACATCTGCAACGTGAA CCACAAGCCCTCCAACACCA AAGTGGACAAGCGGGTGGAA CCCAAGTCCTGCGACAAGAC CCACACCTGTCCTCCCTGCC CTGCCCCTGAGCTGCTGGGC GGACCCTCCGTGTTCCTGTT CCCTCCAAAGCCCAAGGACA CCCTGATGATCTCCCGGACC CCTGAAGTGACCTGCGTGGT GGTGGACGTGTCCCACGAGG ATCCCGAAGTGAAGTTCAAT TGGTACGTGGACGGCGTGGA AGTGCACAACGCCAAGACCA AGCCCAGAGAGGAACAGTAC AACTCCACCTACCGGGTGGT GTCCGTGCTGACCGTGCTGC ACCAGGACTGGCTGAACGGC AAAGAGTACAAGTGCAAAGT GTCCAACAAGGCCCTGCCTG CCCCAATCGAAAAGACCATC TCCAAGGCCAAGGGCCAGCC CCGCGAGCCCCAAGTGTACA CACTGCCTCCCAGCCGGGAA GAGATGACCAAGAACCAAGT GTCCCTGACCTGCCTCGTGA AGGGCTTCTACCCCTGCGAT ATCGCCGTGGAGTGGGAGTC CAACGGCCAGCCCGAGAACA ACTACAAGACCACCCCTCCC GTGCTGGACTCCGACGGCTC ATTCTTCCTGTACTCCAAGC TGACCGTGGACAAGTCCCGG TGGCAGCAGGGCAACGTGTT CTCCTGCTCCGTGATGCACG AGGCCCTGCACAACCACTAC ACCCAGAGTCCCTGTCCCT GAGCCCCGGCAAG |
| | SEQ ID NO: 25 | Light Chain | DIQMTQSPSSLSASVGDRVT ITCRASQSISSYLNWYQQKP GKAPKLLIYAASSLQSGVPS RFSGSGSGTDFTLTISSLQP EDFATYYCQQYSTPLTFGQ |

TABLE 3-continued

Amino acid and nucleic acid sequences of full length mAb IgG chains

| Ab | SEQ ID NO | IgG chain | Amino acid sequence |
|---|---|---|---|
| | | | GTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | SEQ ID NO: 26 | DNA Light Chain | GATATTCAGATGACCCAGTCCCCGTCGTCGCTGAGCGCCAGCGTGGGAGACAGAGTGACCATTACCTGTCGGGCCAGCCAGTCGATCTCCTCCTACCTTAACTGGTATCAGCAGAAGCCAGGAAAGGCACCGAAACTGCTGATCTACGCCGCGTCCTCCTTGCAATCCGGAGTGCCCTCAAGGTTCTCCGGGTCGGGTTCTGGCACTGACTTTACCCTGACCATCAGCAGCCTCCAGCCCGAGGACTTCGCCACCTACTACTGCCAGCAGTCATACTCCACCCCTCTGACATTCGGCCAAGGGACCAAGGTCGAAATCAAGCGTACGGTGGCCGCTCCCAGCGTGTTCATCTTCCCCCCCAGCGACGAGCAGCTGAAGAGCGGCACCGCCAGCGTGGTGTGCCTGCTGAACAACTTCTACCCCCGGGAGGCCAAGGTGCAGTGGAAGGTGGACAACGCCCTGCAGAGCGGCAACAGCCAGGAGAGCGTCACCGAGCAGGACAGCAAGGACTCCACCTACAGCCTGAGCAGCACCCTGACCCTGAGCAAGGCCGACTACGAGAAGCATAAGGTGTACGCCTGCGAGGTGACCCACCAGGGCCTGTCAGCCCCGTGACCAAGAGCTTCAACAGGGGCGAGTGC |
| NY920 CysMab DAPA | SEQ ID NO: 14 | Heavy Chain | EVQLLESGGGLVQPGGSLRLSCAASGFTFSSFAMSWVRQAPGKGLEWVSAISGFGGSTYYADSVKGRFTISRDNSKNTLYLQMNSLRAEDTAVYYCARQFWEDQPPFYFDYWGQGTLVTVSSASTKGPSVFPLAPSSKSTSGGTAALGCLVKDYFPCPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVAVSHEDPEVKFNWYVDGVEVHNAKTKPREEQYNSTYRVVSVLTVLHQDWLNGKEYKCKVSNKALAAPIEKTISKAKGQPREPQVYTLPPSREEMTKNQVSLTCLVKGFYPCDIAVEWESNGQPENNYKTTPPVLDSDGSFFLYSKLTVDKSRWQQGNVFSCSVMHEALHNHYTQKSLSLSPGK |
| | SEQ ID NO: 15 | DNA Heavy Chain | GAAGTGCAGCTGCTGGAGTCCGGGGGTGGACTGGTGCAGCCCGGAGGTTCCCTGCGGTTGTCTTTGTGCCGCCTCGGGATTCACCTTCTCGTCCTTCGCGATGAGCTGGGTCCGCCAAGCTCCTGGAAAAGGGCTCGAATGGGTGTCCGCGATCAGCGGATTTTGGCGGCTCCACCTACTAC GCCGATTCAGTGAAGGGCCGGTTCACCATCTCACGGGACAACAGCAAGAACACGCTGTATCTGCAAATGAACTCCCTGCGCGCTGAGGACACCGCAGTGTACTACTGCGCGAGACAGTTCTGGGAGGACCAGCCGTTCTACTTCGACTACTGGGGACAGGGGACCCTCGTGACTGTCTCCTCCGCCTCCACTAAGGGCCCTAGCGTGTTCCCACTGGCGCCTTCCTCGAAATCGACTAGCGGGGGTACCGCCGCTCTGGGATGCTTGGTAAAGACTACTTTCCGTGTCCGGTGACCGTGAGCTGGAACTCCGGGGCACTCACCTCCGGTGTGCATACTTTCCCTGCTGTCTTGCAGTCCTCGGGCCTGTACAGCCTGTCCTCCGTGGTGACCGTGCCTTCGTCGTCCCTGGGAACCCAGACGTACATCTGCAACGTGAACCACAAGCCGAGCAACACCAAGTCGATAAGGAGTCGAGCCCAAGAGCTGCGATAAGACCCACACTTGTCCGCCTTGTCCTGCCCCTGAGCTTCTGGGTGGCCCATCGGTGTTTCTGTTTCCCCCGAAGCCCAAAGACACCCTGATGATCTCGCGCACTCCGGAGGTCACTTGCGTGGTCGTGGCGGTGTCCCACGAGGACCCGGAAGTGAAGTTTAACTGGTACGTGGACGGAGTGGAAGTCCACAACGCGAAAACTAAGCCCCGGGAGGAACAATACAACTCCACCTACCGCGTCGTGTCCGTGCTCACTGTGCTGCACCAGGATTGGCTGAACGGTAAAGAGTACAAGTGTAAGGTGTCGAACAAAGCCCTCGCCGCC CCTATCGAAAAGACTATTTCGAAAGCTAAGGGCCAGCCGCGAGAACCCCAAGTGTATACCCTGCCCCCTTCACGGGAAGAGATGACTAAGAATCAGGTGTCGCTCACCTGTCTGGTGAAGGGATTTTATCCCTGCGACATTGCCGTGGAGTGGGAATCGAACGGCCAGCCTGAGAACAACTACAAGACCACTCCGCCGGTGCTTGACAGCGACGGTTCGTCTTCCTCTACTCTAAGCTCACCGTGGACAAGTCACGGTGCAACAGGGCAACGTGTTCTCGTGCTCTGTGATGCACGAAGCTCTCCACAACCATTACACCCAGAAGTCCCTCAGCCTCAGCCCGGGGAAG |
| | SEQ ID NO: 25 | Light Chain | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 3-continued

Amino acid and nucleic acid sequences of full length mAb IgG chains

| Ab | SEQ ID NO | IgG chain | Amino acid sequence |
|---|---|---|---|
| | SEQ ID NO: 26 | DNA Light Chain | GATATTCAGATGACCCAGTCCCCGTCGTCGCTGAGCGCCAGCGTGGGAGACAGAGTGACCATTACCTGTCGGGCCAGCCAGTCGATCTCCTCCTACCTTAACTGGTATCAGCAGAAGCCAGGAAAGGCACCGAAACTGCTGATCTACGCCGCGTCCTCCTTGCAATCCGGAGTGCCCTCAAGGTTCTCCGGGTCGGGTTCTGGCACTGACTTTACCCTGACCATCAGCAGCCTCCAGCCCGAGGACTTCGCCACCTACTACTGCCAGCAGTCATACTCCACCCCTCTGACATTCGGCCAAGGGACCAAGGTCGAAATCAAGCGTACGGTGGCCGCTCCCAGCGTGTTCATCTTCCCCCCCAGCGACGAGCAGCTGAAGAGCGGCACCGCCAGCGTGGTGTGCCTGCTGAACAACTTCTACCCCGGGAGGCCAAGGTGCAGTGGAAGGTGGACAACGCCCTGCAGAGCGGCAACAGCCAGGAGAGCGTCACCGAGCAGGACAGCAAGGACTCCACCTACAGCCTGAGCAGCACCCTGACCCTGAGCAAGGCCGACTACGAAAGCATAAGGTGTACGCCTGCGAGGTGACCCACCAGGGCCTGTCCAGCCCCGTGACCAAGAGCTTCAACAGGGGCGAGTGC |
| NY938 CysMab | SEQ ID NO: 38 | Heavy Chain | QVQLVQSGAEVKKPGASVKVSCKASGYTFTEYTMHWVRQAPGQGLEWMGGINPDTGDTSYNQKFTGRATLTVDKSTSTAYMELSSLRSEDTAVYYCARAQFWTTPRFAYWGQGTLVTVSSASTKGPSVFPLAPSSKSTSGGTAALGCLVKDYFPCPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPCDIAVEWESNGQPENNYKTTPPVLDSDGSFFLYSKLTVDKSRWQQGNVFSCSVMHEALHNHYTQKSLSLSPGK |
| | SEQ ID NO: 39 | DNA Heavy Chain | CAAGTGCAGCTCGTGCAGTCCGGAGCGGAAGTGAAAAAGCCCGGAGCCTCAGTGAAAGTGTCCTGCAAAGCCTCGGGGTACACCTTCACCGAGTACACTATGCATTGGGTCCGCCAAGCTCCTGGTCAAGGCCTCGAATGGATGGGCGGCATCAATCCGGACACCGGCGACACCAGCTATAACCAGAAGTTCACCGGACGCGCCACTCTGACTGTCGATAAGAGCACAAGCACCGCCTACATGGAACTGTCGTCCTTGCGGTCCGAGGATACCGCCGTGTACTACTGCGCGAGAGCGCAGTTTTGGACTACCCCGCGGTTCGCCTACTGGGGACAGGGCACTCTCGTGACTGTGTCATCGGCGTCCACCAAGGGCCCATCCGTGTTCCCTCTGGCCCCTTCCAGCAAGTCCACCTCTGGCGGCACCGCCGCTCTGGGCTGCCTGGTCAAGGACTACTTCCCCTGTCCCGTGACCGTGTCCTGGAACTCTGGCGCCCTGACCTCCGGCGTGCACACCTTCCCTGCCGTGCTGCAGTCCTCCGGCCTGTACTCCCTGTCCTCCGTCGTGACCGTGCCCTCCAGCTCTCTGGGCACCCAGACCTACATCTGCAACGTGAACCACAAGCCCTCCAACACCAAGGTGGACAAGCGGGTGGAACCCAAGTCCTGCGACAAGACCCACACCTGTCCTCCCTGCCCTGCCCCTGAGCTGCTGGGCGGACCCTCCGTGTTCCTGTTCCCTCCAAAGCCCAAGGACACCCTGATGATCTCCCGGACCCCTGAAGTGACCTGCGTGGTGGTGGACGTGTCCCACGAGGATCCCGAAGTGAAGTTCAATTGGTACGTGGACGGCGTGGAAGTGCACAACGCCAAGACCAAGCCCAGAGAGGAACAGTACAACTCCACCTACCGGGTGGTGTCCGTGCTGACCGTGCTGCACCAGGACTGGCTGAACGGCAAGGAGTACAAGTGCAAAGTGTCCAACAAGGCCCTGCCTGCCCAATCGAAAAGACCATCTCCAAGGCCAAGGGCCAGCCCCGCGAGCCCCAAGTGTACACACTGCCTCCCAGCCGGGAAGAGATGACCAAGAACCAAGTGTCCCTGACCTGCCTCGTGAAGGGCTTCTACCCCTGCGATATCGCCGTGGAGTGGGAGTCCAACGGCCAGCCCGAGAACAACTACAAGACCACCCCTCCCGTGCTGGACTCCGACGGCTCATTCTTCCTGTACTCCAAGCTGACCGTGGACAAGTCCCGGTGGCAGCAGGGCAACGTGTTCTCCTGCTCCGTGATGCACGAGGCCCTGCACAACCACTACACCCAGAAGTCCCTGTCCCTGAGCCCCGGCAAG |
| | SEQ ID NO: 51 | Light Chain | DIQMTQSPSSLSASVGDRVTITCKASQDVGTAVAWYQQKPGKVPKLLIYWASTRHTGVPSRFSGSGSGTDFTLTISSLQPEDVATYYCQQYSTYPITFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | SEQ ID NO: 52 | DNA Light Chain | GACATCCAAATGACCCAGAGCCCCTTCGAGCCTGTCAGCCTCCGGTGGGCGACAGAGTGACCATTACTTGCAAAGCCAGCCAGGACGTGGGAACTGCAGTCGCCTGGTATCAGCAGAAGCCAGGAAAGGTCCCCAAGCTCCTGATCTACTGGGCTTCCACCC |

TABLE 3-continued

Amino acid and nucleic acid sequences of full length mAb IgG chains

| Ab | SEQ ID NO | IgG chain | Amino acid sequence |
|---|---|---|---|
| | | | GGCACACTGGCGTGCCGTCA AGGTTTTCGGGATCGGGTTC CGGGACTGATTTCACCCTGA CCATTTCCTCCCTCCAACCC GAGGATGTGGCCACCTACTA CTGCCAGCAGTACTCCACCT ACCCGATCACATTCGGACAG GGCACCAAGCTCGAAATCAA GCGTACGGTGGCCGCTCCCA GCGTGTTCATCTTCCCCCCC AGCGACGAGCAGCTGAAGAG CGGCACCGCCAGCGTGGTGT GCCTGCTGAACAACTTCTAC CCCCGGGAGGCCAAGGTGCA GTGGAAGGTGGACAACGCCC TGCAGAGCGGCAACAGCCAG GAGAGCGTCACCGAGCAGGA CAGCAAGGACTCCACCTACA GCCTGAGCAGCACCCTGACC CTGAGCAAGGCCGACTACGA GAAGCATAAGGTGTACGCCT GCGAGGTGACCCACCAGGGC CTGTCCAGCCCCGTGACCAA GAGCTTCAACAGGGGCGAGT GC |
| NY938 CysMab DAPA | SEQ ID NO: 40 | Heavy Chain | QVQLVQSGAEVKKPGASVKV SCKASGYTFTEYTMHWVRQA PGQGLEWMGGINPDTGDTSY NQKFTGRATLTVDKSTSTAY MELSSLRSEDTAVYYCARAQ FWTTPRFAYWGQGTLVTVSS ASTKGPSVFPLAPSSKSTSG GTAALGCLVKDYFPCPVTVS WNSGALTSGVHTFPAVLQSS GLYSLSSVVTVPSSSLGTQT YICNVNHKPSNTKVDKRVEP KSCDKTHTCPPCPAPELLGG PSVFLFPPKPKDTLMISRTP EVTCVVVAVSHEDPEVKFNW YVDGVEVHNAKTKPREEQYN STYRVVSVLTVLHQDWLNGK EYKCKVSNKALAAPIEKTIS KAKGQPREPQVYTLPPSREE MTKNQVSLTCLVKGFYPCDI AVEWESNGQPENNYKTTPPV LDSDGSFFLYSKLTVDKSRW QQGNVFSCSVMHEALHNHYT QKSLSLSPGK |
| | SEQ ID NO: 41 | DNA Heavy Chain | CAAGTGCAGCTCGTGCAGTC CGGAGCGGAAGTGAAAAAGC CCGGAGCCTCAGTGAAAGTG TCCTGCAAAGCCTCGGGGTA CACCTTCACCGAGTACACTA TGCATTGGGTCCGCCAAGCT CCTGGTCAAGGCCTCGAATG GATGGGCGGCATCAATCCCG ACACCGGCGACACCAGCTAT AACCAGAAGTTCACCGGACG CGCCACTCTGACTGTCGATA AGAGCACAAGCACCGCCTAC ATGGAACTGTCGTCCTTGCG GTCCGAGGATACCGCCGTGT ACTACTGCGCGAGAGCGCAG TTTTGGACTACCCCGCGGTT CGCCTACTGGGGACAGGGCA CTCTCGTGACTGTGTCATCG GCGTCCACCAAGGGCCCTAG CGTGTTCCCACTGGCGCCTT CCTCGAAATCGACTAGCGGG GGTACCGCCGCTCTGGGATG CTTGGTGAAGACTACTTTTC CGTGTCCGGTGACCGTGAGC TGGAACTCCGGGGCACTCAC CTCCGGTGTGCATACTTTCC CTGCTGTCTTGCAGTCCTCG GGCCTGTACAGCCTGTCCTC CGTGGTGACCGTGCCTTCGT CGTCCCTGGGAACCCAGACG TACATCTGCAACGTGAACCA CAAGCCGAGCAACACCAAAG TCGATAAGAGAGTCGAGCCC AAGAGCTGCGATAAGACCCA CACTTGTCCGCCTTGTCCTG CCCCTGAGCTTCTGGGTGGC CCATCGGTGTTTCTGTTTCC CCCGAAGCCCAAAGACACCC TGATGATCTCGCGCACTCCG GAGGTCACTTGCGTGGTCGT GGCGGTGTCCCACGAGGACC CAGAAGTGAAGTTTAACTGG TACGTGGACGGAGTGGAAGT CCACAACGCGAAAACTAAGC CCCGGGAGGAACAATACAAC TCCACCTACCGCGTCGTGTC CGTGCTCACTGTGCTGCACC AGGATTGGCTGAACGGTAAA GAGTACAAGTGTAAGGTGTC GAACAAGCCCTCGCCGCCC TATCGAAAAGACTATTTCCG AAAGCTAAGGGCCAGCCGCG AGAACCCCAAGTGTATACCC TGCCCCCTTCACGGGAAGAG ATGACTAAGAATCAGGTGTC GCTCACCTGTCTGGTGAAGG GATTTTATCCCTGCGACATT GCCGTGGAGTGGGAATCGAA CGGCCAGCCTGAGAACAACT ACAAGACCACTCCGCCGGTG CTTGACAGCGACGGTTCGTT CTTCCTCTACTCTAAGCTCA CCGTGGACAAGTCACGGTGG CAACAGGGCAACGTGTTCTC GTGCTCTGTGATGCACGAAG CTCTCCACAACCATTACACC CAGAAGTCCCTCAGCCTCAG CCCGGGGAAG |
| | SEQ ID NO: 51 | Light Chain | DIQMTQSPSSLSASVGDRVT ITCKASQDVGTAVAWYQQKP GKVPKLLIYWASTRHTGVPS RFSGSGSGTDFTLTISSLQP EDVATYYCQQYSTYPITFGQ GTKLEIKRTVAAPSVFIFPP SDEQLKSGTASVVCLLNNFY PREAKVQWKVDNALQSGNSQ ESVTEQDSKDSTYSLSSTLT LSKADYEKHKVYACEVTHQG LSSPVTKSFNRGEC |
| | SEQ ID NO: 52 | DNA Light Chain | GACATCCAAATGACCCAGAG CCCCTTCGAGCCTGTCAGCCT CCGTGGGCGACAGAGTGACC ATTACTTGCAAAGCCAGCCA GGACGTGGGAACTGCAGTCG CCTGGTATCAGCAGAAGCCA GGAAAGGTCCCCAAGCTCCT GATCTACTGGGCTTCCACCC GGCACACTGGCGTGCCGTCA AGGTTTTCGGGATCGGGTTC CGGGACTGATTTCACCCTGA CCATTTCCTCCCTCCAACCC GAGGATGTGGCCACCTACTA CTGCCAGCAGTACTCCACCT ACCCGATCACATTCGGACAG GGCACCAAGCTCGAAATCAA GCGTACGGTGGCCGCTCCCA |

TABLE 3-continued

Amino acid and nucleic acid sequences of full length mAb IgG chains

| Ab | SEQ ID NO | IgG chain | Amino acid sequence |
|---|---|---|---|
| | | | GCGTGTTCATCTTCCCCCCC AGCGACGAGCAGCTGAAGAG CGGCACCGCCAGCGTGGTGT GCCTGCTGAACAACTTCTAC CCCCGGGAGGCCAAGGTGCA GTGGAAGGTGGACAACGCCC TGCAGAGCGGCAACAGCCAG GAGAGCGTCACCGAGCAGGA CAGCAAGGACTCCACCTACA GCCTGAGCAGCACCCTGACC CTGAGCAAGGCCGACTACGA GAAGCATAAGGTGTACGCCT GCGAGGTGACCCACCAGGGC CTGTCCAGCCCCGTGACCAA GAGCTTCAACAGGGGCGAGT GC |
| NY920 | SEQ ID NO: 63 | Heavy Chain | EVQLLESGGGLVQPGGSLRL SCAASGFTFSSFAMSWVRQA PGKGLEWVSAISGFGGSTYY ADSVKGRFTISRDNSKNTLY LQMNSLRAEDTAVYYCARQF WEDQPFYFDYWGQGTLVTVS SASTKGPSVFPLAPSSKSTS GGTAALGCLVKDYFPEPVTV SWNSGALTSGVHTFPAVLQS SGLYSLSSVVTVPSSSLGTQ TYICNVNHKPSNTKVDKRVE PKSCDKTHTCPPCPAPELLG GPSVFLFPPKPKDTLMISRT PEVTCVVVDVSHEDPEVKFN WYVDGVEVHNAKTKPREEQY NSTYRVVSVLTVLHQDWLNG KEYKCKVSNKALPAPIEKTI SKAKGQPREPQVYTLPPSRE EMTKNQVSLTCLVKGFYPSD IAVEWESNGQPENNYKTTPP VLDSDGSFFLYSKLTVDKSR WQQGNVFSCSVMHEALHNHY TQKSLSLSPGK |
| | SEQ ID NO: 75 | DNA Heavy Chain | GAGGTCCAATTGCTGGAATC TGGCGGAGGACTGGTTCAGC CTGGTGGCTCTCTGAGACTG TCTTGTGCCGCCAGCGGCTT CACCTTCAGCAGCTTTGCCA TGTCCTGGGTTCGACAGGCC CCTGGAAAAGGACTCGAGTG GGTGTCCGCTATCTCTGGCT TTGGCGGCAGCACATATTAC GCCGATAGCGTGAAGGGCAG ATTCACCATCAGCCGGGACA ACAGCAAGAACACCCTGTAC CTGCAGATGAACAGCCTGAG AGCCGAGGACACAGCCGTGT ATTACTGCGCGCGTCAGTTC TGGGAAGATCAGCCCCTTCTA CTTCGACTACTGGGGCCAGG GCACACTGGTCACAGTTAGC TCAGCTAGCACCAAGGGCCC CAGCGTGTTCCCCCTGGCCC CCAGCAGCAAGAGCACCAGC GGCGGCACAGCCGCCCTGGG CTGCCTGGTGAAGGACTACT TCCCCGAGCCCGTGACCGTG TCCTGGAACAGCGGAGCCCT GACCTCCGGCGTGCACACCT TCCCCGCCGTGCTGCAGAGC AGCGGCCTGTACAGCCTGTC CAGCGTGGTGACAGTGCCCA GCAGCAGCCTGGGCACCCAG ACCTACATCTGCAACGTGAA CCACAAGCCCAGCAACACCA AGGTGGACAAGAGAGTGGAG CCCAAGAGCTGCGACAAGAC CCACACATGCCCCCCCTGCC CGGCGCCAGAGCTGCTGGGC GGACCCTCCGTGTTCCTGTT CCCCCCCAAGCCCAAGGACA CCCTGATGATCAGCAGGACC CCCGAGGTGACCTGCGTGGT GGTGGACGTGAGCCACGAGG ACCCAGAGGTGAAGTTCAAC TGGTACGTGGACGGCGTGGA GGTGCACAACGCCAAGACCA AGCCCAGAGAGGAGCAGTAC AACAGCACCTACAGGGTGGT GTCCGTGCTGACCGTGCTGC ACCAGGACTGGCTGAACGGC AAGGAATACAAGTGCAAGGT CTCCAACAAGGCCCTGCCAG CCCCCATCGAAAAGACCATC AGCAAGGCCAAGGGCCAGCC ACGGGAGCCCCAGGTGTACA CCCTGCCCCCCTCCCGGGAG GAGATGACCAAGAACCAGGT GTCCCTGACCTGTCTGGTGA AGGGCTTCTACCCCAGCGAC ATCGCCGTGGAGTGGGAGAG CAACGGCCAGCCCGAGAACA ACTACAAGACCACCCCCCCA GTGCTGGACAGCGACGGCAG CTTCTTCCTGTACAGCAAGC TGACCGTGGACAAGTCCAGG TGGCAGCAGGGCAACGTGTT CAGCTGCAGCGTGATGCACG AGGCCCTGCACAACCACTAC ACCCAGAAGAGCCTGAGCTT AAGCCCCGGCAAG |
| | SEQ ID NO: 25 | Light Chain | DIQMTQSPSSLSASVGDRVT ITCRASQSISSYLNWYQQKP GKAPKLLIYAASSLQSGVPS RFSGSGSGTDFTLTISSLQP EDFATYYCQQSYSTPLTFGQ GTKVEIKRTVAAPSVFIFPP SDEQLKSGTASVVCLLNNFY PREAKVQWKVDNALQSGNSQ ESVTEQDSKDSTYSLSSTLT LSKADYEKHKVYACEVTHQG LSSPVTKSFNRGEC |
| | SEQ ID NO: 26 | DNA Light Chain | GATATTCAGATGACCCAGTC CCCGTCGTCGCTGAGCGCCA GCGTGGGAGACAGAGTGACC ATTACCTGTCGGGCCCAGCCA GTCGATCTCCTCCTACCTTA ACTGGTATCAGCAGAAGCCA GGAAAGGCACCGAAACTGCT GATCTACGCCGCGTCCTCCT TGCAATCCGGAGTGCCCTCA AGGTTCTCCGGGTCGGGTTC TGGCACTGACTTTACCCTGA CCATCAGCAGCCTCCAGCCC GAGGACTTCGCCACCTACTA CTGCCAGCAGTCATACTCCA CCCCTCTGACATTCGGCCAA GGGACCAAGGTCGAAATCAA GCGTACGGTGGCCGCTCCCA GCGTGTTCATCTTCCCCCCC AGCGACGAGCAGCTGAAGAG CGGCACCGCCAGCGTGGTGT GCCTGCTGAACAACTTCTAC CCCCGGGAGGCCAAGGTGCA GTGGAAGGTGGACAACGCCC TGCAGAGCGGCAACAGCCAG GAGAGCGTCACCGAGCAGGA CAGCAAGGACTCCACCTACA |

TABLE 3-continued

Amino acid and nucleic acid sequences of full length mAb IgG chains

| Ab | SEQ ID NO | IgG chain | Amino acid sequence |
|---|---|---|---|
| | | | GCCTGAGCAGCACCCTGACC CTGAGCAAGGCCGACTACGA GAAGCATAAGGTGTACGCCT GCGAGGTGACCCACCAGGGC CTGTCCAGCCCCGTGACCAA GAGCTTCAACAGGGGCGAGT GC |
| NY938 | SEQ ID NO: 65 | Heavy Chain | QVQLVQSGAEVKKPGASVKV SCKASGYTFTEYTMHWVRQA PGQGLEWMGGINPDTGDTSY NQKFTGRATLTVDKSTSTAY MELSSLRSEDTAVYYCARAQ FWTTPRFAYWGQGTLVTVSS ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKRVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSREE MTKNQVSLTCLVKGFYPSDI AVEWESNGQPENNYKTTPPV LDSDGSFFLYSKLTVDKSRW QQGNVFSCSVMHEALHNHYT QKSLSLSPGK |
| | SEQ ID NO: 77 | DNA Heavy Chain | CAGGTCCAATTGGTGCAGTC TGGCGCCGAAGTGAAGAAAC CAGGCGCCAGCGTGAAGGTG TCCTGTAAAGCCAGCGGCTA CACCTTTACCGAGTACACCA TGCACTGGGTCCGACAGGCT CCAGGACAAGGACTCGAGTG GATGGGCGGCATCAATCCTG ATACCGGCGACACCAGCTAC AACCAGAAGTTCACAGGCAG AGCCACACTGACCGTGGACA AGAGCACAAGCACCGCCTAC ATGGAACTGAGCAGCCTGAG AAGCGAGGACACCGCCGTGT ATTATTGCGCGCGTGCCCAG TTTTGGACCACACCTAGATT TGCCTACTGGGGCCAGGGCA CCCTGGTCACAGTTAGCTCA GCTAGCACCAAGGGCCCCAG CGTGTTCCCCCTGGCCCCCA GCAGCAAGAGCACCAGCGGC GGCACAGCCGCCCTGGGCTG CCTGGTGAAGGACTACTTCC CCGAGC CCGTGACCGTGTCCTGGAAC AGCGGAGCCCTGACCTCCGG CGTGCACACCTTCCCCGCCG TGCTGCAGAGCAGCGGCCTG TACGCCTGTCCAGCGTGGT GACAGTGCCCAGCAGCAGCC TGGGCACCCAGACCTACATC TGCAACGTGAACCACAAGCC CAGCAACACCAAGGTGGACA AGAGAGTGGAGCCCAAGAGC TGCGACAAGACCCACACATG CCCCCCCTGCCCGGCGCCAG AGCTGCTGGGCGGACCCTCC GTGTTCCTGTTCCCCCCCAA GCCCAAGGACACCCTGATGA TCAGCAGGACCCCCGAGGTG ACCTGCGTGGTGGTGGACGT GAGCCACGAGGACCCAGAGG TGAAGTTCAACTGGTACGTG GACGGCGTGGAGGTGCACAA CGCCAAGACCAAGCCCAGAG AGGAGCAGTACAACAGCACC TACAGGGTGGTGTCCGTGCT GACCGTGCTGCACCAGGACT GGCTGAACGGCAAGGAATAC AAGTGCAAGGTCTCCAACAA GGCCCTGCCAGCCCCCATCG AAAAGACCATCAGCAAGGCC AAGGGCCAGCCACGGGAGCC CCAGGTGTACACCCTGCCCC CCTCCCGGGAGGAGATGACC AAGAACCAGGTGTCCCTGAC CTGTCTGGTGAAGGGCTTCT ACCCCAGCGACATCGCCGTG GAGTGGGAGAGCAACGGCCA GCCCGAGAACAACTACAAGA CCACCCCCCCAGTGCTGGAC AGCGACGGCAGCTTCTTCCT GTACAGCAAGCTGACCGTGG ACAAGTCCAGGTGGCAGCAG GGCAACGTGTTCAGCTGCAG CGTGATGCACGAGGCCCTGC ACAACCACTACACCCAGAAG AGCCTGAGCTTAAGCCCCGG CAAG |
| | SEQ ID NO: 51 | Light Chain | DIQMTQSPSSLSASVGDRVT ITCKASQDVGTAVAWYQQKP GKVPKLLIYWASTRHTGVPS RFSGSGSGTDFTLTISSLQP EDVATYYCQQYSTYPITFGQ GTKLEIKRTVAAPSVFIFPP SDEQLKSGTASVVCLLNNFY PREAKVQWKVDNALQSGNSQ ESVTEQDSKDSTYSLSSTLT LSKADYEKHKVYACEVTHQG LSSPVTKSFNRGEC |
| | SEQ ID NO: 52 | DNA Light Chain | GACATCCAAATGACCCAGAG CCCCTTCGAGCCTGTCAGCC CCGTGGGCGACAGAGTGACC ATTACTTGCAAAGCCAGCCA GGACGTGGGAACTGCAGTCG CCTGGTATCAGCAGAAGCCA GGAAAAGGTCCCCAAGCTCCT GATCTACTGGGCTTCCACCC GGCACACTGGCGTGCCGTCA AGGTTTTCGGGATCGGGTTC CGGGACTGATTTCACCCTGA CCATTTCCTCCCTCCAACCC GAGGATGTGGCCACCTACTA CTGCCAGCAGTACTCCACCT ACCCGATCACATTCGGACAG GGCACCAAGCTCGAAATCAA GCGTACGGTGGCCGCTCCCA GCGTGTTCATCTTCCCCCCC AGCGACGAGCAGCTGAAGAG CGGCACCGCCAGCGTGGTGT GCCTGCTGAACAACTTCTAC CCCCGGGAGGCCAAGGTGCA GTGGAAGGTGGACAACGCCC TGCAGAGCGGCAACAGCCAG GAGAGCGTCACCGAGCAGGA CAGCAAGGACTCCACCTACA GCCTGAGCAGCACCCTGACC CTGAGCAAGGCCGACTACGA GAAGCATAAGGTGTACGCCT GCGAGGTGACCCACCAGGGC CTGTCCAGCCCCGTGACCAA GAGCTTCAACAGGGGCGAGT GC |

In some embodiments, the antibody or antigen-binding fragment thereof disclosed herein may comprise any set of heavy and light chain variable domains listed in the tables above or a set of six CDRs from any set of heavy and light chain variable domains listed in the tables above. In some embodiments, the antibody or antigen-binding fragment thereof disclosed herein may comprise amino acid sequences that are conservatively modified and/or homologous to the sequences listed in the tables above, so long as the antibody retains the ability to bind to its target cancer antigen (e.g., with a KD of less than $1 \times 10^{-8}$ M) and retains one or more functional properties of the antibodies disclosed herein (e.g., ability to internalize, bind to an antigen target, e.g., an antigen expressed on a tumor or other cancer cell, etc.).

In some embodiments, the antibody or antigen-binding fragment thereof disclosed herein further comprises human heavy and light chain constant domains or fragments thereof. For instance, the antibody or antigen-binding fragment of antibody drug conjuges (ADCs) as described herein may comprise a human IgG heavy chain constant domain (such as an IgG1) and a human kappa or lambda light chain constant domain. In some embodiments, the antibody or antigen-binding fragment of ADCs as described herein comprises a human immunoglobulin G subtype 1 (IgG1) heavy chain constant domain with a human Ig kappa light chain constant domain.

In some embodiments, the anti-CD48 antibody or antigen-binding fragment thereof comprises three heavy chain CDRs and three light chain CDRs as follows: heavy chain CDR1 (HCDR1) consisting of the amino acid sequence set forth in SEQ ID NO:1, heavy chain CDR2 (HCDR2) consisting of the amino acid sequence set forth in SEQ ID NO:2, heavy chain CDR3 (HCDR3) consisting of the amino acid sequence set forth in SEQ ID NO:3; light chain CDR1 (LCDR1) consisting of the amino acid sequence set forth in SEQ ID NO:16, light chain CDR2 (LCDR2) consisting of the amino acid sequence set forth in SEQ ID NO:17, and light chain CDR3 (LCDR3) consisting of the amino acid sequence set forth in SEQ ID NO:18.

In some embodiments, the anti-CD48 antibody or antigen-binding fragment thereof comprises three heavy chain CDRs and three light chain CDRs as follows: heavy chain CDR1 (HCDR1) consisting of the amino acid sequence set forth in SEQ ID NO:4, heavy chain CDR2 (HCDR2) consisting of the amino acid sequence set forth in SEQ ID NO:2, heavy chain CDR3 (HCDR3) consisting of the amino acid sequence set forth in SEQ ID NO:3; light chain CDR1 (LCDR1) consisting of the amino acid sequence set forth in SEQ ID NO:16, light chain CDR2 (LCDR2) consisting of the amino acid sequence set forth in SEQ ID NO:17, and light chain CDR3 (LCDR3) consisting of the amino acid sequence set forth in SEQ ID NO:18.

In some embodiments, the anti-CD48 antibody or antigen-binding fragment thereof comprises three heavy chain CDRs and three light chain CDRs as follows: heavy chain CDR1 (HCDR1) consisting of the amino acid sequence set forth in SEQ ID NO:5, heavy chain CDR2 (HCDR2) consisting of the amino acid sequence set forth in SEQ ID NO:6, heavy chain CDR3 (HCDR3) consisting of the amino acid sequence set forth in SEQ ID NO:3; light chain CDR1 (LCDR1) consisting of the amino acid sequence set forth in SEQ ID NO:19, light chain CDR2 (LCDR2) consisting of the amino acid sequence set forth in SEQ ID NO:20, and light chain CDR3 (LCDR3) consisting of the amino acid sequence set forth in SEQ ID NO:21.

In some embodiments, the anti-CD48 antibody or antigen-binding fragment thereof comprises three heavy chain CDRs and three light chain CDRs as follows: heavy chain CDR1 (HCDR1) consisting of the amino acid sequence set forth in SEQ ID NO:7, heavy chain CDR2 (HCDR2) consisting of the amino acid sequence set forth in SEQ ID NO:8, heavy chain CDR3 (HCDR3) consisting of the amino acid sequence set forth in SEQ ID NO:9; light chain CDR1 (LCDR1) consisting of the amino acid sequence set forth in SEQ ID NO:22, light chain CDR2 (LCDR2) consisting of the amino acid sequence set forth in SEQ ID NO:20, and light chain CDR3 (LCDR3) consisting of the amino acid sequence set forth in SEQ ID NO:18.

In some embodiments, the anti-CD48 antibody or antigen-binding fragment thereof comprises three heavy chain CDRs and three light chain CDRs as follows: heavy chain CDR1 (HCDR1) consisting of the amino acid sequence set forth in SEQ ID NO:27, heavy chain CDR2 (HCDR2) consisting of the amino acid sequence set forth in SEQ ID NO:28, heavy chain CDR3 (HCDR3) consisting of the amino acid sequence set forth in SEQ ID NO:29; light chain CDR1 (LCDR1) consisting of the amino acid sequence set forth in SEQ ID NO:42, light chain CDR2 (LCDR2) consisting of the amino acid sequence set forth in SEQ ID NO:43, and light chain CDR3 (LCDR3) consisting of the amino acid sequence set forth in SEQ ID NO:44.

In some embodiments, the anti-CD48 antibody or antigen-binding fragment thereof comprises three heavy chain CDRs and three light chain CDRs as follows: heavy chain CDR1 (HCDR1) consisting of the amino acid sequence set forth in SEQ ID NO:30, heavy chain CDR2 (HCDR2) consisting of the amino acid sequence set forth in SEQ ID NO:28, heavy chain CDR3 (HCDR3) consisting of the amino acid sequence set forth in SEQ ID NO:29; light chain CDR1 (LCDR1) consisting of the amino acid sequence set forth in SEQ ID NO:42, light chain CDR2 (LCDR2) consisting of the amino acid sequence set forth in SEQ ID NO:43, and light chain CDR3 (LCDR3) consisting of the amino acid sequence set forth in SEQ ID NO:44.

In some embodiments, the anti-CD48 antibody or antigen-binding fragment thereof comprises three heavy chain CDRs and three light chain CDRs as follows: heavy chain CDR1 (HCDR1) consisting of the amino acid sequence set forth in SEQ ID NO:31, heavy chain CDR2 (HCDR2) consisting of the amino acid sequence set forth in SEQ ID NO:32, heavy chain CDR3 (HCDR3) consisting of the amino acid sequence set forth in SEQ ID NO:29; light chain CDR1 (LCDR1) consisting of the amino acid sequence set forth in SEQ ID NO:45, light chain CDR2 (LCDR2) consisting of the amino acid sequence set forth in SEQ ID NO:46, and light chain CDR3 (LCDR3) consisting of the amino acid sequence set forth in SEQ ID NO:47.

In some embodiments, the anti-CD48 antibody or antigen-binding fragment thereof comprises three heavy chain CDRs and three light chain CDRs as follows: heavy chain CDR1 (HCDR1) consisting of the amino acid sequence set forth in SEQ ID NO:33, heavy chain CDR2 (HCDR2) consisting of the amino acid sequence set forth in SEQ ID NO:34, heavy chain CDR3 (HCDR3) consisting of the amino acid sequence set forth in SEQ ID NO:35; light chain CDR1 (LCDR1) consisting of the amino acid sequence set forth in SEQ ID NO:48, light chain CDR2 (LCDR2) consisting of the amino acid sequence set forth in SEQ ID NO:46, and light chain CDR3 (LCDR3) consisting of the amino acid sequence set forth in SEQ ID NO:44.

In some embodiments, the anti-CD48 antibody or antigen-binding fragment thereof comprises a heavy chain variable region comprising the amino acid sequence of SEQ ID NO:10, and a light chain variable region comprising the amino acid sequence of SEQ ID NO:23. In some embodiments, the anti-CD48 antibody or antigen-binding fragment thereof comprises the heavy chain variable region amino acid sequence of SEQ ID NO:10 and the light chain variable region amino acid sequence of SEQ ID NO:23, or sequences that are at least 95% identical to the disclosed sequences. In some embodiments, the anti-CD48 antibody or antigen-binding fragment thereof has a heavy chain variable region amino acid sequence that is at least 96%, at least 97%, at least 98%, or at least 99% identical to SEQ ID NO:10 and/or a light chain variable region amino acid sequence that is at least 96%, at least 97%, at least 98%, or at least 99% identical to SEQ ID NO:23.

In some embodiments, the anti-CD48 antibody or antigen-binding fragment thereof comprises a heavy chain variable region comprising the amino acid sequence of SEQ ID NO:36, and a light chain variable region comprising the amino acid sequence of SEQ ID NO:49. In some embodiments, the anti-CD48 antibody or antigen-binding fragment thereof comprises the heavy chain variable region amino acid sequence of SEQ ID NO:36 and the light chain variable region amino acid sequence of SEQ ID NO:49, or sequences that are at least 95% identical to the disclosed sequences. In some embodiments, the anti-CD48 antibody or antigen-binding fragment thereof has a heavy chain variable region amino acid sequence that is at least 96%, at least 97%, at least 98%, or at least 99% identical to SEQ ID NO:36 and/or a light chain variable region amino acid sequence that is at least 96%, at least 97%, at least 98%, or at least 99% identical to SEQ ID NO:49.

In some embodiments, the anti-CD48 antibody comprises the heavy chain amino acid sequence of SEQ ID NO:12 or a sequence that is at least 95% identical to SEQ ID NO:12, and the light chain amino acid sequence of SEQ ID NO:25 or a sequence that is at least 95% identical to SEQ ID NO:25. In some embodiments, the anti-CD48 antibody comprises the heavy chain amino acid sequence of SEQ ID NO:12 and the light chain amino acid sequence of SEQ ID NO:25, or sequences that are at least 95% identical to the disclosed sequences. In some embodiments, the anti-CD48 antibody has a heavy chain amino acid sequence that is at least 96%, at least 97%, at least 98%, or at least 99% identical to SEQ ID NO:12 and a light chain amino acid sequence that is at least 96%, at least 97%, at least 98%, or at least 99% identical to SEQ ID NO:25.

In some embodiments, the anti-CD48 antibody comprises the heavy chain amino acid sequence of SEQ ID NO:14 or a sequence that is at least 95% identical to SEQ ID NO:14, and the light chain amino acid sequence of SEQ ID NO:25 or a sequence that is at least 95% identical to SEQ ID NO:25. In some embodiments, the anti-CD48 antibody comprises the heavy chain amino acid sequence of SEQ ID NO:14 and the light chain amino acid sequence of SEQ ID NO:25, or sequences that are at least 95% identical to the disclosed sequences. In some embodiments, the anti-CD48 antibody has a heavy chain amino acid sequence that is at least 96%, at least 97%, at least 98%, or at least 99% identical to SEQ ID NO:14 and a light chain amino acid sequence that is at least 96%, at least 97%, at least 98%, or at least 99% identical to SEQ ID NO:25.

In some embodiments, the anti-CD48 antibody comprises the heavy chain amino acid sequence of SEQ ID NO:38 or a sequence that is at least 95% identical to SEQ ID NO:38, and the light chain amino acid sequence of SEQ ID NO:51 or a sequence that is at least 95% identical to SEQ ID NO:51. In some embodiments, the anti-CD48 antibody comprises the heavy chain amino acid sequence of SEQ ID NO:38 and the light chain amino acid sequence of SEQ ID NO:51, or sequences that are at least 95% identical to the disclosed sequences. In some embodiments, the anti-CD48 antibody has a heavy chain amino acid sequence that is at least 96%, at least 97%, at least 98%, or at least 99% identical to SEQ ID NO:38 and a light chain amino acid sequence that is at least 96%, at least 97%, at least 98%, or at least 99% identical to SEQ ID NO:51.

In some embodiments, the anti-CD48 antibody comprises the heavy chain amino acid sequence of SEQ ID NO:40 or a sequence that is at least 95% identical to SEQ ID NO:40, and the light chain amino acid sequence of SEQ ID NO:51 or a sequence that is at least 95% identical to SEQ ID NO:51. In some embodiments, the anti-CD48 antibody comprises the heavy chain amino acid sequence of SEQ ID NO:40 and the light chain amino acid sequence of SEQ ID NO:51, or sequences that are at least 95% identical to the disclosed sequences. In some embodiments, the anti-CD48 antibody has a heavy chain amino acid sequence that is at least 96%, at least 97%, at least 98%, or at least 99% identical to SEQ ID NO:40 and a light chain amino acid sequence that is at least 96%, at least 97%, at least 98%, or at least 99% identical to SEQ ID NO:51.

Residues in two or more polypeptides are said to "correspond" if the residues occupy an analogous position in the polypeptide structures. Analogous positions in two or more polypeptides can be determined by aligning the polypeptide sequences based on amino acid sequence or structural similarities. Those skilled in the art understand that it may be necessary to introduce gaps in either sequence to produce a satisfactory alignment.

In some embodiments, amino acid substitutions are of single residues. Insertions usually will be on the order of from about 1 to about 20 amino acid residues, although considerably larger insertions may be tolerated as long as biological function is retained (e.g., binding to a target antigen). Deletions usually range from about 1 to about 20 amino acid residues, although in some cases deletions may be much larger. Substitutions, deletions, insertions, or any combination thereof may be used to arrive at a final derivative or variant. Generally, these changes are done on a few amino acids to minimize the alteration of the molecule, particularly the immunogenicity and specificity of the antigen binding protein. However, larger changes may be tolerated in certain circumstances. Conservative substitutions can be made in accordance with the following chart depicted as Table 4.

TABLE 4

Amino Acid Substitutions

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |

TABLE 4-continued

Amino Acid Substitutions

| Original Residue | Exemplary Substitutions |
|---|---|
| Phe | Met, Leu, Tyr |
| Ser | Thr |
| Thr | Ser |
| Trp | Tyr |
| Tyr | Trp, Phe |
| Val | Ile, Leu |

The antibody or antigen-binding fragment thereof disclosed herein includes within its scope any antibody or antigen-binding fragment that specifically binds to a target antigen (e.g. human CD48) on a cancer cell. The antibody or antigen-binding fragment may bind to a target antigen (e.g. human CD48) with a dissociation constant (KD) of ≤1 mM, ≤100 nM or ≤10 nM, or any amount in between, as measured by, e.g., BIAcore® analysis. In some embodiments, the KD is 1 pM to 500 pM. In some embodiments, the KD is between 500 μM to 1 μM, 1 pM to 100 nM, or 100 mM to 10 nM. In some embodiments, the KD is between 500 nM to 10 pM.

In some embodiments, the antibody or antigen-binding fragment is a four-chain antibody (also referred to as an immunoglobulin or a full-length or intact antibody), comprising two heavy chains and two light chains. In some embodiments, the antibody or antigen-binding fragment is an antigen-binding fragment of an immunoglobulin. In some embodiments, the antibody or antigen-binding fragment is an antigen-binding fragment of an immunoglobulin that retains the ability to bind a target cancer antigen (e.g. CD48) and/or provide at least one function of the immunoglobulin.

In one embodiment, the antibody molecule is a full antibody or fragment thereof (e.g., a Fab, Fab', F(ab')$_2$, dAb, Fd, Fv, disulfide-linked Fv (sdFv), or a single chain Fv (scFv) fragment). In other embodiments, the antibody molecule is a half antibody, a one-arm antibody, a single domain antibody, a maxibody, a minibody, a nanobody, an intrabody, or a diabody. In yet other embodiments, the antibody molecule has a heavy chain constant region (Fc) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1 or IgG4 (e.g., human IgG1 or IgG4). In one embodiment, the heavy chain constant region is human IgG1 or human IgG4. In one embodiment, the constant region is altered, e.g., mutated, to modify the properties of the antibody molecule (e.g., to increase or decrease one or more of: Fc receptor binding, antibody glycosylation, the number of cysteine residues, effector cell function, or complement function).

In certain embodiments, the antibody molecule is in the form of a bispecific or multispecific antibody molecule. In one embodiment, the bispecific antibody molecule has a first binding specificity to human CD48 and a second binding specificity to CD3. In one embodiment, the anti-CD48 antibody is a bispecific T-cell engager (BiTE) antibody.

In one embodiment, the antibody, or antigen binding fragment thereof, (e.g. an scFv fragment) is in the form of a chimeric antigen receptor T-cell (CAR-T or CART).

The antibodies, antibody fragments (e.g., antigen binding fragments) or functional equivalents of the present disclosure can also be conjugated to a radioactive isotope to generate cytotoxic radiopharmaceuticals, referred to as radioimmunoconjugates. Examples of radioactive isotopes that can be conjugated to antibodies for use diagnostically or therapeutically include, but are not limited to, iodine-131, indium-111, yttrium-90, and lutetium-177. Methods for preparing radioimmunoconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies disclosed herein. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., (1998) Clin Cancer Res. 4(10):2483-90; Peterson et al., (1999) Bioconjug. Chem. 10(4):553-7; and Zimmerman et al., (1999) Nucl. Med. Biol. 26(8):943-50, each incorporated by reference in their entireties.

The antibodies, antibody fragments (e.g., antigen binding fragments) or functional equivalents of the present disclosure can also be conjugated to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the disclosure provides fusion proteins comprising an antibody fragment (e.g., antigen binding fragment) described herein (e.g., a Fab fragment, Fd fragment, Fv fragment, Fab' fragment, F(ab')$_2$ fragment, a VH domain, a VH CDR, a VL domain or a VL CDR) and a heterologous protein, polypeptide, or peptide.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the disclosure or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., (1997) Curr. Opinion Biotechnol. 8:724-33; Harayama, (1998) Trends Biotechnol. 16(2):76-82; Hansson et al., (1999) J. Mol. Biol. 287:265-76; and Lorenzo and Blasco, (1998) Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to an antigen may be recombined with one or more components, motifs, sections, parts, domains, fragments, etc. of one or more heterologous molecules.

Moreover, the antibodies, antibody fragments (e.g., antigen binding fragments) or functional equivalents of the present disclosure can be conjugated to marker sequences, such as a peptide, to facilitate purification. In preferred embodiments, the marker amino acid sequence is a hexahistidine peptide (SEQ ID NO: 84), such as the tag provided in a pQE vector (QIAGEN, Inc., 9259 Eton Avenue, Chatsworth, CA, 91311), among others, many of which are commercially available. As described in Gentz et al., (1989) Proc. Natl. Acad. Sci. USA 86:821-824, for instance, hexahistidine (SEQ ID NO: 84) provides for convenient purification of the fusion protein. Other peptide tags useful for purification include, but are not limited to, the hemagglutinin ("HA") tag, which corresponds to an epitope derived from the influenza hemagglutinin protein (Wilson et al., (1984) Cell 37:767), and the "FLAG" tag (A. Einhauer et al., J. Biochem. Biophys. Methods 49: 455-465, 2001). According to the present disclosure, antibodies or antigen binding fragments can also be conjugated to tumor-penetrating peptides in order to enhance their efficacy.

In other embodiments, the antibodies, antibody fragments (e.g., antigen binding fragments) or functional equivalents of the present disclosure are conjugated to a diagnostic or detectable agent. Such immunoconjugates can be useful for monitoring or prognosing the onset, development, progression and/or severity of a disease or disorder as part of a clinical testing procedure, such as determining the efficacy of a particular therapy. Such diagnosis and detection can be accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, umbelliferone, fluorescein, fluorescein isothiocyanate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I, $^{125}$I, $^{123}$I, and $^{121}$I), carbon ($^{14}$C), sulfur ($^{35}$S), tritium ($^{3}$H), indium ($^{115}$In, $^{113}$In, $^{112}$In, and $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P $^{153}$Gd, $^{169}$Yb, $^{51}$Cr, $^{54}$Mn, $^{75}$Se, $^{64}$Cu, $^{113}$Sn, and $^{117}$Sn; and positron emitting metals using various positron emission tomographies, and non-radioactive paramagnetic metal ions.

The antibodies, antibody fragments (e.g., antigen binding fragments) or functional equivalents of the present disclosure may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

In some embodiments, the antibody or antigen-binding fragment is an internalizing antibody or internalizing antigen-binding fragment thereof. In some embodiments, the internalizing antibody or internalizing antigen-binding fragment thereof binds to a target cancer antigen (e.g. CD48) expressed on the surface of a cell and enters the cell upon binding. In some embodiments, the drug moiety of the ADC is released from the antibody or antigen-binding fragment of the ADC after the ADC enters and is present in a cell expressing the target cancer antigen (i.e., after the ADC has been internalized), e.g., by cleavage, by degradation of the antibody or antigen-binding fragment, or by any other suitable release mechanism. In some embodiments where variant antibody sequences are used in an ADC, the variants typically exhibit the same qualitative biological activity and will elicit the same immune response, although variants may also be selected to modify the characteristics of the antigen binding proteins as needed. Alternatively, the variant may be designed such that the biological activity of the antigen binding protein is altered. For example, glycosylation sites may be altered or removed.

The antibodies, antibody fragments (e.g., antigen binding fragments) or functional equivalents of the disclosure may comprise modified antibodies or antigen binding fragments thereof that further comprise modifications to framework residues within VH and/or VL, e.g. to improve the properties of the antibody. In some embodiments, the framework modifications are made to decrease the immunogenicity of the antibody. For example, one approach is to "back-mutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back-mutated" to the germline sequence by, for example, site-directed mutagenesis. Such "back-mutated" antibodies are also intended to be encompassed herein.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 20030153043 by Carr et al.

In addition or in the alternative to modifications made within the framework or CDR regions, antibodies of the disclosure may be engineered to include modifications within the Fc region, typically to alter one or more functional properties of the antibody, such as serum half-life, complement fixation, Fc receptor binding, and/or antigen-dependent cellular cytotoxicity (ADCC). Furthermore, an antibody of the disclosure may be chemically modified (e.g., one or more chemical moieties can be attached to the antibody) or be modified to alter its glycosylation, again to alter one or more functional properties of the antibody. Each of these embodiments is described in further detail below.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In some embodiments, the antibody or antibody fragment disclosed herein include modified or engineered amino acid residues, e.g., one or more cysteine residues, as sites for conjugation to a drug moiety (Junutula J R, et al., Nat Biotechnol 2008, 26:925-932). In one embodiment, the disclosure provides a modified antibody or antibody fragment comprising a substitution of one or more amino acids with cysteine at the positions described herein. Sites for cysteine substitution are in the constant regions of the antibody or antibody fragment and are thus applicable to a variety of antibody or antibody fragment, and the sites are selected to provide stable and homogeneous conjugates. A modified antibody or fragment can have one, two or more cysteine substitutions, and these substitutions can be used in combination with other modification and conjugation methods as described herein. Methods for inserting cysteine at specific locations of an antibody are known in the art, see, e.g., Lyons et al., (1990) Protein Eng., 3:703-708, WO 2011/005481, WO2014/124316, WO 2015/138615. In certain embodiments, a modified antibody comprises a substitution of one or more amino acids with cysteine on its constant region selected from positions 117, 119, 121, 124, 139, 152, 153, 155, 157, 164, 169, 171, 174, 189, 191, 195, 197, 205, 207, 246, 258, 269, 274, 286, 288, 290, 292, 293, 320, 322, 326, 333, 334, 335, 337, 344, 355, 360, 375, 382, 390, 392, 398, 400 and 422 of a heavy chain of the antibody, and wherein the positions are numbered according to the EU system. In some embodiments a modified antibody or antibody fragment comprises a substitution of one or more amino acids with cysteine on its constant region selected from positions 107, 108, 109, 114, 129, 142, 143, 145, 152, 154, 156, 159, 161, 165, 168, 169, 170, 182, 183, 197, 199, and 203 of a light chain of the antibody or antibody fragment, wherein the positions are numbered according to the EU system, and wherein the light chain is a human kappa light chain. In certain embodiments a modified antibody or antibody fragment thereof comprises a combination of substitution of two or more amino acids with cysteine on its constant regions wherein the combinations comprise substitutions at positions 375 of an antibody heavy chain, position 152 of an antibody heavy chain, position 360 of an antibody heavy chain, or position 107 of an antibody light chain and wherein the positions are numbered according to the EU system. In certain embodiments a modified antibody or antibody fragment thereof comprises a substitution of one amino acid with cysteine on its constant regions wherein the substitution is position 375 of an antibody heavy chain, position 152 of an antibody heavy chain, position 360 of an antibody heavy chain, position 107 of an antibody light chain, position 165 of an antibody light chain or position 159 of an antibody light chain and wherein the positions are numbered according to the EU system, and wherein the light chain is a kappa chain. In particular embodiments a modified antibody or antibody fragment thereof comprises a combination of substitution of two amino acids with cysteine on its constant regions wherein the combinations comprise substitutions at positions 375 of an antibody heavy chain and position 152 of an antibody heavy chain, wherein the positions are numbered according to the EU system. In particular embodiments a modified antibody or antibody fragment thereof comprises a substitution of one amino acid with cysteine at position 360 of an antibody heavy chain, wherein the positions are numbered according to the EU system. In other particular embodiments a modified antibody or antibody fragment thereof comprises a substitution of one amino acid with cysteine at position 107 of an antibody light chain and wherein the positions are numbered according to the EU system, and wherein the light chain is a kappa chain.

In additional embodiments antibodies or antibody fragments (e.g., antigen binding fragment) useful in immunoconjugates of the present disclosure include modified or engineered antibodies, such as an antibody modified to introduce one or more other reactive amino acid (other than cysteine), including Pcl, pyrrolysine, peptide tags (such as S6, A1 and ybbR tags), and non-natural amino acids, in place of at least one amino acid of the native sequence, thus providing a reactive site on the antibody or antigen binding fragment for conjugation to a drug moiety or a linker-drug moiety with complementary reactivity. For example, the antibodies or antibody fragments can be modified to incorporate Pcl or pyrrolysine (W. Ou, et al., (2011) PNAS 108 (26), 10437-10442; WO2014124258) or unnatural amino acids (J. Y. Axup, et al., Proc Natl Acad Sci USA, 109 (2012), pp. 16101-16106; for review, see C. C. Liu and P. G. Schultz (2010) Annu Rev Biochem 79, 413-444; C. H. Kim, et al., (2013) Curr Opin Chem Biol. 17, 412-419) as sites for conjugation to a drug. Similarly, peptide tags for enzymatic conjugation methods can be introduced into an antibody (Strop P., et al., Chem Biol. 2013, 20(2):161-7; Rabuka D., Curr Opin Chem Biol. 2010 December; 14(6):790-6; Rabuka D, et al., Nat Protoc. 2012, 7(6):1052-67). One other example is the use of 4'-phosphopantetheinyl transferases (PPTase) for the conjugation of Co-enzyme A analogs (WO2013184514), and (Grunewald et al., (2015) Bioconjugate Chem. 26 (12), 2554-62). Methods for conjugating such modified or engineered antibodies with payloads or linker-payload combinations are known in the art.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in, e.g., U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in, e.g., U.S. Pat. No. 6,194,551 by Idusogie et al.

In another embodiment, one or more amino acid residues are altered to thereby alter the ability of the antibody to fix complement. This approach is described in, e.g., the PCT Publication WO 94/29351 by Bodmer et al. Allotypic amino acid residues include, but are not limited to, constant region of a heavy chain of the IgG1, IgG2, and IgG3 subclasses as well as constant region of a light chain of the kappa isotype as described by Jefferis et al., MAbs. 1:332-338 (2009).

In some embodiments, the antibodies comprise mutations that mediate reduced or no antibody-dependent cellular cytotoxicity (ADCC) or complement-dependent cytotoxicity (CDC). In some embodiments, these mutations are known as Fc Silencing, Fc Silent, or Fc Silenced mutations. In some embodiments, amino acid residues L234 and L235 of the IgG1 constant region are substituted to A234 and A235 (also known as "LALA"). In some embodiments, amino acid residue N297 of the IgG1 constant region is substituted to A297 (also known as "N297A"). In some embodiments, amino acid residues D265 and P329 of the IgG1 constant region are substituted to A265 and A329 (also known as "DAPA"). Other antibody Fc silencing mutations may also be used. In some embodiments, the Fc silencing mutations are used in combination, for example D265A, N297A and P329A (also known as "DANAPA").

In another embodiment, one or more amino acid residues are altered to thereby alter the ability of the antibody to fix complement. This approach is described in, e.g., the PCT Publication WO 94/29351 by Bodmer et al. In a specific embodiment, one or more amino acids of an antibody or antigen binding fragment thereof of the present disclosure are replaced by one or more allotypic amino acid residues. Allotypic amino acid residues also include, but are not limited to, the constant region of the heavy chain of the IgG1, IgG2, and IgG3 subclasses as well as the constant region of the light chain of the kappa isotype as described by Jefferis et al., MAbs. 1:332-338 (2009).

In still another embodiment, the glycosylation of an antibody is modified. For example, an aglycosylated antibody can be made (i.e., the antibody lacks glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in, e.g., U.S. Pat. Nos. 5,714,350 and 6,350,861 by Co et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

Antibodies that Bind to the Same Epitope

The present disclosure provides an antibody or antibody fragment (e.g., antigen binding fragment) that specifically binds to an epitope within the extracellular domain of human CD48. In certain aspects the antibody or antibody fragment can bind to an epitope within amino acids 29-130 of human CD48. In some embodiments, the epitope is within amino acids 54-64 or amino acids 105-121 of human CD48 (SEQ ID NO:53). In some embodiments, the epitope comprises one or more of amino acids 54, 58, 60, 61, 62, 64, 105, 107, 119, 111, 114, 115, 117, 119, and 121 of the amino acid sequence set forth in SEQ ID NO:53.

The present disclosure also provides antibodies or antibody fragments (e.g., antigen binding fragment) that bind to the same epitope as the anti-CD48 antibody or antibody fragment (e.g., antigen binding fragment) described in Table 1, Table 2, and Table 3. Additional antibodies or antibody fragments (e.g., antigen binding fragment) can therefore be identified based on their ability to cross-compete with (e.g., to competitively inhibit the binding of, in a statistically significant manner) another antibody or antibody fragment in CD48 binding assays. A high throughput process for "binning" antibodies based upon their cross-competition is described, for example, in International Patent Publication No. WO 2003/48731. The ability of a test antibody or antibody fragment to inhibit the binding of antibody or antibody fragment disclosed herein to a CD48 protein (e.g., human CD48) demonstrates that the test antibody or antibody fragment can compete with that antibody or antibody fragment for binding to CD48; such an antibody or antibody fragment may, according to non-limiting theory, bind to the same, overlapping, or a related (e.g., a structurally similar or spatially proximal) epitope on the CD48 protein as the antibody or antibody fragment with which it competes. In a certain aspect, the antibody or antibody fragment that binds to the same epitope on CD48 as the antibody or antibody fragment disclosed herein is a human or humanized antibody or antibody fragment. Such human or humanized antibody or antibody fragment can be prepared and isolated as described herein.

Production of CD48 Antibodies or Antibody Fragments

Anti-CD48 antibodies or antibody fragments (e.g., antigen binding fragment) can be produced by any means known in the art, including but not limited to, recombinant expression, chemical synthesis, or enzymatic digestion of full-length monoclonal antibodies, which can be obtained by, e.g., hybridoma or recombinant production. Recombinant expression can be from any appropriate host cells known in the art, for example, mammalian host cells, bacterial host cells, yeast host cells, insect host cells, or made by a cell-free system (e.g., Sutro's Xpress CF™ Platform, World Wide Web at sutrobio.com/technology/).

The disclosure further provides polynucleotides encoding the antibody or antibody fragment (e.g., antigen binding fragment) described herein, e.g., polynucleotides encoding heavy or light chain variable regions or segments comprising the complementarity determining regions as described herein. In some aspects, the polynucleotide encoding the heavy chain variable regions (VH) has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 11 and 37. In some aspects, the polynucleotide encoding the light chain variable regions (VL) has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 24 and 50.

In some aspects, the polynucleotide encoding the antibody heavy chain has at least 85%, 89%, 90%, 91%, 92%, 93%, 94%, 95%, 96%, 97%, 98%, 99%, or 100% nucleic acid sequence identity with a polynucleotide of SEQ ID NO: 13 or 15. In some aspects, the polynucleotide encoding the antibody light chain has at least 85%, 89%, 90%, 91%, 92%, 93%, 94%, 95%, 96%, 97%, 98%, 99%, or 100% nucleic acid sequence identity with a polynucleotide of SEQ ID NO: 26 or 52.

The polynucleotides of the present disclosure can encode only the variable region sequence of an anti-CD48 antibody or antibody fragment (e.g., antigen binding fragment). They can also encode both a variable region and a constant region of the antibody or antibody fragment (e.g., antigen binding fragment). Some of the polynucleotide sequences encode a polypeptide that comprises variable regions of both the heavy chain and the light chain of one of an exemplified anti-CD48 antibody or antibody fragment (e.g., antigen binding fragment).

The polynucleotide sequences can be produced by de novo solid-phase DNA synthesis or by PCR mutagenesis of an existing sequence (e.g., sequences as described in the Examples below) encoding an anti-CD48 antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, NY, 1992; PCR Protocols: A Guide to Methods and Applications, Innis et al. (Ed.), Academic Press, San Diego, CA, 1990; Mattila et al., Nucleic Acids Res. 19:967, 1991; and Eckert et al., PCR Methods and Applications 1:17, 1991.

Also provided in the present disclosure are expression vectors and host cells for producing any of the anti-CD48 antibodies or antibody fragments (e.g., antigen binding fragments) described herein. Various expression vectors can be employed to express the polynucleotides encoding the anti-CD48 antibodies or antibody fragments (e.g., antigen binding fragments). Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet. 15:345, 1997). For example, nonviral vectors useful for expression of the anti-CD48 polynucleotides and polypeptides in mammalian (e.g., human) cells include pThioHis A, B & C, pcDNA3.1/His, pEBVHis A, B & C (Invitrogen, San Diego, CA), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an anti-CD48 antibody or antibody fragment (e.g., antigen binding fragment). In some aspects, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an anti-CD48 antibody or antibody fragment (e.g., antigen binding fragment). These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted anti-CD48 antibody or antibody fragment (e.g., antigen binding fragment) sequences. More often, the inserted anti-CD48 antibody or antibody fragment (e.g., antigen binding fragment) sequences are linked to a signal sequences before inclusion in the vector. Vectors to be used to receive sequences encoding anti-CD48 antibody or antibody fragment (e.g., antigen binding fragment) light and heavy chain variable domains sometimes also encode constant regions or parts thereof. Such vectors allow expression of the variable regions as fusion proteins with the constant regions thereby leading to production of intact antibodies or fragments thereof.

The host cells for harboring and expressing the anti-CD48 antibody or antibody fragment (e.g., antigen binding fragment) chains can be either prokaryotic or eukaryotic. E. coli is one prokaryotic host useful for cloning and expressing the polynucleotides of the present disclosure. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-CD48 antibody or antibody fragment (e.g., antigen binding fragment) polypeptides. Insect cells in combination with baculovirus vectors can also be used.

In other aspects, mammalian host cells are used to express and produce the anti-CD48 antibody or antibody fragment (e.g., antigen binding fragment) polypeptides of the present disclosure. For example, they can be either a hybridoma cell line expressing endogenous immunoglobulin genes (e.g., the myeloma hybridoma clones as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed, including the CHO cell lines, various COS cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express anti-CD48 antibody or antibody fragment (e.g., antigen binding fragment) chains can be prepared using expression vectors which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Antibody fragments, such as antigen binding fragments, may be produced by proteolytic cleavage of immunoglobulin molecules, using enzymes such as papain (to produce Fab fragments), or pepsin (to produce Fab' fragments), etc. Compared to Fab fragments, Fab' fragments also contain the hinge region which includes the two natural cysteines that form disulfide bonds between two heavy chains of an immunoglobulin molecule.

Drum Moiety (D)

In one aspect, the present application provides immunoconjugates that specifically bind to human CD48. The antibody drug conjugates of the present disclosure comprise anti-CD48 antibodies, antibody fragments (e.g., antigen binding fragments) or functional equivalents that are conjugated to a drug moiety, e.g., a diagnostic agent, an anti-cancer agent, an autoimmune treatment agent, an anti-inflammatory agent, an antifungal agent, an antibacterial agent, an anti-parasitic agent, an anti-viral agent, or an anesthetic agent. The antibodies, antibody fragments (e.g., antigen binding fragments) or functional equivalents thereof can be conjugated to several identical or different drug moieties using any methods known in the art.

In certain embodiments, the drug moiety of the immunoconjugates of the present disclosure is selected from a group consisting of an Eg5 inhibitor, a V-ATPase inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitors, a kinesin inhibitor, an HDAC inhibitor, a DNA damaging agent, a DNA alkylating agent, a DNA intercalator, a DNA minor groove binder, an RNA polymerase inhibitor, an amanitin, a spliceosome inhibitor, a topoisomerase inhibitor, a DHFR inhibitor, and a pro-apoptotic agent, but excluding BCL-2 inhibitors, MCL-1 inhibitors, and BCL-XL inhibitors.

In one embodiment, the drug moiety of the immunoconjugates of the present disclosure is a maytansinoid drug moiety, such as but not limited to, DM1, DM3, or DM4.

Further, the antibodies, antibody fragments (e.g., antigen binding fragments) or functional equivalents of the present disclosure may be conjugated to a drug moiety that modifies a given biological response. Drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, pseudomonas exotoxin, cholera toxin, or diphtheria toxin, a protein such as tumor necrosis factor, α-interferon, β-interferon, nerve growth factor, platelet derived growth factor, tissue plasminogen activator, a cytokine, an apoptotic agent, an anti-angiogenic agent, or a biological response modifier such as, for example, a lymphokine.

In one embodiment, the antibodies, antibody fragments (e.g., antigen binding fragments) or functional equivalents of the present disclosure are conjugated to a drug moiety, such as a cytotoxin, a drug (e.g., an immunosuppressant) or a radiotoxin. Examples of cytotoxins include but are not limited to, pyrrolobenzodiazepines (PBDs, see, e.g. tesirine described in Tiberghien et al., ACS Med Chem Lett 7(11): 983-987 (2016), indolinobenzodiazepine dimer payloads (IGN described in Singh et al., Mol Pharm 2020 17(1), 50-58)), taxanes (see, e.g., International (PCT) Patent Application Nos. WO 01/38318 and PCT/US03/02675), DNA-alkylating agents (e.g., CC-1065 analogs), anthracyclines, tubulysin analogs, duocarmycin analogs, auristatin E (MMAE), auristatin F (MMAF), maytansinoids, and cytotoxic agents comprising a reactive polyethylene glycol moiety (see, e.g., Sasse et al., J. Antibiot. (Tokyo), 53, 879-85 (2000), Suzawa et al., Bioorg. Med. Chem., 8, 2175-84 (2000), Ichimura et al., J. Antibiot. (Tokyo), 44, 1045-53 (1991), Francisco et al., Blood (2003) (electronic publication prior to print publication), U.S. Pat. Nos. 5,475,092, 6,340,701, 6,372,738, and 6,436,931, U.S. Patent Application Publication No. 2001/0036923 A1, Pending U.S. patent application Ser. Nos. 10/024,290 and 10/116,053, and International (PCT) Patent Application No. WO 01/49698), taxon, cytochalasin B, gramicidin D, ethidium bromide, emetine, mitomycin, etoposide, tenoposide, vincristine, vinblastine, t. colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, anti-metabolites (e.g., methotrexate, 6-mercaptopurine, 6-thioguanine, cytarabine, 5-fluorouracil decarbazine), ablating agents (e.g., mechlorethamine, thiotepa chlorambucil, meiphalan, carmustine (BSNU) and lomustine (CCNU), cyclophosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). (See e.g., Seattle Genetics US20090304721).

Other examples of cytotoxins that can be conjugated to the antibodies, antibody fragments (antigen binding fragments) or functional equivalents of the present disclosure include duocarmycins, calicheamicins, maytansines and auristatins, and derivatives thereof.

Various types of cytotoxins, linkers and methods for conjugating therapeutic agents to antibodies are known in the art, see, e.g., Saito et al., (2003) Adv. Drug Deliv. Rev. 55:199-215; Trail et al., (2003) Cancer Immunol. Immunother. 52:328-337; Payne, (2003) Cancer Cell 3:207-212; Allen, (2002) Nat. Rev. Cancer 2:750-763; Pastan and Kreitman, (2002) Curr. Opin. Investig. Drugs 3:1089-1091; Senter and Springer, (2001) Adv. Drug Deliv. Rev. 53:247-264.

In one aspect, the Drug moiety of the present disclosure is a compound of Formula (A):

Formula A

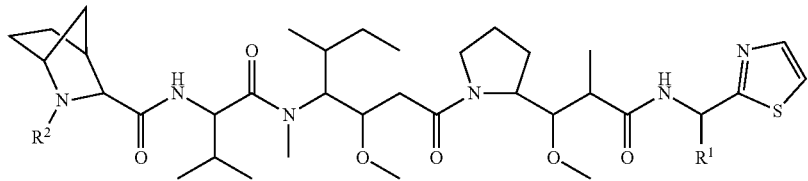

wherein:
R¹ is

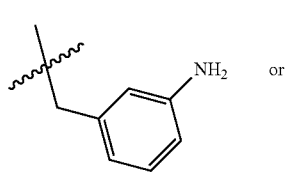 or

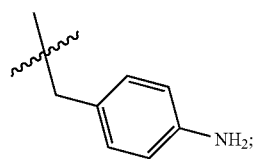

R² is H, $C_1$-$C_6$alkyl, —C(=O)R³, —(CH$_2$)$_m$OH, —C(=O)(CH$_2$)$_m$OH, —C(=O)((CH$_2$)$_m$O)$_n$R⁴, —((CH$_2$)$_m$O)$_n$R⁴ or $C_1$-$C_6$alkyl which is optionally substituted with —CN, —C(=O)NH$_2$ or 1 to 5 hydroxyl;
each R³ is independently selected from $C_1$-$C_6$alkyl and $C_1$-$C_6$alkyl, which is optionally substituted with 1 to 5 hydroxyl;
and each R⁴ is independently selected from H and $C_1$-$C_6$alkyl.

In one aspect, the Drug moiety of the present disclosure is a compound of Formula (B):

Formula (B)

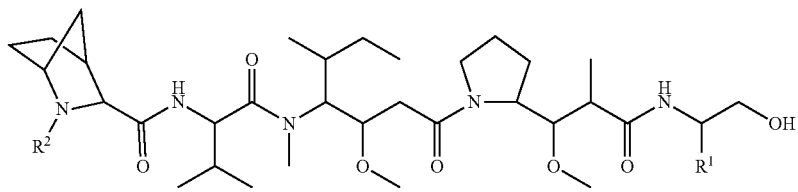

wherein:
R¹ is

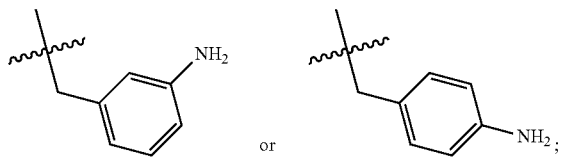 [SMILES: *Cc1cccc(N)c1 ; *Cc1ccc(N)cc1]

R² is H, $C_1$-$C_6$alkyl, —C(=O)R³, —(CH$_2$)$_m$OH, —C(=O)(CH$_2$)$_m$OH, —C(=O)((CH$_2$)$_m$O)$_n$R⁴, —((CH$_2$)$_m$O)$_n$R⁴ or $C_1$-$C_6$alkyl which is optionally substituted with —CN, —C(=O)NH$_2$ or 1 to 5 hydroxyl;

each R³ is independently selected from $C_1$-$C_6$alkyl and $C_1$-$C_6$alkyl, which is optionally substituted with 1 to 5 hydroxyl;

and each R⁴ is independently selected from H and $C_1$-$C_6$alkyl.

Certain aspects and examples of the Drug moiety of the present disclosure are provided in the following listing of additional, enumerated embodiments. It will be recognized that features specified in each embodiment may be combined with other specified features to provide further embodiments of the present disclosure.

Embodiment 1. The compound of Formula (A), or a pharmaceutically acceptable salt thereof, having the structure of Formula (A-1), or a pharmaceutically acceptable salt thereof:

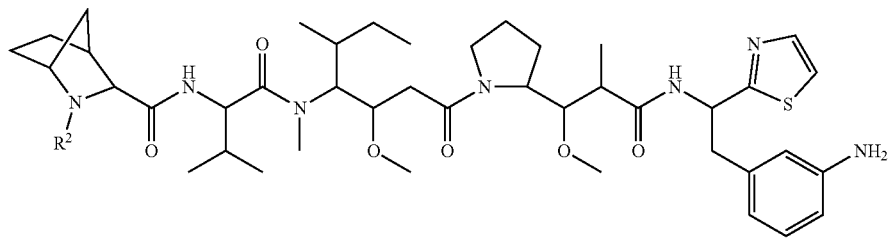

Formula (A-1)

wherein:
R² is H, $C_1$-$C_6$alkyl, —C(=O)R³, —(CH$_2$)$_m$OH, —C(=O)(CH$_2$)$_m$OH, —C(=O)((CH$_2$)$_m$O)$_n$R⁴, —((CH$_2$)$_m$O)$_n$R⁴ or $C_1$-$C_6$alkyl which is optionally substituted with —CN, —C(=O)NH$_2$ or 1 to 5 hydroxyl;

each R³ is independently selected from $C_1$-$C_6$alkyl and $C_1$-$C_6$alkyl, which is optionally substituted with 1 to 5 hydroxyl;

and each R⁴ is independently selected from H and $C_1$-$C_6$alkyl.

Embodiment 2. The compound of Formula (A), or a pharmaceutically acceptable salt thereof, having the structure of Formula (A-2), or a pharmaceutically acceptable salt thereof:

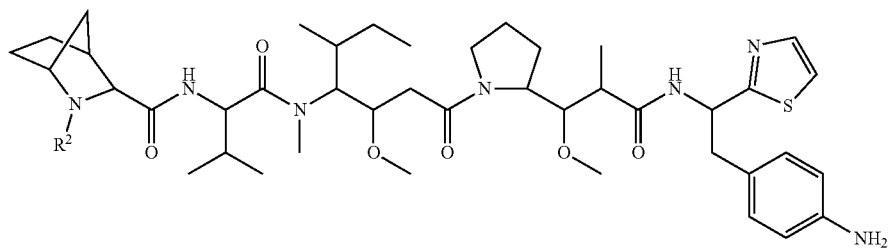

Formula (A-2)

wherein:
R² is H, C₁-C₆alkyl, —C(=O)R³, —(CH₂)ₘOH, —C(=O)(CH₂)ₘOH, —C(=O)((CH₂)ₘO)ₙR⁴, —((CH₂)ₘO)ₙR⁴ or C₁-C₆alkyl which is optionally substituted with —CN, —C(=O)NH₂ or 1 to 5 hydroxyl;

each R³ is independently selected from C₁-C₆alkyl and C₁-C₆alkyl, which is optionally substituted with 1 to 5 hydroxyl;

and each R⁴ is independently selected from H and C₁-C₆alkyl.

Embodiment 3. The compound of Formula (A), or a pharmaceutically acceptable salt thereof, having the structure of Formula (A-3), or a pharmaceutically acceptable salt thereof:

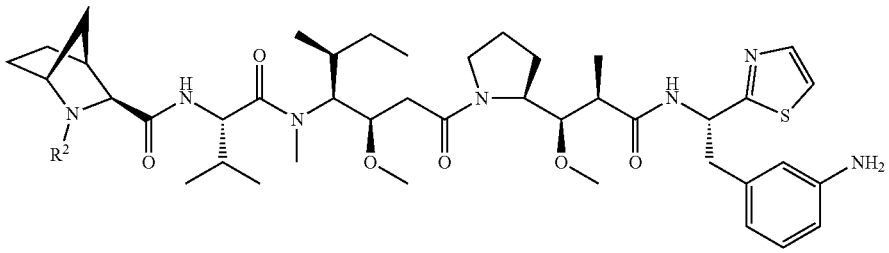

Formula (A-3)

wherein:
R² is H, C₁-C₆alkyl, —C(=O)R³, —(CH₂)ₘOH, —C(=O)(CH₂)ₘOH, —C(=O)((CH₂)ₘO)ₙR⁴, —((CH₂)ₘO)ₙR⁴ or C₁-C₆alkyl which is optionally substituted with —CN, —C(=O)NH₂ or 1 to 5 hydroxyl;

each R³ is independently selected from C₁-C₆alkyl and C₁-C₆alkyl, which is optionally substituted with 1 to 5 hydroxyl;

and each R⁴ is independently selected from H and C₁-C₆alkyl.

Embodiment 4. The compound of Formula (A), or a pharmaceutically acceptable salt thereof, having the structure of Formula (A-4), or a pharmaceutically acceptable salt thereof:

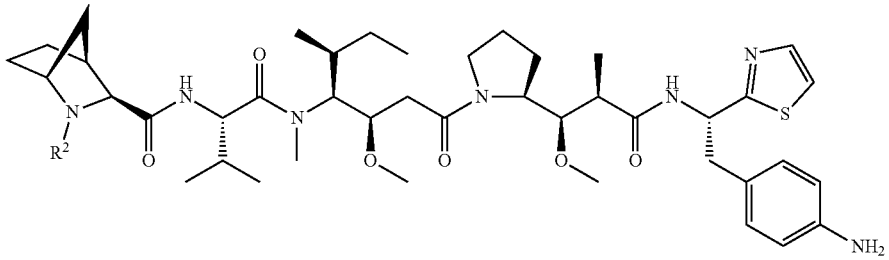

Formula (A-4)

wherein:
R² is H, C₁-C₆alkyl, —C(=O)R³, —(CH₂)ₘOH, —C(=O)(CH₂)ₘOH, —C(=O)((CH₂)ₘO)ₙR⁴, —((CH₂)ₘO)ₙR⁴ or C₁-C₆alkyl which is optionally substituted with —CN, —C(=O)NH₂ or 1 to 5 hydroxyl;

each R³ is independently selected from C₁-C₆alkyl and C₁-C₆alkyl, which is optionally substituted with 1 to 5 hydroxyl;

and each R⁴ is independently selected from H and C₁-C₆alkyl.

Embodiment 5. The compound of Formula (A), Formula (A-1), Formula (A-2), Formula (A-3) or Formula (A-4), or a pharmaceutically acceptable salt thereof, wherein: R² is H or C₁-C₆alkyl.

Embodiment 6. The compound of Formula (A), Formula (A-1), Formula (A-2), Formula (A-3) or Formula (A-4), or a pharmaceutically acceptable salt thereof, wherein: R² is H or methyl.

Embodiment 7. The compound of Formula (A), Formula (A-1), Formula (A-2), Formula (A-3) or Formula (A-4), or a pharmaceutically acceptable salt thereof, wherein: R² is H.

Embodiment 8. The compound of Formula (A), Formula (A-1), Formula (A-2), Formula (A-3) or Formula (A-4), or a pharmaceutically acceptable salt thereof, wherein: R² is methyl.

Embodiment 9. The compound of Formula (A), Formula (A-1) or Formula (A-3), or a pharmaceutically acceptable salt thereof, wherein the compound is

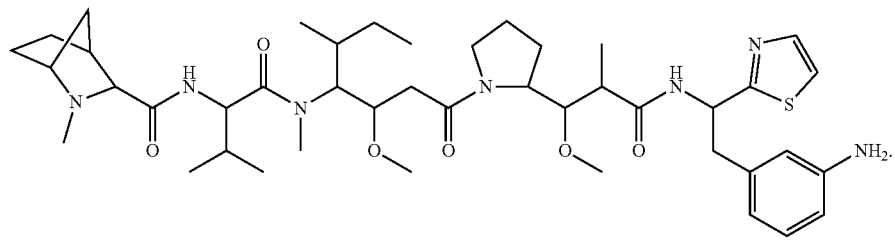 [SMILES: CCC(C)C(C(CC(=O)N1CCCC1C(OC)C(C)C(=O)NC(Cc1cccc(N)c1)c1nccs1)OC)N(C)C(=O)C(NC(=O)C1C2CCC(C2)N1C)C(C)C]

Embodiment 10. The compound of Formula (A), Formula (A-1) or Formula (A-3), or a pharmaceutically acceptable salt thereof, wherein the compound is

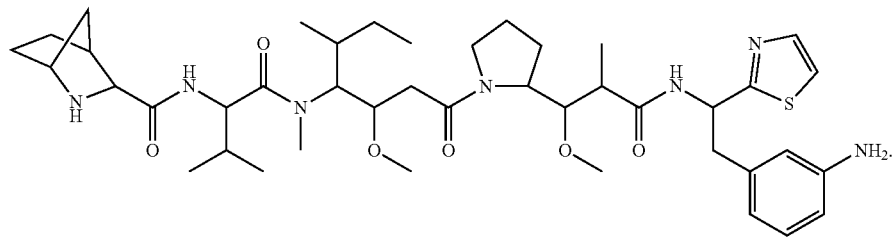 [SMILES: CCC(C)C(C(CC(=O)N1CCCC1C(OC)C(C)C(=O)NC(Cc1cccc(N)c1)c1nccs1)OC)N(C)C(=O)C(NC(=O)C1NC2CCC1C2)C(C)C]

Embodiment 11. The compound of Formula (A), Formula (A-1) or Formula (A-3), or a pharmaceutically acceptable salt thereof, wherein the compound is

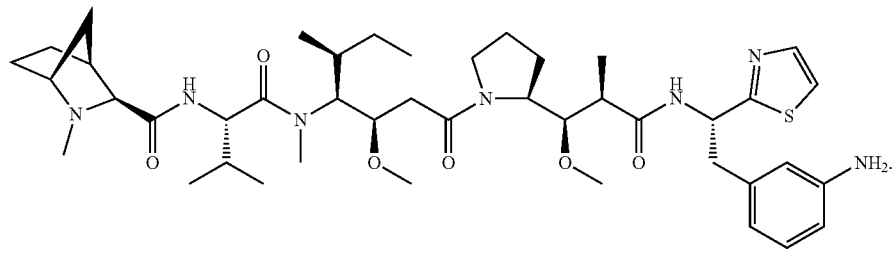 [SMILES: CC[C@H](C)[C@@H]([C@@H](CC(=O)N1CCC[C@H]1[C@H](OC)[C@@H](C)C(=O)N[C@@H](Cc1cccc(N)c1)c1nccs1)OC)N(C)C(=O)[C@@H](NC(=O)[C@@H]1[C@H]2CC[C@@H](C2)N1C)C(C)C]

Embodiment 12. The compound of Formula (A), Formula (A-1) or Formula (A-3), or a pharmaceutically acceptable salt thereof, wherein the compound is

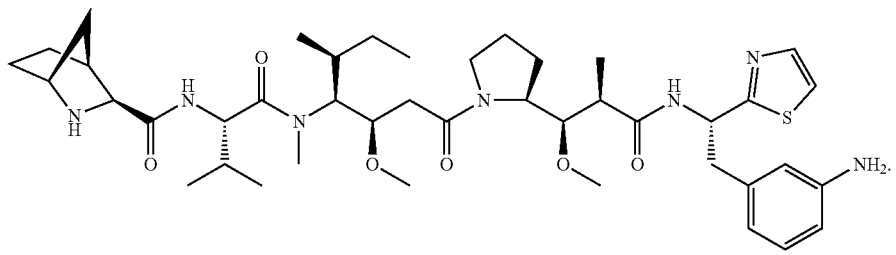 [SMILES: CC[C@H](C)[C@@H]([C@@H](CC(=O)N1CCC[C@H]1[C@H](OC)[C@@H](C)C(=O)N[C@@H](Cc1cccc(N)c1)c1nccs1)OC)N(C)C(=O)[C@@H](NC(=O)[C@H]1N[C@H]2CC[C@H]1C2)C(C)C]

Embodiment 13. The compound of Formula (A), Formula (A-2) or Formula (A-4), or a pharmaceutically acceptable salt thereof, wherein the compound is

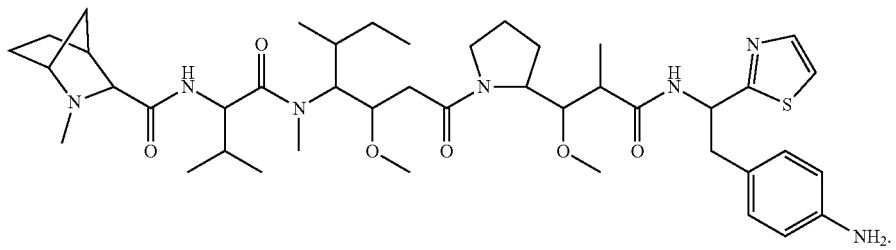 [SMILES: CCC(C)C(C(CC(=O)N1CCCC1C(OC)C(C)C(=O)NC(Cc1ccc(N)cc1)c1nccs1)OC)N(C)C(=O)C(NC(=O)C1C2CCC(C2)N1C)C(C)C]

Embodiment 14. The compound of Formula (A), Formula (A-2) or Formula (A-4), or a pharmaceutically acceptable salt thereof, wherein the compound is

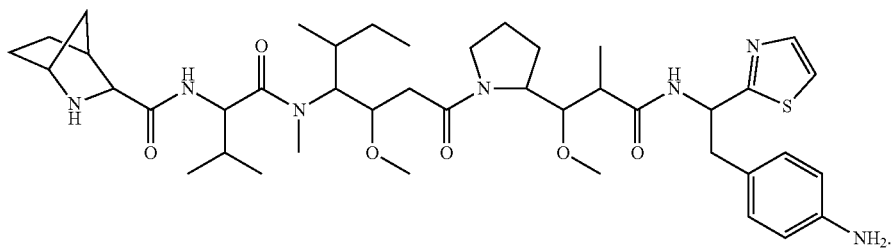 [SMILES: CCC(C)C(C(CC(=O)N1CCCC1C(OC)C(C)C(=O)NC(Cc1ccc(N)cc1)c1nccs1)OC)N(C)C(=O)C(NC(=O)C1NC2CCC1C2)C(C)C]

Embodiment 15. The compound of Formula (A), Formula (A-2) or Formula (A-4), or a pharmaceutically acceptable salt thereof, wherein the compound is

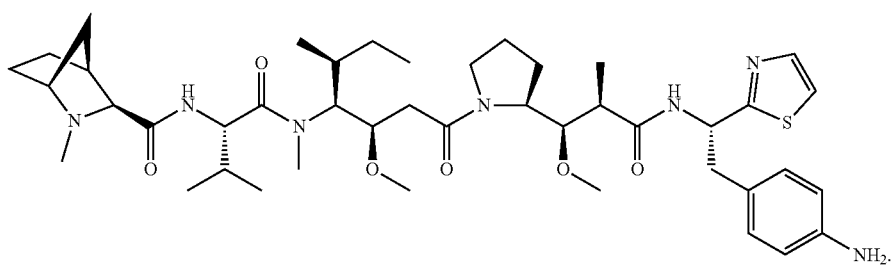 [SMILES: CC[C@H](C)[C@@H]([C@@H](CC(=O)N1CCC[C@H]1[C@H](OC)[C@@H](C)C(=O)N[C@@H](Cc1ccc(N)cc1)c1nccs1)OC)N(C)C(=O)[C@@H](NC(=O)[C@@H]1[C@H]2CC[C@@H](C2)N1C)C(C)C]

Embodiment 16. The compound of Formula (A), Formula (A-2) or Formula (A-4), or a pharmaceutically acceptable salt thereof, wherein the compound is

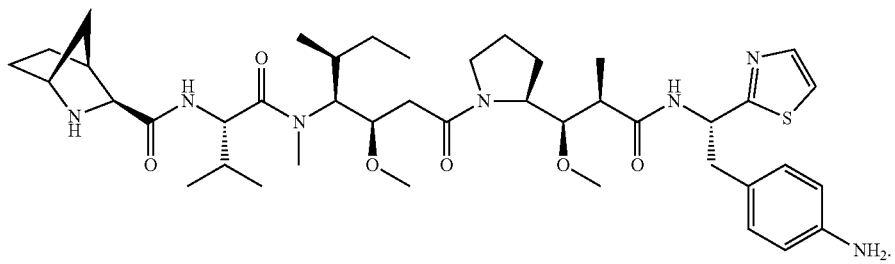 [SMILES: CC[C@H](C)[C@@H]([C@@H](CC(=O)N1CCC[C@H]1[C@H](OC)[C@@H](C)C(=O)N[C@@H](Cc1ccc(N)cc1)c1nccs1)OC)N(C)C(=O)[C@@H](NC(=O)[C@H]1N[C@H]2CC[C@H]1C2)C(C)C]

Embodiment 17. The compound of Formula (B), or a pharmaceutically acceptable salt thereof, having the structure of Formula (B-1), or a pharmaceutically acceptable salt thereof:

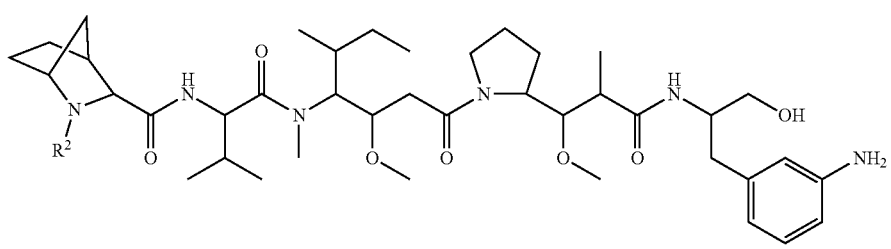

Formula (B-1)

wherein:
$R^2$ is H, $C_1$-$C_6$alkyl, —C(=O)$R^3$, —(CH$_2$)$_m$OH, —C(=O)(CH$_2$)$_m$OH, —C(=O)((CH$_2$)$_m$O)$_n$$R^4$, —((CH$_2$)$_m$O)$_n$$R^4$ or $C_1$-$C_6$alkyl which is optionally substituted with —CN, —C(=O)NH$_2$ or 1 to 5 hydroxyl;

each $R^3$ is independently selected from $C_1$-$C_6$alkyl and $C_1$-$C_6$alkyl, which is optionally substituted with 1 to 5 hydroxyl;

and each $R^4$ is independently selected from H and $C_1$-$C_6$alkyl.

Embodiment 18. The compound of Formula (B), or a pharmaceutically acceptable salt thereof, having the structure of Formula (B-2), or a pharmaceutically acceptable salt thereof:

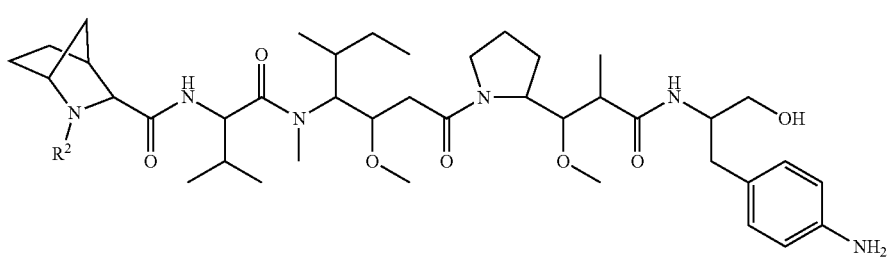

Formula (B-2)

wherein:
R² is H, C₁-C₆alkyl, —C(=O)R³, —(CH₂)ₘOH, —C(=O)(CH₂)ₘOH, —C(=O)((CH₂)ₘO)ₙR⁴, —((CH₂)ₘO)ₙR⁴ or C₁-C₆alkyl which is optionally substituted with —CN, —C(=O)NH₂ or 1 to 5 hydroxyl;

each R³ is independently selected from C₁-C₆alkyl and C₁-C₆alkyl, which is optionally substituted with 1 to 5 hydroxyl;

and each R⁴ is independently selected from H and C₁-C₆alkyl.

Embodiment 19. The compound of Formula (B), or a pharmaceutically acceptable salt thereof, having the structure of Formula (B-3), or a pharmaceutically acceptable salt thereof:

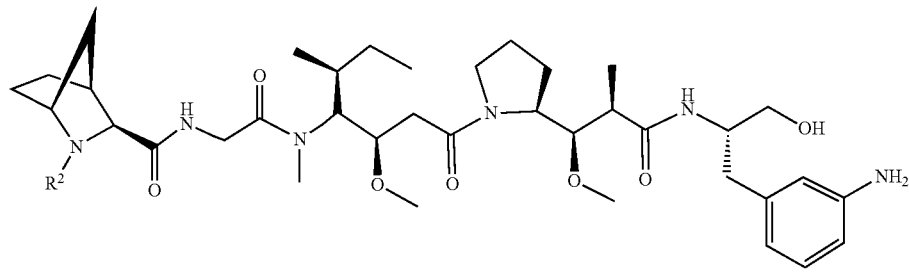

Formula (B-3)

wherein:
R² is H, C₁-C₆alkyl, —C(=O)R³, —(CH₂)ₘOH, —C(=O)(CH₂)ₘOH, —C(=O)((CH₂)ₘO)ₙR⁴, —((CH₂)ₘO)ₙR⁴ or C₁-C₆alkyl which is optionally substituted with —CN, —C(=O)NH₂ or 1 to 5 hydroxyl;

each R³ is independently selected from C₁-C₆alkyl and C₁-C₆alkyl, which is optionally substituted with 1 to 5 hydroxyl;

and each R⁴ is independently selected from H and C₁-C₆alkyl.

Embodiment 20. The compound of Formula (B), or a pharmaceutically acceptable salt thereof, having the structure of Formula (B-4), or a pharmaceutically acceptable salt thereof:

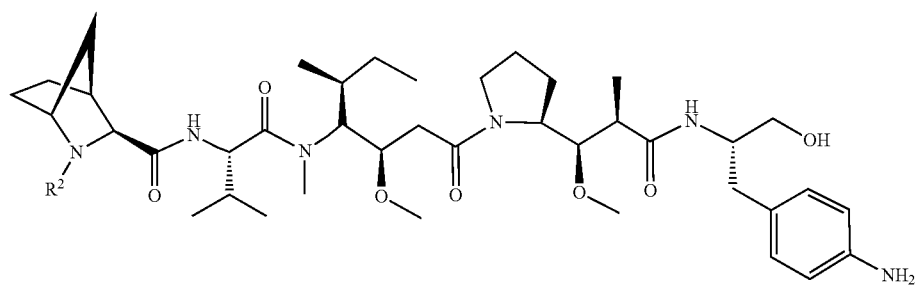

Formula (B-4)

wherein:
R$^2$ is H, C$_1$-C$_6$alkyl, —C(=O)R$^3$, —(CH$_2$)$_m$OH, —C(=O)(CH$_2$)$_m$OH, —C(=O)((CH$_2$)$_m$O)$_n$R$^4$, —((CH$_2$)$_m$O)$_n$R$^4$ or C$_1$-C$_6$alkyl which is optionally substituted with —CN, —C(=O)NH$_2$ or 1 to 5 hydroxyl;
each R$^3$ is independently selected from C$_1$-C$_6$alkyl and C$_1$-C$_6$alkyl, which is optionally substituted with 1 to 5 hydroxyl;
and each R$^4$ is independently selected from H and C$_1$-C$_6$alkyl.

Embodiment 21. The compound of Formula (B), Formula (B-1), Formula (B-2), Formula (B-3) or Formula (B-4), or a pharmaceutically acceptable salt thereof, wherein: R$^2$ is H or C$_1$-C$_6$alkyl.

Embodiment 22. The compound Formula (B), Formula (B-1), Formula (B-2), Formula (B-3) or Formula (B-4), or a pharmaceutically acceptable salt thereof, wherein: R$^2$ is H or methyl.

Embodiment 23. The compound of Formula (B), Formula (B-1), Formula (B-2), Formula (B-3) or Formula (B-4), or a pharmaceutically acceptable salt thereof, wherein: R$^2$ is H.

Embodiment 24. The compound of Formula (B), Formula (B-1), Formula (B-2), Formula (B-3) or Formula (B-4), or a pharmaceutically acceptable salt thereof, wherein: R$^2$ is methyl.

Embodiment 25. The compound of Formula (B), Formula (B-1) or Formula (B-3), or a pharmaceutically acceptable salt thereof, wherein the compound is

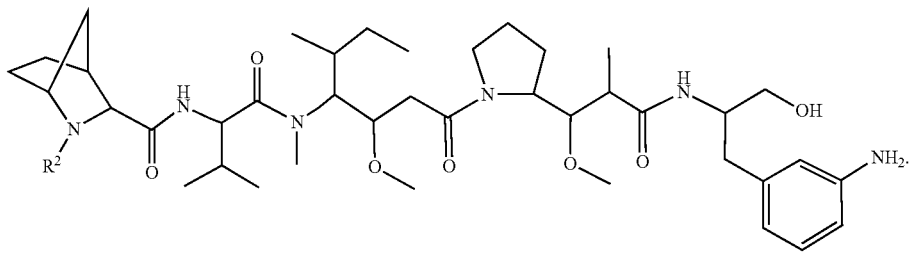

Embodiment 26. The compound of Formula (B), Formula (B-1) or Formula (B-3), or a pharmaceutically acceptable salt thereof, wherein the compound is

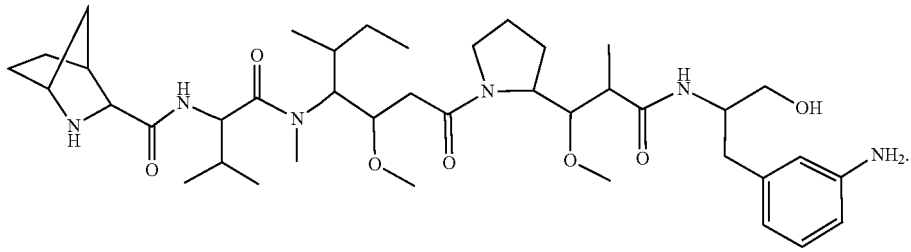 [SMILES: CCC(C)C(CN(C)C(=O)C(CNC(=O)C1NC2CCCC1C2)C(C)C)C(CC(=O)N1CCCC1C(OC)C(C)C(=O)NC(CO)Cc1cccc(N)c1)OC]

Embodiment 27. The compound of Formula (B), Formula (B-1) or Formula (B-3), or a pharmaceutically acceptable salt thereof, wherein the compound is

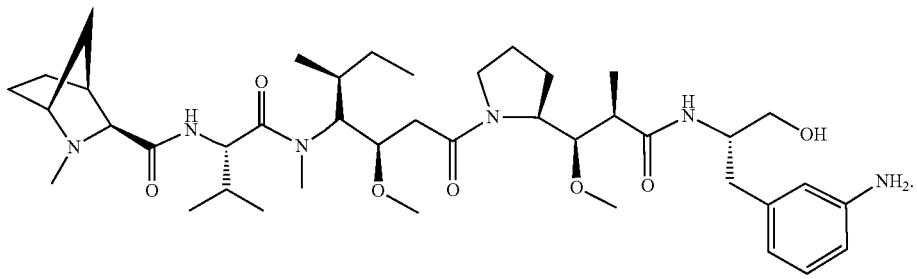 [SMILES: CC[C@H](C)C(CN(C)C(=O)[C@@H](CNC(=O)[C@@H]1[C@H]2CCC[C@@H](C2)N1C)C(C)C)[C@@H](CC(=O)N1CCC[C@H]1[C@H](OC)[C@@H](C)C(=O)N[C@H](CO)Cc1cccc(N)c1)OC]

Embodiment 28. The compound of Formula (B), Formula (B-1) or Formula (B-3), or a pharmaceutically acceptable salt thereof, wherein the compound is

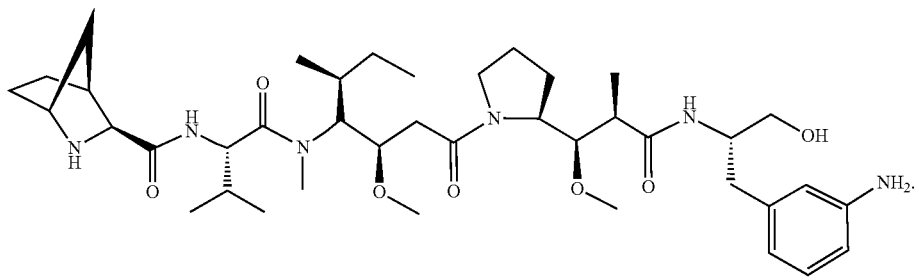 [SMILES: CC[C@H](C)C(CN(C)C(=O)[C@@H](CNC(=O)[C@H]1N[C@H]2CCC[C@H]1C2)C(C)C)[C@@H](CC(=O)N1CCC[C@H]1[C@H](OC)[C@@H](C)C(=O)N[C@H](CO)Cc1cccc(N)c1)OC]

Embodiment 29. The compound of Formula (B), Formula (B-2) or Formula (B-4), or a pharmaceutically acceptable salt thereof, wherein the compound is

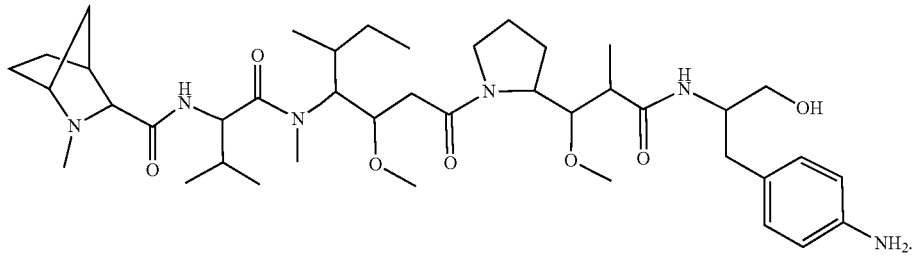 [SMILES: CCC(C)C(CN(C)C(=O)C(CNC(=O)C1C2CCCC(C2)N1C)C(C)C)C(CC(=O)N1CCCC1C(OC)C(C)C(=O)NC(CO)Cc1ccc(N)cc1)OC]

Embodiment 30. The compound of Formula (B), Formula (B-2) or Formula (B-4), or a pharmaceutically acceptable salt thereof, wherein the compound is

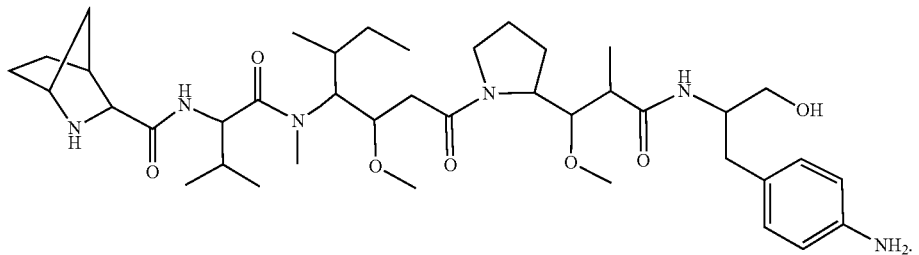 [SMILES: CCC(C)C(CN(C)C(=O)C(CNC(=O)C1NC2CCCC1C2)C(C)C)C(CC(=O)N1CCCC1C(OC)C(C)C(=O)NC(CO)Cc1ccc(N)cc1)OC]

Embodiment 31. The compound of Formula (B), Formula (B-2) or Formula (B-4), or a pharmaceutically acceptable salt thereof, wherein the compound is

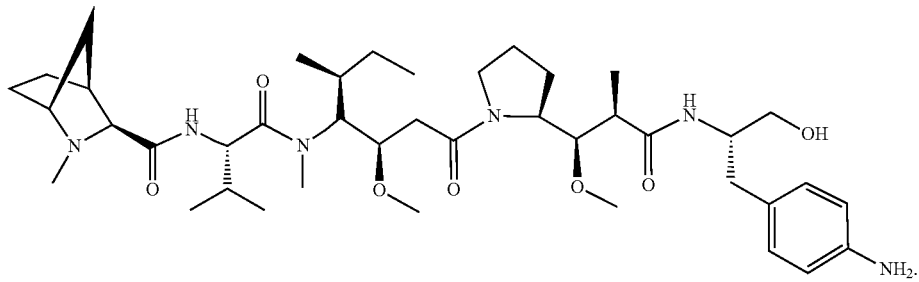 [SMILES: CC[C@H](C)C(CN(C)C(=O)[C@@H](CNC(=O)[C@@H]1[C@H]2CCC[C@@H](C2)N1C)C(C)C)[C@@H](CC(=O)N1CCC[C@H]1[C@H](OC)[C@@H](C)C(=O)N[C@H](CO)Cc1ccc(N)cc1)OC]

Embodiment 32. The compound of Formula (A), Formula (A-2) or Formula (A-4), or a pharmaceutically acceptable salt thereof, wherein the compound is

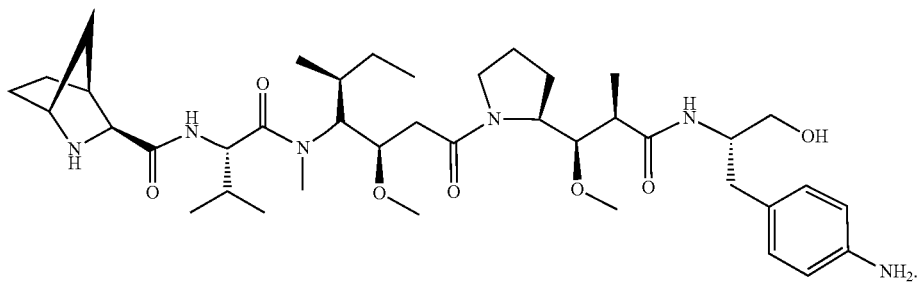 [SMILES: CC[C@H](C)C(CN(C)C(=O)[C@@H](CNC(=O)[C@H]1N[C@H]2CCC[C@H]1C2)C(C)C)[C@@H](CC(=O)N1CCC[C@H]1[C@H](OC)[C@@H](C)C(=O)N[C@H](CO)Cc1ccc(N)cc1)OC]

Linkers

In one aspect, the antibody drug conjugates of the present disclosure may include linkers. As used herein, a "linker" is any chemical moiety that is capable of linking an antibody, antibody fragment (e.g., antigen binding fragments) or functional equivalent to another moiety, such as a drug moiety. Linkers can be susceptible to cleavage (cleavable linker), such as, acid-induced cleavage, photo-induced cleavage, peptidase-induced cleavage, esterase-induced cleavage, and disulfide bond cleavage, at conditions under which the compound or the antibody remains active. Alternatively, linkers can be substantially resistant to cleavage (e.g., stable linker or noncleavable linker). In some aspects, the linker is a procharged linker, a hydrophilic linker, or a dicarboxylic acid based linker.

In one aspect, the linker used in the present invention is derived from a crosslinking reagent such as N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)-2-sulfo-butanoate (sulfo-SPDB), N-succinimidyl iodoacetate (SIA), N-succinimidyl(4-iodoacetyl)aminobenzoate (SIAB), maleimide PEG NHS, N-succinimidyl 4-(maleimidomethyl) cyclohexanecarboxylate (SMCC), N-sulfosuccinimidyl 4-(maleimidomethyl) cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1).

Non-cleavable linkers are any chemical moiety capable of linking a drug, such as a maytansinoid, to an antibody in a stable, covalent manner and does not fall off under the categories listed above for cleavable linkers. Thus, non-cleavable linkers are substantially resistant to acid-induced cleavage, photo-induced cleavage, peptidase-induced cleavage, esterase-induced cleavage and disulfide bond cleavage. Furthermore, non-cleavable refers to the ability of the chemical bond in the linker or adjoining to the linker to withstand cleavage induced by an acid, photolabile-cleaving agent, a peptidase, an esterase, or a chemical or physiological compound that cleaves a disulfide bond, at conditions under which the drug, such as maytansionoid or the antibody does not lose its activity.

Acid-labile linkers are linkers cleavable at acidic pH. For example, certain intracellular compartments, such as endosomes and lysosomes, have an acidic pH (pH 4-5), and provide conditions suitable to cleave acid-labile linkers.

Photo-labile linkers are linkers that are useful at the body surface and in many body cavities that are accessible to light. Furthermore, infrared light can penetrate tissue.

Some linkers can be cleaved by peptidases, i.e. peptidase cleavable linkers. Only certain peptides are readily cleaved inside or outside cells, see e.g. Trout et al., 79 Proc. Natl. Acad. Sci. USA, 626-629 (1982) and Umemoto et al. 43 Int. J. Cancer, 677-684 (1989). Furthermore, peptides are composed of α-amino acids and peptidic bonds, which chemically are amide bonds between the carboxylate of one amino acid and the amino group of a second amino acid. Other amide bonds, such as the bond between a carboxylate and the α-amino group of lysine, are understood not to be peptidic bonds and are considered non-cleavable.

Some linkers can be cleaved by esterases, i.e. esterase cleavable linkers. Again, only certain esters can be cleaved by esterases present inside or outside of cells. Esters are formed by the condensation of a carboxylic acid and an alcohol. Simple esters are esters produced with simple alcohols, such as aliphatic alcohols, and small cyclic and small aromatic alcohols.

Procharged linkers are derived from charged cross-linking reagents that retain their charge after incorporation into an antibody drug conjugate. Examples of procharged linkers can be found in US 2009/0274713.

Linker-Drug Moiety

In one aspect, the Linker-Drug moiety $(L_B\text{-}(D)_n)$ of the present disclosure comprises one or more cytotoxins covalently attached to a linker $(L_B)$, wherein the one or more cytotoxins are independently selected from compound of Formula (A), Formula (A-1), Formula (A-2), Formula (A-3), Formula (A-4), Formula (B), Formula (B-1), Formula (B-2), Formula (B-3) and Formula (B-4) or a compound of any one of Embodiments 9 to 16 or any one of Embodiments 25 to 32.

In one aspect, the Linker-Drug moiety disclosed herein comprises one or more cytotoxins covalently attached to a linker $(L_B)$, wherein the one or more cytotoxins are independently selected from compound of Formula (A), Formula (A-1), Formula (A-2), Formula (A-3) and Formula (A-4), or a compound of any one of Embodiments 7 to 14.

In one aspect, the Linker-Drug moiety of the present disclosure comprises one or more cytotoxins covalently attached to a linker $(L_B)$, wherein the one or more cytotoxins are independently selected from compound of Formula (B), Formula (B-1), Formula (B-2), Formula (B-3) and Formula (B-4) or a compound of any one of Embodiments 23 to 30.

In one aspect the Linker-Drug moiety of the present disclosure is a compound having the structure of Formula (C), or stereoisomers or pharmaceutically acceptable salts thereof, Formula (C)

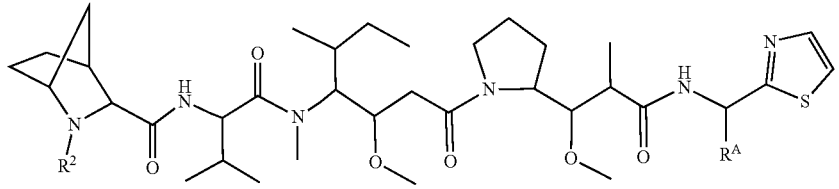

wherein:

$R_A$ is

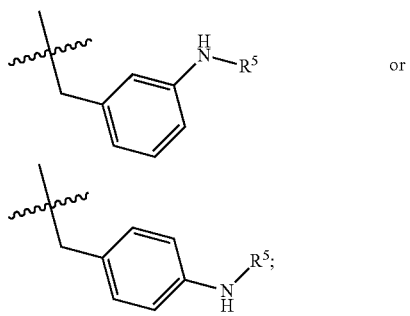 or

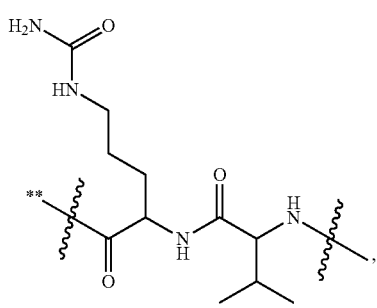;

$R^2$ is H, $C_1$-$C_6$alkyl, —C(=O)$R^3$, —(CH$_2$)$_m$OH, —C(=O)(CH$_2$)$_m$OH, —C(=O)((CH$_2$)$_m$O)$_n$$R^4$, —((CH$_2$)$_m$O)$_n$$R^4$ or $C_1$-$C_6$alkyl which is optionally substituted with —CN, —C(=O)NH$_2$ or 1 to 5 hydroxyl;

each $R^3$ is independently selected from $C_1$-$C_6$alkyl and $C_1$-$C_6$alkyl, which is optionally substituted with 1 to 5 hydroxyl;

each $R^4$ is independently selected from H and $C_1$-$C_6$alkyl;

$R^5$ is -$L_1R^{14}$, -$L_1R^{24}$, -$L_1R^{34}$ or -$L_1R^{44}$;

$L_1$ is —X$_1$C(=O)((CH$_2$)$_m$O)$_p$(CH$_2$)$_m$—, —X$_1$C(=O)(CH$_2$)$_m$—, —X$_2$X$_1$C(=O)((CH$_2$)$_m$O)$_p$(CH$_2$)$_m$—, —X$_2$X$_1$C(=O)(CH$_2$)$_m$—, —X$_3$C(=O)((CH$_2$)$_m$O)$_p$(CH$_2$)$_m$—, —X$_3$C(=O)(CH$_2$)$_m$—, —X$_3$C(=O)(CH$_2$)$_m$NHC(=O)((CH$_2$)$_m$O)$_p$(CH$_2$)$_m$—, —X$_3$C(=O)(CH$_2$)$_m$NHC(=O)(CH$_2$)$_m$—, —X$_3$C(=O)(CH$_2$)$_m$—, —X$_1$C(=O)((CH$_2$)$_m$O)$_p$(CH$_2$)$_m$X$_4$(CH$_2$)$_m$—, —X$_1$C(=O)(CH$_2$)$_m$X$_4$(CH$_2$)$_m$—, —X$_2$X$_1$C(=O)((CH$_2$)$_m$O)$_p$(CH$_2$)$_m$X$_4$(CH$_2$)$_m$— or —X$_2$X$_1$C(=O)(CH$_2$)$_m$X$_4$(CH$_2$)$_m$—, where  indicates the point of attachment to $R^{14}$;

$X_1$ is

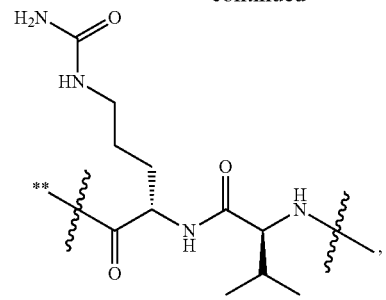

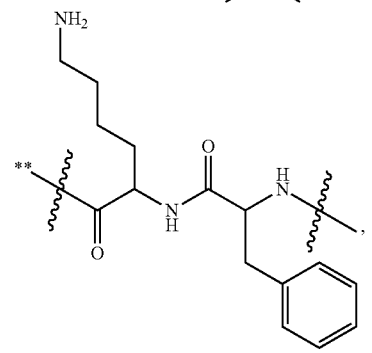

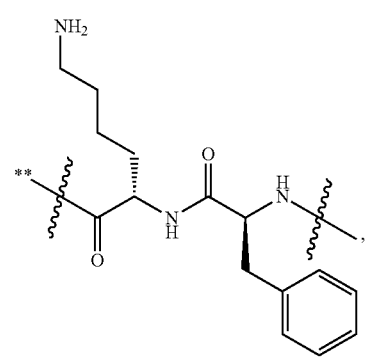

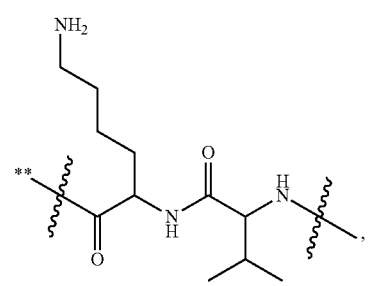

103
-continued
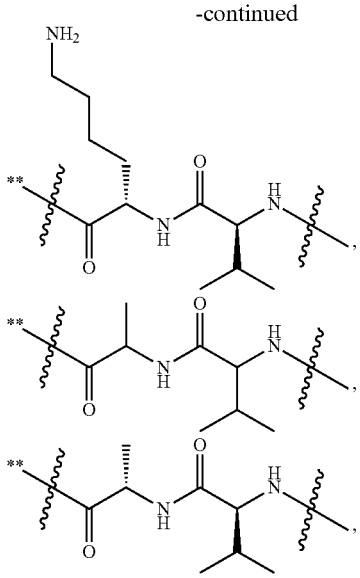
where ** indicates the point of attachment to the —NH— or to $X_2$;
$X_2$ is
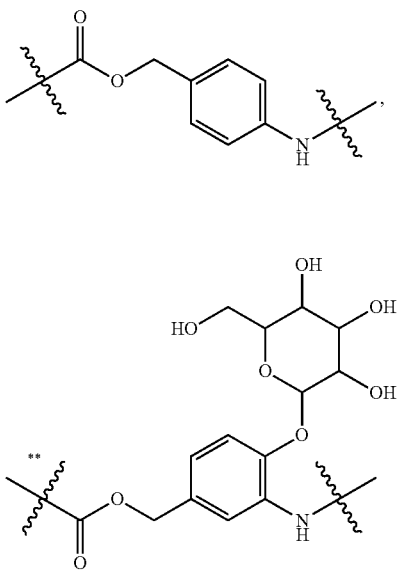
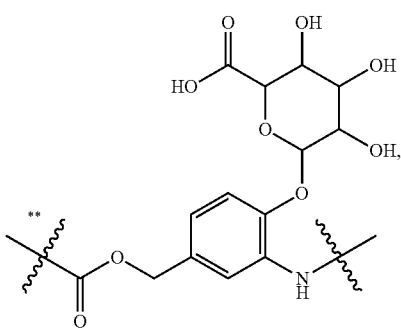
104
where ** indicates the point of attachment to the —NH—;
$X_3$ is
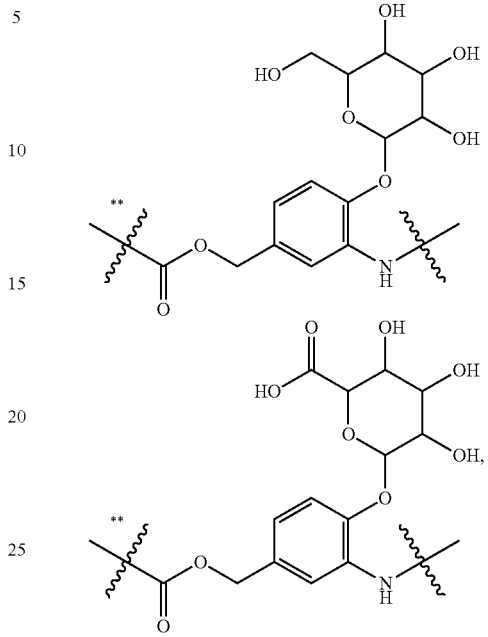
where ** indicates the point of attachment to the —NH—;
$X_4$ is
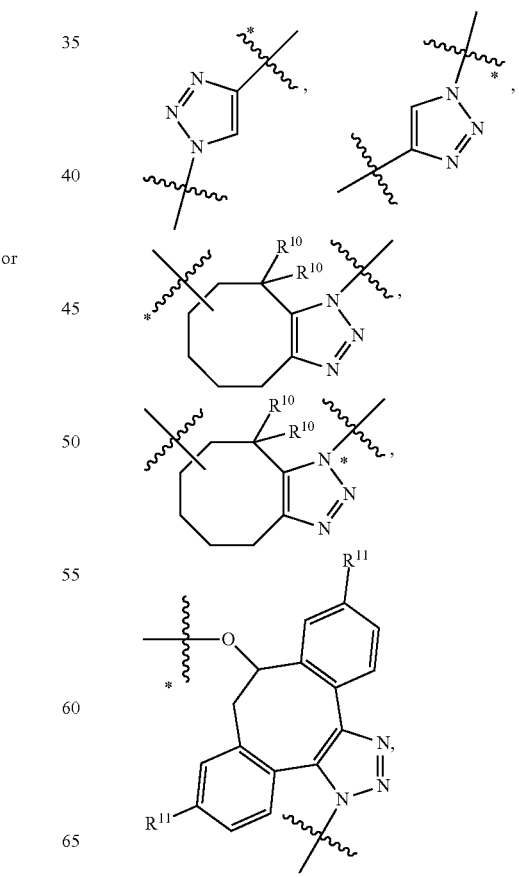

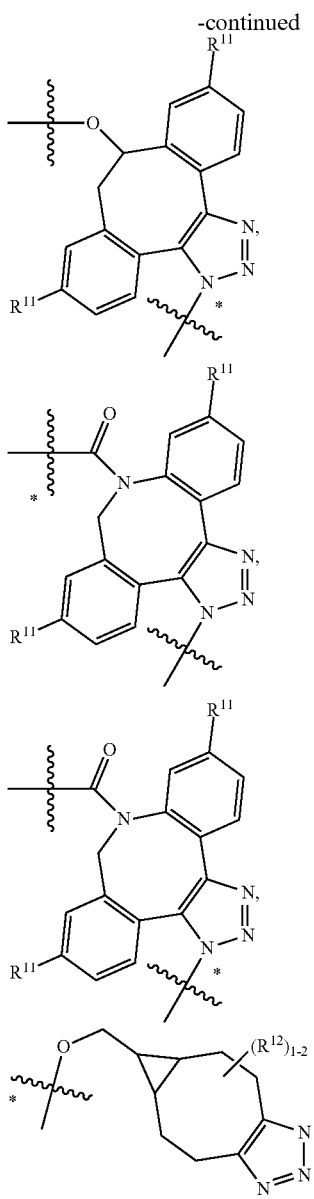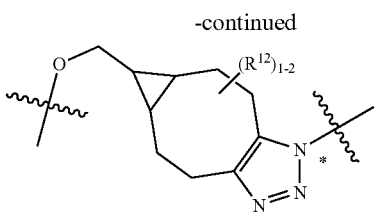
where the * indicates the point of attachment is toward $R^{14}$, $R^{24}$, $R^{34}$ or $R^{44}$,
$R^{14}$ is
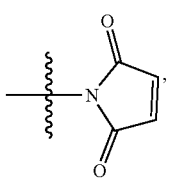 [SMILES: *N1C(=O)C=CC1=O]
—$N_3$, —$ONH_2$, —$NR^6C(=O)CH=CH_2$, SH, —$SSR^7$, —$S(=O)_2(CH=CH_2)$, —$NR^6S(=O)_2(CH=CH_2)$, —$NR^6C(=O)CH_2Br$, —$NR^6C(=O)CH_2I$, —$NHC(=O)CH_2Br$, —$NHC(=O)CH_2I$, —$C(=O)NHNH_2$,
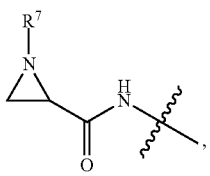
—$CO_2H$, —$NH_2$,
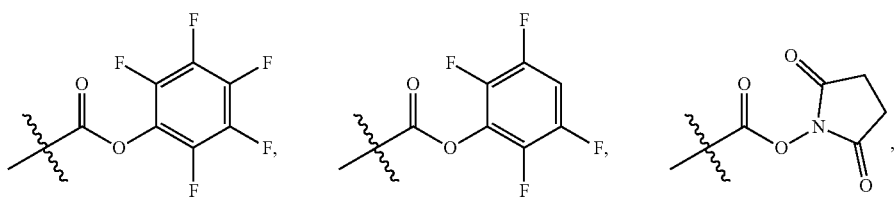
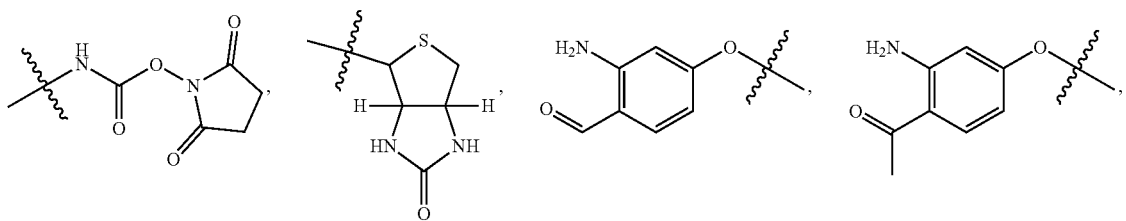

107 108
-continued
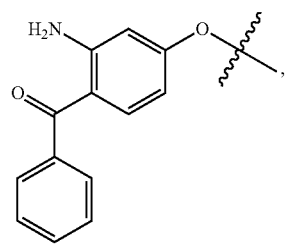
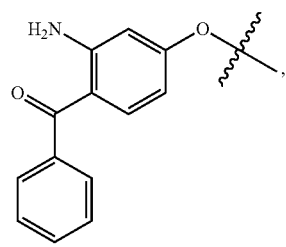
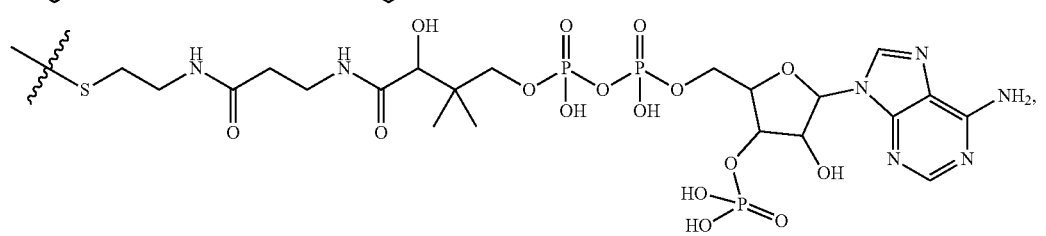
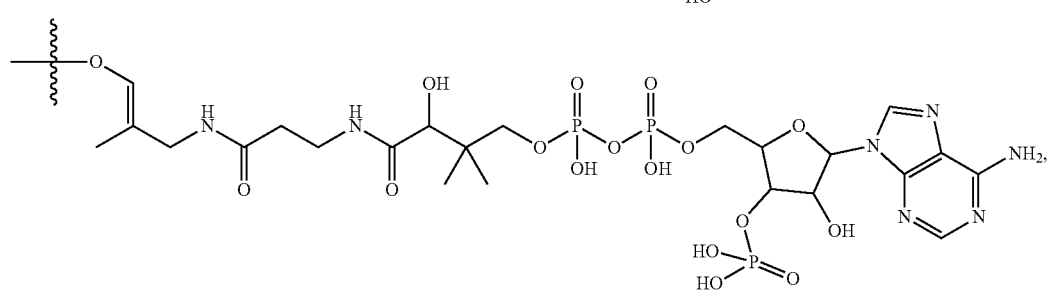
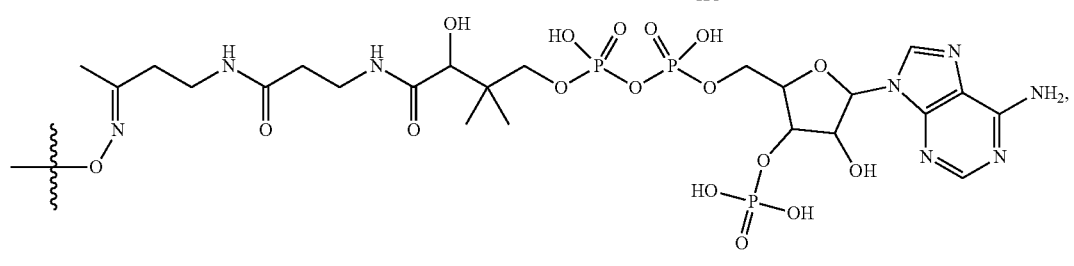
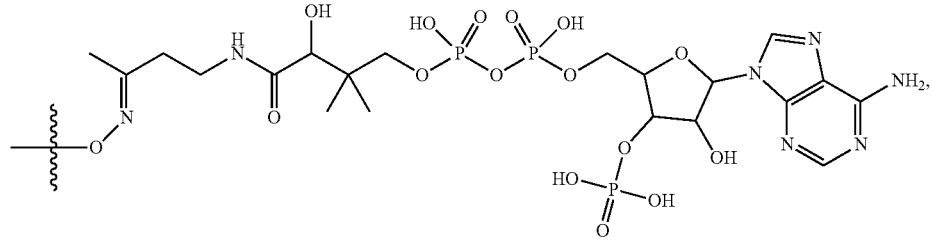
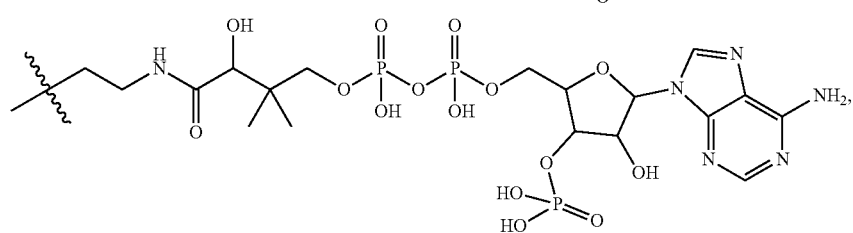
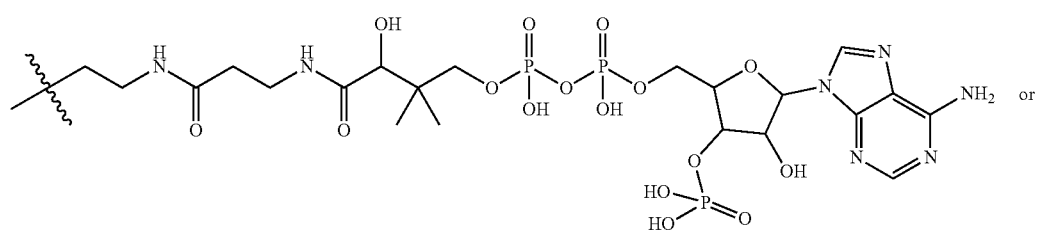 or -continued

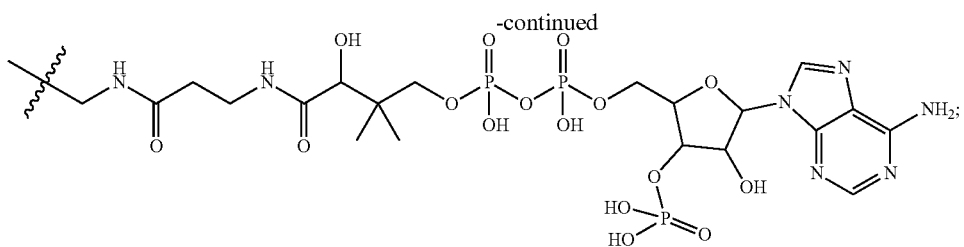

$R^{24}$ is

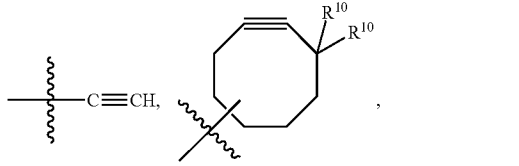

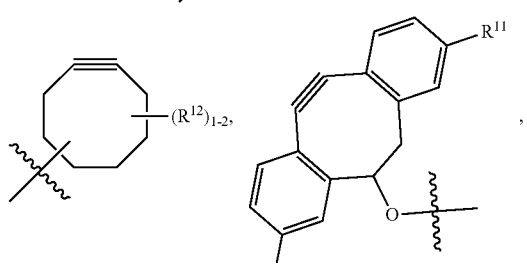

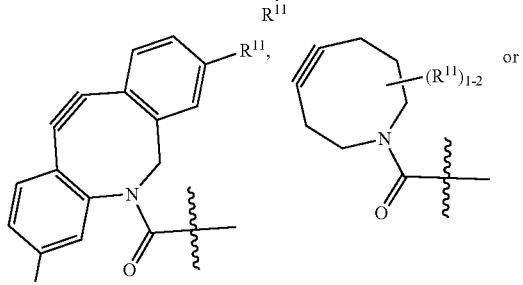

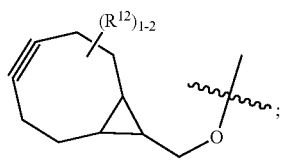

$R^{34}$ is, —$N_3$, —$ONH_2$, —$NR^7C(=O)CH=CH_2$, —$C(=O)NHNH_2$, —$CO_2H$, —$NH_2$, $R^{44}$ is

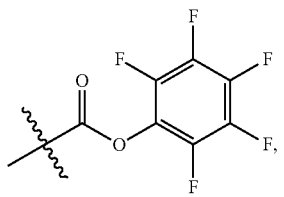

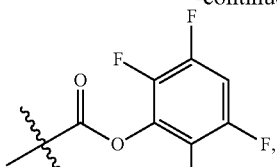

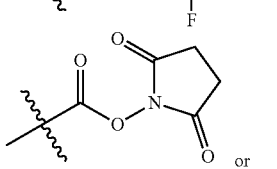

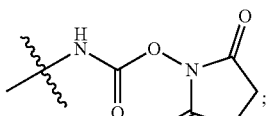

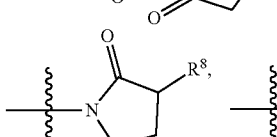

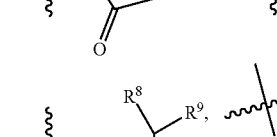

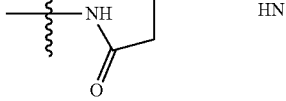

or —$NR^7C(=O)CH_2R^8$;

each $R^6$ is independently selected from H and $C_1$-$C_6$alkyl;
$R^7$ is 2-pyridyl or 4-pyridyl;
$R^8$ is —$S(CH_2)_nCHR^9NH_2$;
$R^9$ is —$C(=O)OR^7$;
each $R^{10}$ is independently selected from H, $C_1$-$C_6$alkyl, F, Cl, and —OH;
each $R^{11}$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;
each $R^{12}$ is independently selected from H, $C_{1-6}$alkyl, fluoro, benzyloxy substituted with —$C(=O)OH$, benzyl substituted with —$C(=O)OH$, $C_{1-4}$alkoxy substituted with —$C(=O)OH$ and $C_{1-4}$alkyl substituted with —$C(=O)OH$;
each m is independently selected from 1, 2, 3, 4, 5, 6, 7, 8, 9 and 10, and
each p is independently selected from 1, 2, 3, 4, 5, 6, 7, 8, 9, 10, 11, 12, 13 and 14.

Certain aspects and examples of the Linker-Drug moiety disclosed herein are provided in the following listing of additional, enumerated embodiments. It will be recognized that features specified in each embodiment may be combined with other specified features to provide further embodiments of the present disclosure.

Embodiment 33. The compound of Formula (C), or a pharmaceutically acceptable salt thereof, having the structure of Formula (C-1), or a pharmaceutically acceptable salt thereof:

Formula (C-1)

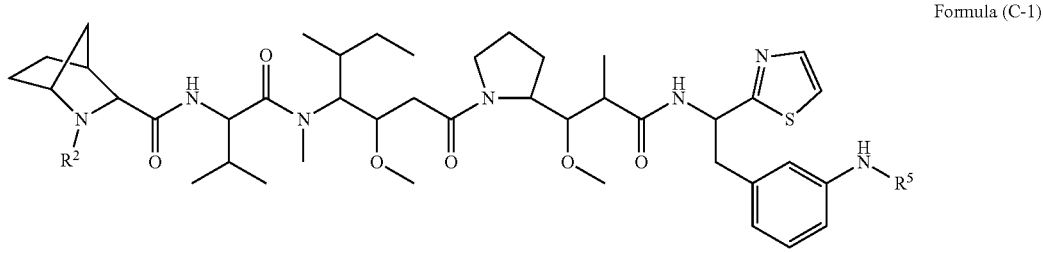

wherein: $R^2$ and $R^5$ are as defined above for compounds of Formula (C).

Embodiment 34. The compound of Formula (C), or a pharmaceutically acceptable salt thereof, having the structure of Formula (C-2), or a pharmaceutically acceptable salt thereof:

Formula (C-2)

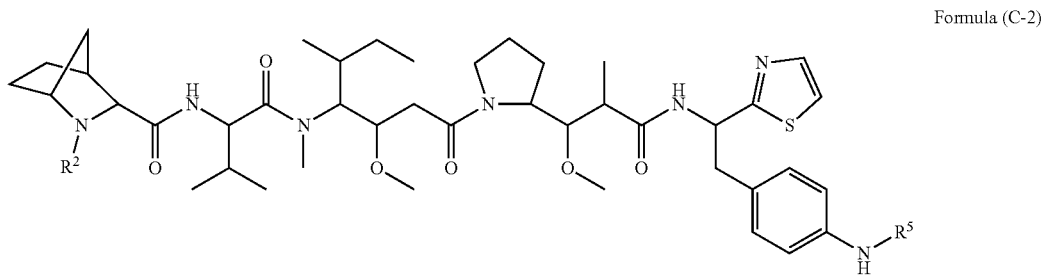

wherein: $R^2$ and $R^5$ are as defined above for compounds of Formula (C).

Embodiment 35. The compound of Formula (C), or a pharmaceutically acceptable salt thereof, having the structure of Formula (C-3), or a pharmaceutically acceptable salt thereof:

Formula (C-3)

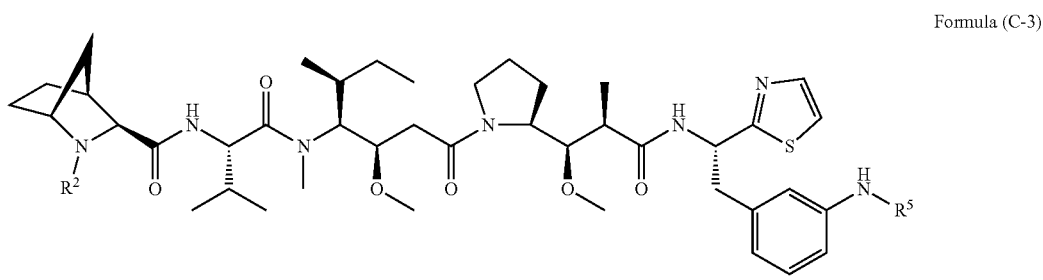

wherein: $R^2$ and $R^5$ are as defined above for compounds of Formula (C).

Embodiment 36. The compound of Formula (C), or a pharmaceutically acceptable salt thereof, having the structure of Formula (C-4), or a pharmaceutically acceptable salt thereof:

Formula (C-4)

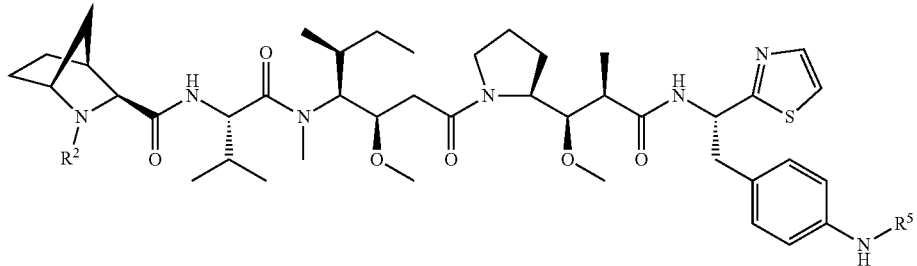

wherein: $R^2$ and $R^5$ are as defined above for compounds of Formula (C).

Embodiment 37. The compound of Formula (C), Formula (C-1), Formula (C-2), Formula (C-3) or Formula (C-4), or a pharmaceutically acceptable salt thereof, wherein: $R^2$ is H or $C_1$-$C_6$alkyl.

Embodiment 38. The compound of Formula (C), Formula (C-1), Formula (C-2), Formula (C-3) or Formula (C-4), or a pharmaceutically acceptable salt thereof, wherein: $R^2$ is H or methyl.

Embodiment 39. The compound of Formula (C), Formula (C-1), Formula (C-2), Formula (C-3) or Formula (C-4), or a pharmaceutically acceptable salt thereof, wherein: $R^2$ is H.

Embodiment 40. The compound of Formula (C), Formula (C-1), Formula (C-2), Formula (C-3) or Formula (C-4), or a pharmaceutically acceptable salt thereof, wherein: $R^2$ is methyl.

Embodiment 41. The compound of Formula (C), Formula (C-1) or Formula (C-3), or a pharmaceutically acceptable salt thereof, having the structure of Formula (C-5), or a pharmaceutically acceptable salt thereof:

Formula (C-5)

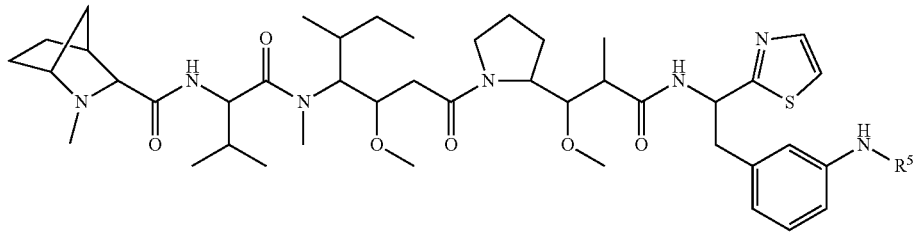

wherein: $R^5$ are as defined above for compounds of Formula (C).

Embodiment 42 The compound of Formula (C), Formula (C-1) or Formula (C-3), or a pharmaceutically acceptable salt thereof, having the structure of Formula (C-6), or a pharmaceutically acceptable salt thereof:

Formula (C-6)

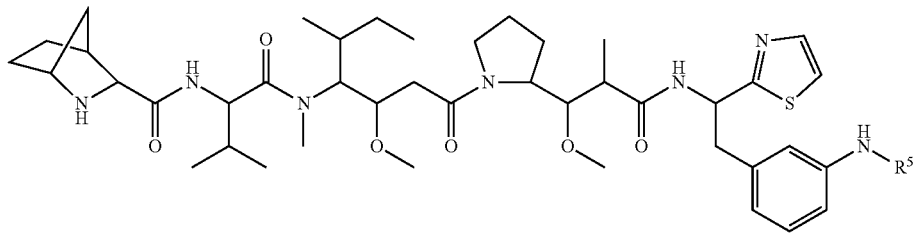

wherein: $R^5$ are as defined above for compounds of Formula (C).

Embodiment 43. The compound of Formula (C), Formula (C-1) or Formula (C-3), or a pharmaceutically acceptable salt thereof, having the structure of Formula (C-7), or a pharmaceutically acceptable salt thereof:

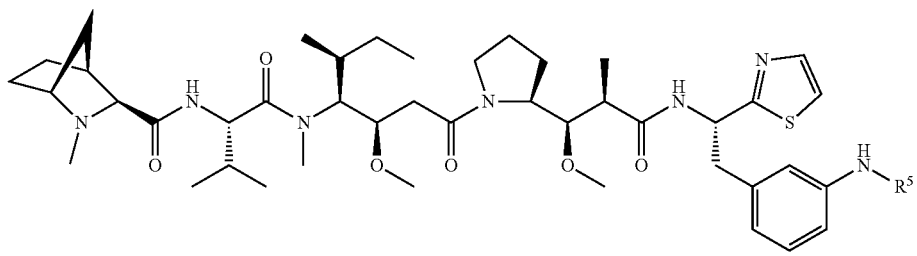

Formula (C-7)

wherein: $R^5$ are as defined above for compounds of Formula (C).

Embodiment 44. The compound of Formula (C), Formula (C-1) or Formula (C-3), or a pharmaceutically acceptable salt thereof, having the structure of Formula (C-8), or a pharmaceutically acceptable salt thereof:

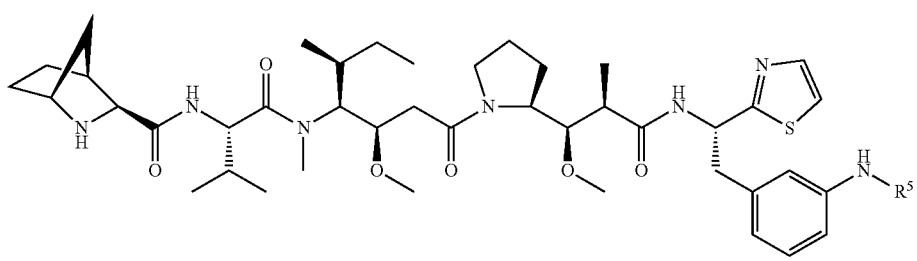

Formula (C-8)

wherein: $R^5$ are as defined above for compounds of Formula (C).

Embodiment 45. The compound of Formula (C), Formula (C-1) or Formula (C-3), or a pharmaceutically acceptable salt thereof, having the structure of Formula (C-9), or a pharmaceutically acceptable salt thereof:

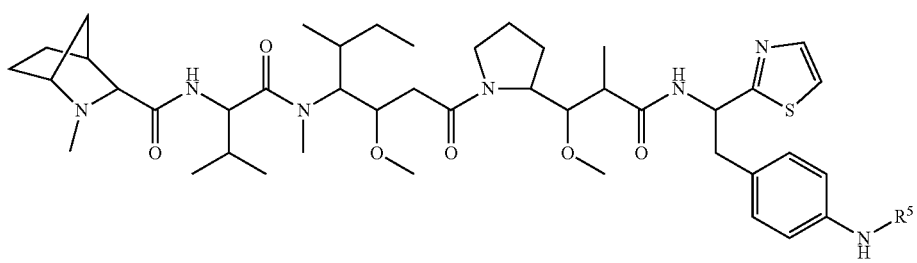

Formula (C-9)

wherein: $R^5$ are as defined above for compounds of Formula (C).

Embodiment 46. The compound of Formula (C), Formula (C-1) or Formula (C-3), or a pharmaceutically acceptable salt thereof, having the structure of Formula (C-10), or a pharmaceutically acceptable salt thereof:

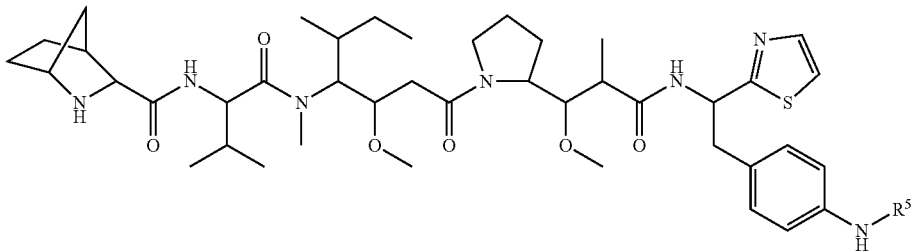

Formula (C-10)

wherein: $R^5$ are as defined above for compounds of Formula (C).

Embodiment 47. The compound of Formula (C), Formula (C-1) or Formula (C-3), or a pharmaceutically acceptable salt thereof, having the structure of Formula (C-11), or a pharmaceutically acceptable salt thereof:

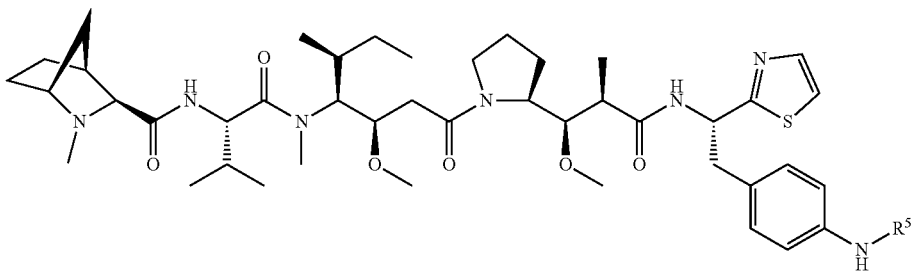

Formula (C-11)

wherein: $R^5$ are as defined above for compounds of Formula (C).

Embodiment 48. The compound of Formula (C), Formula (C-1) or Formula (C-3), or a pharmaceutically acceptable salt thereof, having the structure of Formula (C-12), or a pharmaceutically acceptable salt thereof:

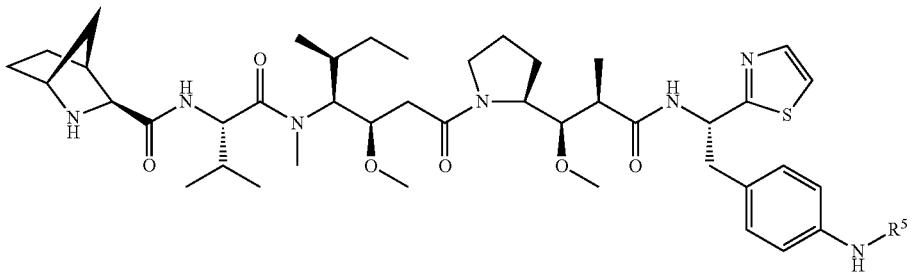

Formula (C-12)

wherein: $R^5$ are as defined above for compounds of Formula (C).

Embodiment 49. The compound of Formula (C), Formula (C-1) or Formula (C-3), or Embodiment 37, wherein the compound is

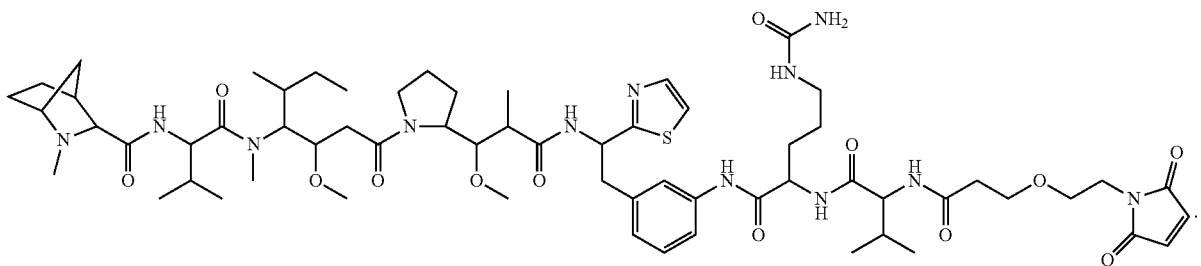 [SMILES: CCC(C)C(C(CC(=O)N1CCCC1C(OC)C(C)C(=O)NC(Cc1cccc(NC(=O)C(CCCNC(N)=O)NC(=O)C(NC(=O)CCOCCN2C(=O)C=CC2=O)C(C)C)c1)c1nccs1)OC)N(C)C(=O)C(NC(=O)C1C2CCC(C2)N1C)C(C)C]

Embodiment 50. The compound of Formula (C), Formula (C-1) or Formula (C-3), or Embodiment 37, wherein the compound is

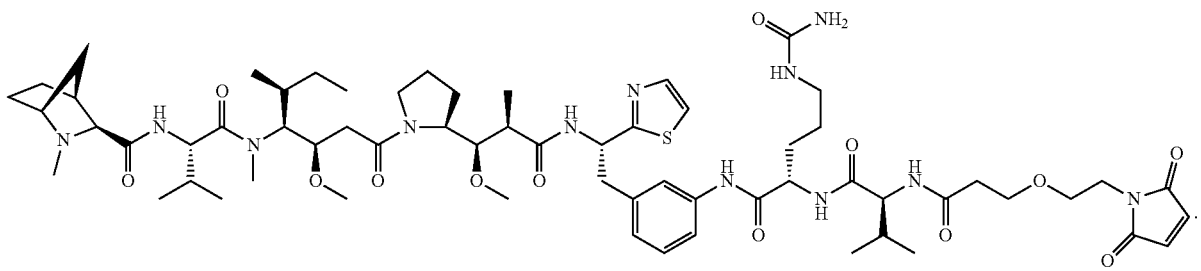 [SMILES: CC[C@H](C)[C@@H]([C@@H](CC(=O)N1CCC[C@H]1[C@H](OC)[C@@H](C)C(=O)N[C@@H](Cc1cccc(NC(=O)[C@H](CCCNC(N)=O)NC(=O)[C@@H](NC(=O)CCOCCN2C(=O)C=CC2=O)C(C)C)c1)c1nccs1)OC)N(C)C(=O)[C@@H](NC(=O)[C@@H]1[C@H]2CC[C@@H](C2)N1C)C(C)C]

Embodiment 51. The compound of Formula (C), Formula (C-1) or Formula (C-3), or Embodiment 38, wherein the compound is

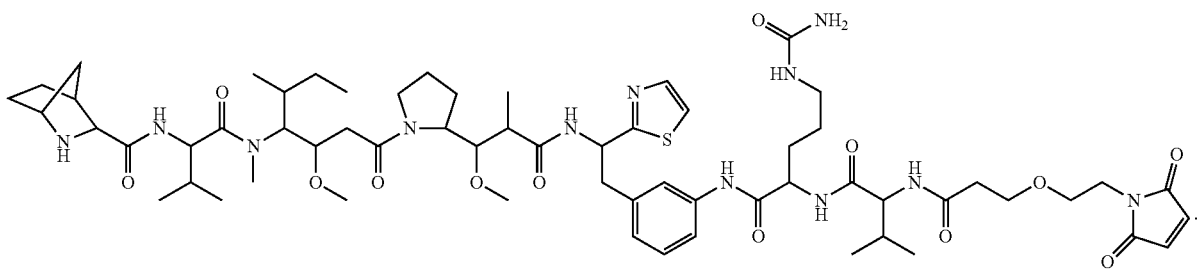 [SMILES: CCC(C)C(C(CC(=O)N1CCCC1C(OC)C(C)C(=O)NC(Cc1cccc(NC(=O)C(CCCNC(N)=O)NC(=O)C(NC(=O)CCOCCN2C(=O)C=CC2=O)C(C)C)c1)c1nccs1)OC)N(C)C(=O)C(NC(=O)C1NC2CCC1C2)C(C)C]

Embodiment 52. The compound of Formula (C), Formula (C-1) or Formula (C-3), or Embodiment 38, wherein the compound is

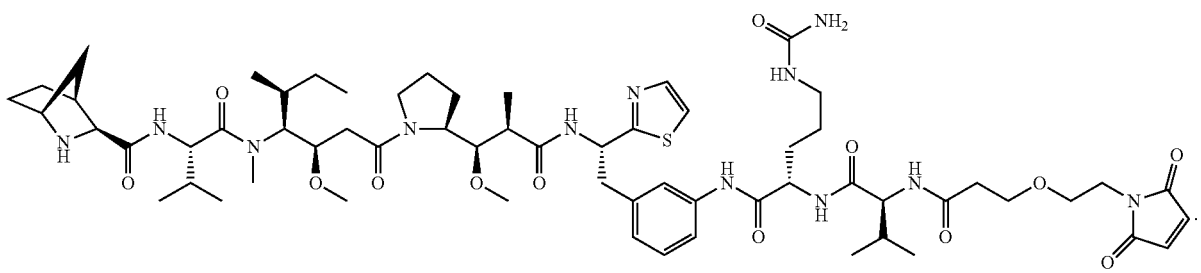 [SMILES: CC[C@H](C)[C@@H]([C@@H](CC(=O)N1CCC[C@H]1[C@H](OC)[C@@H](C)C(=O)N[C@@H](Cc1cccc(NC(=O)[C@H](CCCNC(N)=O)NC(=O)[C@@H](NC(=O)CCOCCN2C(=O)C=CC2=O)C(C)C)c1)c1nccs1)OC)N(C)C(=O)[C@@H](NC(=O)[C@H]1N[C@H]2CC[C@H]1C2)C(C)C]

In one aspect the Linker-Drug moiety is a compound having the structure of Formula (C), or stereoisomers or pharmaceutically acceptable salts thereof, Formula (D)

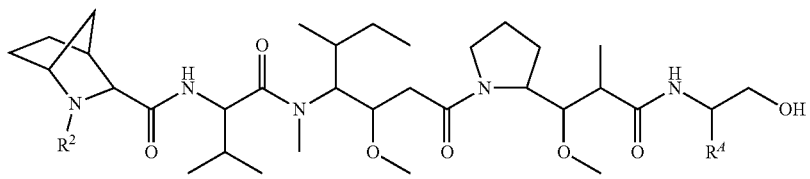

wherein:
$R_A$ is

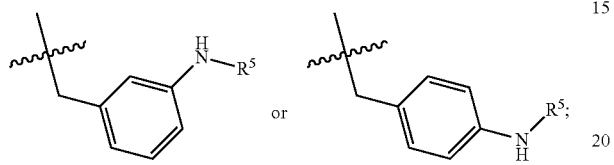

$R^2$ is H, $C_1$-$C_6$alkyl, —C(=O)$R^3$, —(CH$_2$)$_m$OH, —C(=O)(CH$_2$)$_m$OH, —C(=O)((CH$_2$)$_m$O)$_n$$R^4$, —((CH$_2$)$_m$O)$_n$$R^4$ or $C_1$-$C_6$alkyl which is optionally substituted with —CN, —C(=O)NH$_2$ or 1 to 5 hydroxyl;

each $R^3$ is independently selected from $C_1$-$C_6$alkyl and $C_1$-$C_6$alkyl, which is optionally substituted with 1 to 5 hydroxyl;

each $R^4$ is independently selected from H and $C_1$-$C_6$alkyl;

$R^5$ is -$L_1R^{14}$, -$L_1R^{24}$, -$L_1R^{34}$ or -$L_1R^{44}$;

$L_1$ is —X$_1$C(=O)((CH$_2$)$_m$O)$_p$(CH$_2$)$_m$—, —X$_1$C(=O)(CH$_2$)$_m$—, —X$_2$X$_1$C(=O)((CH$_2$)$_m$O)$_p$(CH$_2$)$_m$—, —X$_2$X$_1$C(=O)(CH$_2$)$_m$—, —X$_3$C(=O)((CH$_2$)$_m$O)$_p$(CH$_2$)$_m$—, —X$_3$C(=O)(CH$_2$)$_m$—, —X$_3$C(=O)(CH$_2$)$_m$NHC(=O)((CH$_2$)$_m$O)$_p$(CH$_2$)$_m$—, —X$_3$C(=O)(CH$_2$)$_m$NHC(=O)(CH$_2$)$_m$—, —X$_3$C(=O)(CH$_2$)$_m$—, —X$_1$C(=O)((CH$_2$)$_m$O)$_p$(CH$_2$)$_m$X$_4$(CH$_2$)$_m$—, —X$_1$C(=O)(CH$_2$)$_m$X$_4$(CH$_2$)$_m$—, —X$_2$X$_1$C(=O)((CH$_2$)$_m$O)$_p$(CH$_2$)$_m$X$_4$(CH$_2$)$_m$— or —X$_2$X$_1$C(=O)(CH$_2$)$_m$X$_4$(CH$_2$)$_m$—, where  indicates the point of attachment to $R^{14}$; $X_1$ is

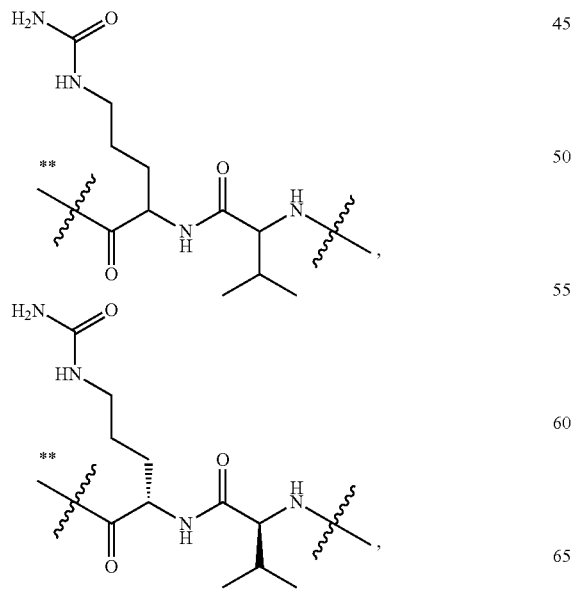

-continued

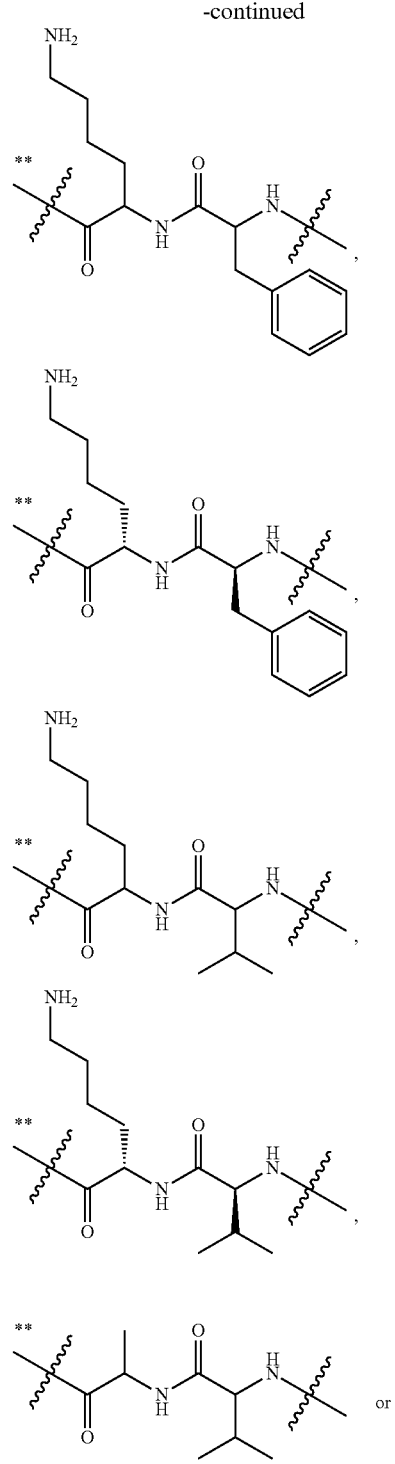

123
-continued
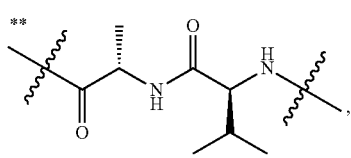
where ** indicates the point of attachment to the —NH— or to X$_2$;
X$_2$ is
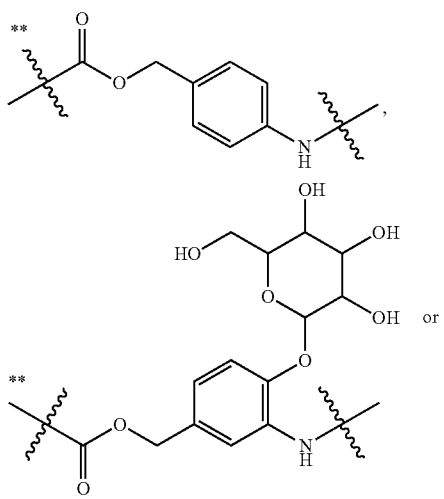
where ** indicates the point of attachment to the —NH—;
X$_3$ is
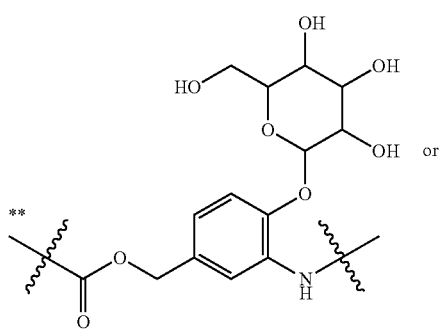
124
-continued
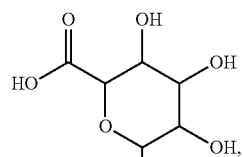
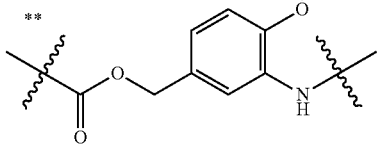
where ** indicates the point of attachment to the —NH—;
X$_4$ is
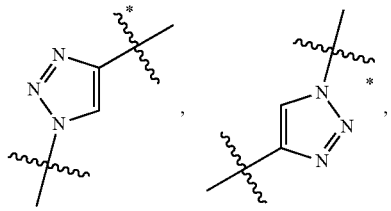
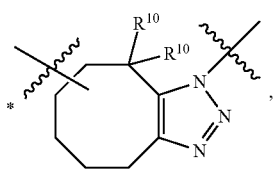
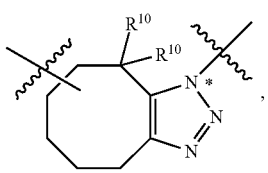
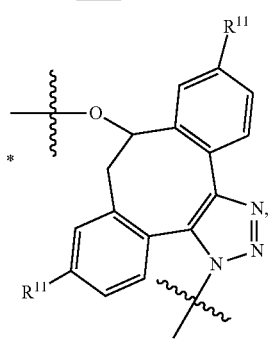
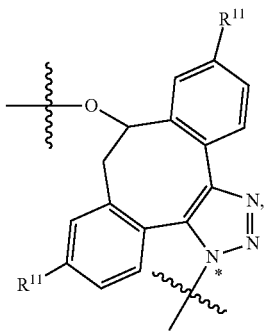

125
-continued
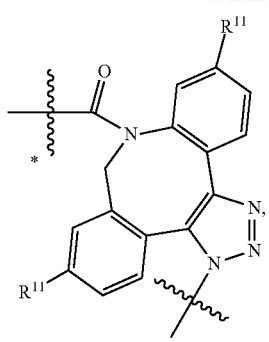
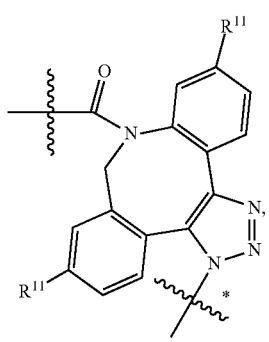
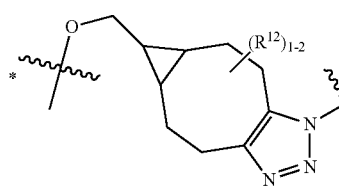
126
-continued
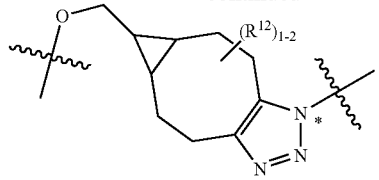
where the * indicates the point of attachment is toward $R^{14}$, $R^{24}$, $R^{34}$ or $R^{44}$;
$R^{14}$ is
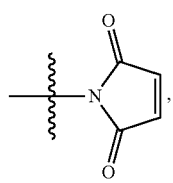
—$N_3$, —$ONH_2$, —$NR^6C(=O)CH=CH_2$, SH, —$SSR^7$, —$S(=O)_2(CH=CH_2)$, —$NR^6S(=O)_2(CH=CH_2)$, —$NR^6C(=O)CH_2Br$, —$NR^6C(=O)CH_2I$, —$NHC(=O)CH_2Br$, —$NHC(=O)CH_2I$, —$C(=O)NHNH_2$,
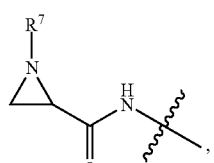
—$CO_2H$, —$NH_2$,
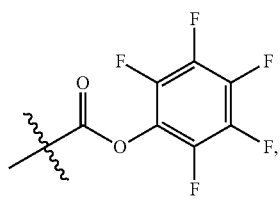
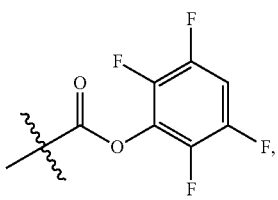
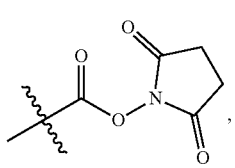
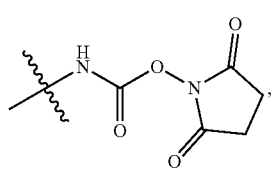
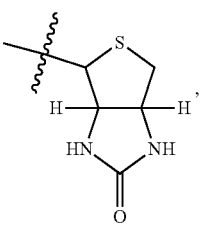
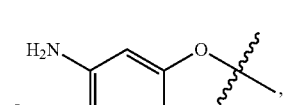
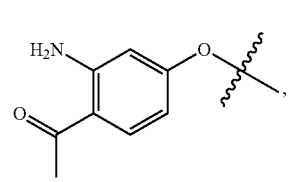
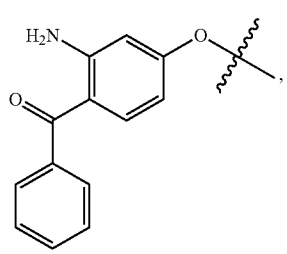
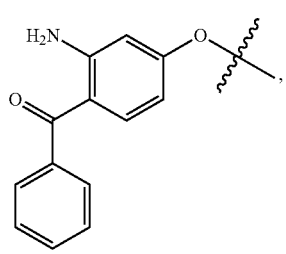

-continued
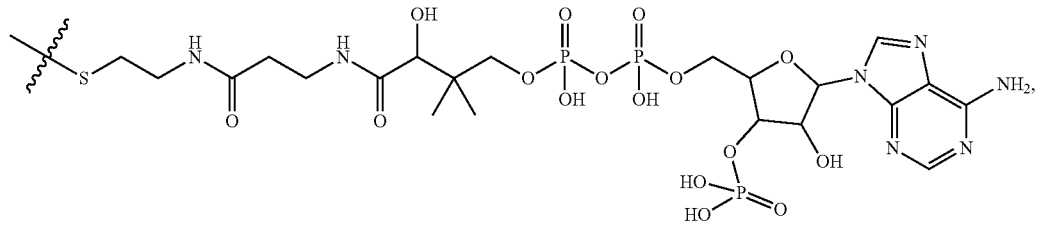
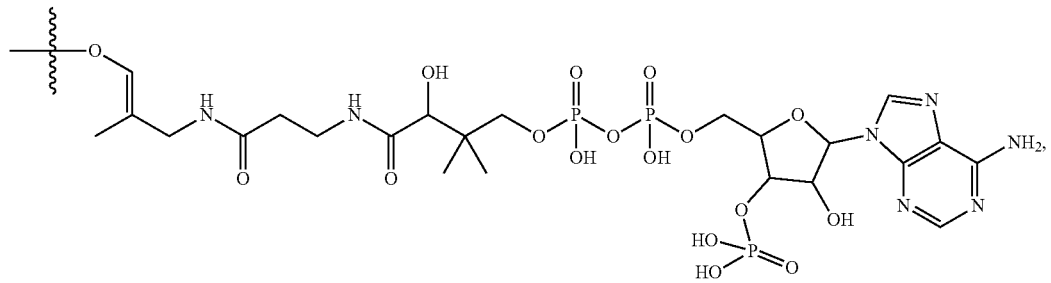
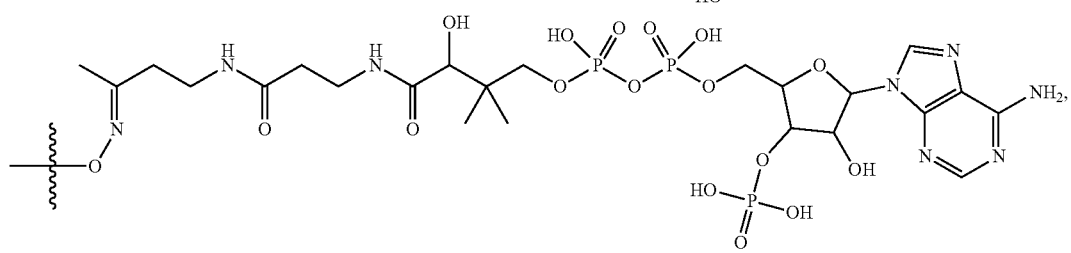
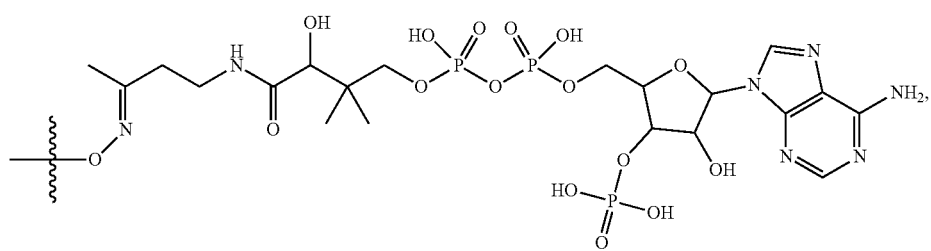
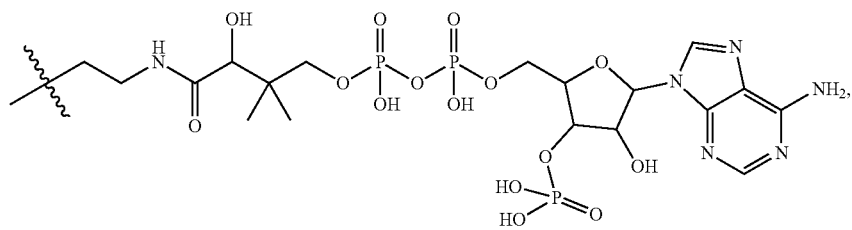
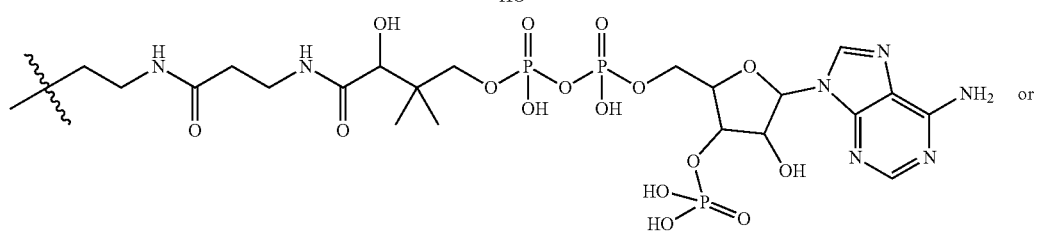 or
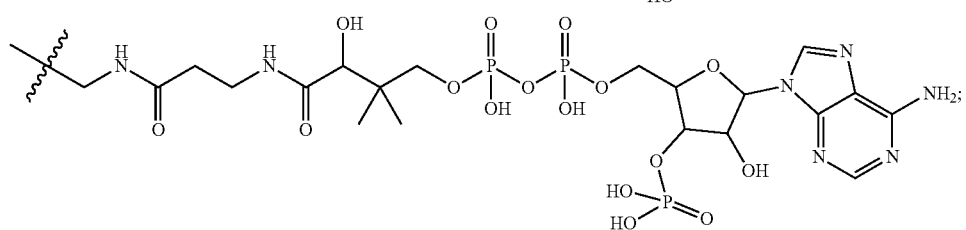

$R^{24}$ is

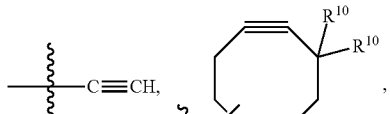

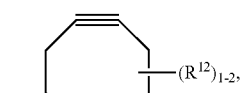

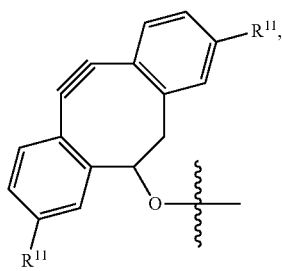

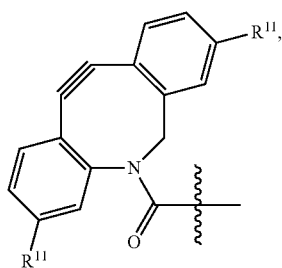

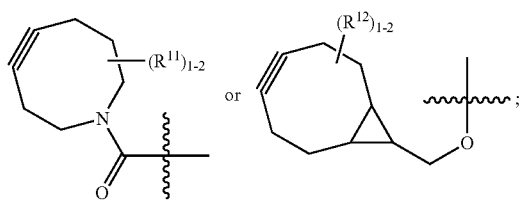

$R^{34}$ is, —$N_3$, —$ONH_2$, —$NR^7C(=O)CH=CH_2$, —$C(=O)NHNH_2$, —$CO_2H$, —$NH_2$,

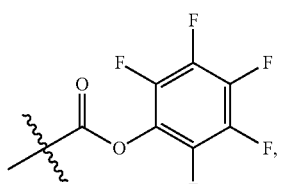

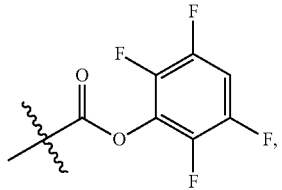

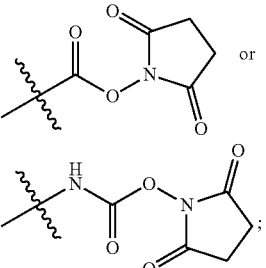

$R^{44}$ is

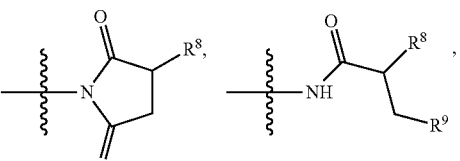

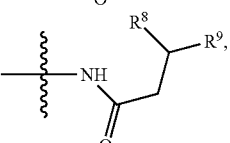

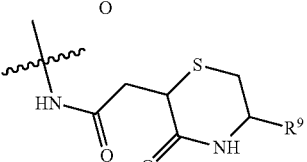

or —$NR^7C(=O)CH_2R^8$;

each $R^6$ is independently selected from H and $C_1$-$C_6$alkyl;

$R^7$ is 2-pyridyl or 4-pyridyl;

$R^8$ is —$S(CH_2)_nCHR^9NH_2$;

$R^9$ is —$C(=O)OR^7$;

each $R^{10}$ is independently selected from H, $C_1$-$C_6$alkyl, F, Cl, and —OH;

each $R^{11}$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;

each $R^{12}$ is independently selected from H, $C_{1-6}$alkyl, fluoro, benzyloxy substituted with —$C(=O)OH$, benzyl substituted with —$C(=O)OH$, $C_{1-4}$alkoxy substituted with —$C(=O)OH$ and $C_{1-4}$alkyl substituted with —$C(=O)OH$;

each m is independently selected from 1, 2, 3, 4, 5, 6, 7, 8, 9 and 10, and each p is independently selected from 1, 2, 3, 4, 5, 6, 7, 8, 9, 10, 11, 12, 13 and 14.

Certain aspects and examples of the Linker-Drug moiety are provided in the following listing of additional, enumerated embodiments. It will be recognized that features specified in each embodiment may be combined with other specified features to provide further embodiments of the present disclosure.

Embodiment 53. The compound of Formula (D), or a pharmaceutically acceptable salt thereof, having the structure of Formula (D-1), or a pharmaceutically acceptable salt thereof:

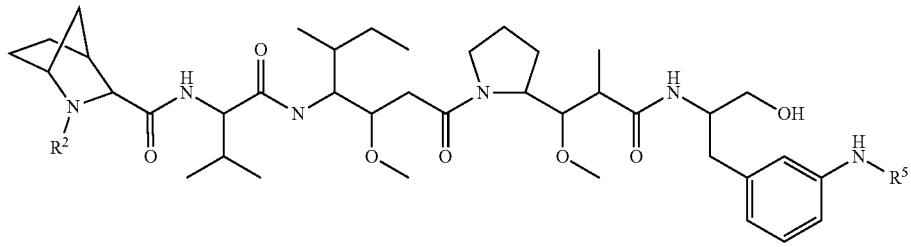

Formula (D-1)

wherein: $R^2$ and $R^5$ are as defined above for compounds of Formula (D).

Embodiment 54. The compound of Formula (D), or a pharmaceutically acceptable salt thereof, having the structure of Formula (D-2), or a pharmaceutically acceptable salt thereof:

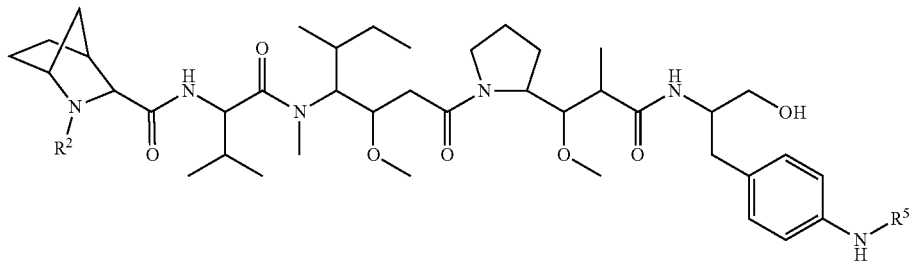

Formula (D-2)

wherein: $R^2$ and $R^5$ are as defined above for compounds of Formula (D).

Embodiment 55. The compound of Formula (D), or a pharmaceutically acceptable salt thereof, having the structure of Formula (D-3), or a pharmaceutically acceptable salt thereof:

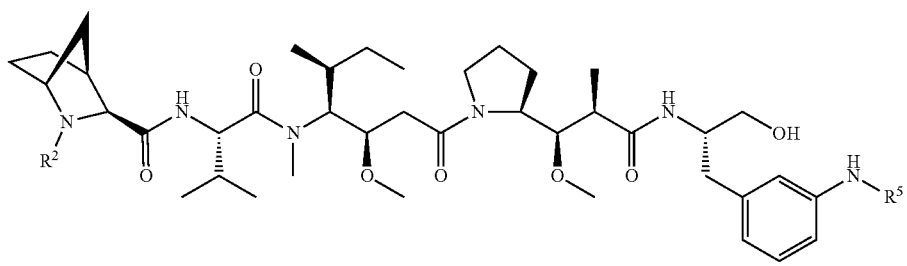

Formula (D-3)

wherein: $R^2$ and $R^5$ are as defined above for compounds of Formula (D).

Embodiment 56. The compound of Formula (D), or a pharmaceutically acceptable salt thereof, having the structure of Formula (D-4), or a pharmaceutically acceptable salt thereof:

Formula (D-4)

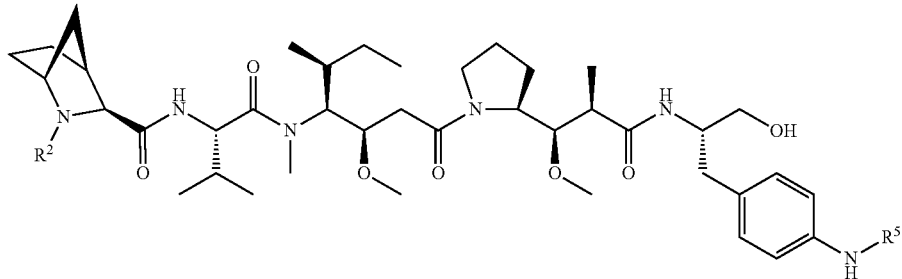

wherein: R² and R⁵ are as defined above for compounds of Formula (D).

Embodiment 57. The compound of Formula (D), Formula (D-1), Formula (D-2), Formula (D-3) or Formula (D-4), or a pharmaceutically acceptable salt thereof, wherein: R² is H or $C_1$-$C_6$alkyl.

Embodiment 58. The compound of Formula (D), Formula (D-1), Formula (D-2), Formula (D-3) or Formula (D-4), or a pharmaceutically acceptable salt thereof, wherein: R² is H or methyl.

Embodiment 59. The compound of Formula (D), Formula (D-1), Formula (D-2), Formula (D-3) or Formula (D-4), or a pharmaceutically acceptable salt thereof, wherein: R² is H.

Embodiment 60. The compound of Formula (D), Formula (D-1), Formula (D-2), Formula (D-3) or Formula (D-4), or a pharmaceutically acceptable salt thereof, wherein: R² is methyl.

Embodiment 61. The compound of Formula (D), Formula (D-1) or Formula (D-3), or a pharmaceutically acceptable salt thereof, having the structure of Formula (D-5), or a pharmaceutically acceptable salt thereof:

Formula (D-5)

wherein: R⁵ are as defined above for compounds of Formula (D).

Embodiment 62. The compound of Formula (D), Formula (D-1) or Formula (D-3), or a pharmaceutically acceptable salt thereof, having the structure of Formula (D-6), or a pharmaceutically acceptable salt thereof:

Formula (D-6)

wherein: $R^5$ are as defined above for compounds of Formula (D).

Embodiment 63. The compound of Formula (D), Formula (D-1) or Formula (D-3), or a pharmaceutically acceptable salt thereof, having the structure of Formula (D-7), or a pharmaceutically acceptable salt thereof:

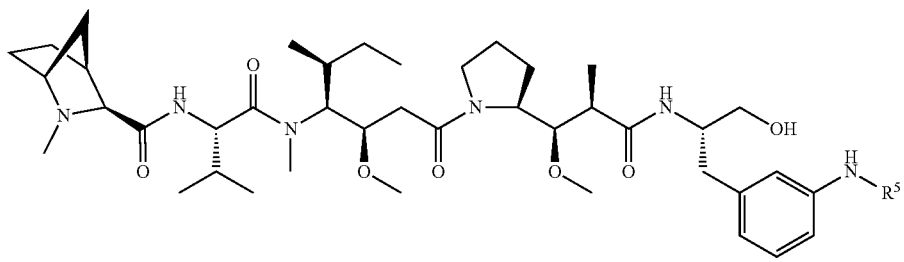

Formula (D-7)

wherein: $R^5$ are as defined above for compounds of Formula (D).

Embodiment 64. The compound of Formula (D), Formula (D-1) or Formula (D-3), or a pharmaceutically acceptable salt thereof, having the structure of Formula (D-8), or a pharmaceutically acceptable salt thereof:

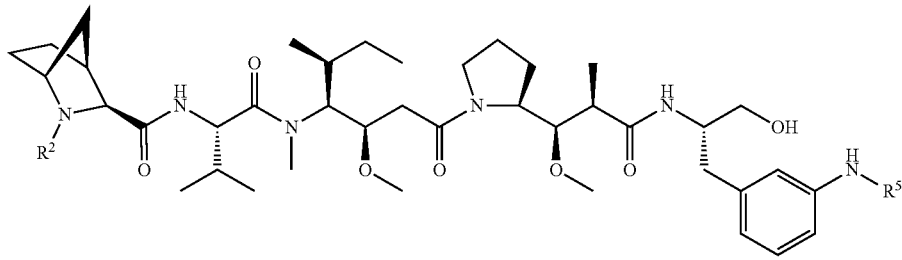

Formula (D-8)

wherein: $R^5$ are as defined above for compounds of Formula (D).

Embodiment 65. The compound of Formula (D), Formula (D-1) or Formula (D-3), or a pharmaceutically acceptable salt thereof, having the structure of Formula (D-9), or a pharmaceutically acceptable salt thereof:

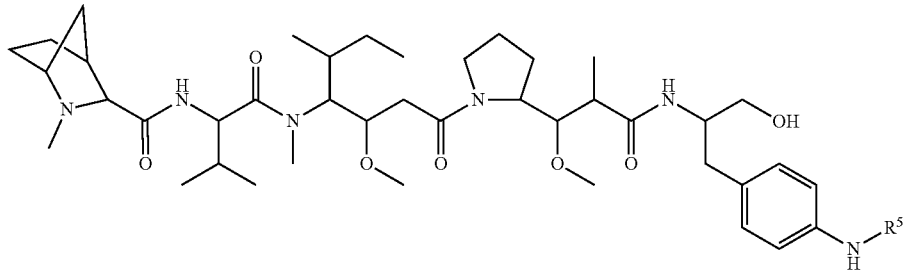

Formula (D-9)

wherein: $R^5$ are as defined above for compounds of Formula (D).

Embodiment 66. The compound of Formula (D), Formula (D-1) or Formula (D-3), or a pharmaceutically acceptable salt thereof, having the structure of Formula (D-10), or a pharmaceutically acceptable salt thereof:

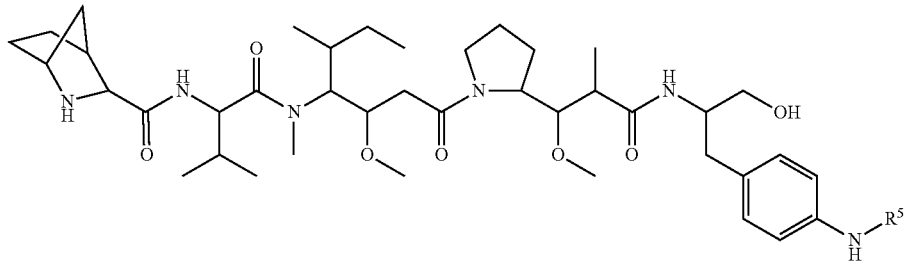

Formula (D-10)

wherein: $R^5$ are as defined above for compounds of Formula (D).

Embodiment 67. The compound of Formula (D), Formula (D-1) or Formula (D-3), or a pharmaceutically acceptable salt thereof, having the structure of Formula (D-11), or a pharmaceutically acceptable salt thereof:

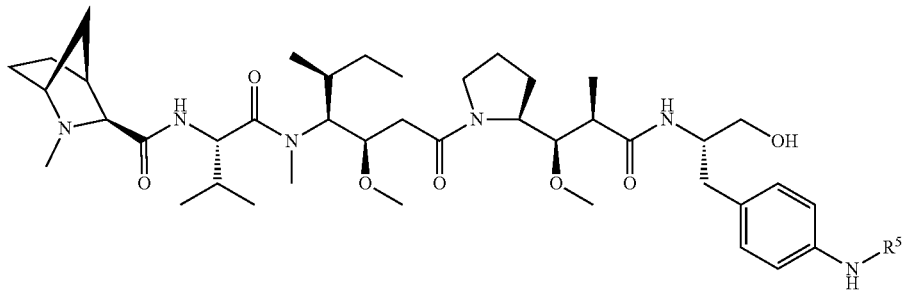

Formula (D-11)

wherein: $R^5$ are as defined above for compounds of Formula (D).

Embodiment 68. The compound of Formula (D), Formula (D-1) or Formula (D-3), or a pharmaceutically acceptable salt thereof, having the structure of Formula (D-12), or a pharmaceutically acceptable salt thereof:

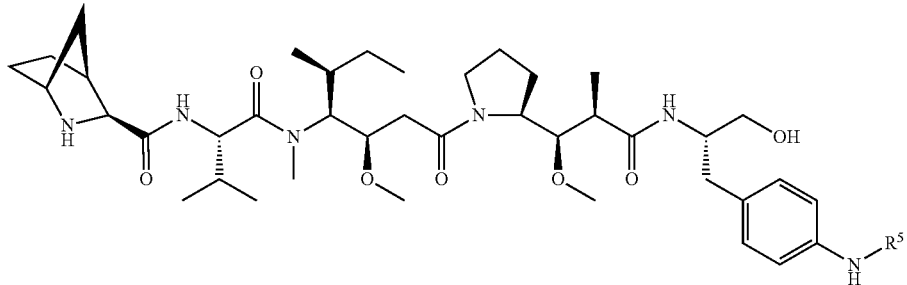

Formula (D-12)

wherein: $R^5$ are as defined above for compounds of Formula (D).

Embodiment 69. The compound of Formula (D), Formula (D-1) or Formula (D-3), or Embodiment 61, wherein the compound is

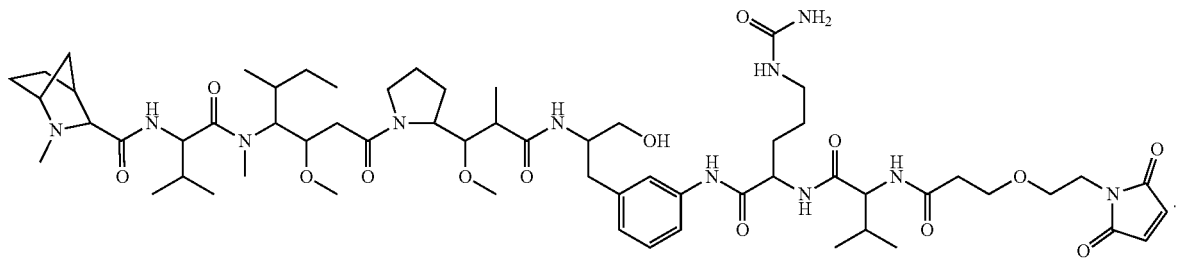 [SMILES: CCC(C)C(C(CC(=O)N1CCCC1C(OC)C(C)C(=O)NC(CO)Cc1cccc(NC(=O)C(CCCNC(N)=O)NC(=O)C(NC(=O)CCOCCN2C(=O)C=CC2=O)C(C)C)c1)OC)N(C)C(=O)C(NC(=O)C1C2CCC(C2)N1C)C(C)C]
Embodiment 70. The compound of Formula (D), Formula (D-1) or Formula (D-3), or Embodiment 61, wherein the compound is
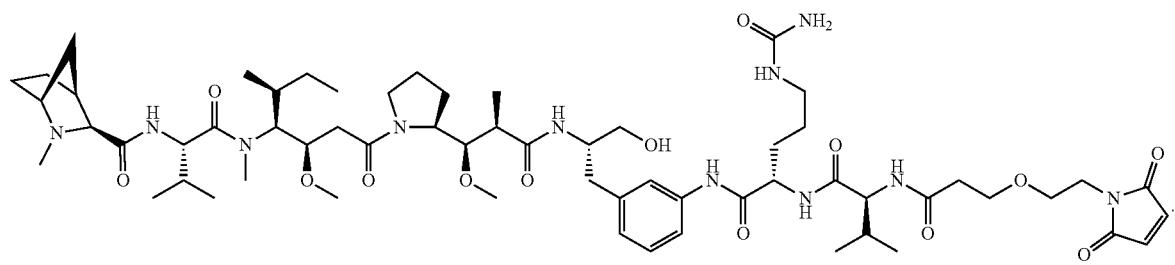 [SMILES: CC[C@H](C)[C@@H]([C@@H](CC(=O)N1CCC[C@H]1[C@H](OC)[C@@H](C)C(=O)N[C@H](CO)Cc1cccc(NC(=O)[C@H](CCCNC(N)=O)NC(=O)[C@@H](NC(=O)CCOCCN2C(=O)C=CC2=O)C(C)C)c1)OC)N(C)C(=O)[C@@H](NC(=O)[C@@H]1[C@H]2CC[C@@H](C2)N1C)C(C)C]
Embodiment 71. The compound of Formula (D), Formula (D-1) or Formula (D-3), or Embodiment 62, wherein the compound is
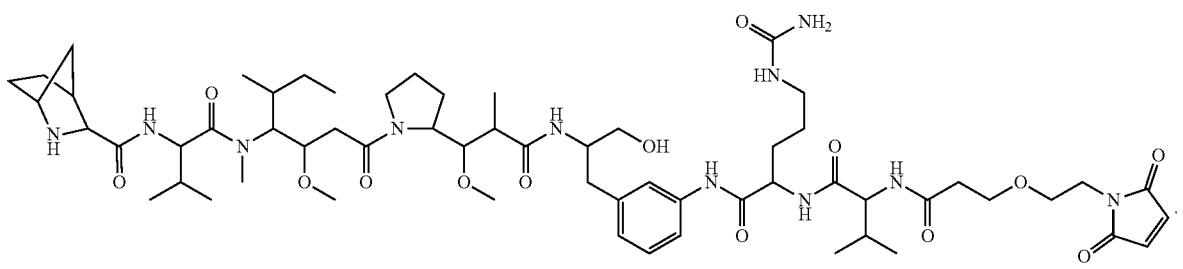 [SMILES: CCC(C)C(C(CC(=O)N1CCCC1C(OC)C(C)C(=O)NC(CO)Cc1cccc(NC(=O)C(CCCNC(N)=O)NC(=O)C(NC(=O)CCOCCN2C(=O)C=CC2=O)C(C)C)c1)OC)N(C)C(=O)C(NC(=O)C1NC2CCC1C2)C(C)C]
Embodiment 72. The compound of Formula (D), Formula (D-1) or Formula (D-3), or Embodiment 62, wherein the compound is
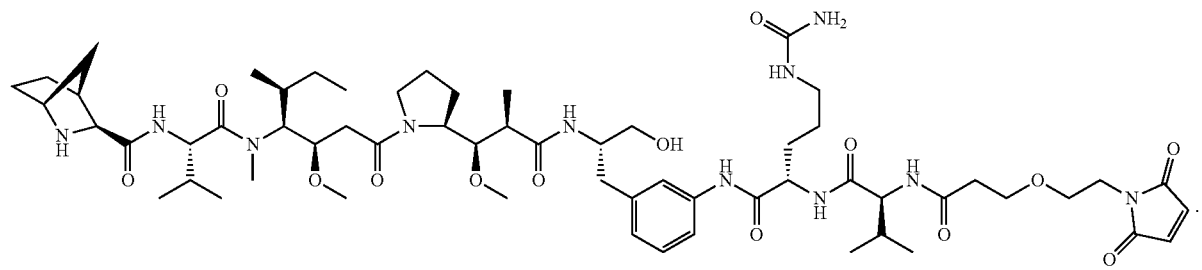 [SMILES: CC[C@H](C)[C@@H]([C@@H](CC(=O)N1CCC[C@H]1[C@H](OC)[C@@H](C)C(=O)N[C@H](CO)Cc1cccc(NC(=O)[C@H](CCCNC(N)=O)NC(=O)[C@@H](NC(=O)CCOCCN2C(=O)C=CC2=O)C(C)C)c1)OC)N(C)C(=O)[C@@H](NC(=O)[C@H]1N[C@H]2CC[C@H]1C2)C(C)C]

In one aspect, the Linker-Drug moiety present disclosure comprises valine-citruline MMAE (valcit-MMAE):

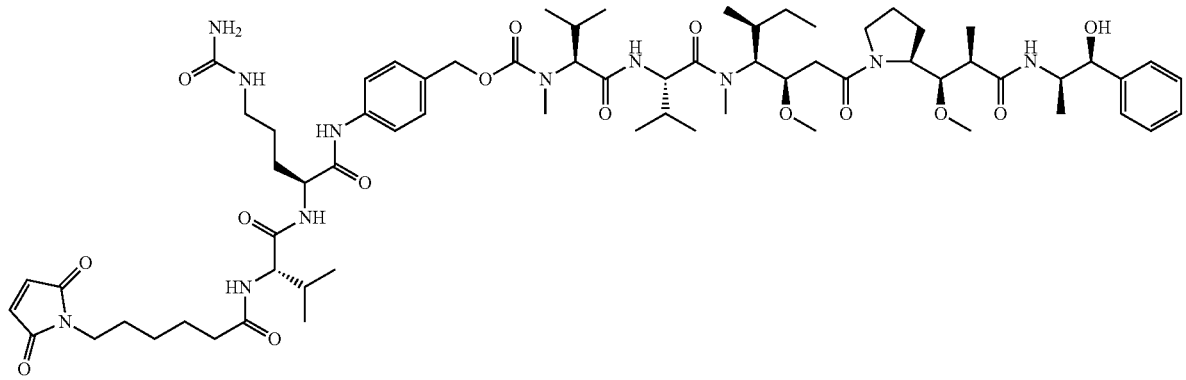 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)C(C)C]

where the Linker-Drug moiety $(L_B\text{-}(D)_n)$ covalently couples the antibody or antibody fragments $A_1$ and $A_2$.

Antibody Drug Conjugates

The present disclosure provides antibody drug conjugates, wherein an antibody or antibody fragment (e.g., antigen binding fragment) (e.g., antigen binding fragment) that specifically binds to CD48 is linked to a drug moiety (e.g., a cytotoxic agent), optionally through a linker. In one aspect, the antibody or antibody fragment (e.g., antigen binding fragment) (e.g., antigen binding fragment) is linked, via covalent attachment by a linker, to a drug moiety that is a cytotoxic agent.

In some embodiments, provided herein are conjugates comprising an antibody or antibody fragment (e.g., antigen binding fragment) (e.g., antigen binding fragment) that specifically binds to CD48, linked to a drug moiety (e.g., a cytotoxic agent), optionally through a linker.

In one aspect, the disclosure provides for an conjugate of Formula (I):

wherein:
  A is an antibody or antibody fragment (e.g., antigen binding fragment) that specifically binds to human CD48;
  $L_B$ is a linker;
  D is a cytotoxic agent;
  n is an integer from 1 to 10, and
  y is an integer from 1 to 10,
where the Linker-Drug moiety $(L_B\text{-}(D)_n)$ is covalently attached to the antibody or antibody fragment (A).

In one aspect, the present disclosure is directed to a conjugate of Formula (II):

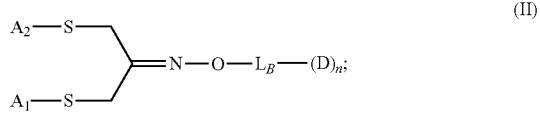

$A_1$ is an antibody or antibody fragment (e.g., antigen binding fragment) that specifically binds to human CD48;
  $A_2$ is an antibody or antibody fragment (e.g., antigen binding fragment) that specifically binds to human CD48;
  $L_B$ is a linker;
  D is a cytotoxic agent, and
  n is an integer from 1 to 10, In one aspect, the conjugates disclosed herein comprise one or more cytotoxins covalently attached to a linker ($L_B$), wherein the one or more cytotoxins are independently selected from compound of Formula (A), Formula (A-1), Formula (A-2), Formula (A-3), Formula (A-4), Formula (B), Formula (B-1), Formula (B-2), Formula (B-3) and Formula (B-4) or a compound of any one of Embodiments 7 to 14 or any one of Embodiments 23 to 30.

In one aspect, the conjugates of the present disclosure comprises one or more cytotoxins covalently attached to a linker ($L_B$), wherein the one or more cytotoxins are independently selected from compound of Formula (A), Formula (A-1), Formula (A-2), Formula (A-3) and Formula (A-4), or a compound of any one of Embodiments 7 to 14.

In one aspect, the conjugates of the disclosure comprises one or more cytotoxins covalently attached to a linker ($L_B$), wherein the one or more cytotoxins are independently selected from compound of Formula (B), Formula (B-1), Formula (B-2), Formula (B-3) and Formula (B-4) or a compound of any one of Embodiments 23 to 30.

In the conjugates of Formula (I), one or more Linker-Drug moiety $(L_B\text{-}(D)_n)$ can be covalently attached to the antibody or antibody fragment, A (e.g. antigen binding fragment), thereby covalently attaching one or more drug moieties, D, to the antibody or antibody fragment, A (e.g. antigen binding fragment), through linker, $L_B$. $L_B$ is any chemical moiety that is capable of linking the antibody or antibody fragment, A (e.g. antigen binding fragment) to one or more drug moieties, D. The conjugates of Formula (I), wherein one or more drug moieties, D, are covalently linked to an antibody or antibody fragment, A (e.g. antigen binding fragment), can be formed using a bifunctional or multifunctional linker reagent having one or more reactive functional groups that are the same or different. One of the reactive functional groups of the bifunctional or multifunctional linker reagent is used to react with a group on the antibody or antibody fragment, A, by way of example, a thiol or an amine (e.g. a cysteine, an N-terminus or amino acid side chain such as lysine) to form a covalent linkage with one end of the linker $L_B$. Such reactive functional groups of the bifunctional or multifunctional linker reagent include, but are not limited to, a maleimide, a thiol and an NHS ester. The other reactive functional group or groups of the bifunctional or multifunctional linker reagent are used to covalently attached one or more drug moieties, D, to linker $L_B$.

In the conjugates of Formula (II), a ketone bridge is formed by reaction of pendent thiols on antibody or antibody fragments $A_1$ and $A_2$ and a 1,3-dihaloacetone, such as 1,3-dichloroacetone, 1,3-dibromoacetone, 1,3-diiodoacetone, and bissulfonate esters of 1, 3-dihydroxyacetone, which thereby covalently couples the antibody or antibody fragments $A_1$ and $A_2$. This ketone bridge moiety is used to covalently attach one or more drug moieties, D, to the antibody or antibody fragments $A_1$ and $A_2$ through a linker $L_B$. $L_B$ is any chemical moiety that is capable of linking the antibody or antibody fragment, $A_1$ and $A_2$ to one or more drug moieties, D. The conjugates of Formula (II), wherein one or more drug moieties, D, are covalently linked to antibody or antibody fragments $A_1$ and $A_2$, can be formed using a bifunctional or multifunctional linker reagent having one or more reactive functional groups that are the same or different. In an embodiment, one the reactive functional groups of the bifunctional or multifunctional linker reagent is an alkoxyamine which is used to react with the ketone bridge to form an oxime linkage with one end of the linker $L_B$, and the other reactive functional group or groups of the bifunctional or multifunctional linker reagent are used to covalently attached one or more drug moieties, D, to linker $L_B$. In another embodiment, one the reactive functional groups of the bifunctional or multifunctional linker reagent is an hydrazine which is used to react with the ketone bridge to form a hydrazone linkage with one end of the linker $L_B$, and the other reactive functional group or groups of the bifunctional or multifunctional linker reagent are used to covalently attached one or more drug moieties, D, to linker $L_B$.

In one aspect, $L_B$ is a cleavable linker. In another aspect, $L_B$ is a non-cleavable linker. In some aspects, $L_B$ is an acid-labile linker, photo-labile linker, peptidase cleavable linker, esterase cleavable linker, glycosidase cleavable linker, phosphodiesterase cleavable linker, a disulfide bond reducible linker, a hydrophilic linker, or a dicarboxylic acid based linker.

While the drug to antibody ratio has an exact integer value for a specific conjugate molecule (e.g., the product of n and y in Formula (I) and "n" in Formula (II)), it is understood that the value will often be an average value when used to describe a sample containing many molecules, due to some degree of inhomogeneity, typically associated with the conjugation step. The average loading for a sample of a conjugate is referred to herein as the drug to antibody (or antibody fragment) ratio, or "DAR." In some aspects, the DAR is between about 1 and about 5, and typically is about 1, 2, 3, or 4. In some aspects, at least 50% of a sample by weight is compound having the average DAR plus or minus 2, and preferably at least 50% of the sample is a conjugate that contains the average DAR plus or minus 1. Other aspects include conjugates wherein the DAR is about 2. In some aspects, a DAR of 'about y' means the measured value for DAR is within 20% of the product of n and y in Formula (I). In some aspects, a DAR of 'about n' means the measured value for DAR is within 20% of n in Formula (II).

In one aspect, the average molar ratio of the drug to the antibody or antibody fragment in the conjugates of Formula (I) (i.e., average value of the product of n and y, also known as drug to antibody ratio (DAR)) is about 1 to about 10, about 1 to about 6 (e.g., 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0), about 1 to about 5, about 1.5 to about 4.5, or about 2 to about 4.

In one aspect, the average molar ratio of the drug to the antibody or antibody fragments $A_1$ and $A_2$ in the conjugates of Formula (II) (i.e., average value of n, also known as drug to antibody ratio (DAR)) is about 1 to about 10, about 1 to about 6 (e.g., 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0), about 1 to about 5, about 1.5 to about 4.5, or about 2 to about 4.

In one aspect provided by the disclosure, the conjugate has substantially high purity and has one or more of the following features: (a) greater than about 90% (e.g., greater than or equal to about 91%, 92%, 93%, 94%, 95%, 96%, 97%, 98%, 99%, or 100%), preferably greater than about 95%, of conjugate species are monomeric, (b) unconjugated linker level in the conjugate preparation is less than about 10% (e.g., less than or equal to about 9%, 8%, 7%, 6%, 5%, 4%, 3%, 2%, 1%, or 0%) (relative to total linker), (c) less than 10% of conjugate species are crosslinked (e.g., less than or equal to about 9%, 8%, 7%, 6%, 5%, 4%, 3%, 2%, 1%, or 0%), (d) free drug (e.g., auristatin, amanitin, maytansinoid or saporin) level in the conjugate preparation is less than about 2% (e.g., less than or equal to about 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, or 0%) (mol/mol relative to total cytotoxic agent).

In one aspect the conjugates disclosed herein have the structure of Formula (E):

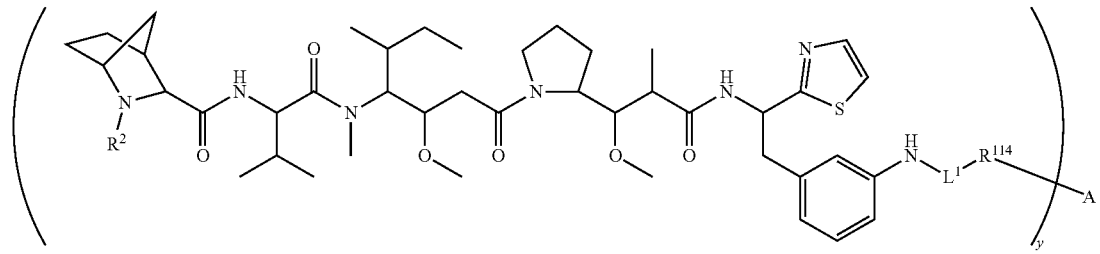

Formula (E)

wherein:

A represents an antibody or antibody fragment (e.g., antigen binding fragment) that specifically binds to human CD48;

y is an integer from 1 to 10;

$R^2$ is H, $C_1$-$C_6$alkyl, —C(=O)$R^3$, —(CH$_2$)$_m$OH, —C(=O)(CH$_2$)$_m$OH, —C(=O)((CH$_2$)$_m$O)$_n$$R^4$, —((CH$_2$)$_m$O)$_n$$R^4$ or $C_1$-$C_6$alkyl which is optionally substituted with —CN, —C(=O)NH$_2$ or 1 to 5 hydroxy;

each $R^3$ is independently selected from $C_1$-$C_6$alkyl and $C_1$-$C_6$alkyl, which is optionally substituted with 1 to 5 hydroxyl;

each $R^4$ is independently selected from H and $C_1$-$C_6$alkyl;

$L_1$ is —$X_1$C(=O)((CH$_2$)$_m$O)$_p$(CH$_2$)$_m$—, —$X_1$C(=O)(CH$_2$)$_m$—, —$X_2$$X_1$C(=O)((CH$_2$)$_m$O)$_p$(CH$_2$)$_m$—, —$X_2$$X_1$C(=O)(CH$_2$)$_m$—, —$X_3$C(=O)((CH$_2$)$_m$O)$_p$(CH$_2$)$_m$—, —$X_3$C(=O)(CH$_2$)$_m$—, —$X_3$C(=O)(CH$_2$)$_m$NHC(=O)((CH$_2$)$_m$O)$_p$(CH$_2$)$_m$—, —$X_3$C(=O)(CH$_2$)$_m$NHC(=O)(CH$_2$)$_m$—, —$X_3$C(=O)(CH$_2$)$_m$—, —$X_1$C(=O)((CH$_2$)$_m$O)$_p$(CH$_2$)$_m$$X_4$(CH$_2$)$_m$—, —$X_1$C(=O)(CH$_2$)$_m$$X_4$(CH$_2$)$_m$—, —$X_2$$X_1$C(=O)((CH$_2$)$_m$O)$_p$(CH$_2$)$_m$$X_4$(CH$_2$)$_m$— or —$X_2$$X_1$C(=O)(CH$_2$)$_m$$X_4$(CH$_2$)$_m$—, where  indicates the point of attachment to $R^{14}$;

$X_1$ is

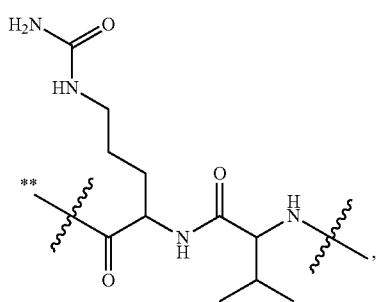

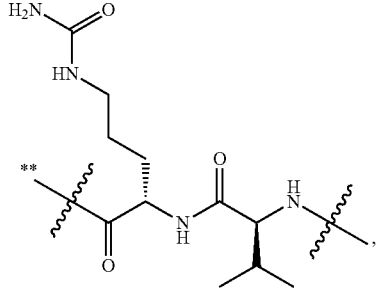

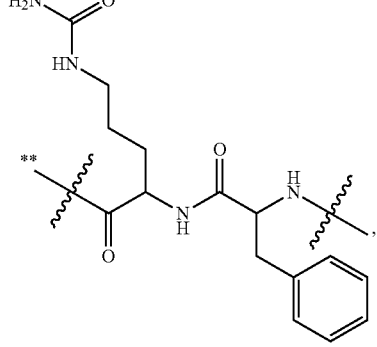

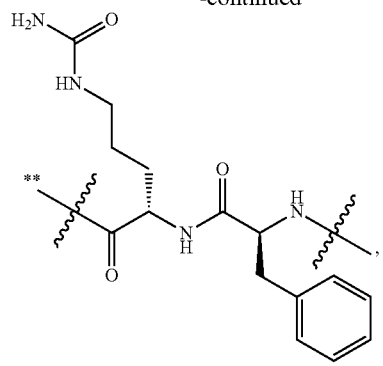

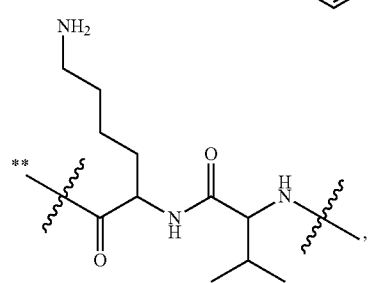

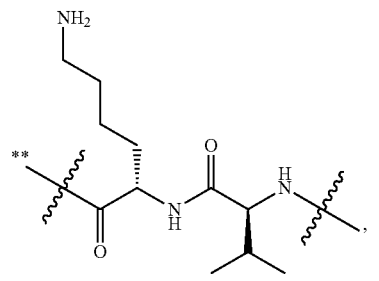

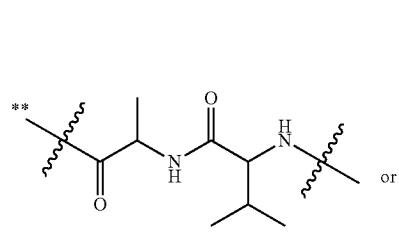

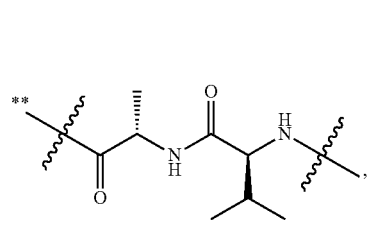

or where ** indicates the point of attachment to the —NH— or to $X_2$;

$X_2$ is

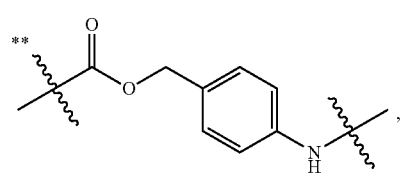

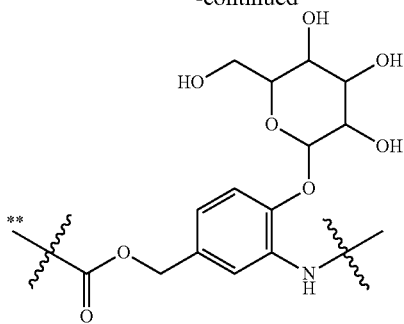
or
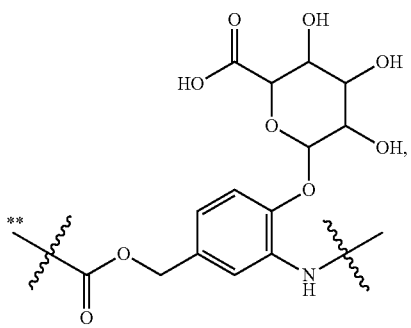
where ** indicates the point of attachment to the —NH—;
X$_3$ is
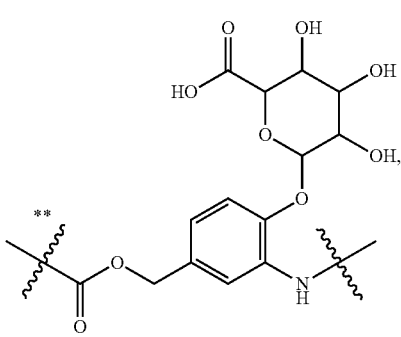
or
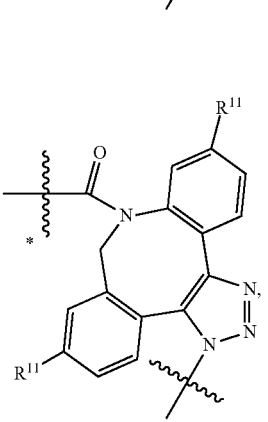
where ** indicates the point of attachment to the —NH—;
X$_4$ is
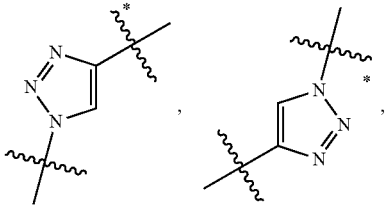
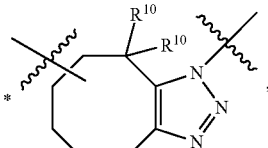
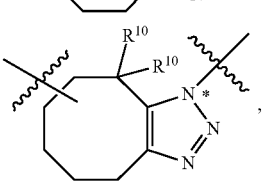
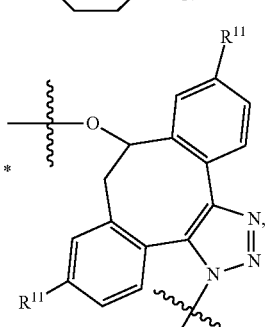
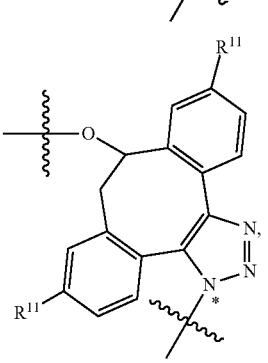
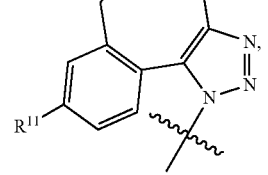

-continued
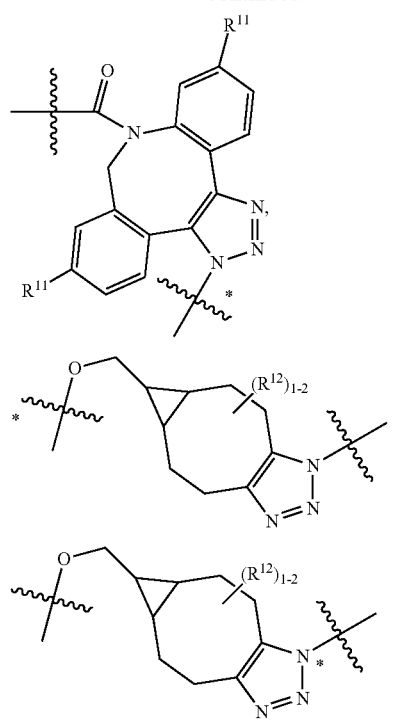
where the * indicates the point of attachment is toward $R^{114}$;
$R^{114}$ is
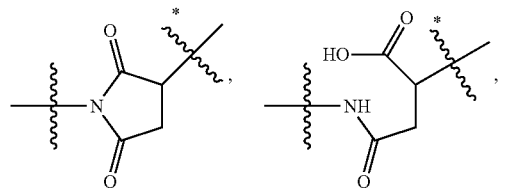
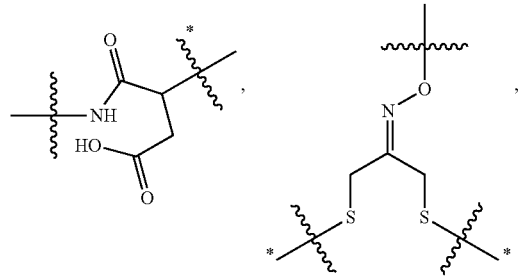
—NR⁶C(=O)CH₂—*,     —NHC(=O)CH₂—*,
—S(=O)₂CH₂CH₂—*,    —(CH₂)₂S(=O)₂CH₂CH₂—*,
—NR⁶S(=O)₂CH₂CH₂—*, —NR⁶C(=O)CH₂CH₂—*,
—NH—,               —C(=O)—,               —NHC(=O)—*,
—CH₂NHCH₂CH₂—*, —NHCH₂CH₂—*, —S—,
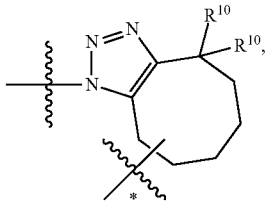
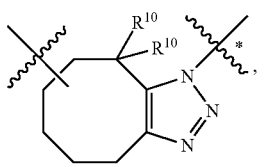
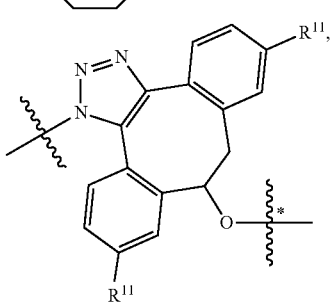
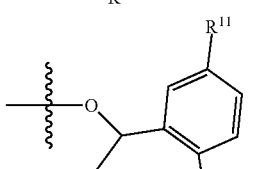
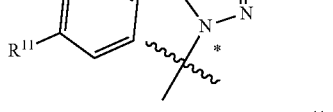
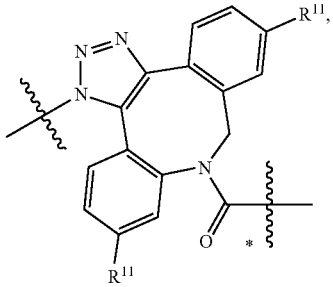
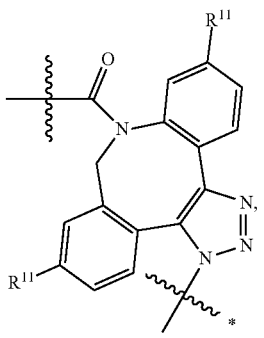

151
-continued

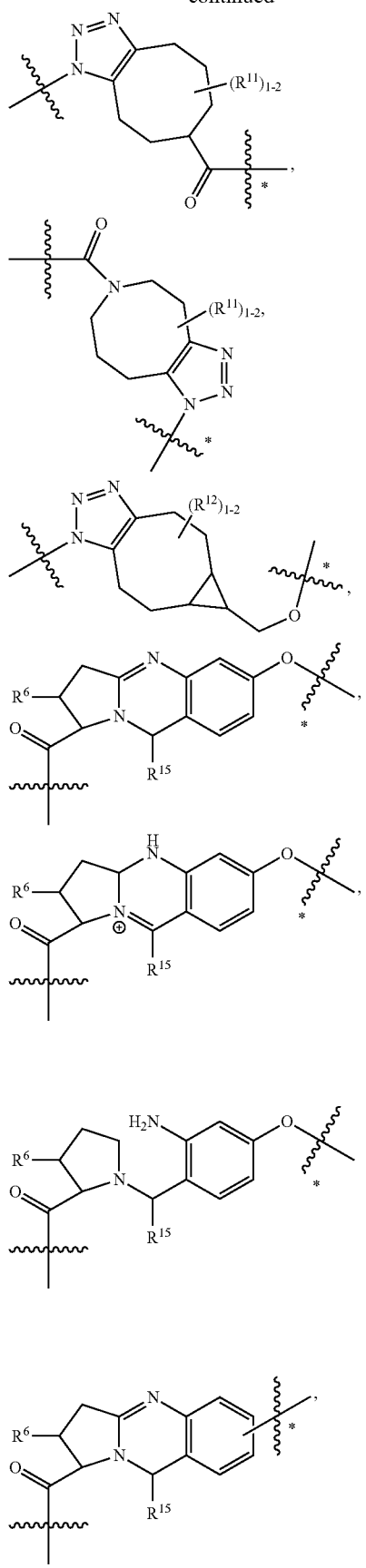

152
-continued

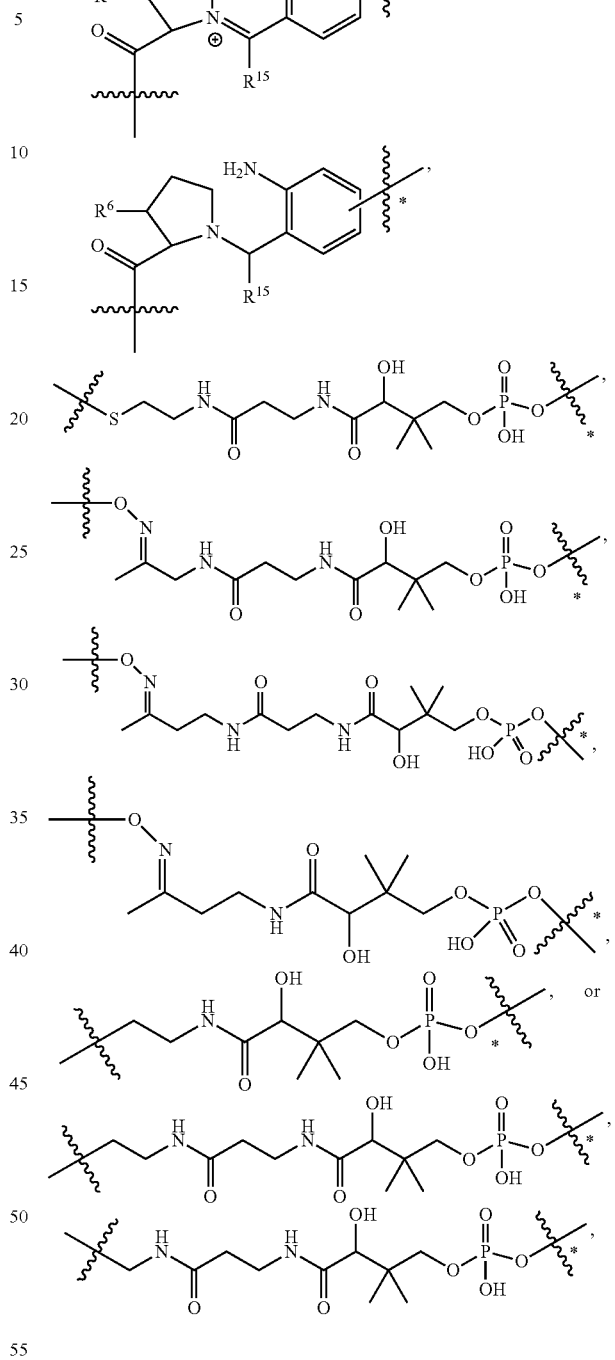

where the * indicates the point of attachment to A;
  each $R^6$ is independently selected from H and $C_1$-$C_6$alkyl;
  each $R^{10}$ is independently selected from H, $C_1$-$C_6$alkyl, F, Cl, and —OH;
  each $R^{11}$ is independently selected from H, $C_1$-$C_6$alkyl, F, Cl, —NH$_2$, —OCH$_3$, —OCH$_2$CH$_3$, —N(CH$_3$)$_2$, —ON, —NO$_2$ and —OH;
  each $R^{12}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each $R^{15}$ is independently selected from H, —OH₃ and phenyl;

each m is independently selected from 1, 2, 3, 4, 5, 6, 7, 8, 9 and 10, and each p is independently selected from 1, 2, 3, 4, 5, 6, 7, 8, 9, 10, 11, 12, 13 and 14.

In one aspect the conjugates of the present disclosure have the structure of Formula (F):

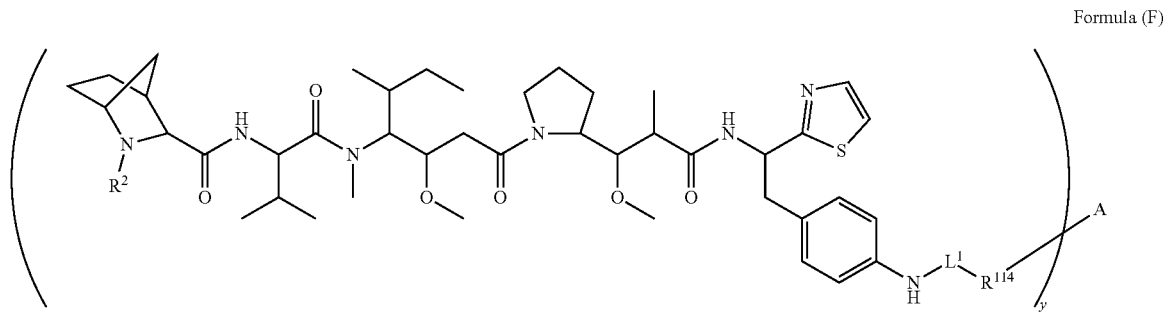

Formula (F)

wherein:

A represents an antibody or antibody fragment (e.g., antigen binding fragment) that specifically binds to human CD48;

y is an integer from 1 to 10;

$R^2$ is H, $C_1$-$C_6$alkyl, —C(=O)$R^3$, —(CH₂)$_m$OH, —C(=O)(CH₂)$_m$OH, —C(=O)((CH₂)$_m$O)$_n$$R^4$, —((CH₂)$_m$O)$_n$$R^4$ or $C_1$-$C_6$alkyl which is optionally substituted with —CN, —C(=O)NH₂ or 1 to 5 hydroxy;

each $R^3$ is independently selected from $C_1$-$C_6$alkyl and $C_1$-$C_6$alkyl, which is optionally substituted with 1 to 5 hydroxyl;

each $R^4$ is independently selected from H and $C_1$-$C_6$alkyl;

$L_1$ is —X₁C(=O)((CH₂)$_m$O)$_p$(CH₂)$_m$—, —X₁C(=O)(CH₂)$_m$—, —X₂X₁C(=O)((CH₂)$_m$O)$_p$(CH₂)$_m$—, —X₂X₁C(=O)(CH₂)$_m$—, —X₃C(=O)((CH₂)$_m$O)$_p$(CH₂)$_m$—, —X₃C(=O)(CH₂)$_m$—, —X₃C(=O)(CH₂)$_m$NHC(=O)((CH₂)$_m$O)$_p$(CH₂)$_m$—, —X₃C(=O)(CH₂)$_m$NHC(=O)(CH₂)$_m$—, —X₃C(=O)(CH₂)$_m$—; —X₁C(=O)((CH₂)$_m$O)$_p$(CH₂)$_m$X₄(CH₂)$_m$—, —X₁C(=O)(CH₂)$_m$X₄(CH₂)$_m$—, —X₂X₁C(=O)((CH₂)$_m$O)$_p$(CH₂)$_m$X₄(CH₂)$_m$— or —X₂X₁C(=O)(CH₂)$_m$X₄(CH₂)$_m$—, where  indicates the point of attachment to $R^{14}$;

$X_1$ is

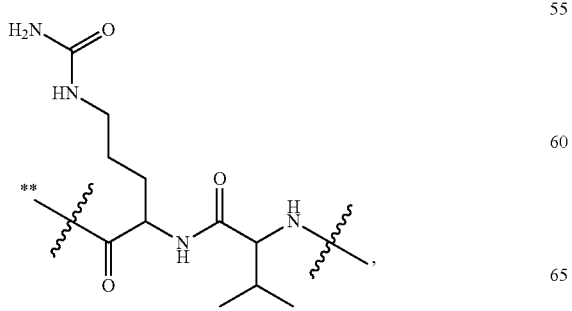

-continued

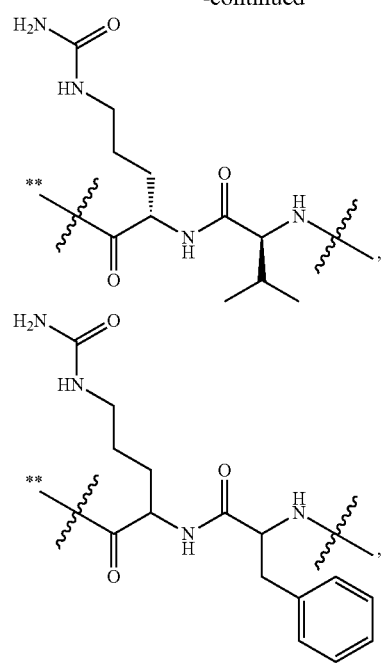

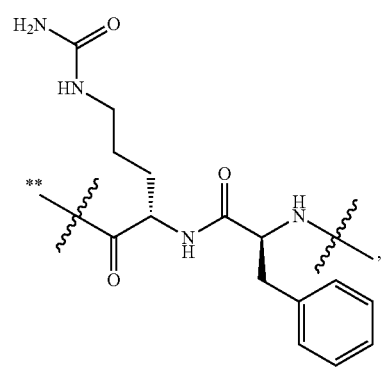

155
-continued
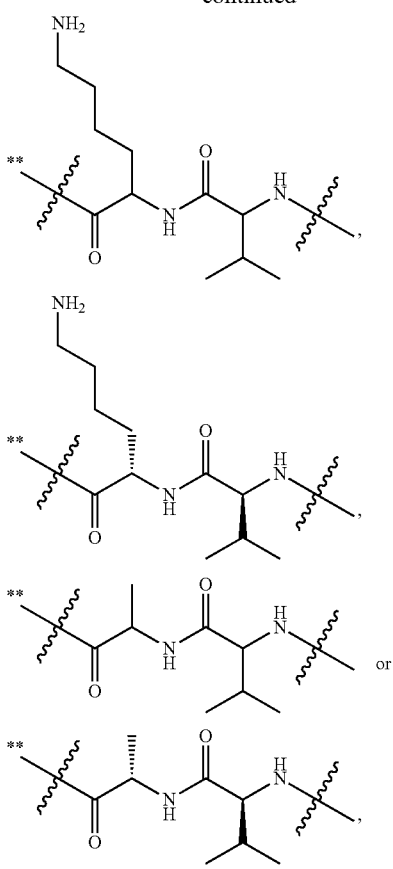
where ** indicates the point of attachment to the —NH— or to $X_2$;
$X_2$ is
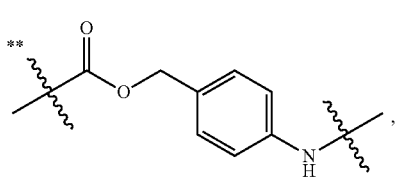
156
-continued
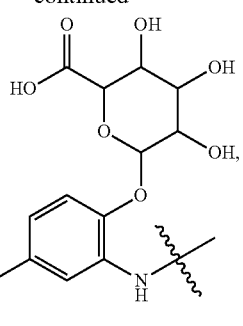
where ** indicates the point of attachment to the —NH—;
$X_3$ is
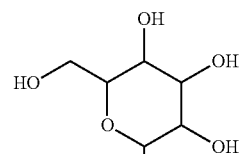
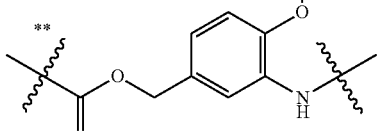
or
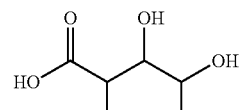
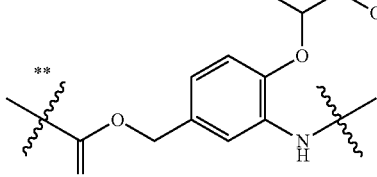
where ** indicates the point of attachment to the —NH—;
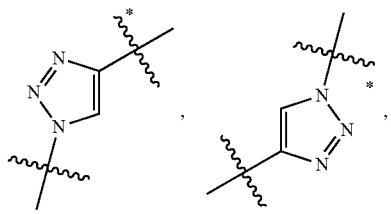
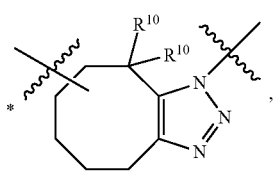

157
-continued
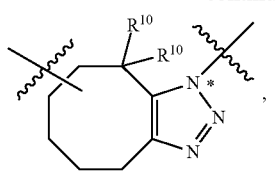
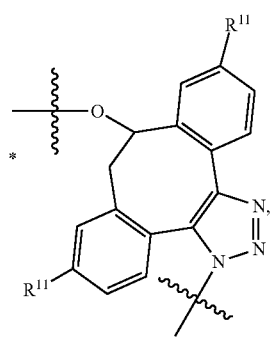
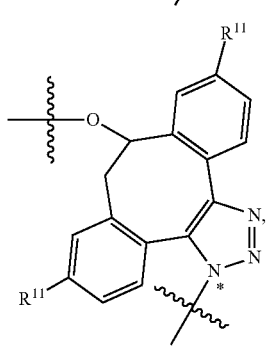
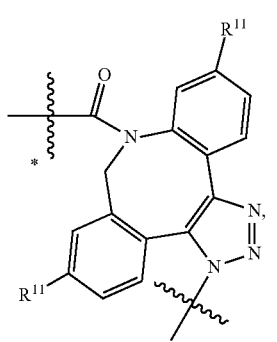
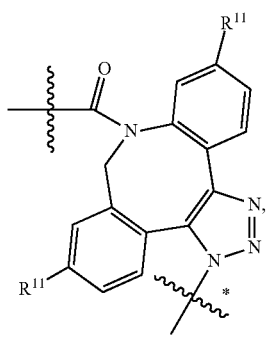
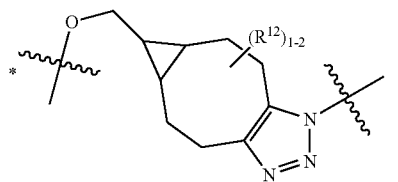 or
158
-continued
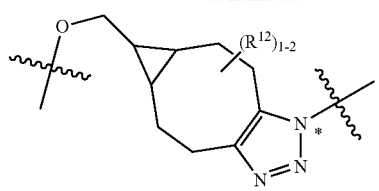
where the * indicates the point of attachment is toward $R^{114}$;
$R^{114}$ is
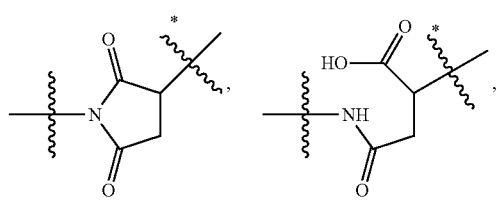
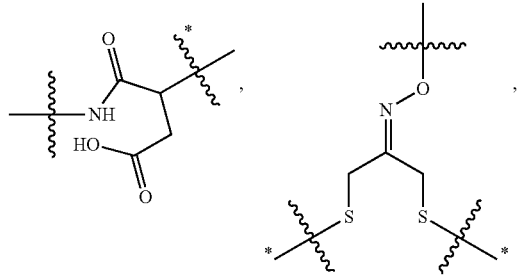
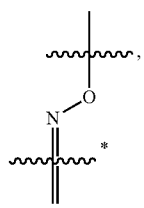
—NR⁶C(=O)CH₂—*, —NHC(=O)CH₂—*,
—S(=O)₂CH₂CH₂—*, —(CH₂)₂S(=O)₂CH₂CH₂—*,
—NR⁶S(=O)₂CH₂CH₂—*, —NR⁶C(=O)CH₂CH₂—*,
—NH—, —C(=O)—, —NHC(=O)—*,
—CH₂NHCH₂CH₂—*, —NHCH₂CH₂—*, —S—,
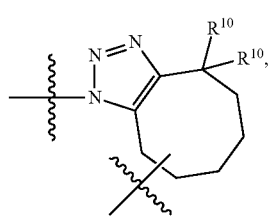
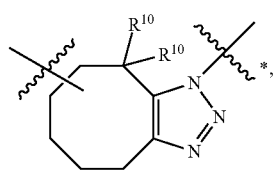

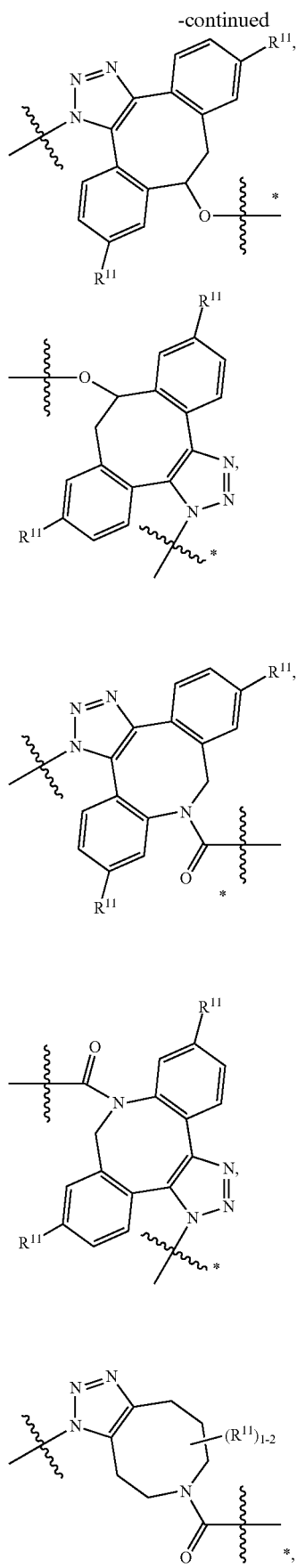
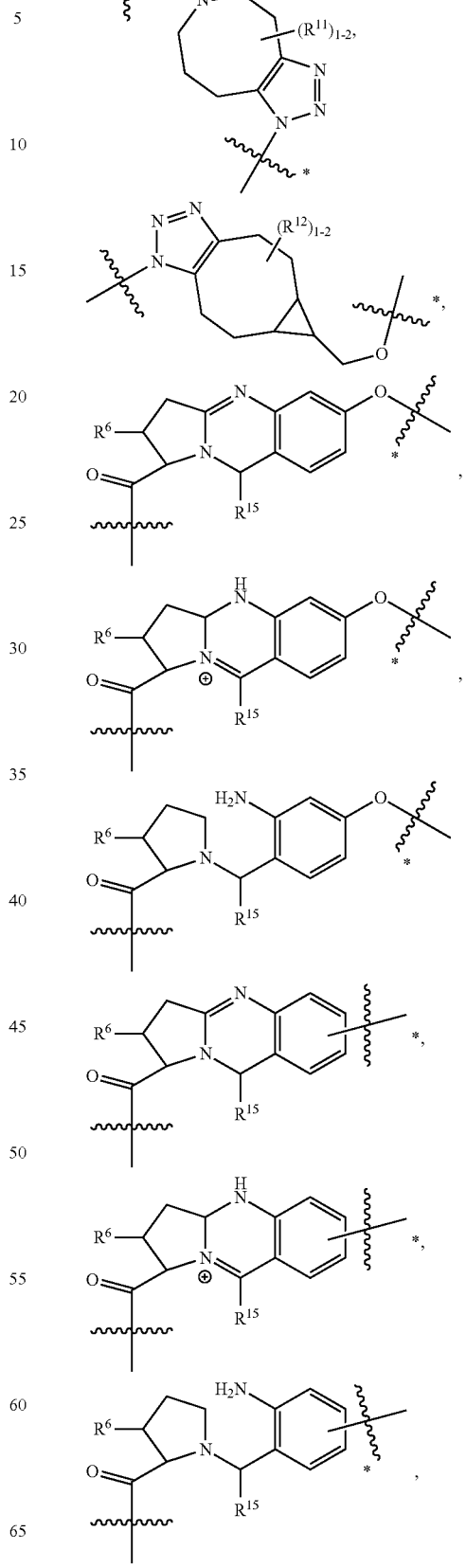

-continued

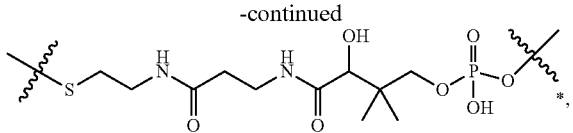

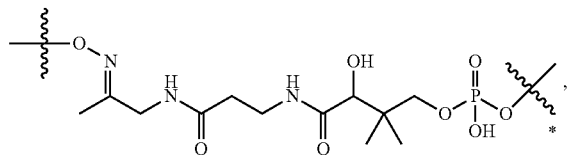

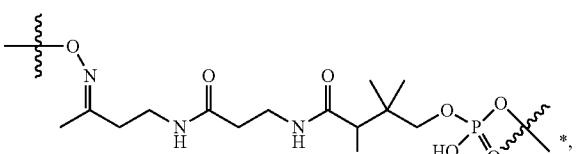

where the * indicates the point of attachment to A;

each $R^6$ is independently selected from H and $C_1$-$C_6$alkyl;

each $R^{10}$ is independently selected from H, $C_1$-$C_6$alkyl, F, Cl, and —OH;

each $R^{11}$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;

each $R^{12}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each $R^{15}$ is independently selected from H, —$CH_3$ and phenyl;

each m is independently selected from 1, 2, 3, 4, 5, 6, 7, 8, 9 and 10, and each p is independently selected from 1, 2, 3, 4, 5, 6, 7, 8, 9, 10, 11, 12, 13 and 14.

In one aspect the conjugates of the disclosure have the structure of Formula (G):

Formula (G)

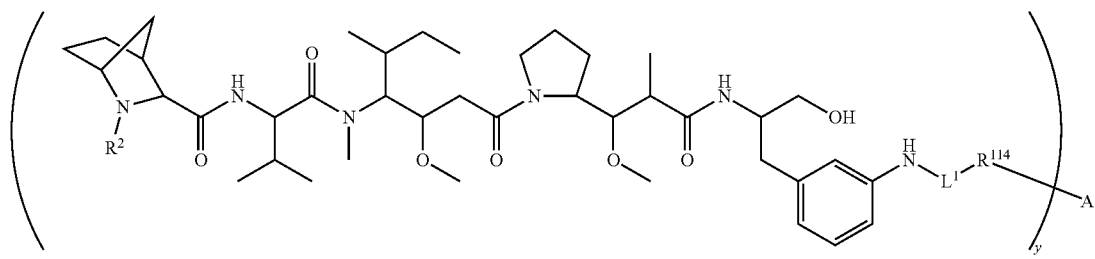

-continued

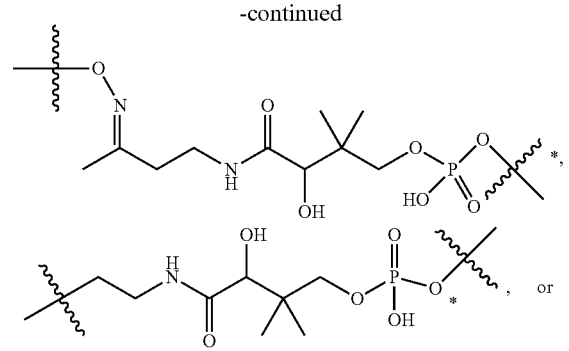

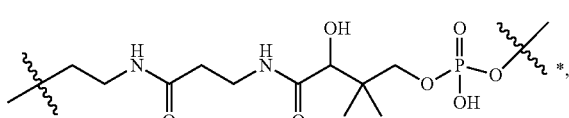

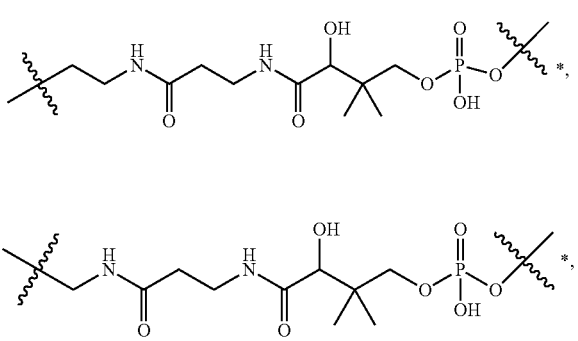

wherein:

A represents an antibody or antibody fragment (e.g., antigen binding fragment) that specifically binds to human CD48;

y is an integer from 1 to 10;

$R^2$ is H, $C_1$-$C_6$alkyl, —C(=O)$R^3$, —$(CH_2)_m$OH, —C(=O)$(CH_2)_m$OH, —C(=O)$((CH_2)_mO)_nR^4$, —$((CH_2)_mO)_nR^4$ or $C_1$-$C_6$alkyl which is optionally substituted with —CN, —C(=O)$NH_2$ or 1 to 5 hydroxy;

each $R^3$ is independently selected from $C_1$-$C_6$alkyl and $C_1$-$C_6$alkyl, which is optionally substituted with 1 to 5 hydroxyl;

each $R^4$ is independently selected from H and $C_1$-$C_6$alkyl;

$L_1$ is —$X_1$C(=O)$((CH_2)_mO)_p(CH_2)_m$—, —$X_1$C(=O)$(CH_2)_m$—, —$X_2X_1$C(=O)$((CH_2)_mO)_p(CH_2)_m$—, —$X_2X_1$C(=O)$(CH_2)_m$—, —$X_3$C(=O)$((CH_2)_mO)_p(CH_2)_m$—, —$X_3$C(=O)$(CH_2)_m$—, —$X_3$C(=O)$(CH_2)_m$NHC(=O)$((CH_2)_mO)_p(CH_2)_m$—, —$X_3$C(=O)$(CH_2)_m$NHC(=O)$(CH_2)_m$—, —$X_3$C(=O)$(CH_2)_m$—, —$X_1$C(=O)$((CH_2)_mO)_p(CH_2)_mX_4(CH_2)_m$—, —$X_1$C(=O)$(CH_2)_mX_4(CH_2)_m$—, —$X_2X_1$C(=O)$((CH_2)_mO)_p(CH_2)_mX_4(CH_2)_m$— or —$X_2X_1$C(=O)$(CH_2)_mX_4(CH_2)_m$—, where  indicates the point of attachment to $R^{114}$;

$X_1$ is
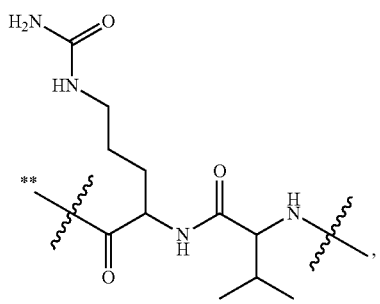
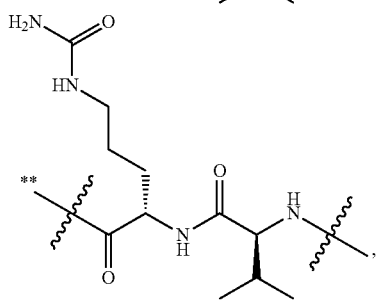
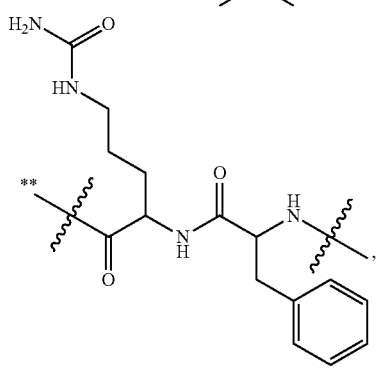
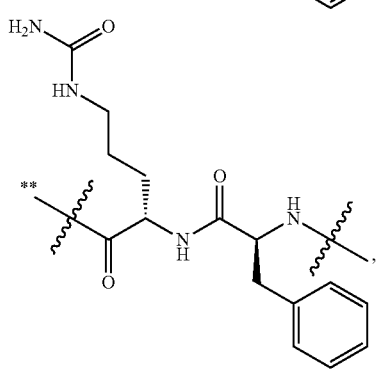
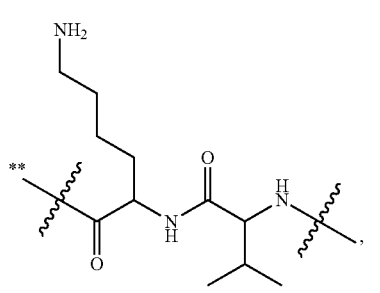
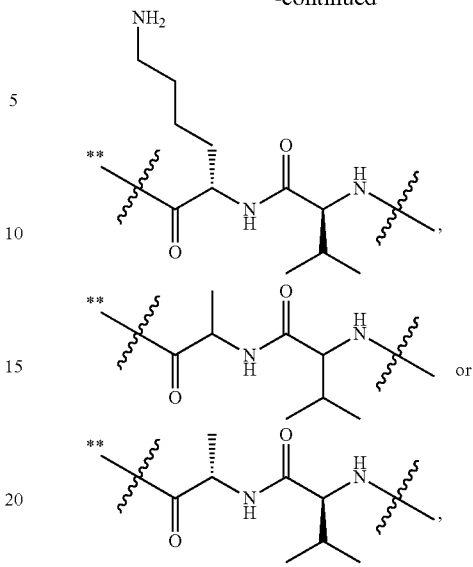
where ** indicates the point of attachment to the —NH— or to $X_2$;
$X_2$ is
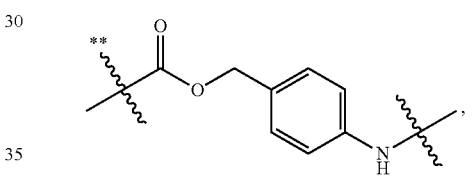
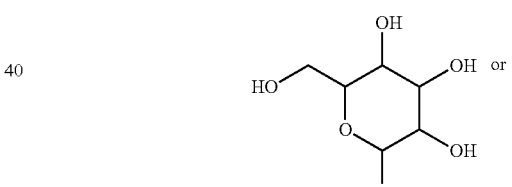
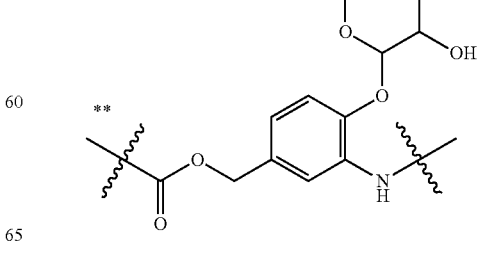

where ** indicates the point of attachment to the —NH—;
$X_3$ is
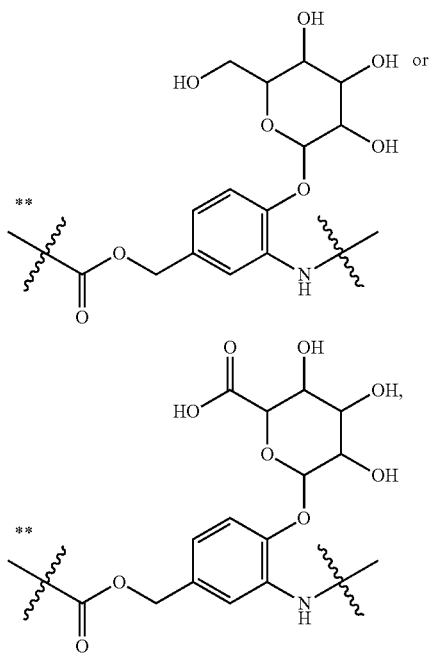
where ** indicates the point of attachment to the —NH—;
$X_4$ is
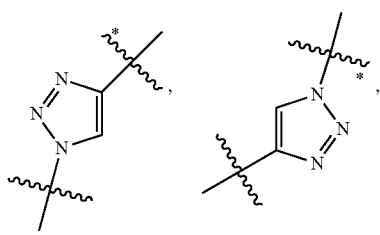
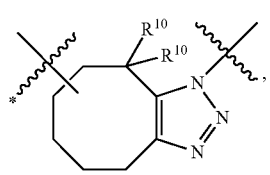
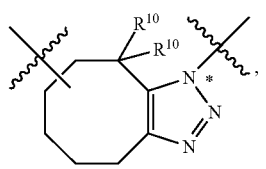
-continued
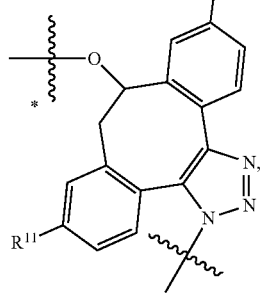
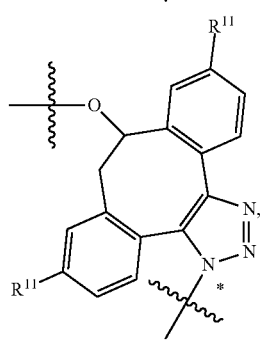
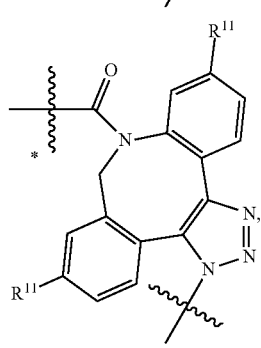
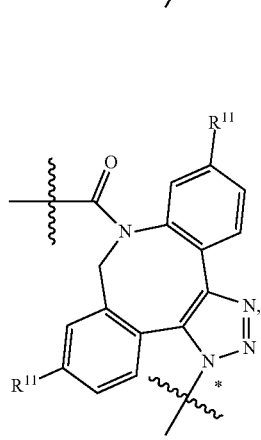
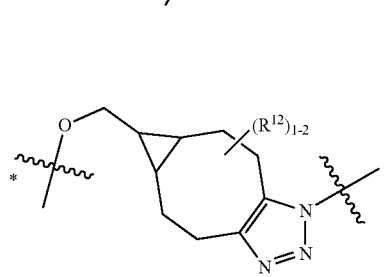
or -continued
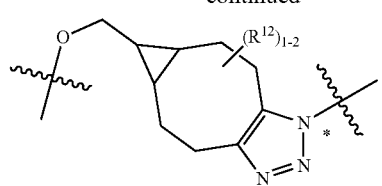
where the * indicates the point of attachment is toward $R^{114}$.
$R^{114}$ is
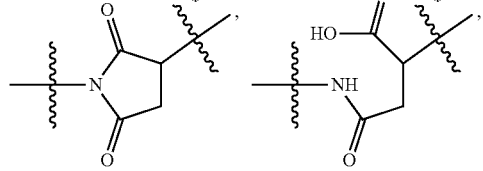
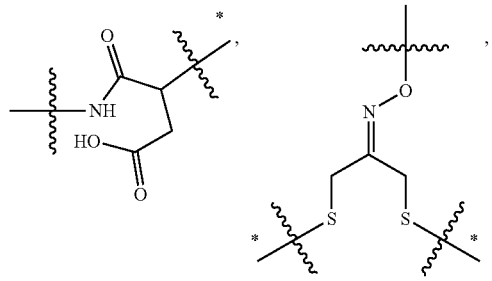
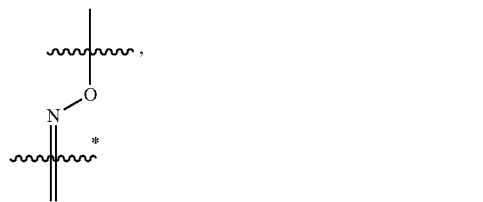
—NR$^6$C(=O)CH$_Z$—*,      —NHC(=O)CH$_2$—*,
—S(=O)$_2$CH$_2$CH$_2$—*,      —(CH$_2$)$_2$S(=O)$_2$CH$_2$CH$_2$—*,
—NR$^6$S(=O)$_2$CH$_2$CH$_2$—*,     —NR$^6$C(=O)CH$_2$CH$_2$—*,
—NH—,        —C(=O)—,        —NHC(=O)—*,
—CH$_2$NHCH$_2$CH$_2$—*, —NHCH$_2$CH$_2$—*, —S—,
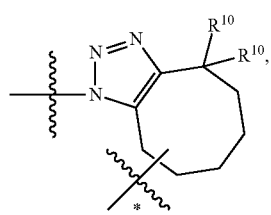
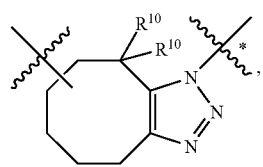
-continued
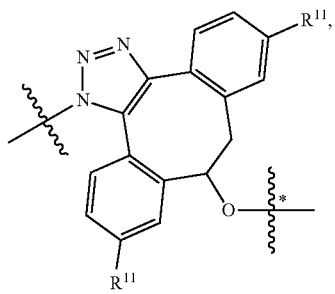
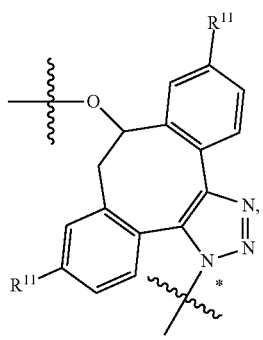
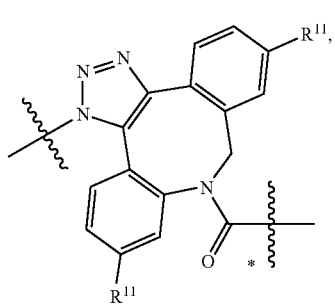
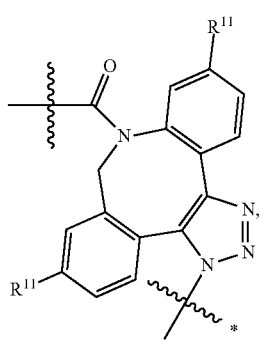
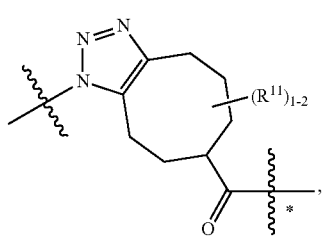

169

-continued

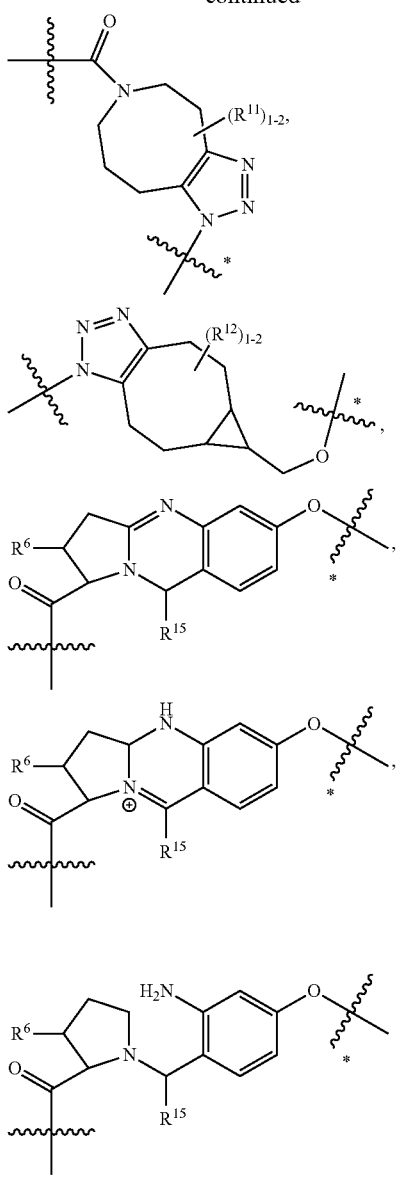

170

-continued

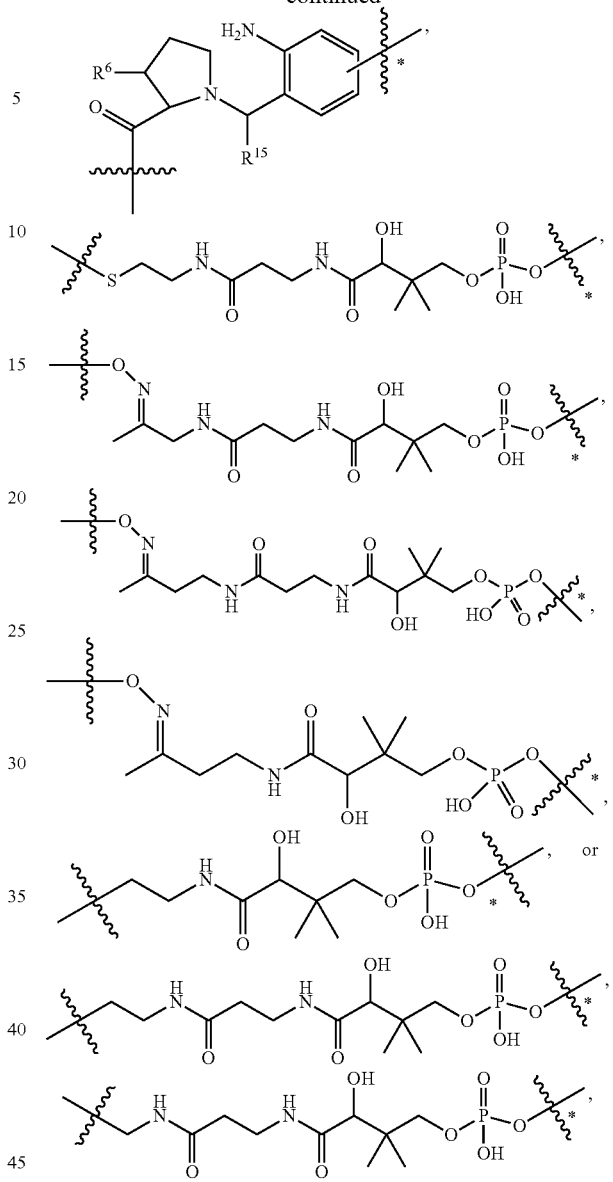

where the indicates the point of attachment to A;

each $R^6$ is independently selected from H and $C_1$-$C_6$alkyl;

each $R^{10}$ is independently selected from H, $C_1$-$C_6$alkyl, F, C, and —OH;

each $R^{11}$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;

each $R^{12}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each $R^{15}$ is independently selected from H, —$CH_3$ and phenyl;

each m is independently selected from 1, 2, 3, 4, 5, 6, 7, 8, 9 and 10, and each p is independently selected from 1, 2, 3, 4, 5, 6, 7, 8, 9, 10, 11, 12, 13 and 14.

In one aspect the conjugates of the disclosure have the structure of Formula (H):

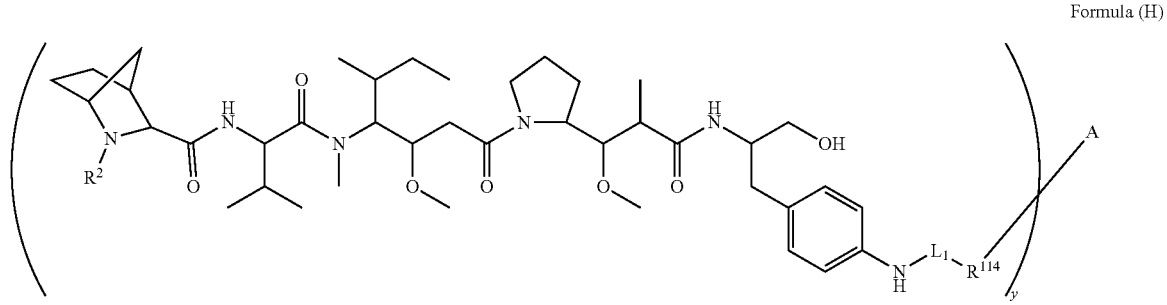

Formula (H)

wherein:
- A represents an antibody or antibody fragment (e.g., antigen binding fragment) that specifically binds to human CD48;
- y is an integer from 1 to 10;
- $R^2$ is H, $C_1$-$C_6$alkyl, —C(=O)$R^3$, —(CH$_2$)$_m$OH, —C(=O)(CH$_2$)$_m$OH, —C(=O)((CH$_2$)$_m$O)$_n$$R^4$, —((CH$_2$)$_m$O)$_n$$R^4$ or $C_1$-$C_6$alkyl which is optionally substituted with —CN, —C(=O)NH$_2$ or 1 to 5 hydroxy;
- each $R^3$ is independently selected from $C_1$-$C_6$alkyl and $C_1$-$C_6$alkyl, which is optionally substituted with 1 to 5 hydroxyl;
- each $R^4$ is independently selected from H and $C_1$-$C_6$alkyl;
- $L_1$ is —X$_1$C(=O)((CH$_2$)$_m$O)$_p$(CH$_2$)$_m$—, —X$_1$C(=O)(CH$_2$)$_m$—, —X$_2$X$_1$C(=O)((CH$_2$)$_m$O)$_p$(CH$_2$)$_m$—, —X$_2$X$_1$C(=O)(CH$_2$)$_m$—, —X$_3$C(=O)((CH$_2$)$_m$O)$_p$(CH$_2$)$_m$—, —X$_3$C(=O)(CH$_2$)$_m$—, —X$_3$C(=O)(CH$_2$)$_m$NHC(=O)((CH$_2$)$_m$O)$_p$(CH$_2$)$_m$—, —X$_3$C(=O)(CH$_2$)$_m$NHC(=O)(CH$_2$)$_m$—, —X$_3$C(=O)(CH$_2$)$_m$—, —X$_1$C(=O)((CH$_2$)$_m$O)$_p$(CH$_2$)$_m$X$_4$(CH$_2$)$_m$—, —X$_1$C(=O)(CH$_2$)$_m$X$_4$(CH$_2$)$_m$—, —X$_2$X$_1$C(=O)((CH$_2$)$_m$O)$_p$(CH$_2$)$_m$X$_4$(CH$_2$)$_m$— or —X$_2$X$_1$C(=O)(CH$_2$)$_m$X$_4$(CH$_2$)$_m$—, where  indicates the point of attachment to $R^{14}$;
- $X_1$ is

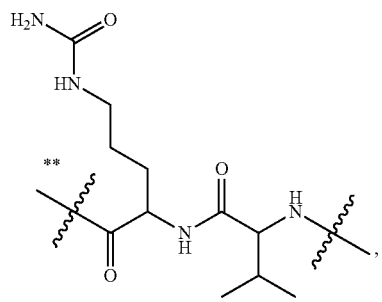

-continued

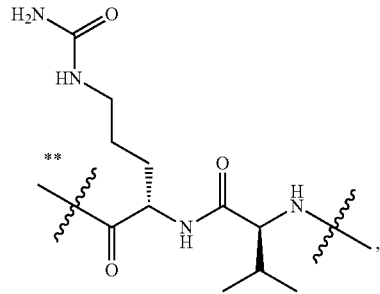

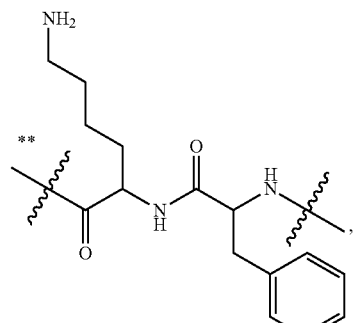

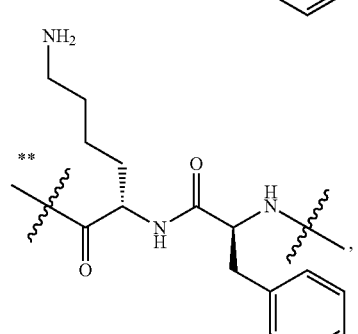

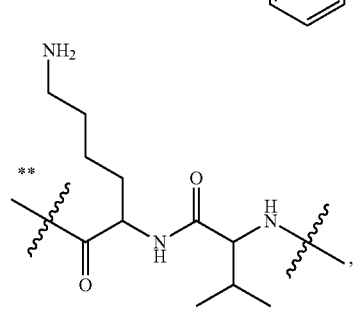

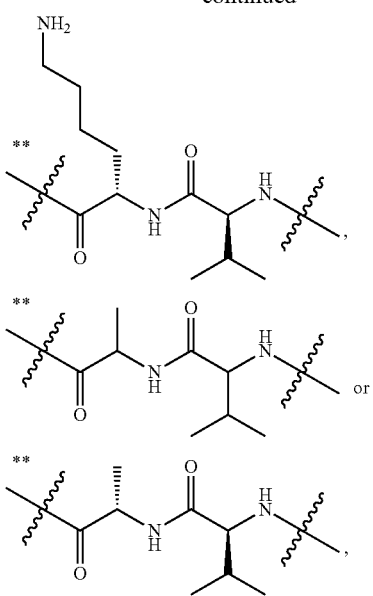
where ** indicates the point of attachment to the —NH— or to $X_2$;
$X_2$ is
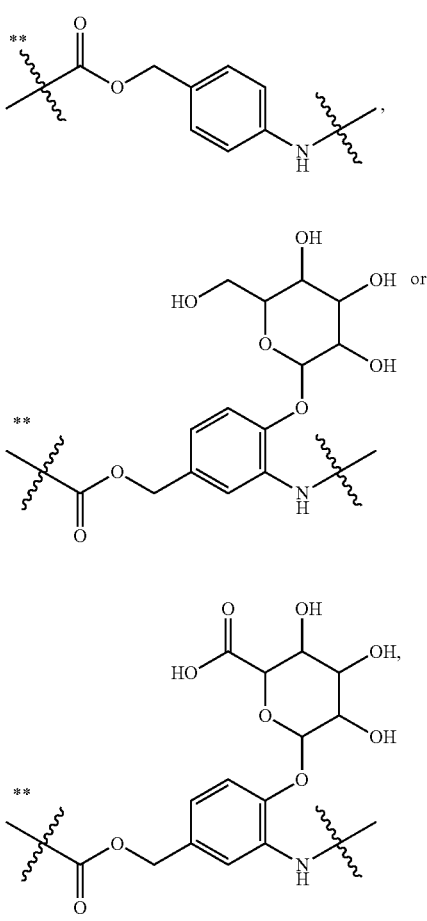
where ** indicates the point of attachment to the —NH—;
$X_3$ is
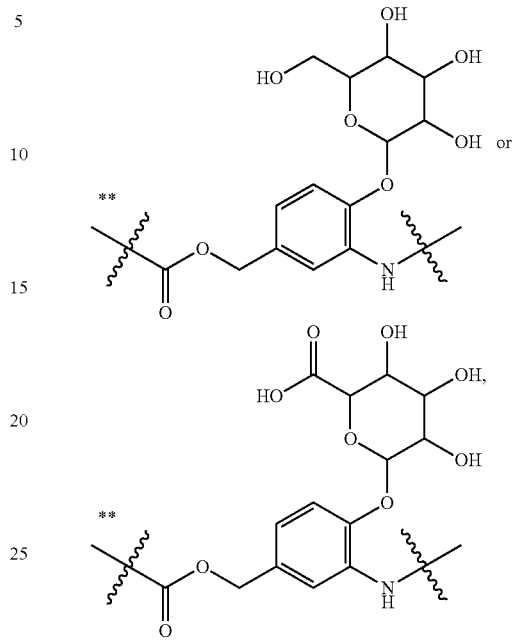
where ** indicates the point of attachment to the —NH—;
$X_4$ is
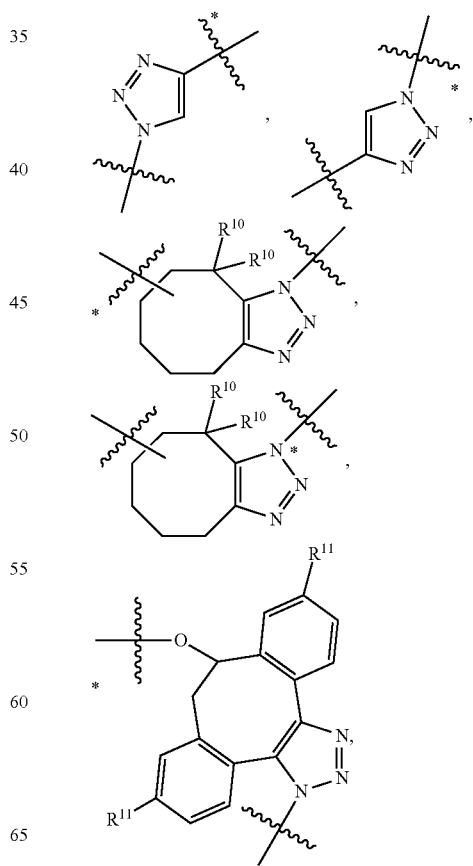

-continued
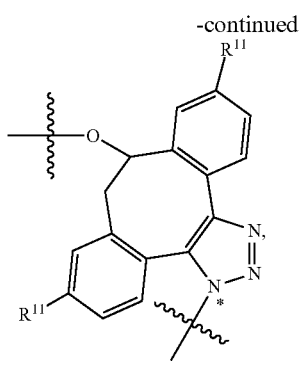
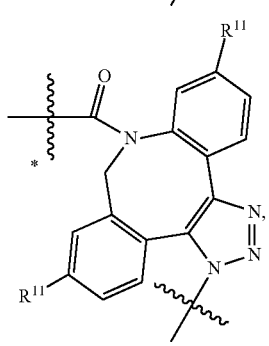
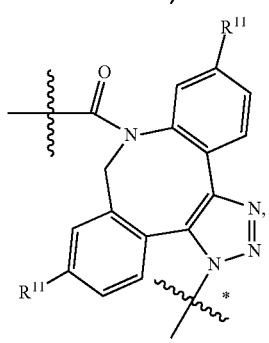
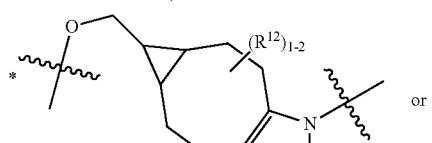
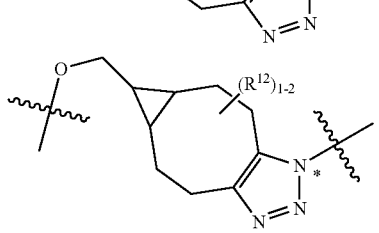
where the * indicates the point of attachment is toward R[114]; R[114] is
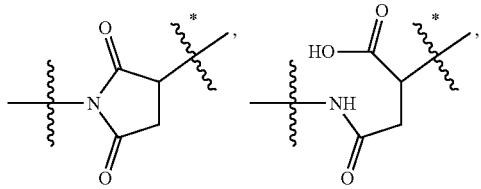
-continued
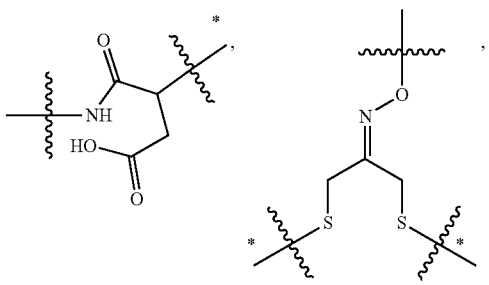
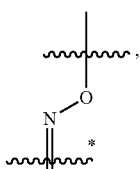
—NR[6]C(=O)CH₂—*,    —NHC(=O)CH₂—*,
—S(=O)₂CH₂CH₂—*,    —(CH₂)₂S(=O)₂CH₂CH₂—*,
—NR[6]S(=O)₂CH₂CH₂—*,    —NR[6]C(=O)CH₂CH₂—*,
—NH—,    —C(=O)—,    —NHC(=O)—*,
—CH₂NHCH₂CH₂—*, —NHCH₂CH₂—*, —S—,
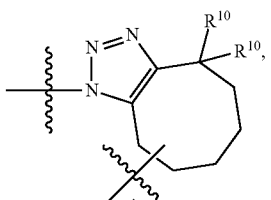
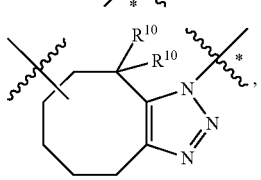
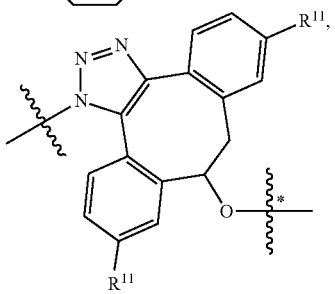
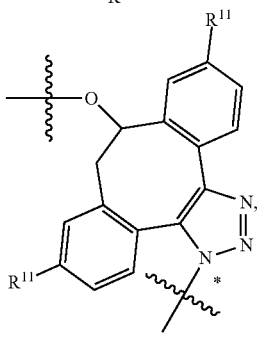

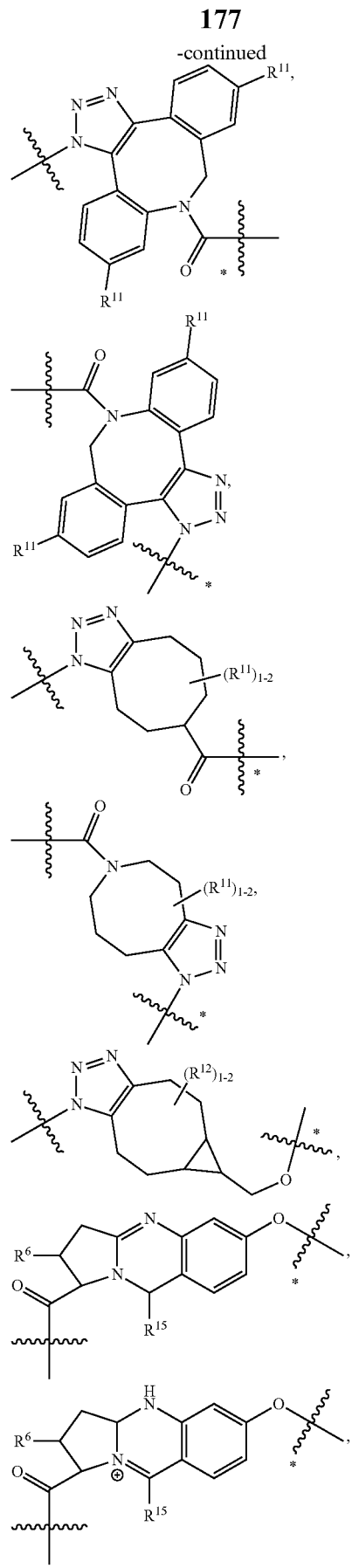
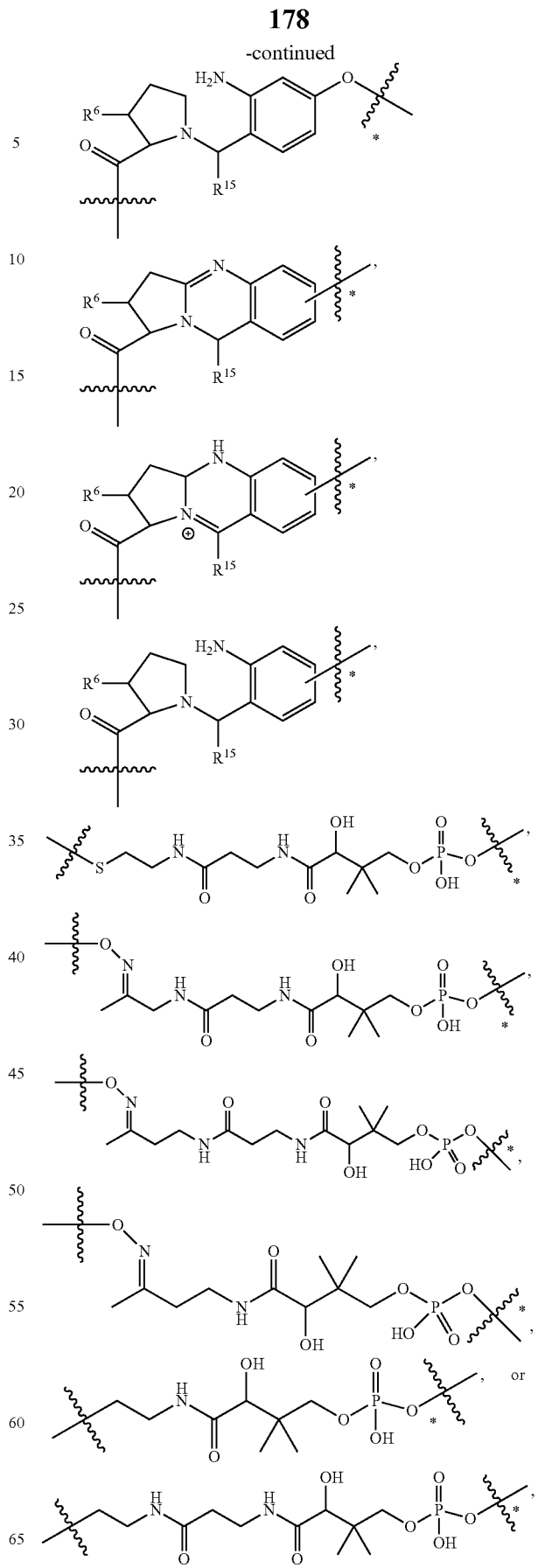

-continued

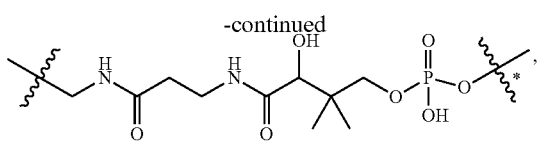

where the * indicates the point of attachment to A;

each $R^6$ is independently selected from H and $C_1$-$C_6$alkyl;

each $R^{10}$ is independently selected from H, $C_1$-$C_6$alkyl, F, Cl, and —OH;

each $R^{11}$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;

each $R^{12}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each $R^{15}$ is independently selected from H, —$CH_3$ and phenyl;

each m is independently selected from 1, 2, 3, 4, 5, 6, 7, 8, 9 and 10, and each p is independently selected from 1, 2, 3, 4, 5, 6, 7, 8, 9, 10, 11, 12, 13 and 14.

Certain aspects and examples of the conjugates are provided in the following listing of additional, enumerated embodiments. It will be recognized that features specified in each embodiment may be combined with other specified features to provide further embodiments of the present disclosure.

Embodiment 73. The conjugate having the structure of Formula (E) is a conjugate having has the structure of Formula (E-1):

Formula (E-1)

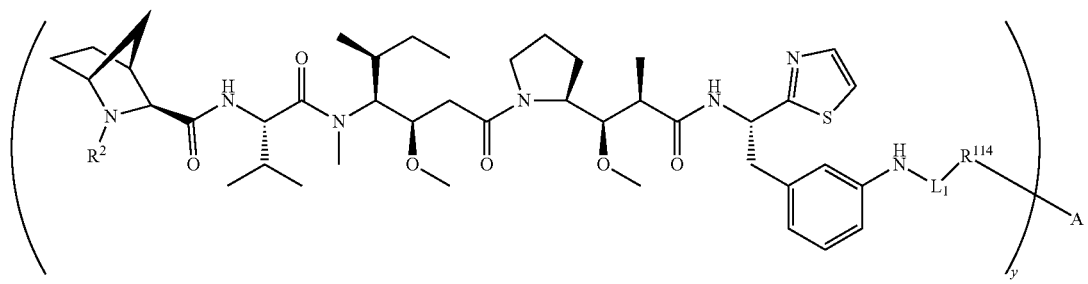

wherein: $R^2$, $R^{114}$, A, y, and $L_1$ are as defined for conjugates of Formula (E) above.

Embodiment 74. The conjugate having the structure of Formula (F) is a conjugate having has the structure of Formula (F-1):

Formula (F-1)

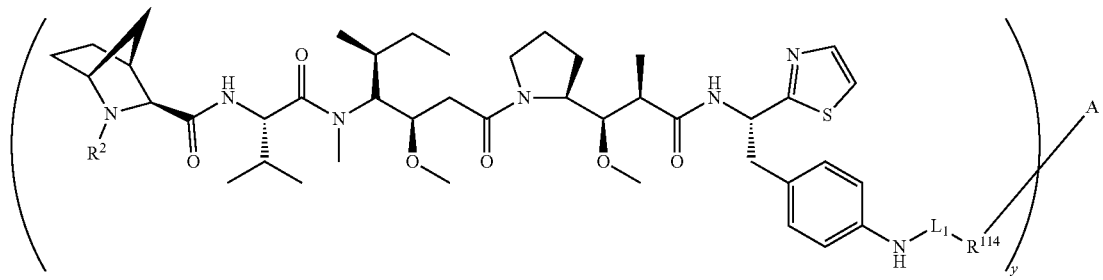

wherein: $R^2$, $R^{114}$, A, y, and $L_1$ are as defined for conjugates of Formula (F) above.

Embodiment 75. The conjugate having the structure of Formula (G) is a conjugate having has the structure of Formula (G-1):

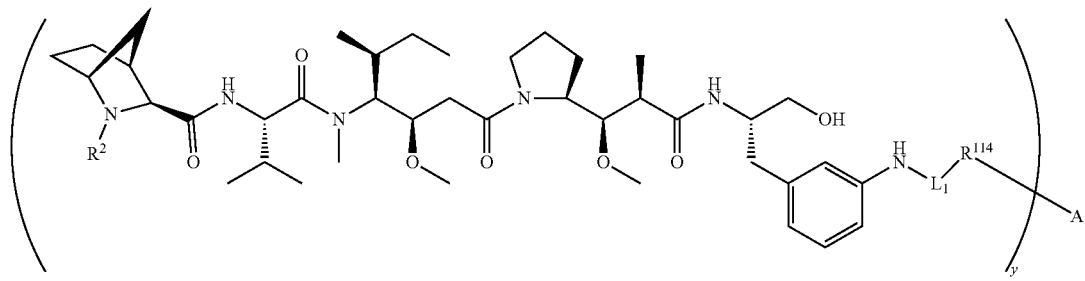

Formula (G-1)

wherein: $R^2$, $R^{114}$, A, y, and $L_1$ are as defined for conjugates of Formula (G) above.

Embodiment 76. The conjugate having the structure of Formula (H) is a conjugate having has the structure of Formula (H-1):

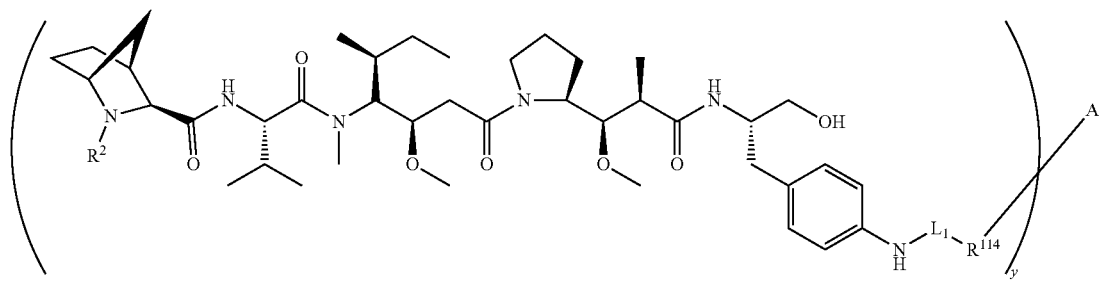

Formula (H-1)

wherein: $R^2$, $R^{114}$, A, y, and $L_1$ are as defined for conjugates of Formula (H) above.

Embodiment 77. The conjugate of Formula (E), Formula (F), Formula (G), Formula (H) or any one of Embodiments 69 to 72, wherein $R^2$ is H or $C_1$-$C_6$alkyl.

Embodiment 78. The conjugate of Formula (E), Formula (F), Formula (G), Formula (H) or any one of Embodiments 69 to 72, wherein $R^2$ is H or methyl.

Embodiment 79. The conjugate of Formula (E), Formula (F), Formula (G), Formula (H) or any one of Embodiments 69 to 72, wherein $R^2$ is H.

Embodiment 80. The conjugate of Formula (E), Formula (F), Formula (G), Formula (H) or any one of Embodiments 69 to 72, wherein $R^2$ is methyl.

Embodiment 81. The conjugate having the structure of Formula (E) is a conjugate having has the structure of Formula (E-2):

Formula (E-2)

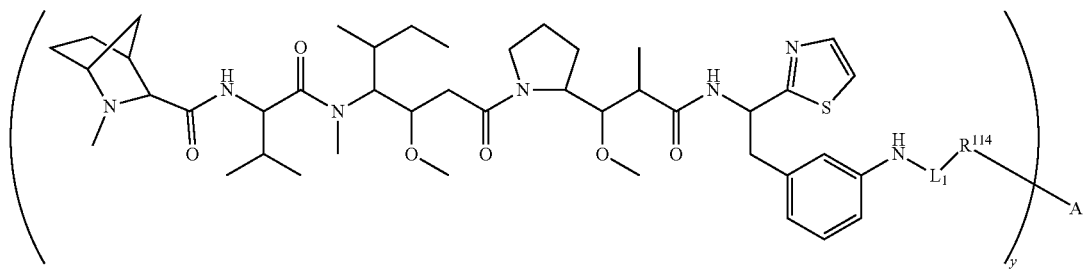

wherein: $R^{114}$, A, y, and $L_1$ are as defined for conjugates of Formula (E) above.

Embodiment 82. The conjugate having the structure of Formula (E) is a conjugate having has the structure of Formula (E-3):

Formula (E-3)

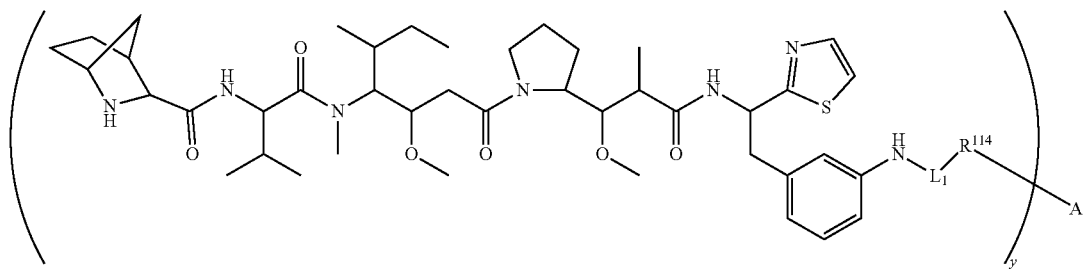

wherein: $R^{114}$, A, y, and $L_1$ are as defined for conjugates of Formula (E) above.

Embodiment 83. The conjugate having the structure of Formula (E) or Formula (E-1) is a conjugate having has the structure of Formula (E-4):

Formula (E-4)

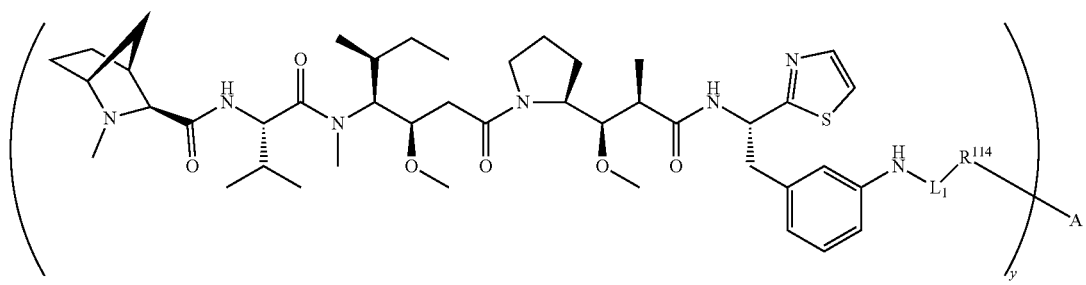

wherein: $R^{114}$, A, y, and $L_1$ are as defined for conjugates of Formula (E) above.

Embodiment 84. The conjugate having the structure of Formula (E) or Formula (E-1) is a conjugate having has the structure of Formula (E-5):

Formula (E-5)

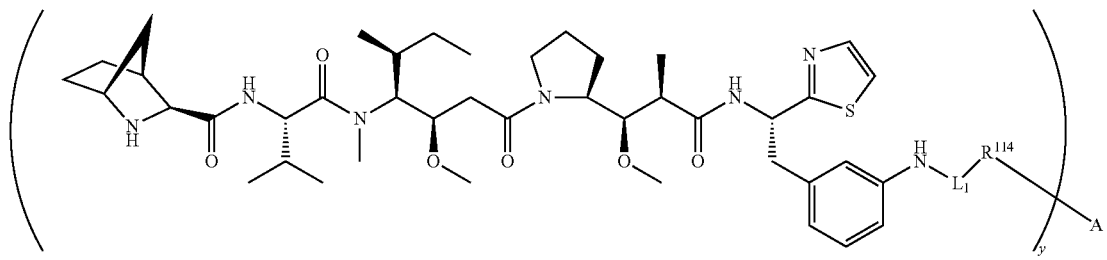

wherein: $R^{114}$, A, y, and $L_1$ are as defined for conjugates of Formula (E) above.

Embodiment 85. The conjugate having the structure of Formula (F) is a conjugate having has the structure of Formula (F-2):

Formula (F-2)

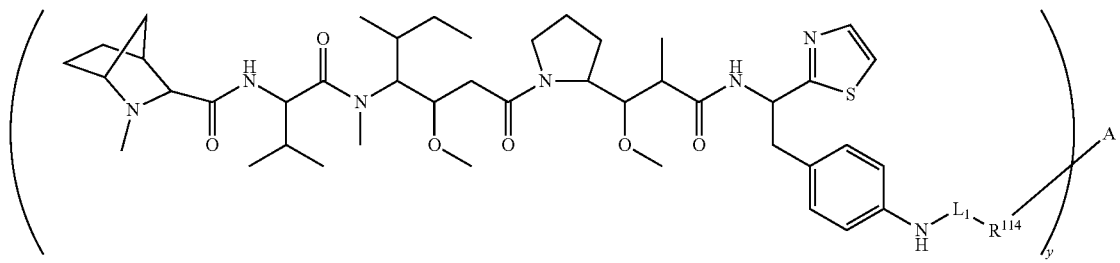

wherein: $R^{114}$, A, y, and $L_1$ are as defined for conjugates of Formula (F) above.

Embodiment 86. The conjugate having the structure of Formula (F) is a conjugate having has the structure of Formula (F-3):

Formula (F-3)

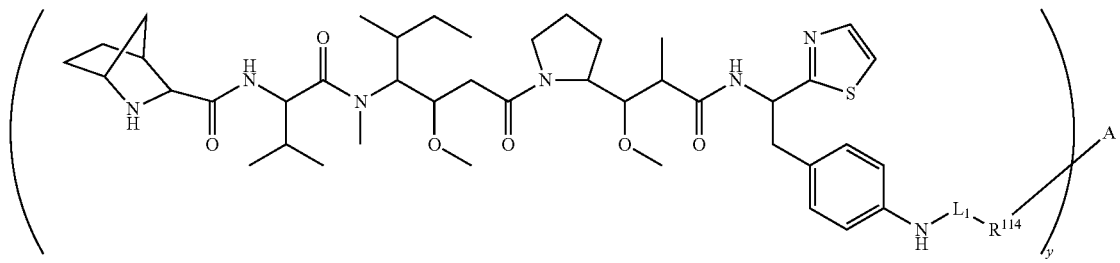

wherein: $R^{114}$, A, y, and $L_1$ are as defined for conjugates of Formula (F) above.

Embodiment 87. The conjugate having the structure of Formula (F) or Formula (F-1) is a conjugate having has the structure of Formula (F-4):

Formula (F-4)

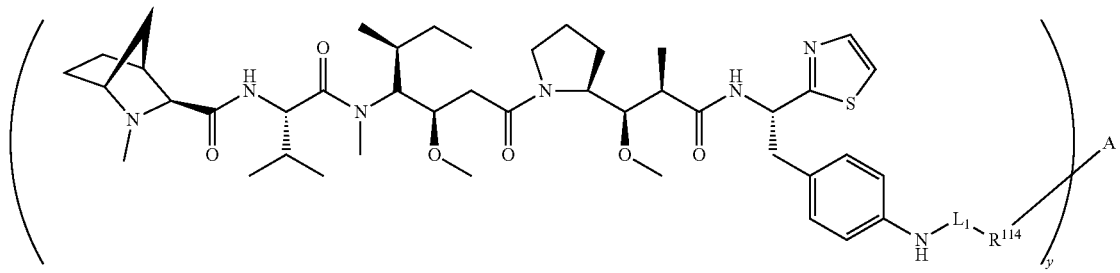

wherein: $R^{114}$, A, y, and $L_1$ are as defined for conjugates of Formula (F) above.

Embodiment 88. The conjugate having the structure of Formula (F) or Formula (F-1) is a conjugate having has the structure of Formula (F-5):

Formula (F-5)

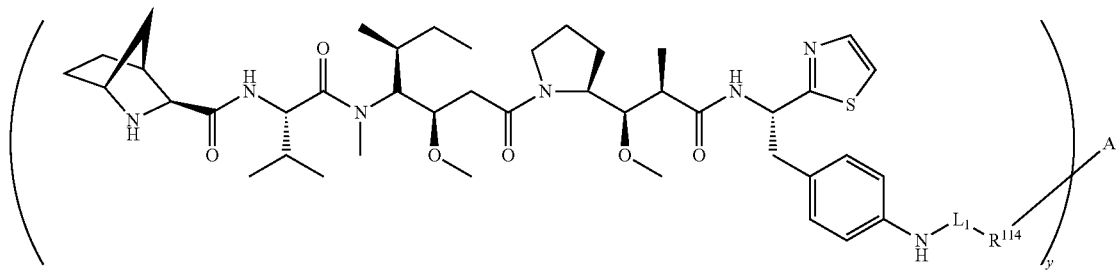

wherein: $R^{114}$, A, y, and $L_1$ are as defined for conjugates of Formula (F) above.

Embodiment 89. The conjugate having the structure of Formula (G) is a conjugate having has the structure of Formula (G-2):

Formula (G-2)

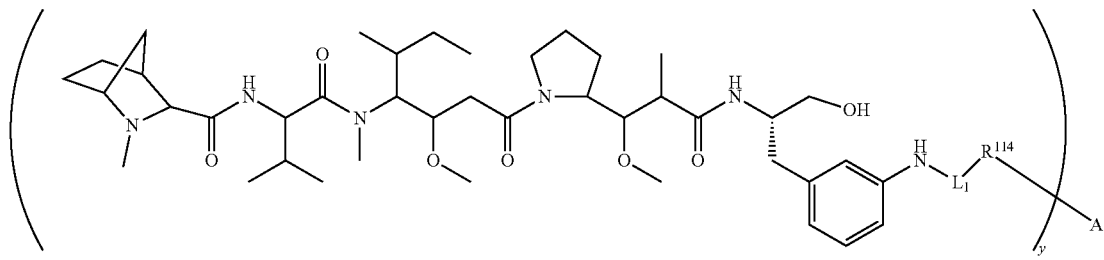

wherein: $R^{114}$, A, y, and $L_1$ are as defined for conjugates of Formula (G) above.

Embodiment 90. The conjugate having the structure of Formula (G) is a conjugate having has the structure of Formula (G-3):

Formula (G-3)

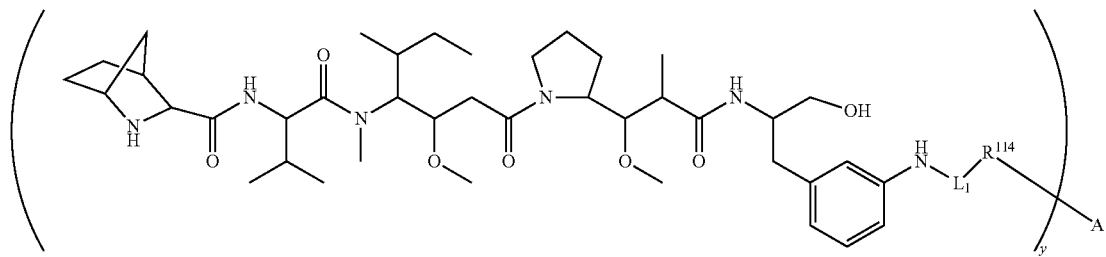

wherein: $R^{114}$, A, y, and $L_1$ are as defined for conjugates of Formula (G) above.

Embodiment 91. The conjugate having the structure of Formula (G) or Formula (G-1) is a conjugate having has the structure of Formula (G-4):

Formula (G-4)

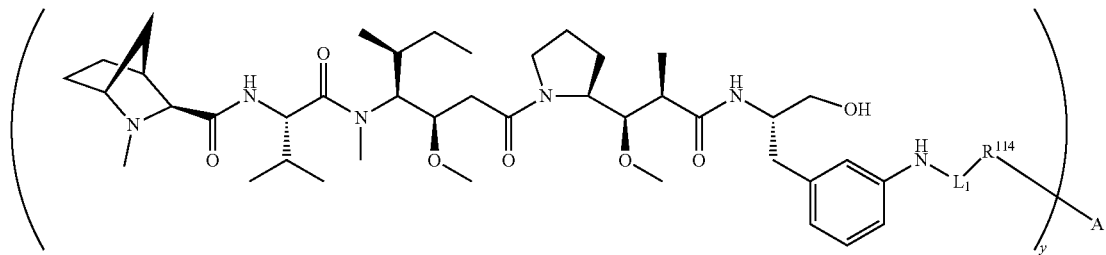

wherein: $R^{114}$, A, y, and $L_1$ are as defined for conjugates of Formula (G) above.

Embodiment 92. The conjugate having the structure of Formula (G) or Formula (G-1) is a conjugate having has the structure of Formula (G-5):

Formula (G-5)

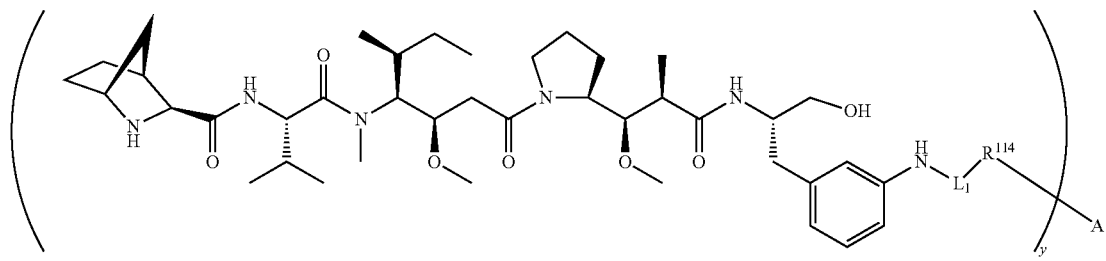

wherein: $R^4$, A, y, and $L_1$ are as defined for conjugates of Formula (G) above.

Embodiment 93. The conjugate having the structure of Formula (H) is a conjugate having has the structure of Formula (H-2):

Formula (H-2)

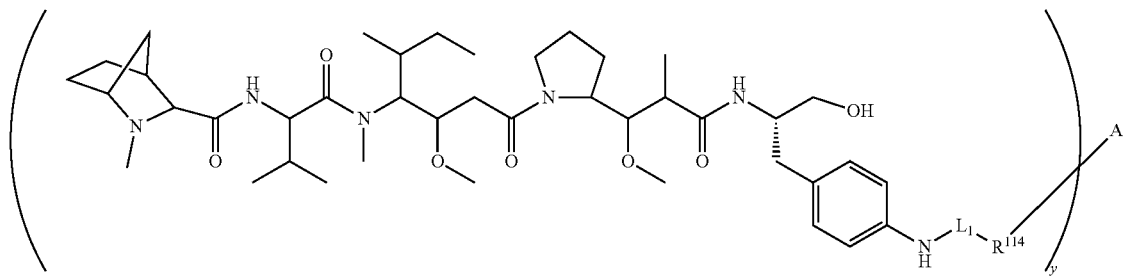

wherein: $R^4$, A, y, and $L_1$ are as defined for conjugates of Formula (H) above.

Embodiment 94. The conjugate having the structure of Formula (H) is a conjugate having has the structure of Formula (H-3):

Formula (H-3)

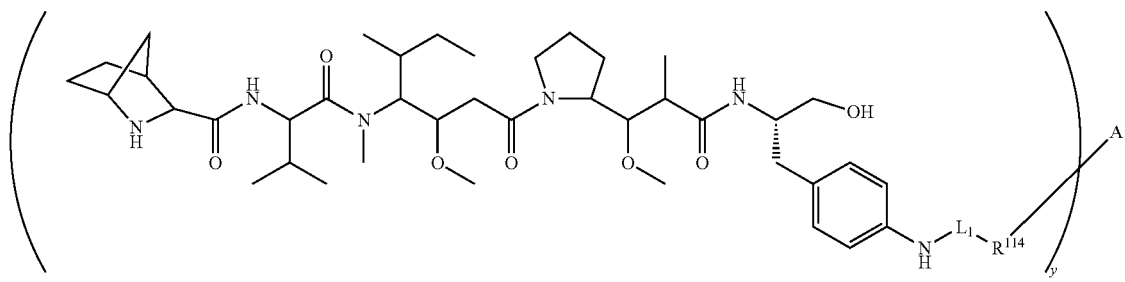

wherein: $R^4$, A, y, and $L_1$ are as defined for conjugates of Formula (H) above.

Embodiment 95. The conjugate having the structure of Formula (H) or Formula (H-1) is a conjugate having has the structure of Formula (H-4):

Formula (H-4)

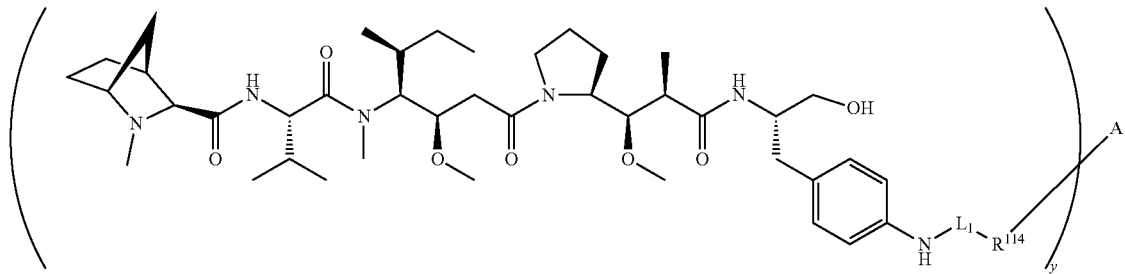

wherein: $R^4$, A, y, and $L_1$ are as defined for conjugates of Formula (H) above.

Embodiment 96. The conjugate having the structure of Formula (H) or Formula (H-1) is a conjugate having has the structure of Formula (H-5):

Formula (H-5)

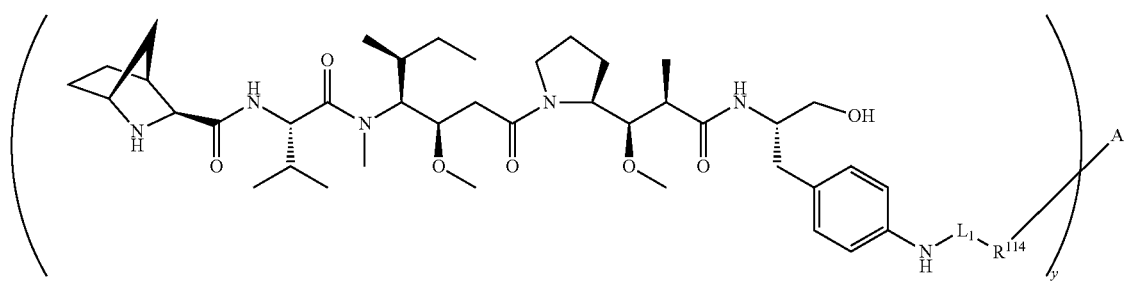

wherein: $R^{114}$, A, y, and $L_1$ are as defined for conjugates of Formula (H) above.

Embodiment 97. The conjugate of Formula (E), Formula (F), Formula (G), Formula (H) or the conjugate of any one of Embodiments 73 to 96, wherein:

$L_1$ is $-X_1C(=O)((CH_2)_mO)_p(CH_2)_m-$ or $-X_1C(=O)(CH_2)_m-$, where ** indicates the point of attachment to $R^{114}$;

and $X_1$ is

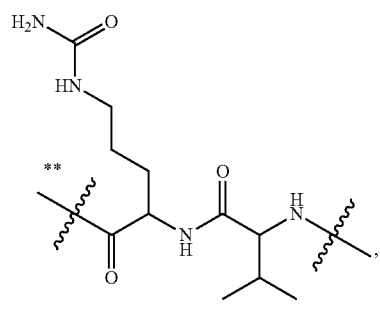

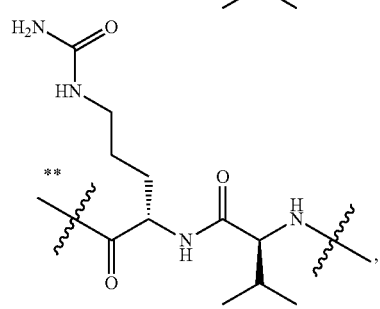

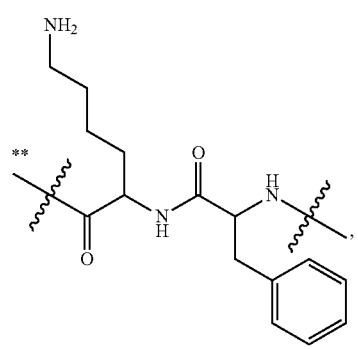

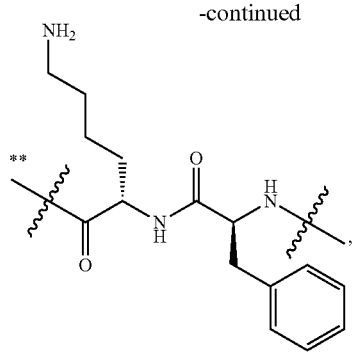

where ** indicates the point of attachment to the —NH— or to $X_2$.

Embodiment 98. The conjugate of Formula (E), Formula (F), Formula (G), Formula (H) or the conjugate of any one of Embodiments 73 to 96, wherein:

$L_1$ is $-X_1C(=O)((CH_2)_mO)_p(CH_2)_m-$, where  indicates the point of attachment to $R^{114}$; and $X_1$ is

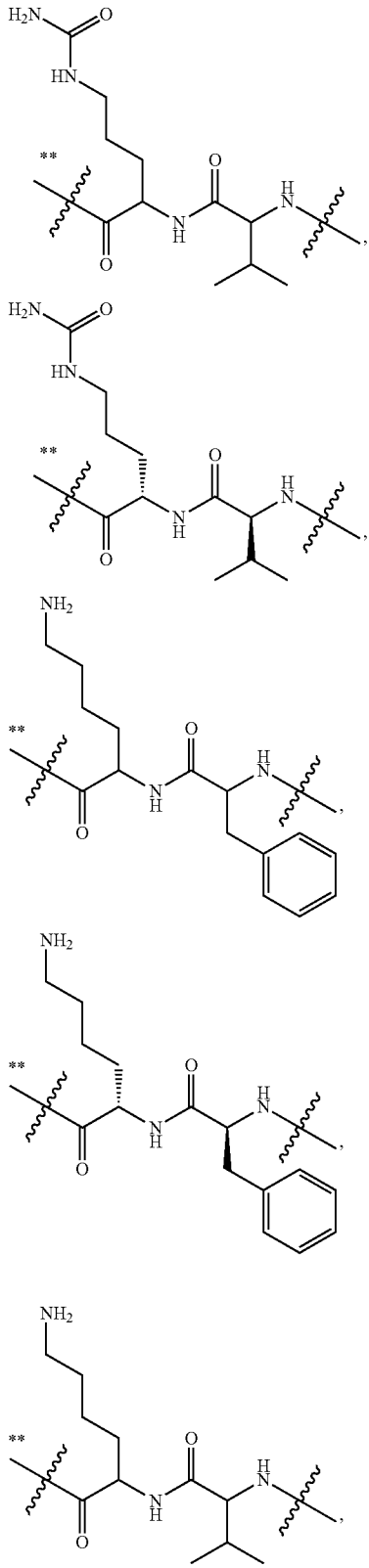

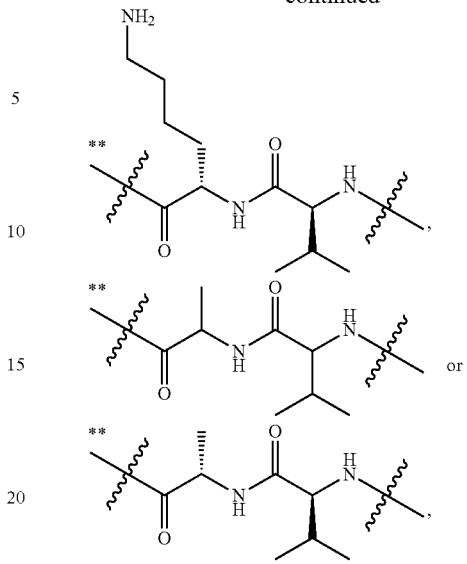

where ** indicates the point of attachment to the —NH— or to $X_2$.

Embodiment 99. The conjugate of Formula (E), Formula (F), Formula (G), Formula (H) or the conjugate of any one of Embodiments 73 to 98, each m is independently selected from 1, 2, 3, 4, 5 and 6.

Embodiment 100. The conjugate of Formula (E), Formula (F), Formula (G), Formula (H) or the conjugate of any one of Embodiments 73 to 98, each m is independently selected from 1, 2, 3, 4 and 5.

Embodiment 101. The conjugate of Formula (E), Formula (F), Formula (G), Formula (H) or the conjugate of any one of Embodiments 73 to 98, each m is independently selected from 1, 2, 3 and 4.

Embodiment 102. The conjugate of Formula (E), Formula (F), Formula (G), Formula (H) or the conjugate of any one of Embodiments 73 to 98, each m is independently selected from 1, 2 and 3.

Embodiment 103. The conjugate of Formula (E), Formula (F), Formula (G), Formula (H) or the conjugate of any one of Embodiments 73 to 98, each m is independently selected from 1 and 2.

Embodiment 104. The conjugate of Formula (E), Formula (F), Formula (G), Formula (H) or the conjugate of any one of Embodiments 73 to 103, each n is independently selected from 1, 2, 3, 4, 5, 6, 7, 8, 9, 10, 11 and 12.

Embodiment 105. The conjugate of Formula (E), Formula (F), Formula (G), Formula (H) or the conjugate of any one of Embodiments 73 to 103, each n is independently selected from 1, 2, 3, 4, 5, 6, 7, 8, 9, 10 and 11.

Embodiment 106. The conjugate of Formula (E), Formula (F), Formula (G), Formula (H) or the conjugate of any one of Embodiments 73 to 103, each n is independently selected from 1, 2, 3, 4, 5, 6, 7, 8, 9 and 10.

Embodiment 107. The conjugate of Formula (E), Formula (F), Formula (G), Formula (H) or the conjugate of any one of Embodiments 73 to 103, each n is independently selected from 1, 2, 3, 4, 5, 6, 7, 8 and 9.

Embodiment 108. The conjugate of Formula (E), Formula (F), Formula (G), Formula (H) or the conjugate of any one of Embodiments 73 to 103, each n is independently selected from 1, 2, 3, 4, 5, 6, 7 and 8.

Embodiment 109. The conjugate of Formula (E), Formula (F), Formula (G), Formula (H) or the conjugate of any one of Embodiments 73 to 103, each n is independently selected from 1, 2, 3, 4, 5, 6 and 7.

Embodiment 110. The conjugate of Formula (E), Formula (F), Formula (G), Formula (H) or the conjugate of any one of Embodiments 73 to 103, each n is independently selected from 1, 2, 3, 4, 5 and 6.

Embodiment 111. The conjugate of Formula (E), Formula (F), Formula (G), Formula (H) or the conjugate of any one of Embodiments 73 to 103, each n is independently selected from 1, 2, 3, 4 and 5.

Embodiment 112. The conjugate of Formula (E), Formula (F), Formula (G), Formula (H) or the conjugate of any one of Embodiments 73 to 103, each n is independently selected from 1, 2, 3 and 4.

Embodiment 113. The conjugate of Formula (E), Formula (F), Formula (G), Formula (H) or the conjugate of any one of Embodiments 73 to 103, each n is independently selected from 1, 2 and 3. In any of the above embodiments, each n is independently selected from 1 and 2.

Embodiment 114. The conjugate of Formula (E), Formula (F), Formula (G), Formula (H) or the conjugate of any one of Embodiments 73 to 113, each y is independently selected from 1, 2, 3, 4, 5, 6, 7, 8, 9, 10, 11 and 12.

Embodiment 115. The conjugate of Formula (E), Formula (F), Formula (G), Formula (H) or the conjugate of any one of Embodiments 73 to 113, each y is independently selected from 1, 2, 3, 4, 5, 6, 7, 8, 9, 10 and 11.

Embodiment 116. The conjugate of Formula (E), Formula (F), Formula (G), Formula (H) or the conjugate of any one of Embodiments 73 to 113, each y is independently selected from 1, 2, 3, 4, 5, 6, 7, 8, 9 and 10.

Embodiment 117. The conjugate of Formula (E), Formula (F), Formula (G), Formula (H) or the conjugate of any one of Embodiments 73 to 113, each y is independently selected from 1, 2, 3, 4, 5, 6, 7, 8 and 9.

Embodiment 118. The conjugate of Formula (E), Formula (F), Formula (G), Formula (H) or the conjugate of any one of Embodiments 73 to 113, each y is independently selected from 1, 2, 3, 4, 5, 6, 7 and 8.

Embodiment 119. The conjugate of Formula (E), Formula (F), Formula (G), Formula (H) or the conjugate of any one of Embodiments 73 to 113, each y is independently selected from 1, 2, 3, 4, 5, 6 and 7.

Embodiment 120. The conjugate of Formula (E), Formula (F), Formula (G), Formula (H) or the conjugate of any one of Embodiments 73 to 113, each y is independently selected from 1, 2, 3, 4, 5 and 6.

Embodiment 121. The conjugate of Formula (E), Formula (F), Formula (G), Formula (H) or the conjugate of any one of Embodiments 73 to 113, each y is independently selected from 1, 2, 3, 4 and 5.

Embodiment 122. The conjugate of Formula (E), Formula (F), Formula (G), Formula (H) or the conjugate of any one of Embodiments 73 to 113, each y is independently selected from 1, 2, 3 and 4.

Embodiment 123. The conjugate of Formula (E), Formula (F), Formula (G), Formula (H) or the conjugate of any one of Embodiments 73 to 113, each y is independently selected from 1, 2 and 3.

Embodiment 124. The conjugate of Formula (E), Formula (F), Formula (G), Formula (H) or the conjugate of any one of Embodiments 73 to 113, each y is independently selected from 1 and 2.

Embodiment 125. The conjugate of Formula (E), Formula (F), Formula (G), Formula (H) or the conjugate of any one of Embodiments 73 to 124, wherein:

$L_1$ is

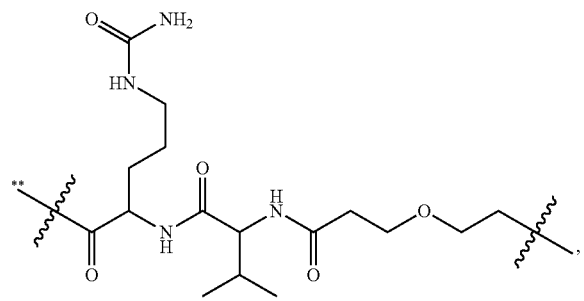

where ** indicates the point of attachment to the —NH— or to $X_2$.

Embodiment 126. The conjugate of Formula (E), Formula (F), Formula (G), Formula (H) or the conjugate of any one of Embodiments 73 to 124, wherein:

$L_1$ is

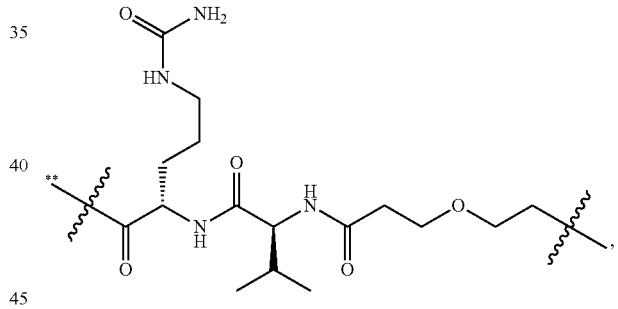

where ** indicates the point of attachment to the —NH— or to $X_2$.

Embodiment 127. The conjugate of Formula (E), Formula (F), Formula (G), Formula (H) or the conjugate of any one of Embodiments 73 to 126, wherein:

$R^{114}$ is

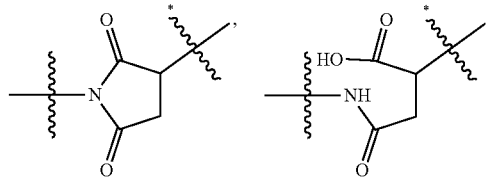

199
-continued
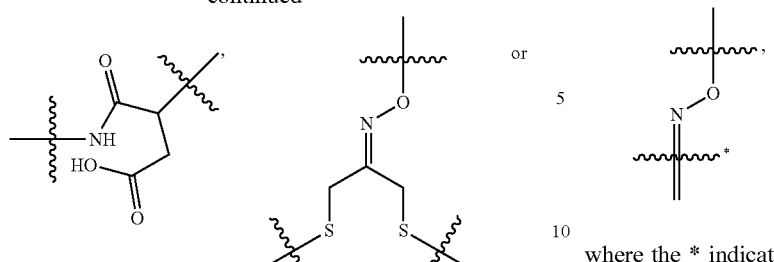
200
-continued
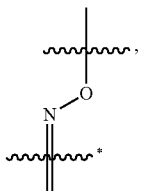
where the * indicates the point of attachment to A.
Embodiment 128. The conjugate of Formula (E), Formula (E-1), Formula (E-2) and Formula (E-4) selected from:
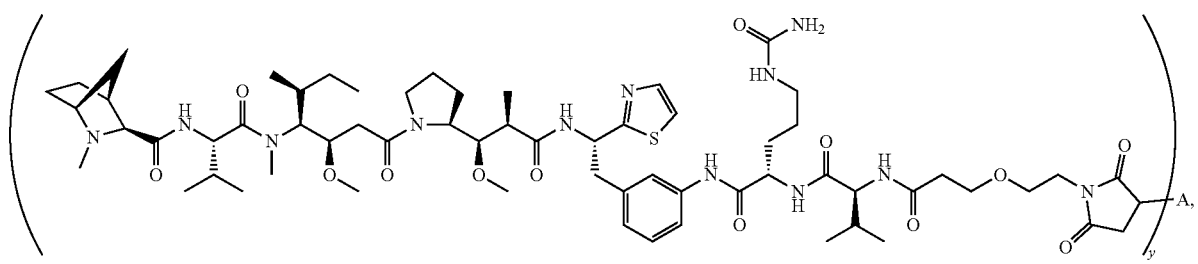
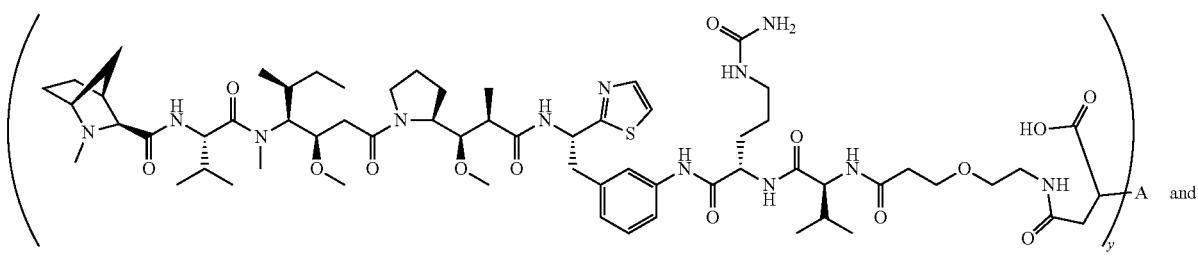
and
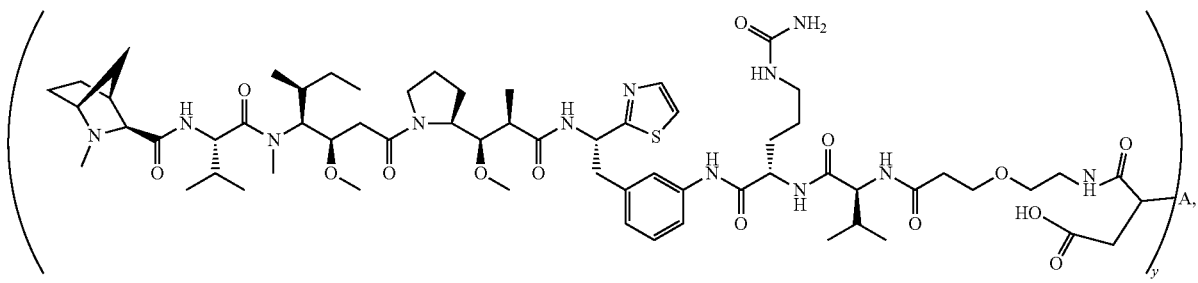

where y and A are as defined for conjugates of Formula (E) above.
Embodiment 129. The conjugate of Formula (E), Formula (E-1), Formula (E-3) and Formula (E-5) selected from:
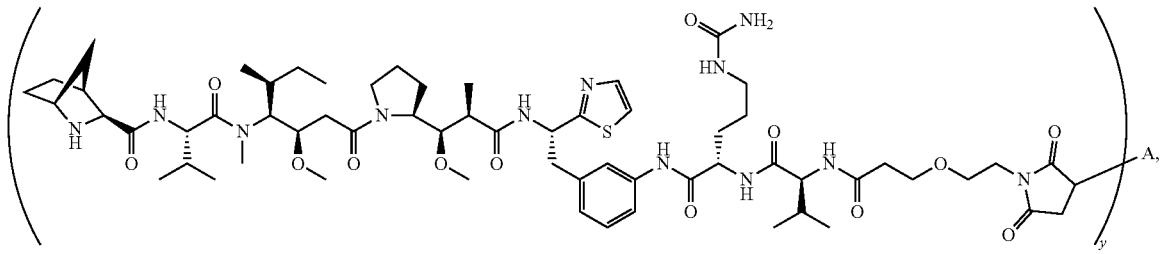
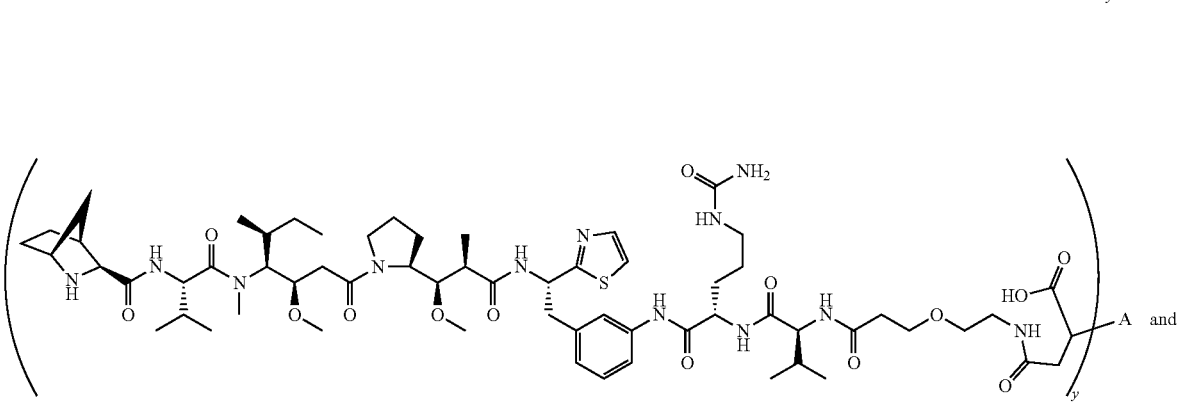
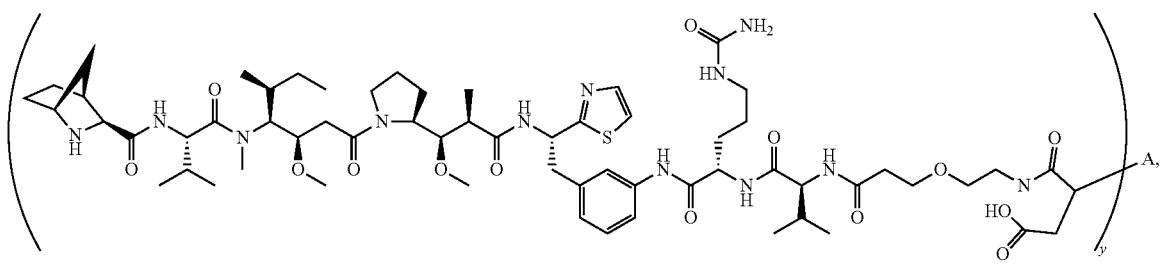
where y and A are as defined for conjugates of Formula (E) above.
Embodiment 130. The conjugate of Formula (F), Formula (F-1), Formula (F-2) and Formula (F-4) selected from:
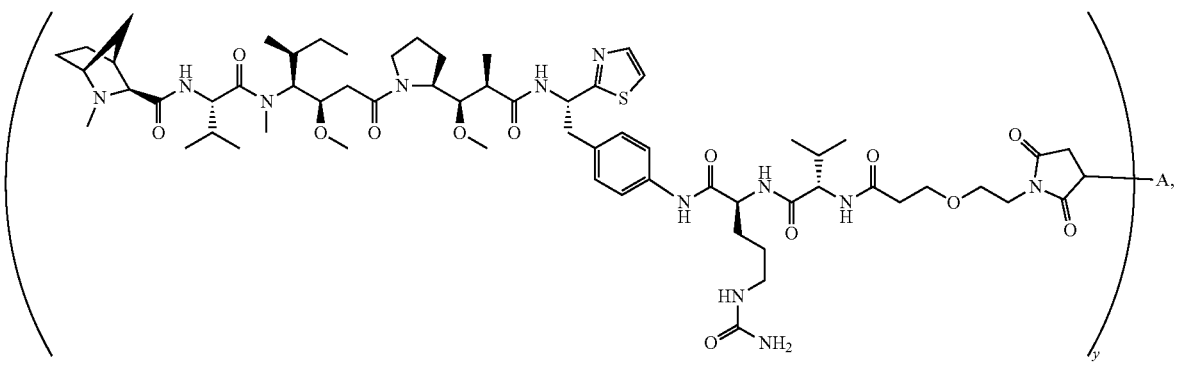

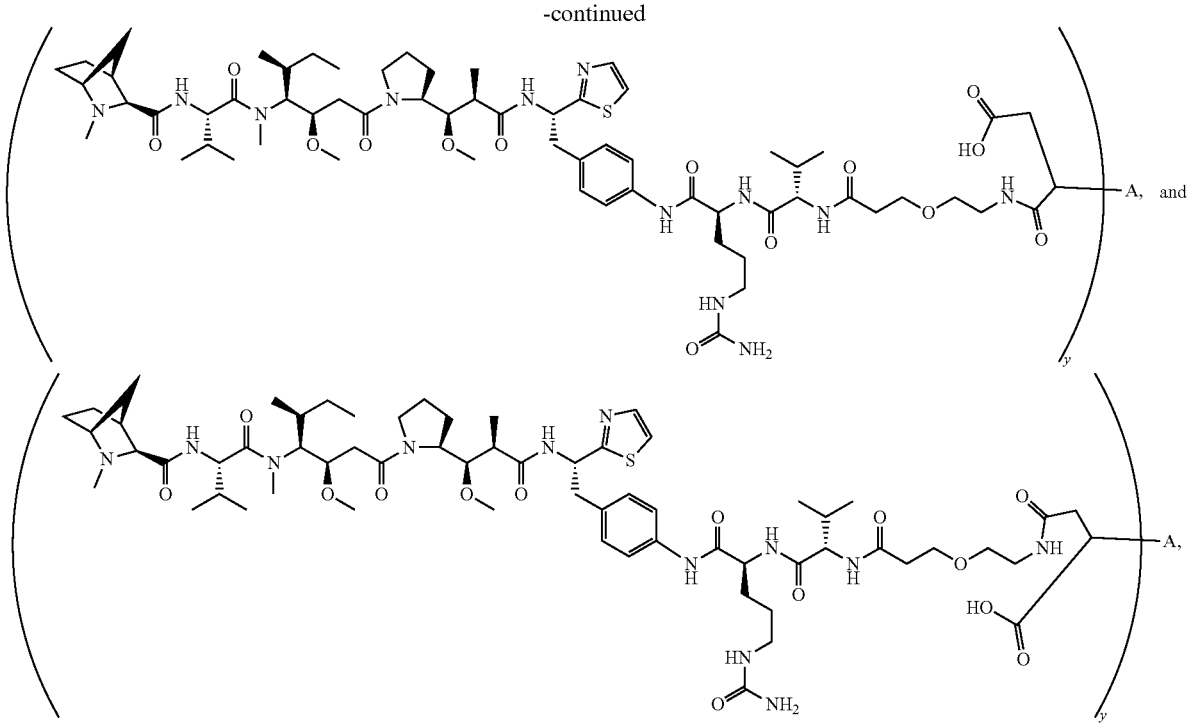
where y and A are as defined for conjugates of Formula (F) above.
Embodiment 131. The conjugate of Formula (F), Formula (F-1), Formula (F-3) and Formula (F-5) selected from:
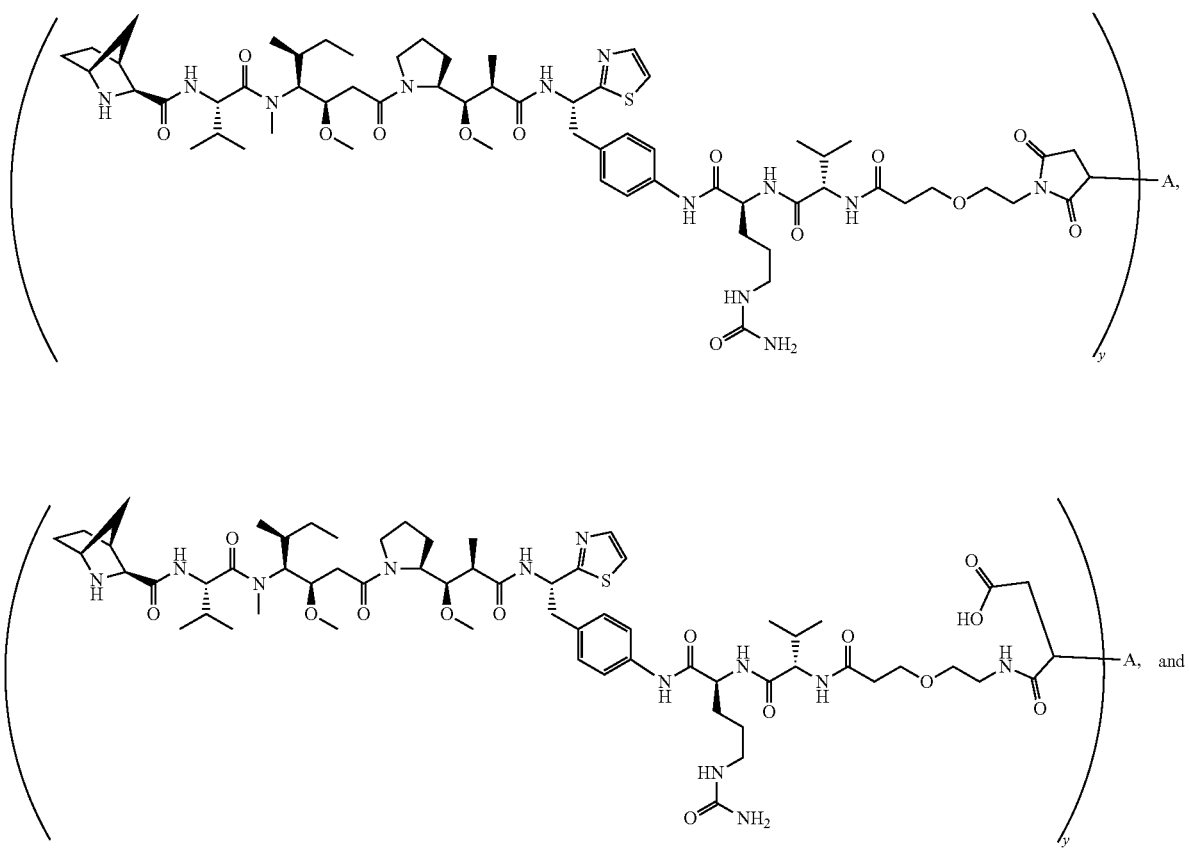

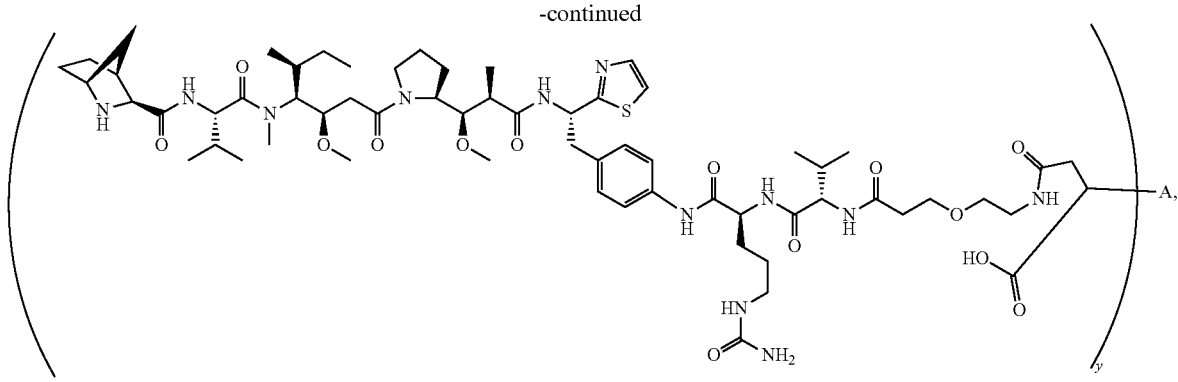
where y and A are as defined for conjugates of Formula (F) above.
Embodiment 132. The conjugate of Formula (G), Formula (G-1), Formula (G-2) and Formula (G-4) selected from:
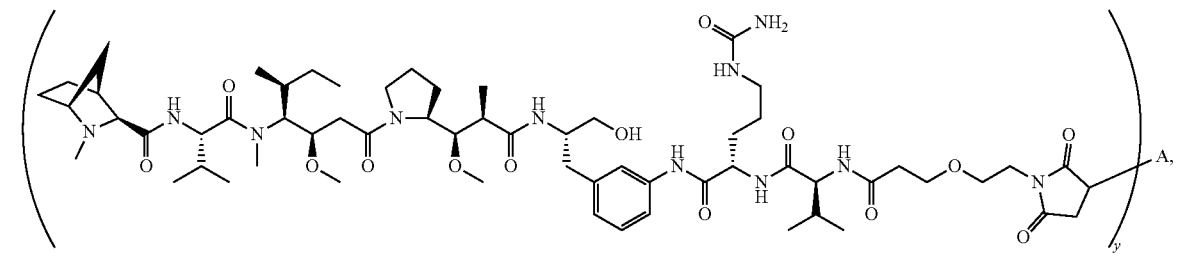
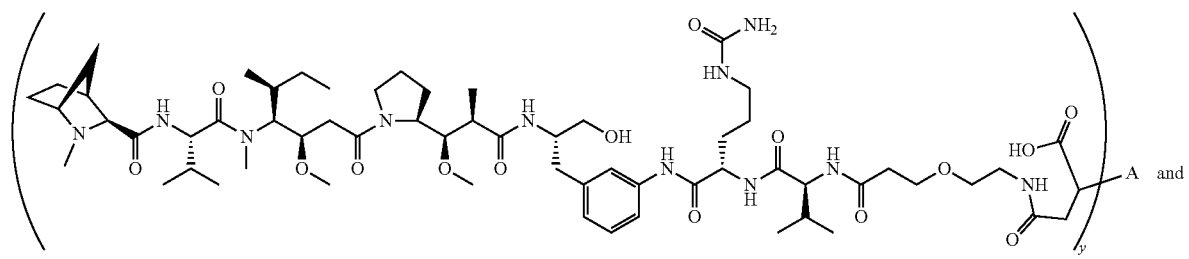
and
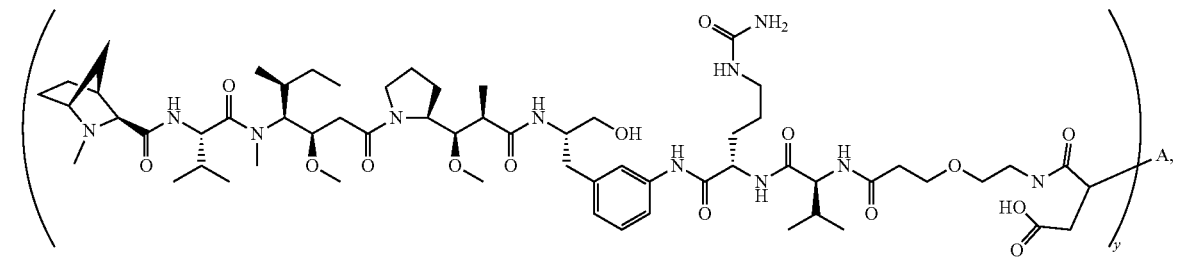

where y and A are as defined for conjugates pf Formula (G) above.
Embodiment 133. The conjugate of Formula (G), Formula (G-1), Formula (G-3) and Formula (G-5) selected from:
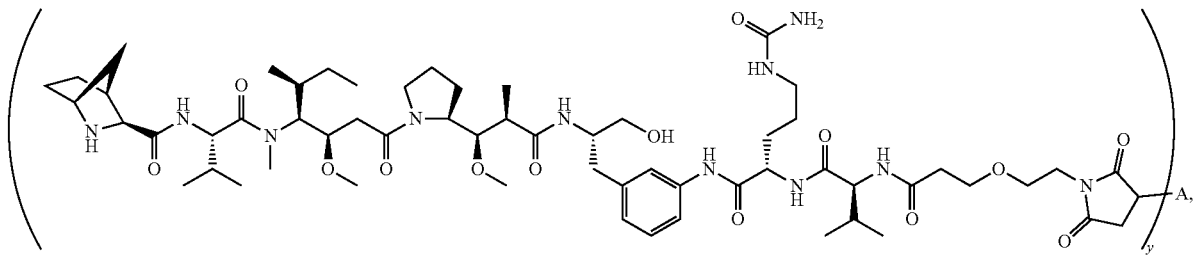
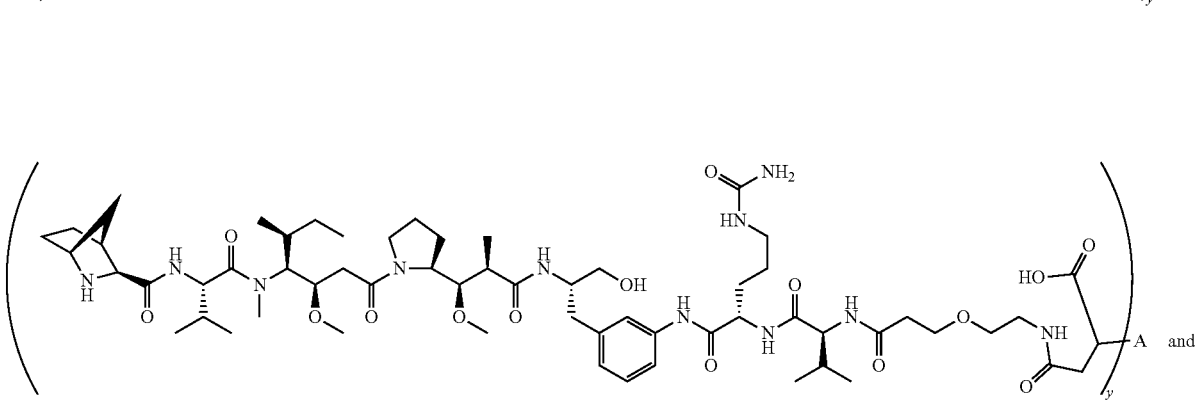
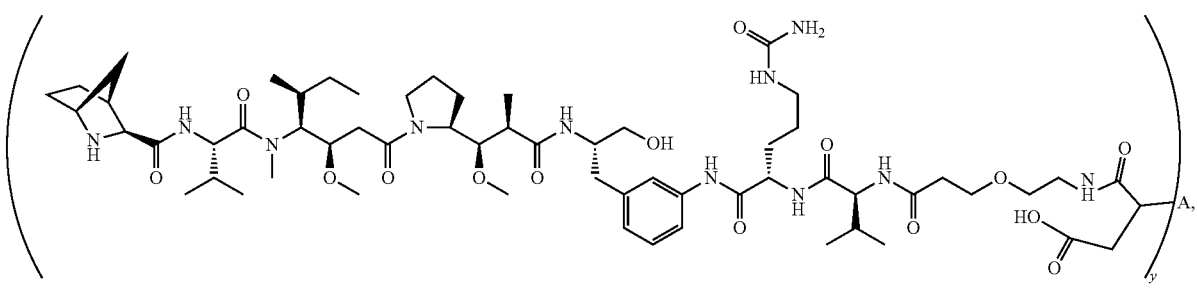
where y and A are as defined for conjugates of Formula (G) above.
Embodiment 134. The conjugate of Formula (H), Formula (H-1), Formula (H-2) and Formula (H-4) selected from:
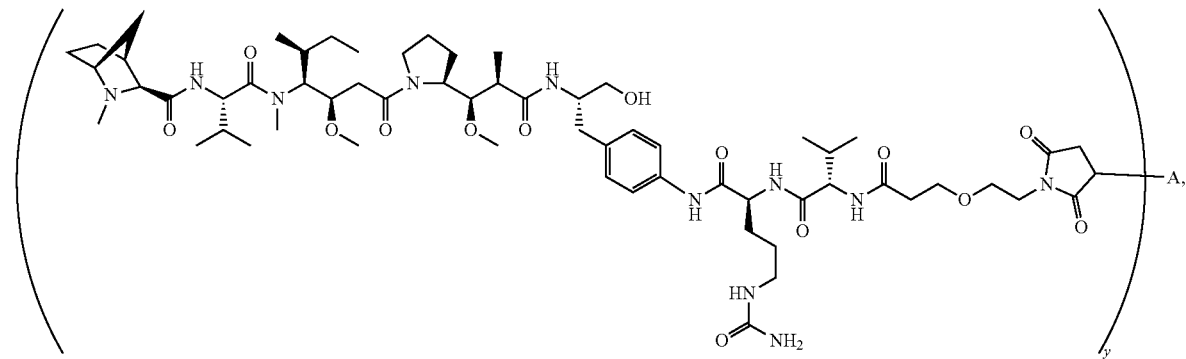

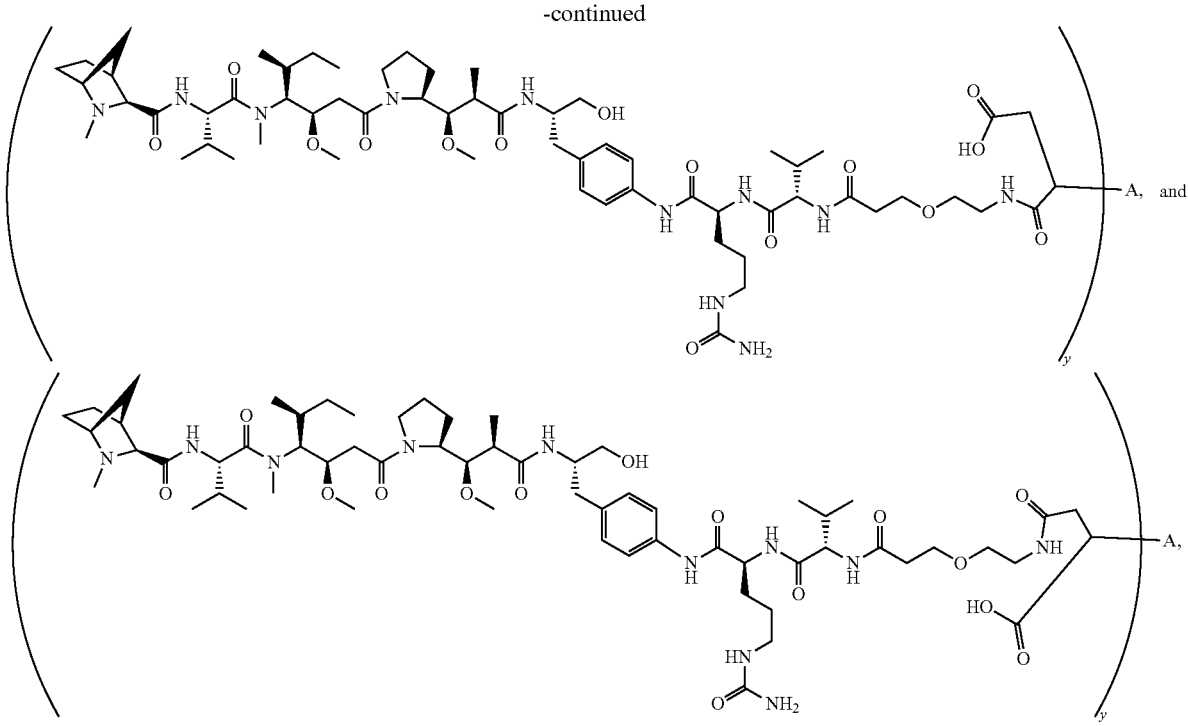
where y and A are as defined for conjugates of Formula (H) above.
Embodiment 135. The conjugate of Formula (H), Formula (H-1), Formula (H-3) and Formula (H-5) selected from:
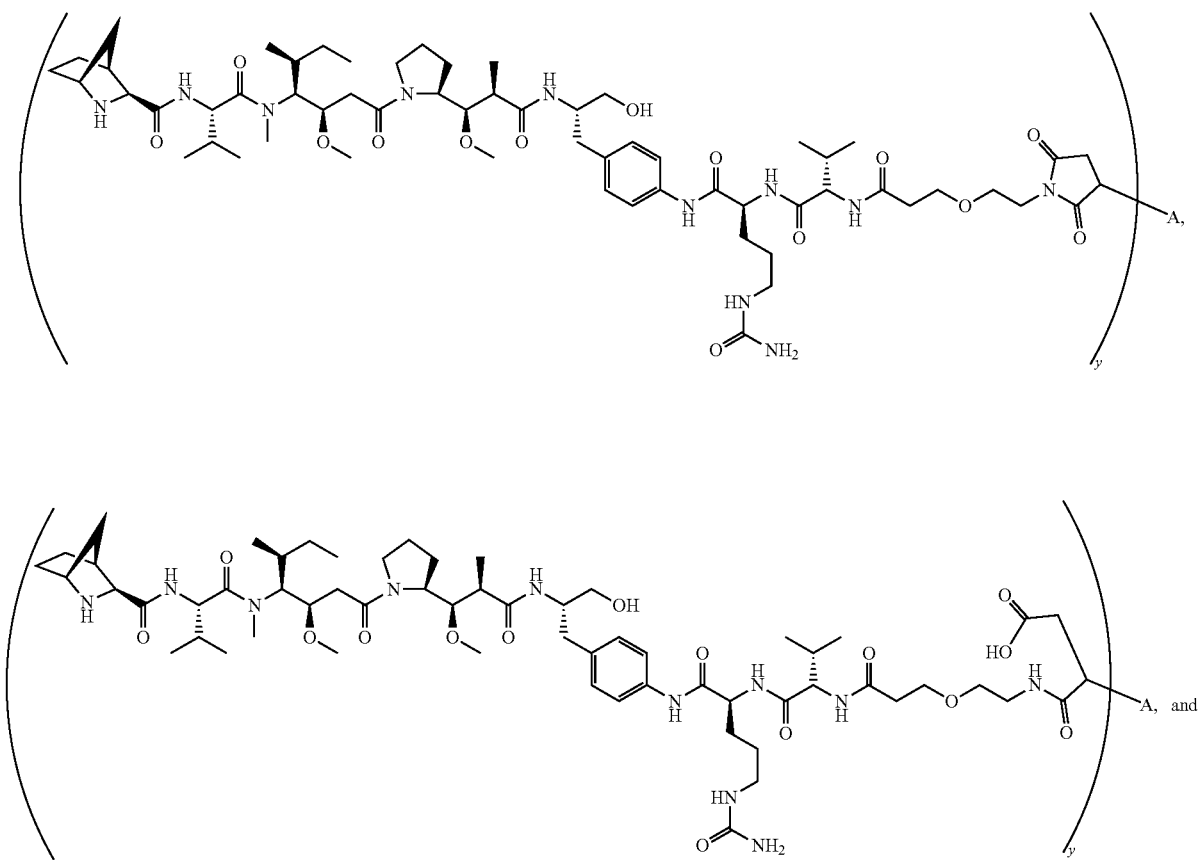

-continued
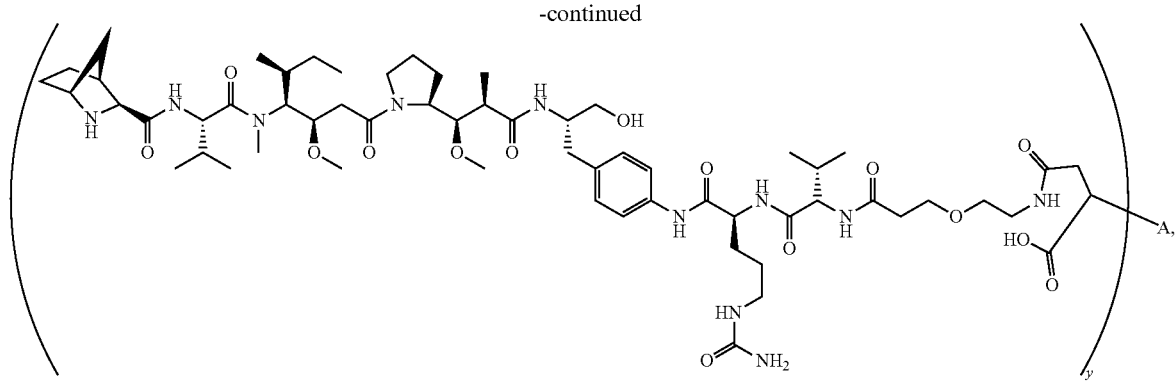
where y and A are as defined for conjugates of Formula (H) above.
Embodiment 136. The conjugate selected from:
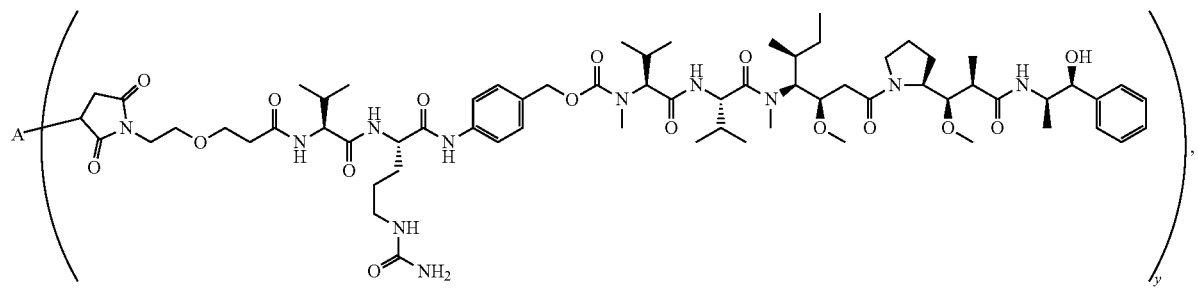
,
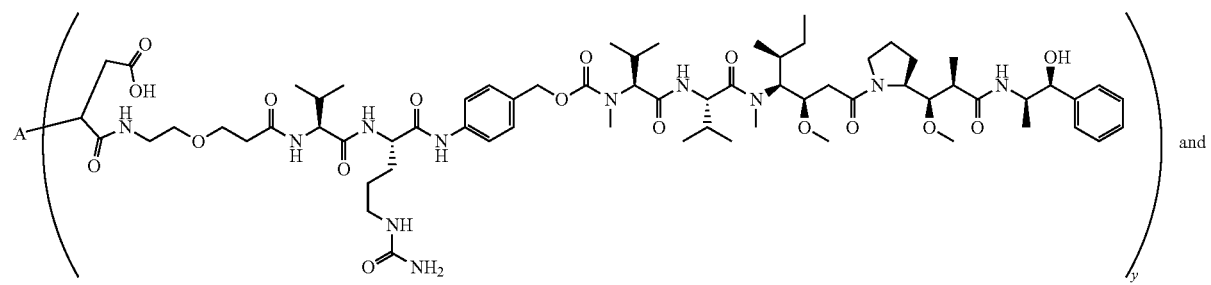
and
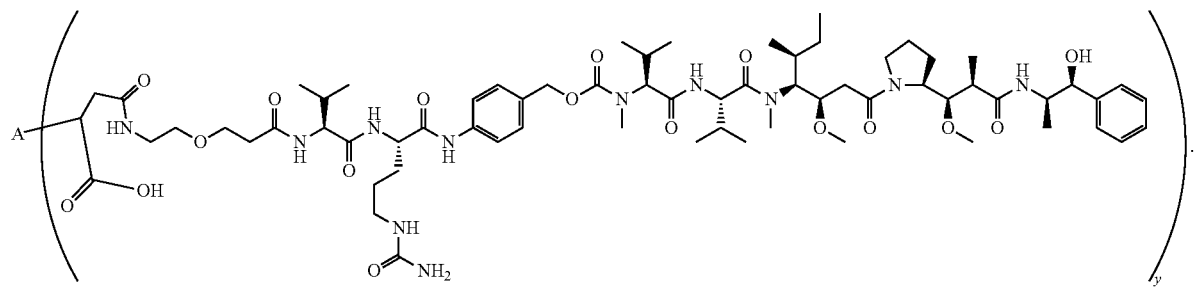
.

Embodiment 137. The conjugate selected from:

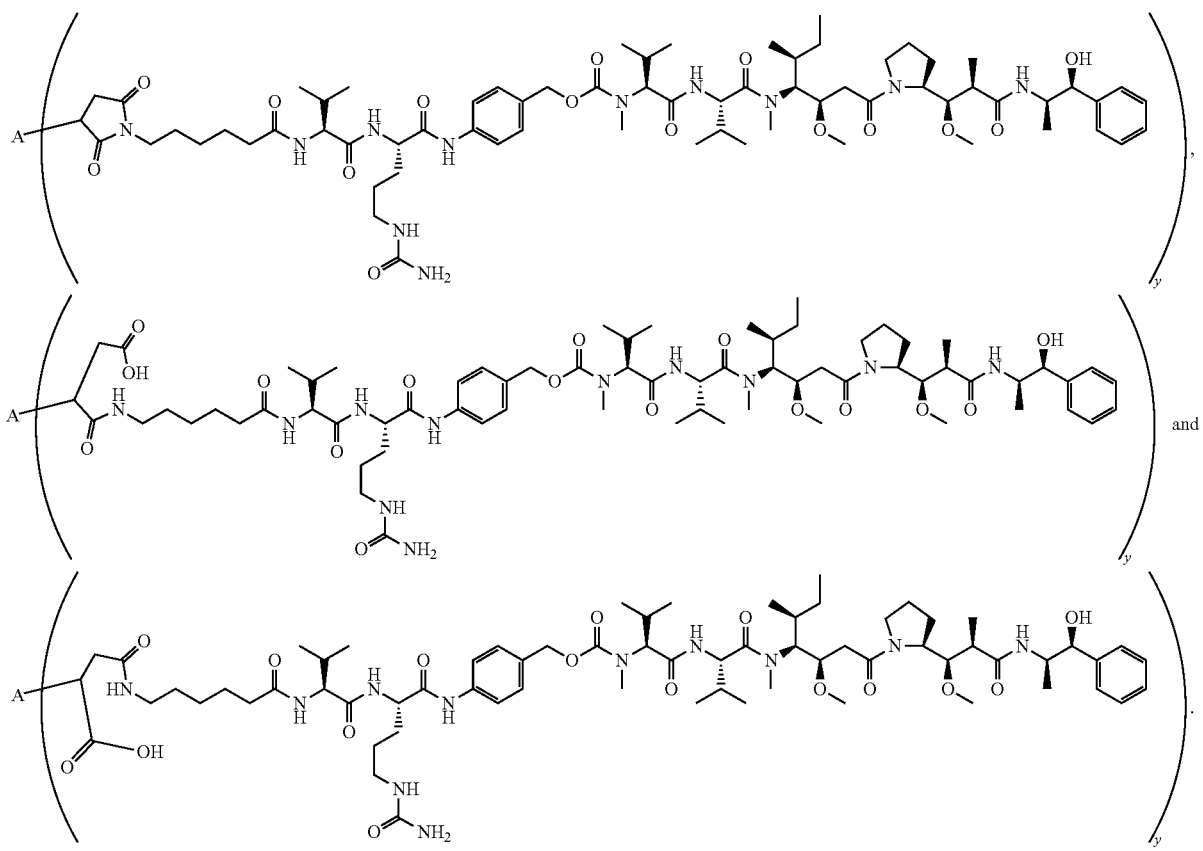

The compounds of any of the Formulae disclosed herein, such as Formula (A), Formula (B), Formula (C), Formula (D), Formula (E), Formula (F), Formula (G) and Formula (H) can be produced using the methods described in the following examples. The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

Abbreviations

| | |
|---|---|
| aq.: aqueous | $Boc_2O$: di-tert-butyl dicarbonate |
| br: broad | Cbz: Carboxybenzyl |
| d: doublet; dd: doublet of doublets | DCM: dichloromethane |
| m: multiplet | DEAD: Diethyl azodicarboxylate, |
| q: quartet | DIEA: N,N-Diisopropylethylamine |
| s: singlet | DIP-chloride ™: (+)-B-Chlorodiisopinocampheylborane |
| t: triplet | DIPEA: N,N-Diisopropylethylamine |
| h, hr: hour(s) | DMF: dimethyl formamide |
| ESI-MS: electrospray ionization mass spectrometry | DMSO: dimethylsulfoxide |
| HPLC: high pressure liquid chromatography | DPPA: Diphenyl phosphoryl azide |

-continued

| | |
|---|---|
| Isco, ISCO: Flash chromatography cartridge containing silica gel provided by Teledyne Isco | EtOAc: ethyl acetate |
| LC and LCMS: liquid chromatography and liquid chromatography-mass spectrometry | EEDQ: 2-Ethoxy-1-ethoxycarbonyl-1,2-dihydroquinoline |
| MS: mass | HATU: 1-[Bis(dimethylamino)methylene]-1H-1,2,3-triazolo[4,5-b]pyridinium 3-oxid-hexafluorophosphate |
| min(s): minute(s) | MeCN: acetonitrile |
| m/z: mass to charge ratio | TFA: trifluoroacetic acid |
| M and mM: molar and millimolar | THF: tetrahydrofuran |
| mg: milligram | TMEDA: N,N,N',N'-Tetramethylethylenediamine |
| μL, mL and L: microliter, milliliter and liter | RT and rt: room temperature |
| mmol and μmol: millimole and micromole | |
| NMR: nuclear magnetic resonance | |
| wt: weight | |

All starting materials, building blocks, reagents, acids, bases, dehydrating agents, solvents, and catalysts utilized to synthesis the compounds of the present disclosure are either commercially available or can be produced by organic synthesis methods known to one of ordinary skill in the art or can be produced by organic synthesis methods as described herein.

Synthesis of Intermediates

Synthesis of (S)-t-butyl (3-(2-amino-3-hydroxypropyl)phenyl)carbamate (i-1)

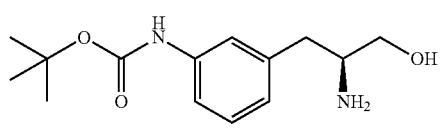

(i-1)

Step 1: BH$_3$ in THF (1M, 10 ml) was added to (S)-2-((t-butoxycarbonyl)amino)-3-(3-nitrophenyl)propanoic acid (562 mg, 1.81 mmol) in THF (10 ml) with stirring at 0° C. Then the reaction was stirred at 50° C. for 1 h. The reaction mixture was cooled at 0° C., quenched with water, diluted with EtOAc and washed with 10% aqueous K$_2$CO$_3$, dried over MgSO$_4$, filtered and concentrated. The crude was purified by a silica gel column (30-70% EtOAc-hexanes) to obtain (S)-t-butyl (1-hydroxy-3-(3-nitrophenyl)propan-2-yl) carbamate as a white solid. MS m/z 319.1 (M+Na). Retention time 1.183 minute. 1H NMR (600 MHz, Chloroform-d) b 8.13-8.04 (m, 2H), 7.57 (d, J=7.7 Hz, 1H), 7.46 (dd, J=8.9, 7.6 Hz, 1H), 4.76 (s, 1H), 3.87 (dq, J=8.0, 4.6, 4.1 Hz, 1H), 3.69 (dd, J=10.9, 3.9 Hz, 1H), 3.58 (dd, J=10.8, 4.7 Hz, 1H), 2.97 (td, J=13.1, 12.5, 7.3 Hz, 2H), 1.37 (s, 9H).

Step 2: To (S)-t-butyl (1-hydroxy-3-(3-nitrophenyl)propan-2-yl)carbamate (0.31 g, 1.0 mmol) in acetonitrile (5 ml) was added 10% hydrochloric acid (5 ml). The reaction mixture was stirred at rt for 48 h and then concentrated to give (S)-2-amino-3-(3-nitrophenyl)propan-1-ol as HCl salt. MS m/z 197.2 (M+H). Retention time 0.775 min.

Step 3: (S)-2-Amino-3-(3-nitrophenyl)propan-1-ol HCl salt (0.243 g, 1.046 mmol) was dissolved in MeOH (10 ml) and 10% palladium on carbon (50 mg, 0.047 mmol) was added. A 2 L hydrogen balloon was attached. The reaction was flushed with H$_2$ three times and then stirred at rt for 1 h. LCMS indicated the reaction was complete. The reaction was filtered through a celite pad and concentrated to give (S)-2-amino-3-(3-aminophenyl)propan-1-ol as HCl salt. MS m/z 167.2 (M+H). Retention time 0.373 min.

Step 4: (S)-2-Amino-3-(3-aminophenyl)propan-1-ol HCl salt (0.212 g, 1.046 mmol) and Boc$_2$O (228 mg, 1.05 mmol) and dioxane-water-AcOH (10:9:1, 20 ml) were combined and stirred at rt for 3 days. LCMS indicated the reaction was 75% complete. Additional Boc$_2$O (150 mg) was added and the reaction was further stirred for 6 h. The reaction mixture was then concentrated and purified with preparative HPLC (10-40% acetonitrile in water with 0.05% TFA) to give (S)-t-butyl (3-(2-amino-3-hydroxypropyl)phenyl)carbamate (i-1) as an oil. MS m/z 267.2 (M+H). Retention time 1.011 min.

Synthesis of (3R,4S,5S)-4-((S)—N,3-dimethyl-2-((1R,3S,4S)-2-methyl-2-azabicyclo[2.2.1]heptane-3-carboxamido)butanamido)-3-methoxy-5-methylheptanoic acid (i-2)

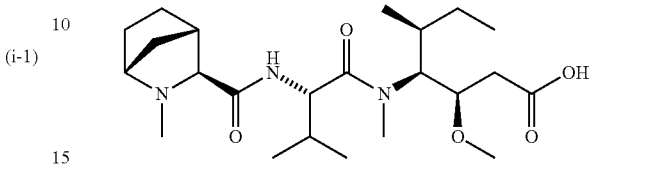

(i-2)

Step 1: Dil-OtBu HCl salt

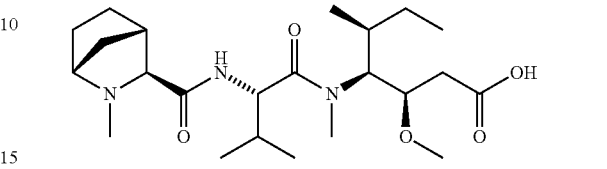

388 mg, 0.982 mmol), (1R,3S,4S)-2-(t-butoxycarbonyl)-2-azabicyclo[2.2.1]heptane-3-carboxylic acid

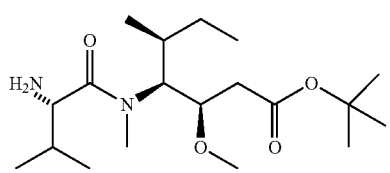

287 mg, 1.19 mmol), HATU (411 mg, 1.08 mmol) and DIEA (0.42 ml, 2.38 mmol) and DMF (5 ml) were combined and stirred at rt for 30 min. The reaction mixture was diluted with water (10 ml) and purified by RP-C18 ISCO to give tert-butyl (1R,3S,4S)-3-(((S)-1-(((3R,4S,5S)-1-(tert-butoxy)-3-methoxy-5-methyl-1-oxoheptan-4-yl)(methyl)amino)-3-methyl-1-oxobutan-2-yl)carbamoyl)-2-azabicyclo[2.2.1]heptane-2-carboxylate

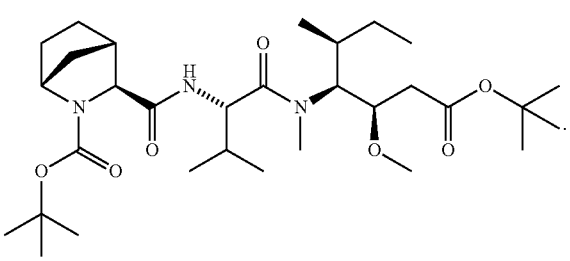

MS (m+1)=582.5, HPLC Peak RT=1.542 min

Step 2: The product obtained in step 1 (540 mg, 0.93 mmol) in 4M HCl in 1,4-dioxane (10 ml) was stirred at rt overnight. The reaction mixture was concentrated in to give (3R,4S,5S)-4-((S)-2-((1R,3S,4S)-2-azabicyclo[2.2.1]heptane-3-carboxamido)-N,3-dimethylbutanamido)-3-methoxy-5-methylheptanoic acid,

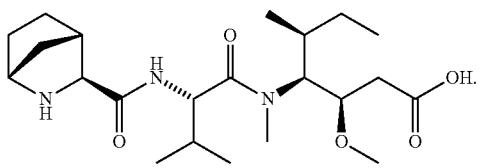

MS (m+1)=426.2, HPLC Peak RT=0.736 min

Step 3: The product obtained in step 2 (430 mg, 0.93 mmol), 37% formaldehyde solution (0.38 ml, 4.7 mmol), acetic acid (0.27 ml, 4.65 mmol), NaBH3CN (585 mg, 9.31 mmol) and MeOH (10 ml) were combined and stirred at rt for 30 min and then concentrated. The residue was purified by RP-C18 ISCO to give 450 mg of (3R,4S,5S)-4-((S)—N,3-dimethyl-2-((1R,3S,4S)-2-methyl-2-azabicyclo[2.2.1]heptane-3-carboxamido)butanamido)-3-methoxy-5-methylheptanoic acid (i-2), as a TFA salt. The TFA salt was treated with 10 ml of 12N HCl solution and concentrated twice to give (3R,4S,5S)-4-((S)—N,3-dimethyl-2-((1R,3S,4S)-2-methyl-2-azabicyclo[2.2.1]heptane-3-carboxamido)butanamido)-3-methoxy-5-methylheptanoic acid HCl salt. MS (m+1)=440.2, HPLC Peak RT=0.754 min.

Synthesis of Dap-OMe: ((2R,3R)-methyl 3-methoxy-2-methyl-3-((S)-pyrrolidin-2-yl)propanoate) (i-3)

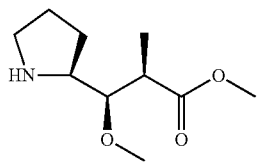

Step 1: Boc-Dap-OH

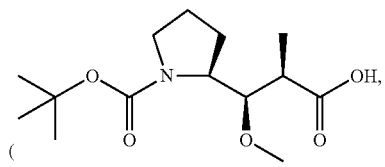 [SMILES: CO[C@H]([C@@H](C)C(=O)O)[C@@H]1CCCN1C(=O)OC(C)(C)C]

3.11 g, 10.8 mmol), K$_2$CO$_3$ (2.99 g, 21.6 mmol), iodomethane (2.95 g) and acetone (55 mL) were combined. The reaction was stirred at 20° C. for 2 h. An additional methyliodide (2.28 g) was added to the reaction and the reaction was stirred at 40° C. for 3 h. The reaction mixture was concentrated. The residue was partitioned between 200 mL EtOAc and 100 mL H2O. The organic layer was separated, washed with 50 mL saturated aq NaCl, dryed over MgSO$_4$, filtered and concentrated, affording Boc-Dap-OMe,

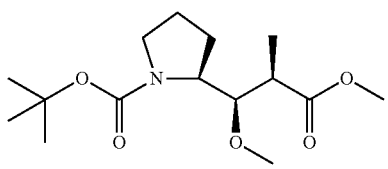

as a yellow oil. MS (ESI+) m/z calc 324.2, found 324.2 (M+23). Retention time 1.245 min.

Step 2: Boc-Dap-OMe (3.107 g, 10.3 mmol) was combined with HCl in diethyl ether (2 M, 10 mL) and concentrated. This operation was repeated. The reaction was complete after the 7$^{th}$ treatment. HCl salt of Dap-OMe (i-3) was obtained as a white solid after being concentrated. MS (ESI+) m/z calc 202.1, found 202.2 (M+1). Retention time 0.486 min. $^1$H NMR (400 MHz, CDCl$_3$): δ 4.065-4.041 (m, 1H), 3.732 (br.s, 1H), 3.706 (s, 3H), 3.615 (s, 3H), 3.368 (br.s, 1H), 3.314 (br.s, 1H), 2.795 (q, 1H, J=6.8 Hz), 2.085-1.900 (m, 4H), 1.287 (d, 3H, J=7.2 Hz).

Synthesis of tert-butyl (S)-(3-(2-amino-2-(thiazol-2-yl)ethyl)phenyl)carbamate (i-4)

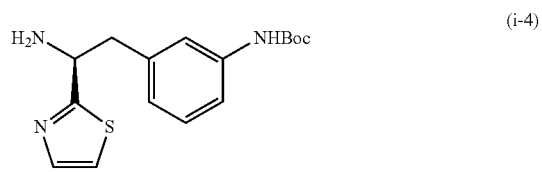 [SMILES: CC(C)(C)OC(=O)Nc1cccc(C[C@H](N)c2nccs2)c1]

Step 1: To a Solution of 2-(3-nitrophenyl)acetic acid (3 g, 16.56 mmol) in DMF (dry, 17 ml) was added HATU (6.93 g, 18.22 mmol), N,O-dimethylhydroxylamine hydrochloride (1.615 g, 16.56 mmol), and DIPEA (14.46 ml, 83 mmol) at RT. The reaction mixture was stirred overnight at RT. The reaction mixture was concentrated under high vacuum to remove most solvent. Then the residue was extracted between DCM and water. The aq. phase was extracted by DCM 2×. Combined DCM phases were concentrated under vacuum. The residue was separated by silica gel flash column (EtOAc/Heptane 0-70%, then 70%) to obtain 3.5 g N-methoxy-N-methyl-2-(3-nitrophenyl)acetamide as white solid. MS m/z 225.1 (M+1). Retention time 1.09 min. $^1$H NMR (400 MHz, Chloroform-d) δ 8.28-8.09 (m, 2H), 7.67 (m, 1H), 7.63-7.46 (m, 1H), 3.90 (s, 2H), 3.74 (s, 3H), 3.24 (s, 3H). Step 2: To a solution of TMEDA (2.63 mL, 17.39 mmol) in THF (dry, 30 ml) under N$_2$ atmosphere at −78° C. (Acetone-dry ice bath), was added dropwise n-butyllithium (2.5 M in hexane) (1.028 g, 16.06 mmol). Then at −78° C., 2-bromothiazole (2.63 g, 16.06 mmol) was also added dropwise to the reaction mixture. The reaction mixture was stirred at −78° C. for 1 h. The mixture of N-methoxy-N-methyl-2-(3-nitrophenyl)acetamide (3 g, 13.38 mmol) in THF (30 ml) was added dropwise to the reaction mixture at −78° C. The reaction mixture was stirred at −78° C. for 1 h, then at −10° C. (Acetone-ice bath) for 2 h. The reaction mixture was quenched by adding sat. KHSO$_4$ aq. solution, then extracted with EtOAc 3×. The combined EtOAc phases were dried over sat. NaCl, NaSO$_4$, and concentrated. The residue was separated by silica gel flash column (EtOAc/Heptane 0-30%, then 30%) to obtain 1.95 g 2-(3-nitrophenyl)-1-(thiazol-2-yl)ethan-1-one as light yellow oil. MS m/z 249.0 (M+1). Retention time 1.34 min. $^1$H NMR (400 MHz, Chloroform-d) δ 8.33-8.22 (m, 1H), 8.17 (ddd, J=8.1, 2.3, 1.0 Hz, 1H), 8.10 (d, J=3.0 Hz, 1H), 7.79-7.67 (m, 2H), 7.54 (t, J=7.9 Hz, 1H), 4.62 (s, 2H).

Step 3: To the solution of (+)-DIP-Chloride™ (9.22 g, 28.8 mmol) in diethyl ether (7 ml) under N$_2$ atmosphere at 0° C. (ice-water bath) was added dropwise a solution of 2-(3-nitrophenyl)-1-(thiazol-2-yl)ethan-1-one (2.38 g, 9.59 mmol) in diethyl ether (37 ml). The reaction mixture was stirred at 0° C. for 24 h. Then the mixture was neutralized with 30 ml of (1:1) mixture of 10% NaOH and 30% $H_2O_2$ at 10° C. in a water-ice bath. The mixture was stirred for 1 h at RT. Then the mixture was diluted with water, extracted with EtOAc 3x. The combined EtOAc phases were washed with sat. $K_2CO_3$, sat NaCl, and dried over $NaSO_4$, and concentrated. The residue was separated by silica gel flash column (EtOAc/Heptane 0-60%, then 60%) to obtain 1.639 g (R)-2-(3-nitrophenyl)-1-(thiazol-2-yl)ethan-1-ol as light yellow solid. MS m/z 251.1 (M+1). Retention time 1.09 min. $^1$H NMR (400 MHz, Chloroform-d) b 8.33-8.07 (m, 2H), 8.07-7.80 (m, 1H), 7.74-7.55 (m, 1H), 7.55-7.36 (m, 2H), 5.55 (dd, J=7.9, 4.1 Hz, 1H), 4.48 (s, 1H), 3.53 (dd, J=13.9, 4.0 Hz, 1H), 3.32 (dd, J=13.9, 8.1 Hz, 1H). 92% e.e. determined by Chiral SFC.

Step 4: To a solution of (R)-2-(3-nitrophenyl)-1-(thiazol-2-yl)ethan-1-ol (1.636 g, 6.54 mmol) in MeOH (20 ml) was added Pd/C (10%, 0.696 g, 0.654 mmol). The reaction mixture was charged with $H_2$ (1 atm) after three vacuum/$H_2$ cycle, and stirred at RT. After overnight stirring, the reaction mixture was filtered through Celite and washed with MeOH. The filtrate was concentrated under vacuum to obtain 1.3 g (R)-2-(3-aminophenyl)-1-(thiazol-2-yl)ethan-1-ol as a solid which was directly used for the next step without further purification. MS m/z 221.1 (M+1). Retention time 0.50 min. $^1$H NMR (400 MHz, DMSO-$d_6$) δ 7.72 (d, J=3.2 Hz, 1H), 7.59 (d, J=3.2 Hz, 1H), 6.88 (t, J=7.7 Hz, 1H), 6.46 (t, J=1.9 Hz, 1H), 6.42-6.29 (m, 2H), 6.14 (d, J=5.7 Hz, 1H), 5.03-4.78 (m, 3H), 3.03 (dd, J=13.7, 4.0 Hz, 1H), 2.72 (dd, J=13.7, 8.7 Hz, 1H).

Step 5: To the mixture of (R)-2-(3-aminophenyl)-1-(thiazol-2-yl)ethan-1-ol (1.3 g, 5.92 mmol) in Dioxane/Water (1/1, 16 ml/16 ml) was added $Boc_2O$ (1.512 ml, 6.51 mmol) and NaOH (0.284 g, 7.10 mmol). The reaction mixture was stirred at RT overnight. The reaction mixture was added 10 ml water, then extracted with EtOAc (3*40 ml). The organic phases were combined, dried over $Na_2SO_4$, then concentrated under vacuum. The residue was then separated by silica gel flash column (EtOAc/Heptane 0 to 80% then 80%) to obtain 1.24 g tert-butyl (R)-(3-(2-hydroxy-2-(thiazol-2-yl)ethyl)phenyl)carbamate as solid. MS m/z 321.3 (M+1). Retention time 1.26 min. $^1$H NMR (400 MHz, DMSO-$d_6$) δ 9.24 (s, 1H), 7.73 (d, J=3.2 Hz, 1H), 7.60 (d, J=3.3 Hz, 1H), 7.39 (t, J=1.8 Hz, 1H), 7.25 (ddd, J=8.2, 2.3, 1.1 Hz, 1H), 7.11 (t, J=7.8 Hz, 1H), 6.80 (dt, J=7.7, 1.2 Hz, 1H), 6.20 (d, J=5.7 Hz, 1H), 4.97 (ddd, J=8.6, 5.7, 4.0 Hz, 1H), 3.13 (dd, J=13.7, 4.0 Hz, 1H), 2.83 (dd, J=13.7, 8.7 Hz, 1H), 1.47 (s, 9H).

Step 6: To an ice-water bath cooled solution of tert-butyl (R)-(3-(2-hydroxy-2-(thiazol-2-yl)ethyl)phenyl)carbamate (1.2 g, 3.75 mmol) in THF (dry, 25 ml) under $N_2$ atmosphere, was added $PPh_3$ (1.670 g, 6.37 mmol). DEAD (40% wt in Toluene) (2.90 ml, 6.37 mmol) was then added dropwise at 0° C., followed by DPPA (1.372 ml, 6.37 mmol). Then the cold bath was removed. the reaction mixture was stirred at RT for overnight. The reaction mixture was concentrated under vacuum, and then subjected to flash silica gel column separation (EtOAc/Heptane 0 to 30%, then 30%) to obtain 1.03 g tert-butyl (S)-(3-(2-azido-2-(thiazol-2-yl)ethyl)phenyl)carbamate as oil. MS m/z 346.3 (M+1). Retention time 1.55 min. $^1$H NMR (400 MHz, DMSO-$d_6$) δ 9.29 (s, 1H), 7.86 (d, J=3.2 Hz, 1H), 7.76 (d, J=3.2 Hz, 1H), 7.41 (t, J=1.9 Hz, 1H), 7.29 (ddd, J=8.3, 2.2, 1.1 Hz, 1H), 7.16 (t, J=7.8 Hz, 1H), 6.86 (dt, J=7.9, 1.2 Hz, 1H), 5.31 (dd, J=8.7, 5.7 Hz, 1H), 3.17 (d, J=5.3 Hz, 1H), 3.09 (dd, J=13.9, 8.7 Hz, 1H), 1.47 (s, 9H).

Step 7: To a solution of tert-butyl (S)-(3-(2-azido-2-(thiazol-2-yl)ethyl)phenyl)carbamate (861 mg, 2.493 mmol) in MeOH (4 ml) was added Pd/C (10% wet, 265 mg, 0.249 mmol). The reaction mixture was charged with $H_2$ (1 atm) after three vacuum/$H_2$ cycle, and stirred at RT. After overnight stirring, the reaction mixture was concentrated and then filtered through Celite and washed with MeOH. The filtrate was concentrated under vacuum. to obtain 781 mg tert-butyl (S)-(3-(2-amino-2-(thiazol-2-yl)ethyl)phenyl)carbamate (i-4) as sticky oil. MS m/z 320.2 (M+1). Retention time 0.91 min. $^1$H NMR (400 MHz, DMSO-$d_6$) δ 9.26 (s, 1H), 7.71 (d, J=3.3 Hz, 1H), 7.55 (d, J=3.3 Hz, 1H), 7.36 (t, J=1.9 Hz, 1H), 7.26 (dt, J=8.3, 1.5 Hz, 1H), 7.13 (t, J=7.8 Hz, 1H), 6.78 (dt, J=7.6, 1.3 Hz, 1H), 4.31 (dd, J=8.7, 4.7 Hz, 1H), 3.14 (dd, J=21.2, 5.0 Hz, 1H), 2.73 (dd, J=13.4, 8.7 Hz, 1H), 2.11 (s, 2H), 1.47 (s, 9H).

Synthesis of Exemplary Drug Moieties

Example A: Synthesis of (1R,3S,4S)—N—((S)-1-(((3R,4S,5S)-1-((S)-2-((1R,2R)-3-(((S)-2-(3-aminophenyl)-1-(thiazol-2-yl)ethyl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (C1)

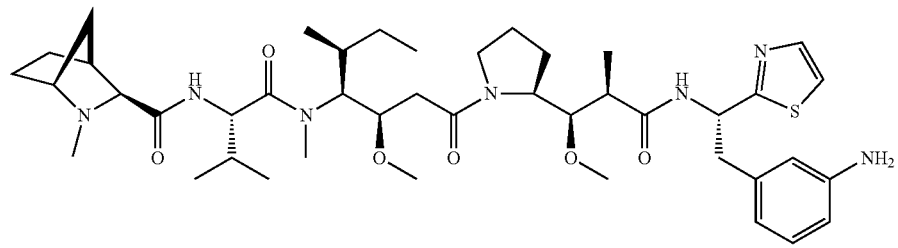

(C1)

Step 1: To a solution of (2R,3R)-3-((S)-1-((3R,4S,5S)-4-((S)—N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanoic acid (250 mg, 0.346 mmol) in DMF (4 ml) was added tert-butyl (S)-(3-(2-amino-2-(thiazol-2-yl)ethyl)phenyl)carbamate (i-4) (110 mg, 0.346 mmol), HATU (158 mg, 0.415 mmol), and DIPEA (362 μl, 2.075 mmol). The reaction mixture was stirred at RT overnight. The reaction mixture was concentrated under vacuum. The residue was then dissolved in MeOH, and was separated by ISCO gold C-18 100 gram reversed phase column (MeCN/H$_2$O 0-100%) to obtain 173 mg tert-butyl (3-((S)-2-((2R,3R)-3-((S)-1-((3R,4S,5S)-4-((S)—N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanamido)-2-(thiazol-2-yl)ethyl)phenyl)carbamate as white powder. MS m/z 911.0 (M+1). Retention time 1.15 min.

Step 2: tert-butyl (3-((S)-2-((2R,3R)-3-((S)-1-((3R,4S,5S)-4-((S)—N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanamido)-2-(thiazol-2-yl)ethyl)phenyl)carbamate (173 mg, 0.190 mmol) was dissolved in 1 ml Dioxane, then 10 ml 4N HCl in Dioxane was added to the mixture. The reaction mixture was stirred at room temperature for 30 min. The reaction mixture was concentrated under high vacuum, and then was partitioned between sat. NaHCO$_3$ and DCM to make the aq. phase pH as 8. The basic aq. phase was extracted with DCM 3×. The combined DCM phases were dried over sat NaCl and Na$_2$SO$_4$, and then concentrated under high vacuum to obtain 155 mg (1R,3S,4S)—N—((S)-1-(((3R,4S,5S)-1-((S)-2-((1R,2R)-3-(((S)-2-(3-aminophenyl)-1-(thiazol-2-yl)ethyl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide as solid. MS m/z 810.5 (M+1). Retention time 0.90 min.

Example B: Synthesis of (1R,3S,4S)—N—((S)-1-(((3R,4S,5S)-1-((S)-2-((1R,2R)-3-(((S)-1-(3-aminophenyl)-3-hydroxypropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (C2)

acid (i-2) (57 mg, 0.12 mmol) in DMF (2 ml). The reaction mixture was stirred at rt for 5 min and then DapOMe (i-3) (28.5 mg, 0.12 mmol) in DMF (1 ml) was added. The reaction mixture was stirred at rt for 1 h and then purified by preparative HPLC (10-50% acetonitrile-H$_2$O containing 0.05% TFA) to obtain (2R,3R)-methyl 3-((S)-1-((3R,4S,5S)-4-((S)—N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanoate. MS m/z 623.5 (M+H). Retention time 1.225 min.

Step 2: LiOH (30 mg, 1.25 mmol) was added to (2R,3R)-methyl 3-((S)-1-((3R,4S,5S)-4-((S)—N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanoate (43.2 mg, 0.059 mmol) in MeOH—H$_2$O (1:1, 4 ml). The reaction mixture was stirred at rt for 18 h, concentrated and acidified with HCl (1N, 1 ml). The crude was purified by preparative HPLC (10-38% acetonitrile-H$_2$O containing 0.05% TFA) obtain (2R,3R)-3-((S)-1-((3R,4S,5S)-4-((S)—N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanoic acid as TFA salt. MS m/z 609.5 (M+H). Retention time 0.962 min.

Step 3: To (2R,3R)-3-((S)-1-((3R,4S,5S)-4-((S)—N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanoic acid (45.7 mg, 0.063 mmol) in DMF (1 ml) were added DIEA (0.055 ml, 0.32 mmol) and HATU (24.0 mg, 0.063 mmol). The reaction mixture was stirred at rt for 10 min and then added to (S)-t-butyl (3-(2-amino-3-hydroxypropyl)phenyl)carbamate TFA salt (i-1) (24.1 mg, 0.063 mmol) in DMF (1 ml). The reaction mixture was stirred at rt for 1 h and then concentrated. The crude was purified by preparative HPLC (20-70% acetonitrile-H$_2$O containing 0.05% TFA) to obtain t-butyl (3-((S)-2-((2R,3R)-3-((S)-1-((3R,4S,5S)-4-((S)—N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanamido)-3-hydroxypropyl)phenyl)carbamate as TFA salt. MS m/z 857.5 (M+H). Retention time 1.145 min.

Step 4: A solution of t-butyl (3-((S)-2-((2R,3R)-3-((S)-1-((3R,4S,5S)-4-((S)—N,3-dimethyl-2-((1R,3S,4S)-2-methyl-2-azabicyclo[2.2.1]heptane-3-carboxamido)butana-

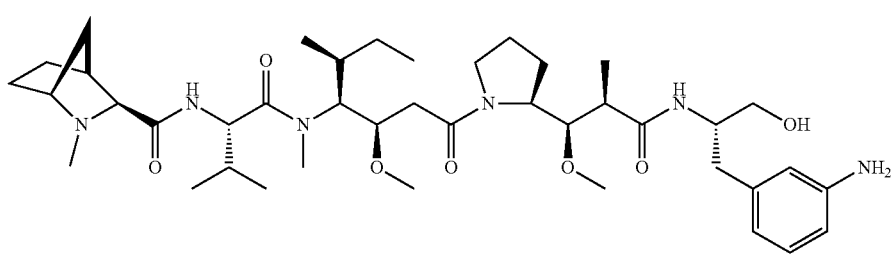

(C2)

Step 1: DIEA (0.105 ml, 0.60 mmol) and HATU (45.5 mg, 0.12 mmol) were added to (3R,4S,5S)-4-((S)—N,3-dimethyl-2-((1R,3S,4S)-2-methyl-2-azabicyclo[2.2.1]heptane-3-carboxamido)butanamido)-3-methoxy-5-methylheptanoic mido)-3-methoxy-5-methylheptanoyl)pyrrolidin-2-yl)-3-methoxy-2-methylpropanamido)-3-hydroxypropyl)phenyl)carbamate (61.4 mg, 0.063 mmol) in acetonitrile-water (1:1, 4 ml) with 5% HCl was stirred at rt for 24 h. The reaction mixture was then concentrated and purified by preparative HPLC (10-30% acetonitrile-H₂O containing 0.05% TFA) to give (1R,3S,4S)—N—((S)-1-(((3R,4S,5S)-1-((S)-2-((1R,2R)-3-(((S)-1-(3-aminophenyl)-3-hydroxypropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (C2) as TFA salt. MS m/z 757.5 (M+H). Retention time 0.744 min.

Synthesis of Exemplary Linker-Drug Compounds

Example C: Synthesis of (1R,3S,4S)—N—((S)-1-(((3R,4S,5S)-1-((S)-2-((1R,2R)-3-(((S)-2-(3-((S)-2-((S)-2-(3-(2-(2,5-dioxo-2,5-dihydro-1H-pyrrol-1-yl)ethoxy)propanamido)-3-methylbutanamido)-5-ureidopentanamido)phenyl)-1-(thiazol-2-yl)ethyl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (LP1)

yl)amino)-3-methyl-1-oxobutan-2-yl)carbamate as TFA salt. MS m/z 1167.3 (M+1). Retention time 1.10 min. Step 2: To tert-butyl ((S)-1-(((S)-1-((3-((S)-2-((2R,3R)-3-((S)-1-((3R,4S,5S)-4-((S)—N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanamido)-2-(thiazol-2-yl)ethyl)phenyl)amino)-1-oxo-5-ureidopentan-2-yl)amino)-3-methyl-1-oxobutan-2-yl)carbamate (232 mg, 0.181 mmol) was added to a cold solution of TFA/DCM (25%, 6 ml) at 0° C. with ice-water bath, then the mixture was stirred at 0° C. for 15 min, then was allowed to warm to RT. The mixture was stirred at RT for 30 min. The reaction mixture was concentrated under vacuum. The residue was then dissolved in DMSO and was separated by ISCO gold C-18 50 gram reversed phase column (MeCN/H₂O containing 0.05% TFA, 0-100%) to obtain 219 mg ((1R,2R)-3-(((S)-2-(3-((S)-2-((S)-2-amino-3-methylbutanamido)-5-ureidopentanamido)phenyl)-1-(thiazol-2-yl)ethyl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide as TFA salt. MS m/z 1067.2 (M+1). Retention time 0.88 min.

(LP1)

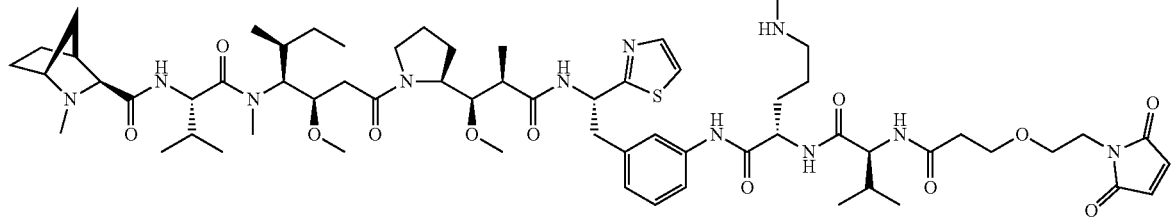

Step 1: To the mixture of (1R,3S,4S)—N—((S)-1-(((3R,4S,5S)-1-((S)-2-((1R,2R)-3-(((S)-2-(3-aminophenyl)-1-(thiazol-2-yl)ethyl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (C1) (154 mg, 0.190 mmol) and Boc-Val-Cit-OH (

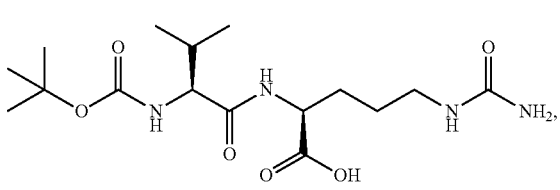 [SMILES: CC(C)[C@H](NC(=O)OC(C)(C)C)C(=O)N[C@@H](CCCNC(N)=O)C(=O)O]

92 mg, 0.247 mmol) in DCM (5 ml)/MeOH (0.1 ml) was added EEDQ (94 mg, 0.380 mmol). The reaction mixture was stirred at RT overnight. The reaction mixture was concentrated under vacuum. The residue was then dissolved in MeOH, and was separated by ISCO gold C-18 50 gram reversed phase column (MeCN/H₂O containing 0.05% TFA, 0-100%) to obtain 232 mg tert-butyl ((S)-1-(((S)-1-((3-((S)-2-((2R,3R)-3-((S)-1-((3R,4S,5S)-4-((S)—N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanamido)-2-(thiazol-2-yl)ethyl)phenyl)amino)-1-oxo-5-ureidopentan-2-

Step 3: ((1R,2R)-3-(((S)-2-(3-((S)-2-((S)-2-amino-3-methylbutanamido)-5-ureidopentanamido)phenyl)-1-(thiazol-2-yl)ethyl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (219 mg 0.18 mmol) was dissolved in DMF (2 ml), then MAL-PEG1-NHS ester

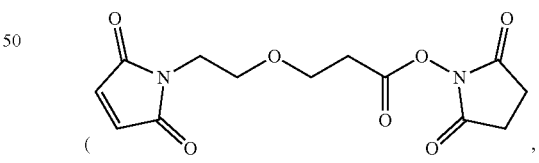

73.1 mg, 0.236 mmol) and DIPEA (190 µl, 1.087 mmol) were added. The reaction mixture was stirred at RT for 1 h. The reaction mixture was concentrated under vacuum. The residue was then dissolved in DMSO and was separated by ISCO gold C-18 50 gram reversed phase column (MeCN/H₂O containing 0.05% TFA, 0-100%) to obtain 174 mg (1R,3S,4S)—N—((S)-1-(((3R,4S,5S)-1-((S)-2-((1R,2R)-3-(((S)-2-(3-((S)-2-((S)-2-(3-(2-(2,5-dioxo-2,5-dihydro-1H-pyrrol-1-yl)ethoxy)propanamido)-3-methylbutanamido)-5-ureidopentanamido)phenyl)-1-(thiazol-2-yl)ethyl)amino)-1-methoxy-2-methyl-3-oxopropyl)pyrrolidin-1-yl)-3- methoxy-5-methyl-1-oxoheptan-4-yl)(methyl)amino)-3-methyl-1-oxobutan-2-yl)-2-methyl-2-azabicyclo[2.2.1]heptane-3-carboxamide (LP1) as TFA salt. MS m/z 1262.4 (M+1). Retention time 1.02 min.

Example D: Synthesis of (1R,3S,4S)—N—((S)-1-(((3R,4S,5S)-1-((S)-2-((1R,2R)-3-(((S)-1-(3-((S)-2-((S)-2-(3-(2-(2,5-dioxo-2,5-dihydro-1H-pyrrol-1-yl)ethoxy)propanamido)-3-methylbutanamido)-5-ureidopentanamido)phenyl)-3-hydroxypropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (LP2)

phenyl)amino)-1-oxo-5-ureidopentan-2-yl)carbamate (31.5 mg, 0.025 mmol) TFA salt was dissolved in MeOH (1 mL). Then Pd/C (10 mg, 9.40 µmol) was added. A 2 L hydrogen balloon was attached and the reaction mixture was vacuum flushed three times with H₂ and then stirred under H₂ at rt for 30 min. The catalyst was then removed by filtration through celite and the mixture was concentrated and treated with 1N NaOH. The crude mixture was purified by reverse phase HPLC, using C18 column, eluted with 5-37% acetonitrile-H₂O containing 0.05% TFA. The fractions containing desired product were lyophilized to obtain (1R,3S,4S)—N—((S)-1-(((3R,4S,5S)-1-((S)-2-((1R,2R)-3-(((S)-1-(3-((S)-2-amino-5-ureidopentanamido)phenyl)-3-hydroxypropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-

(LP2)

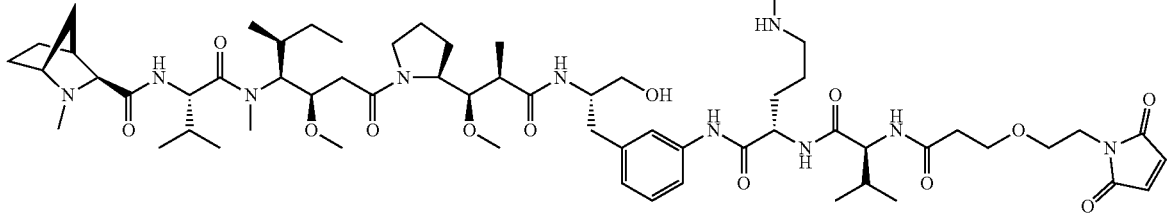

Step 1: To a solution of Fmoc-Cit-OH

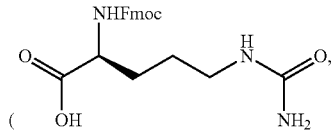

10.0 mg, 0.025 mmol) in DMF (1 ml) was added DIEA (13.0 mg, 0.10 mmol) and then HATU (9.6 mg, 0.025 mmol) and the reaction mixture was stirred at rt for 5 min and the solution was then added to (1R,3S,4S)—N—((S)-1-(((3R,4S,5S)-1-((S)-2-((1R,2R)-3-(((S)-1-(3-aminophenyl)-3-hydroxypropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (C2) (20 mg, 0.025 mmol). This reaction mixture was stirred at rt for 1 hour and then purified by reverse phase HPLC, using C18 column, eluted with 10-45% acetonitrile-H₂O containing 0.05% TFA. The fractions containing the desired product were concentrated to obtain (9H-fluoren-9-yl)methyl ((S)-1-((3-((S)-2-((2R,3R)-3-((S)-1-((3R,4S,5S)-4-((S)—N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanamido)-3-hydroxypropyl)phenyl)amino)-1-oxo-5-ureidopentan-2-yl)carbamate as TFA salt. LCMS MS m/z 1136.6 (M+1), Retention time 1.042 minutes.

Step 2: (9H-fluoren-9-yl)methyl ((S)-1-((3-((S)-2-((2R,3R)-3-((S)-1-((3R,4S,5S)-4-((S)—N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanamido)-3-hydroxypropyl)phenyl)amino)-1-oxo-5-ureidopentan-2-yl)carbamate as TFA salt. LCMS m/z 914.6 (M+1), Retention time 0.773 min.

Step 3: To a solution of Cbz-Val-OH

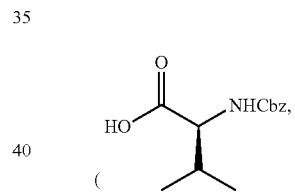

2.6 mg, 0.011 mmol) in DMF (1 ml) was added DIEA (0.011 ml, 0.061 mmol) and then HATU (3.86 mg, 0.011 mmol). The reaction mixture was stirred at rt for 5 min and then added to a solution of (1R,3S,4S)—N—((S)-1-(((3R,4S,5S)-1-((S)-2-((1R,2R)-3-(((S)-1-(3-((S)-2-amino-5-ureidopentanamido)phenyl)-3-hydroxypropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (11.6 mg, 0.011 mmol) TFA salt in DMF (1 ml). The reaction mixture was stirred at rt for 1 hour and then the crude was purified by reverse phase HPLC, using C18 column, eluted with 10-50% acetonitrile-H₂O containing 0.05% TFA. The fractions containing desired product were lyophilized to obtain benzyl ((S)-1-(((S)-1-((3-((S)-2-((2R,3R)-3-((S)-1-((3R,4S,5S)-4-((S)—N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanamido)-3-hydroxypropyl)phenyl)amino)-1-oxo-5-ureidopentan-2-yl)amino)-3-methyl-1-oxobutan-2-yl)carbamate as TFA salt. LCMS m/z 1147.6 (M+1), Retention time 0.986 min.

Step 4: Benzyl ((S)-1-(((S)-1-((3-((S)-2-((2R,3R)-3-((S)-1-((3R,4S,5S)-4-((S)—N,3-dimethyl-2-((1R,3S,4S)-2- methyl-2-azabicyclo[2.2.1]heptane-3-carboxamido)butanamido)-3-methoxy-5-methylheptanoyl)pyrrolidin-2-yl)-3-methoxy-2-methylpropanamido)-3-hydroxypropyl)phenyl)amino)-1-oxo-5-ureidopentan-2-yl)amino)-3-methyl-1-oxobutan-2-yl)carbamate (7.7 mg, 0.006 mmol) TFA salt was dissolved in MeOH (2 ml) and then Pd/C (5 mg, 4.70 µmol) was added. A 2 L hydrogen balloon was attached and the reaction mixture was vacuum flushed with H$_2$ three times and then stirred under H$_2$ for 30 mins. LCMS indicated the reaction was complete. The catalyst was then removed by filtration through celite and the mixture was then concentrated to give (1R,3S,4S)—N—((S)-1-(((3R,4S,5S)-1-((S)-2-((1R,2R)-3-(((S)-1-(3-((S)-2-((S)-2-amino-3-methylbutanamido)-5-ureidopentanamido)phenyl)-3-hydroxypropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide as TFA salt. LCMS m/z 1013.6 (M+1) Retention time 0.774 min.

Step 5: To a solution of Mal-PEG1-acid

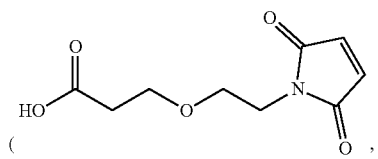 [SMILES: O=C(O)CCOCCN1C(=O)C=CC1=O]

1.0 mg, 0.005 mmol) in DMF (0.5 ml) was added DIEA (2.8 mg, 0.022 mmol) and then HATU (1.8 mg, 0.005 mmol). The reaction was stirred at rt for 5 min and then added to a solution of (1R,3S,4S)—N—((S)-1-(((3R,4S,5S)-1-((S)-2-((1R,2R)-3-(((S)-1-(3-((S)-2-((S)-2-amino-3-methylbutanamido)-5-ureidopentanamido)phenyl)-3-hydroxypropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (4.8 mg, 0.005 mmol) TFA salt in DMF (1 ml). The reaction was stirred at rt for 1 hour and then the crude was purified by reverse phase HPLC, using C18 column, eluted with 10-38% acetonitrile-H$_2$O containing 0.05% TFA. The fractions containing desired product were lyophilized to obtain (1R,3S,4S)—N—((S)-1-(((3R,4S,5S)-1-((S)-2-((1R,2R)-3-(((S)-1-(3-((S)-2-((S)-2-(3-(2-(2,5-dioxo-2,5-dihydro-1H-pyrrol-1-yl)ethoxy)propanamido)-3-methylbutanamido)-5-ureidopentanamido)phenyl)-3-hydroxypropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide as TFA salt (LP-2). LCMS m/z 1208.5 (M+1) Retention time 0.882 min.

Conjugation and Preparation of ADCs

Processes for Making Antibody Conjugate of Formula (I)

A general reaction scheme for the formation of conjugates of Formula (I) is shown in Scheme 1 below:

Scheme 1

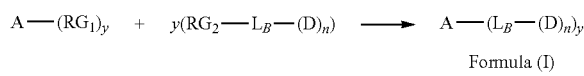

Formula (I)

where: RG$_1$ is a reactive group, by way of example only a thiol or amine or ketone, which reacts with a compatible reactive group, RG$_2$, attached to the linker-drug moiety thereby covalently linking antibody or antibody fragment, A, to one or more linker-drug moieties. Non-limiting examples of such reactions of RG$_1$ and RG$_2$ groups is a maleimide (RG$_2$) reacting with a thiol (RG$_1$) to give a succinimide ring, or a hydroxylamine (RG$_2$) reacting with a ketone (RG$_1$) to give an oxime.

A general reaction scheme for the formation of conjugates of Formula (II) is shown in Scheme 2 below:

Scheme 2

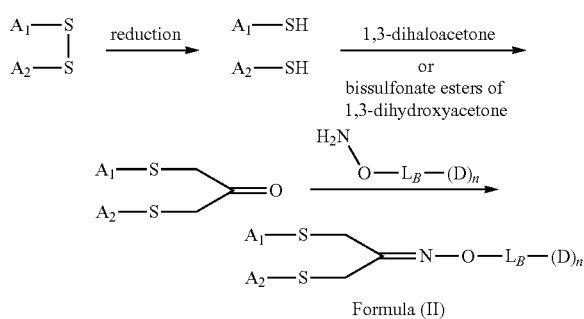

Formula (II)

where: A$_1$, A$_2$, L$_B$, D and n are as defined herein, the 1,3-dihaloacetone is selected from 1,3-dichloroacetone, 1,3-dibromoacetone, and 1,3-diiodoacetone, and the reduction step is accomplished using a reducing agent selected from dithiothreitol (DTT) and Tris(2-carboxyethyl)phosphine hydrochloride (TCEP-HCl).

A general reaction scheme for the formation of conjugates of Formula (E) is shown in Scheme 3 below:

Scheme 3

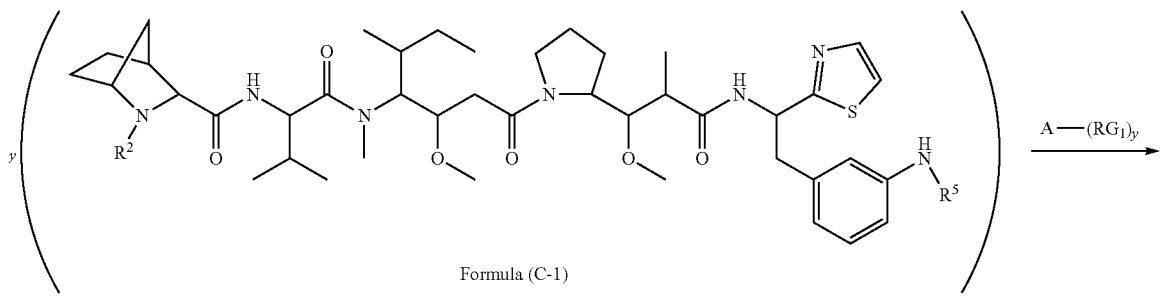

Formula (C-1)

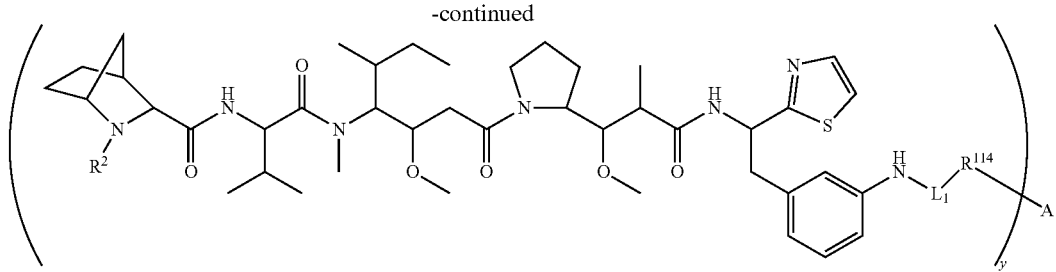

Formula (E)

where: $R^5$ is $-L_1R^{14}$, $-L_1R^{24}$, $-L_1R^{34}$ or $-L_1R^{44}$ and $RG_1$ is a reactive group, by way of example only a thiol or amine or ketone, which reacts with a compatible $R^{14}$, $R^{24}$, $R^{34}$ or $R^{44}$ group of a compound of Formula (C-1) to form a corresponding $R^{14}$ group. By way of example, a maleimide reacting with a thiol to give a succinimide ring, or a hydroxylamine reacting with a ketone to give an oxime. A, y, $L_1$, $R^2$, $R^5$ and $R^{14}$ are as defined herein.

A general reaction scheme for the formation of conjugates of Formula (F) is shown in Scheme 4 below:

Scheme 4

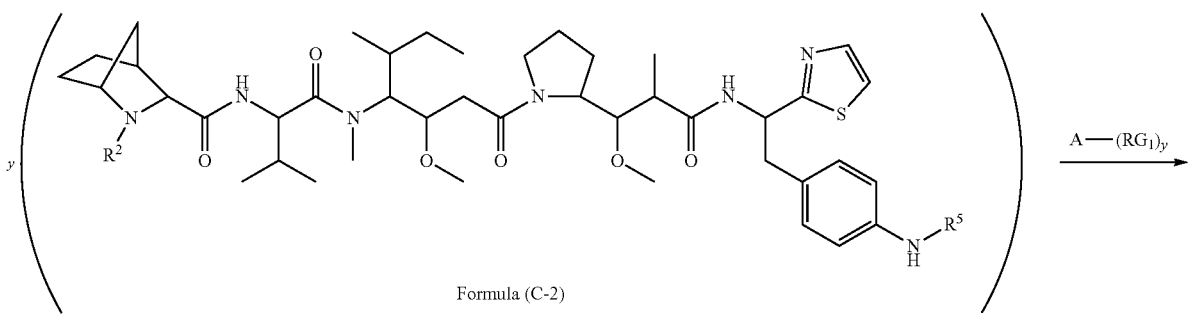

Formula (C-2)

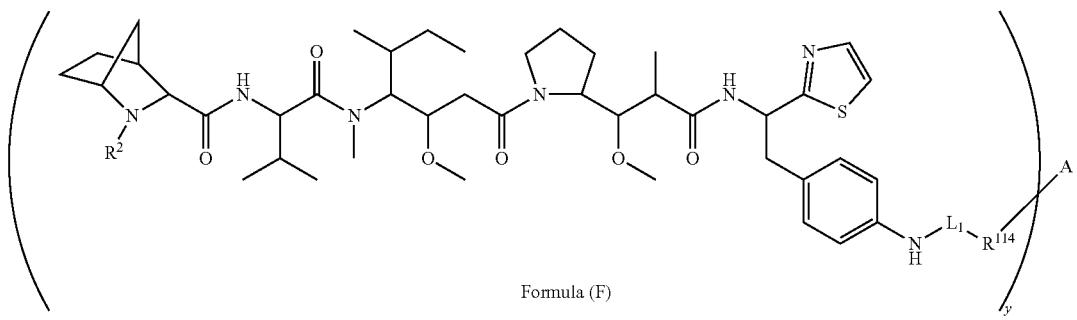

Formula (F)

where: $R^5$ is $-L_1R^{14}$, $-L_1R^{24}$, $-L_1R^{34}$ or $-L_1R^{44}$ and $RG_1$ is a reactive group, by way of example only a thiol or amine or ketone, which reacts with a compatible $R^{14}$, $R^{24}$, $R^{34}$ or $R^{44}$ group of a compound of Formula (C-2) to form a corresponding $R^{114}$ group. By way of example, a maleimide reacting with a thiol to give a succinimide ring, or a hydroxylamine reacting with a ketone to give an oxime. A, y, $L_1$, $R^2$, $R^5$ and $R^{114}$ are as defined herein.

A general reaction scheme for the formation of conjugates of Formula (G) is shown in Scheme 5 below:

Scheme 5

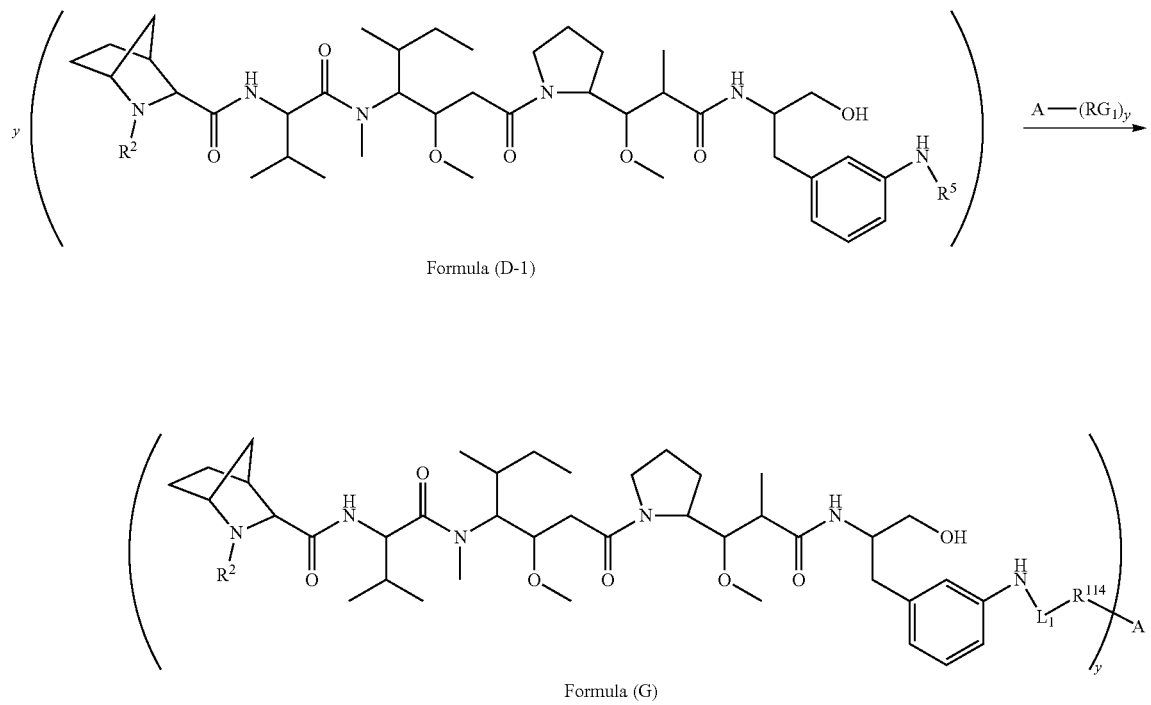

Formula (D-1)

Formula (G)

where: $R^5$ is $-L_1R^{14}$, $-L_1R^{24}$, $-L_1R^{34}$ or $-L_1R^{44}$ and $RG_1$ is a reactive group, by way of example only a thiol or amine or ketone, which reacts with a compatible $R^{14}$, $R^{24}$, $R^{34}$ or $R^{44}$ group of a compound of Formula (D-1) to form a corresponding $R^{14}$ group. By way of example, a maleimide reacting with a thiol to give a succinimide ring, or a hydroxylamine reacting with a ketone to give an oxime. A, y, $L_1$, $R^2$, $R^5$ and $R^{114}$ are as defined herein.

A general reaction scheme for the formation of conjugates of Formula (H) is shown in Scheme 6 below:

Scheme 6

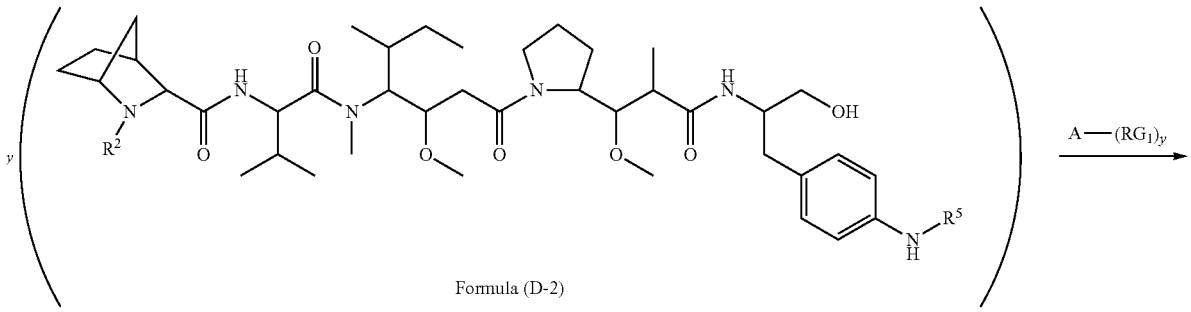

Formula (D-2)

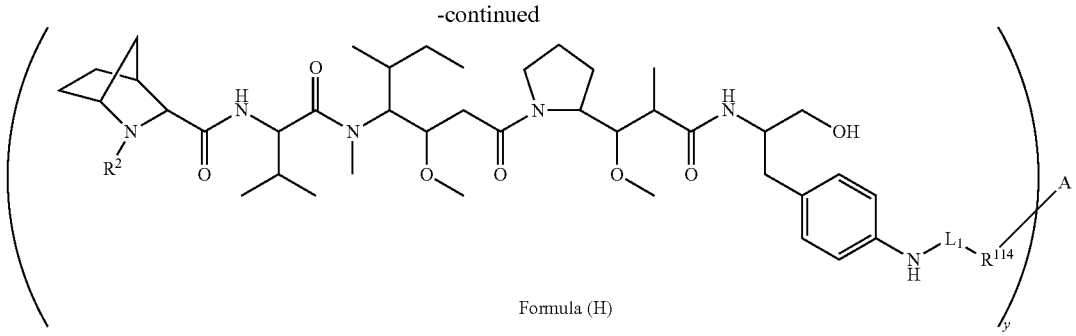

Formula (H)

where: $R^5$ is $-L_1R^{14}$, $-L_1R^{24}$, $-L_1R^{34}$ or $-L_1R^{44}$ and $RG_1$ is a reactive group, by way of example only a thiol or amine or ketone, which reacts with a compatible $R^{14}$, $R^{24}$, $R^{34}$ or $R^{44}$ group of a compound of Formula (D-2) to form a corresponding $R^{114}$ group. By way of example, a maleimide reacting with a thiol to give a succinimide ring, or a hydroxylamine reacting with a ketone to give an oxime. A, y, $L_1$, $R^2$, $R^5$ and $R^{11}4$ are as defined herein.

Therapeutic Uses

The antibodies, antibody fragments (e.g. antigen binding fragments), and antibody drug conjugates disclosed herein are useful in treating any CD48-expressing cancer such as hematologic diseases or hematological malignancies. Hematological diseases/malignancies that are treatable with the antibodies, antibody fragments (e.g. antigen binding fragments), and antibody drug conjugates disclosed herein includes: multiple myeloma, acute lymphoblastic leukemia (ALL), acute myelogenous leukemia (AML), acute monocytic leukemia (AMoL), chronic lymphocytic leukemia (CLL), chronic myelogenous leukemia (CML), hairy cell leukemia (HCL), T-cell prolymphocytic leukemia (T-PLL), large granular lymphocytic leukemia and adult T-cell leukemia, lymphoma, B-cell lymphoma, precursor T-cell leukemia/lymphoma, Burkitt lymphoma, follicular lymphoma, diffuse large B cell lymphoma, mantle cell lymphoma, B-cell chronic lymphocytic leukemia/lymphoma, MALT lymphoma, Mycosis fungoides, Peripheral T-cell lymphoma not otherwise specified, Hodgkin lymphoma, non-Hodgkin lymphoma, Nodular sclerosis form of Hodgkin lymphoma, Mixed-cellularity subtype of Hodgkin lymphoma, and myelodysplastic syndrome.

In some embodiments, the antibodies, antibody fragments (e.g. antigen binding fragments), and antibody drug conjugates disclosed herein are useful in treating any CD48-expressing solid tumors selected from any of the following: lung cancer, non-small cell lung cancer (NSCLC), small cell lung cancer (SCLC), colon cancer, colorectal cancer, rectal cancer, renal-cell carcinoma, liver cancer, hepatocellular carcinoma, cancer of the small intestine, cancer of the esophagus, pancreatic cancer, breast cancer, head and neck cancer, head and neck squamous cell carcinoma, thyroid cancer, cervical cancer, ovarian cancer, skin cancer, melanoma, and prostate cancer. The cancer may be at an early, intermediate, late stage or metastatic cancer.

In some embodiments, antibodies, antibody fragments (e.g. antigen binding fragments), and antibody drug conjugates disclosed herein are useful in treating breast cancer, multiple myeloma, B-cell lymphoma, plasma cell myeloma, leukemia, lymphoma, gastric cancer, acute myeloid leukemia, bladder cancer, brain cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, prostate cancer, small cell lung cancer, or spleen cancer.

Combination Therapy

In certain instances, the antibodies, antibody fragments (e.g. antigen binding fragments), and antibody drug conjugates of the present disclosure can be used in combination with another conditioning regiment such as radiation therapy or chemotherapy.

In certain instances, the antibodies, antibody fragments (e.g. antigen binding fragments), and antibody drug conjugates of the present disclosure can be used in combination with another therapeutic agent, such as an anti-cancer agent, anti-nausea agent (or anti-emetic), pain reliever, mobilizing agent, or combinations thereof.

General chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclosporine (Sandimmune®, Neoral® or Restasis®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

In one aspect, the antibodies, antibody fragments (e.g. antigen binding fragments), and antibody drug conjugates of the present disclosure can be combined in a pharmaceutical combination formulation, or dosing regimen as combination therapy, with a second compound having anti-cancer properties. The second compound of the pharmaceutical combination formulation or dosing regimen can have complementary activities to the conjugate of the combination such that they do not adversely affect each other.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In some embodiments, the present disclosure provides methods of treatment wherein the antibody-drug conjugates disclosed herein are administered in combination with one or more additional therapeutic agents. Exemplary combination partners are disclosed herein.

In certain embodiments, a combination described herein comprises a PD-1 inhibitor. In some embodiments, the PD-1 inhibitor is chosen from PDR001 (Novartis), Nivolumab (Bristol-Myers Squibb), Pembrolizumab (Merck & Co), Pidilizumab (CureTech), MED10680 (Medimmune), REGN2810 (Regeneron), TSR-042 (Tesaro), PF-06801591 (Pfizer), BGB-A317 (Beigene), BGB-108 (Beigene), INCSHR1210 (Incyte), or AMP-224 (Amplimmune). In some embodiments, the PD-1 inhibitor is PDR001. PDR001 is also known as Spartalizumab.

In certain embodiments, a combination described herein comprises a LAG-3 inhibitor. In some embodiments, the LAG-3 inhibitor is chosen from LAG525 (Novartis), BMS-986016 (Bristol-Myers Squibb), or TSR-033 (Tesaro).

In certain embodiments, a combination described herein comprises a TIM-3 inhibitor. In some embodiments, the TIM-3 inhibitor is MBG453 (Novartis), TSR-022 (Tesaro), LY-3321367 (Eli Lily), Sym23 (Symphogen), BGB-A425 (Beigene), INCAGN-2390 (Agenus), BMS-986258 (BMS), RO-7121661 (Roche), or LY-3415244 (Eli Lilly). MBG453 is also known as sabatolimab In certain embodiments, a combination described herein comprises a PDL1 inhibitor. In one embodiment, the PDL1 inhibitor is chosen from FAZ053 (Novartis), atezolizumab (Genentech), durvalumab (Astra Zeneca), or avelumab (Pfizer).

In certain embodiments, a combination described herein comprises a GITR agonist. In some embodiments, the GITR agonist is chosen from GWN323 (NVS), BMS-986156, MK-4166 or MK-1248 (Merck), TRX518 (Leap Therapeutics), INCAGN1876 (Incyte/Agenus), AMG 228 (Amgen) or INBRX-110 (Inhibrx).

In some embodiments, a combination described herein comprises an IAP inhibitor. In some embodiments, the IAP inhibitor comprises LCL161 or a compound disclosed in International Application Publication No. WO 2008/016893.

In an embodiment, the combination comprises an mTOR inhibitor, e.g., RAD001 (also known as everolimus).

In an embodiment, the combination comprises a HDAC inhibitor, e.g., LBH589. LBH589 is also known as panobinostat.

In an embodiment, the combination comprises an IL-17 inhibitor, e.g., CJM112.

In certain embodiments, a combination described herein comprises an estrogen receptor (ER) antagonist. In some embodiments, the estrogen receptor antagonist is used in combination with a PD-1 inhibitor, a CDK4/6 inhibitor, or both. In some embodiments, the combination is used to treat an ER positive (ER+) cancer or a breast cancer (e.g., an ER+ breast cancer).

In some embodiments, the estrogen receptor antagonist is a selective estrogen receptor degrader (SERD). SERDs are estrogen receptor antagonists which bind to the receptor and result in e.g., degradation or down-regulation of the receptor (Boer K. et al., (2017) *Therapeutic Advances in Medical Oncology* 9(7): 465-479). ER is a hormone-activated transcription factor important for e.g., the growth, development and physiology of the human reproductive system. ER is activated by, e.g., the hormone estrogen (17beta estradiol). ER expression and signaling is implicated in cancers (e.g., breast cancer), e.g., ER positive (ER+) breast cancer. In some embodiments, the SERD is chosen from LSZ102, fulvestrant, brilanestrant, or elacestrant.

In some embodiments, the SERD comprises a compound disclosed in International Application Publication No. WO 2014/130310, which is hereby incorporated by reference in its entirety.

In some embodiments, the SERD comprises LSZ102. LSZ102 has the chemical name: (E)-3-(4-((2-(2-(1,1-difluoroethyl)-4-fluorophenyl)-6-hydroxybenzo[b]thiophen-3-yl)oxy)phenyl)acrylic acid. In some embodiments, the SERD comprises fulvestrant (CAS Registry Number: 129453-61-8), or a compound disclosed in International Application Publication No. WO 2001/051056, which is hereby incorporated by reference in its entirety. In some embodiments, the SERD comprises elacestrant (CAS Registry Number: 722533-56-4), or a compound disclosed in U.S. Pat. No. 7,612,114, which is incorporated by reference in its entirety. Elacestrant is also known as RAD1901, ER-306323 or (6R)-6-{2-[Ethyl({4-[2-(ethylamino)ethyl]phenyl}methyl)amino]-4-methoxyphenyl}-5,6,7,8-tetrahydronaphthalen-2- ol. Elacestrant is an orally bioavailable, non-steroidal combined selective estrogens receptor modulator (SERM) and a SERD. Elacestrant is also disclosed, e.g., in Garner F et al., (2015) *Anticancer Drugs* 26(9):948-56. In some embodiments, the SERD is brilanestrant (CAS Registry Number: 1365888-06-7), or a compound disclosed in International Application Publication No. WO 2015/136017, which is incorporated by reference in its entirety.

In some embodiments, the SERD is chosen from RU 58668, GW7604, AZD9496, bazedoxifene, pipendoxifene, arzoxifene, OP-1074, or acolbifene, e.g., as disclosed in McDonell et al. (2015) *Journal of Medicinal Chemistry* 58(12) 4883-4887.

Other exemplary estrogen receptor antagonists are disclosed, e.g., in WO 2011/156518, WO 2011/159769, WO 2012/037410, WO 2012/037411, and US 2012/0071535, all of which are hereby incorporated by reference in their entirety In certain embodiments, a combination described herein comprises an inhibitor of Cyclin-Dependent Kinases 4 or 6 (CDK4/6). In some embodiments, the CDK4/6 inhibitor is used in combination with a PD-1 inhibitor, an estrogen receptor (ER) antagonist, or both. In some embodiments, the combination is used to treat an ER positive (ER+) cancer or a breast cancer (e.g., an ER+ breast cancer). In some embodiments, the CDK4/6 inhibitor is chosen from ribociclib, abemaciclib (Eli Lilly), or palbociclib.

In some embodiments, the CDK4/6 inhibitor comprises ribociclib (CAS Registry Number: 1211441-98-3), or a compound disclosed in U.S. Pat. Nos. 8,415,355 and 8,685,980, which are incorporated by reference in their entirety.

In some embodiments, the CDK4/6 inhibitor comprises a compound disclosed in International Application Publication No. WO 2010/020675 and U.S. Pat. Nos. 8,415,355 and 8,685,980, which are incorporated by reference in their entirety.

In some embodiments, the CDK4/6 inhibitor comprises ribociclib (CAS Registry Number: 1211441-98-3). Ribociclib is also known as LEE011, KISQALI®, or 7-cyclopentyl-N,N-dimethyl-2-((5-(piperazin-1-yl)pyridin-2-yl)amino)-7H-pyrrolo[2,3-d]pyrimidine-6-carboxamide.

In some embodiments, the CDK4/6 inhibitor comprises abemaciclib (CAS Registry Number: 1231929-97-7). Abemaciclib is also known as LY835219 or N-[5-[(4-Ethyl-1-piperazinyl)methyl]-2-pyridinyl]-5-fluoro-4-[4-fluoro-2-methyl-1-(1-methylethyl)-1H-benzimidazol-6-yl]-2-pyrimidinamine. Abemaciclib is a CDK inhibitor selective for CDK4 and CDK6 and is disclosed, e.g., in Torres-Guzman R et al. (2017) Oncotarget 10.18632/oncotarget.17778.

In some embodiments, the CDK4/6 inhibitor comprises palbociclib (CAS Registry Number: 571190-30-2). Palbociclib is also known as PD-0332991, IBRANCE® or 6-Acetyl-8-cyclopentyl-5-methyl-2-{[5-(1-piperazinyl)-2-pyridinyl]amino}pyrido[2,3-d]pyrimidin-7(8H)-one. Palbociclib inhibits CDK4 with an IC50 of 11 nM, and inhibits CDK6 with an IC50 of 16 nM, and is disclosed, e.g., in Finn et al. (2009) Breast Cancer Research 11(5):R77.

In certain embodiments, a combination described herein comprises an inhibitor of chemokine (C-X-C motif) receptor 2 (CXCR2). In some embodiments, the CXCR2 inhibitor is chosen from 6-chloro-3-((3,4-dioxo-2-(pentan-3-ylamino)cyclobut-1-en-1-yl)amino)-2-hydroxy-N-methoxy-N-methylbenzenesulfonamide, danirixin, reparixin, or navarixin.

In some embodiments, the CSF-1/1R binding agent is chosen from an inhibitor of macrophage colony-stimulating factor (M-CSF), e.g., a monoclonal antibody or Fab to M-CSF (e.g., MCS110), a CSF-1R tyrosine kinase inhibitor (e.g., 4-((2-(((1R,2R)-2-hydroxycyclohexyl)amino)benzo[d]thiazol-6-yl)oxy)-N-methylpicolinamide or BLZ945), a receptor tyrosine kinase inhibitor (RTK) (e.g., pexidartinib), or an antibody targeting CSF-1R (e.g., emactuzumab or FPA008). In some embodiments, the CSF-1/1R inhibitor is BLZ945. In some embodiments, the CSF-1/1R binding agent is MCS110. In other embodiments, the CSF-1/1R binding agent is pexidartinib.

In certain embodiments, a combination described herein comprises a c-MET inhibitor. C-MET, a receptor tyrosine kinase overexpressed or mutated in many tumor cell types, plays key roles in tumor cell proliferation, survival, invasion, metastasis, and tumor angiogenesis. Inhibition of c-MET may induce cell death in tumor cells overexpressing c-MET protein or expressing constitutively activated c-MET protein. In some embodiments, the c-MET inhibitor is chosen from capmatinib (INC280), JNJ-3887605, AMG 337, LY2801653, MSC2156119J, crizotinib, tivantinib, or golvatinib.

In certain embodiments, a combination described herein comprises a transforming growth factor beta (also known as TGF-β TGFβ, TGFb, or TGF-beta, used interchangeably herein) inhibitor. In some embodiments, the TGF-β inhibitor is chosen from fresolimumab or XOMA 089.

In certain embodiments, a combination described herein comprises an adenosine A2a receptor (A2aR) antagonist (e.g., an inhibitor of A2aR pathway, e.g., an adenosine inhibitor, e.g., an inhibitor of A2aR or CD-73). In some embodiments, the A2aR antagonist is used in combination with a PD-1 inhibitor, and one or more (e.g., two, three, four, five, or all) of a CXCR2 inhibitor, a CSF-1/1R binding agent, LAG-3 inhibitor, a GITR agonist, a c-MET inhibitor, or an IDO inhibitor. In some embodiments, the combination is used to treat a pancreatic cancer, a colorectal cancer, a gastric cancer, or a melanoma (e.g., a refractory melanoma). In some embodiments, the A2aR antagonist is chosen from PBF509 (NIR178) (Palobiofarma/Novartis), CPI444/V81444 (Corvus/Genentech), AZD4635/HTL-1071 (AstraZeneca/Heptares), Vipadenant (Redox/Juno), GBV-2034 (Globavir), AB928 (Arcus Biosciences), Theophylline, Istradefylline (Kyowa Hakko Kogyo), Tozadenant/SYN-115 (Acorda), KW-6356 (Kyowa Hakko Kogyo), ST-4206 (Leadiant Biosciences), or Preladenant/SCH 420814 (Merck/Schering). Without wishing to be bound by theory, it is believed that in some embodiments, inhibition of A2aR leads to upregulation of IL-1b.

In certain embodiments, a combination described herein comprises an inhibitor of indoleamine 2,3-dioxygenase (IDO) and/or tryptophan 2,3-dioxygenase (TDO). In some embodiments, the IDO inhibitor is used in combination with a PD-1 inhibitor, and one or more (e.g., two, three, four, or all) of a TGF-β inhibitor, an A2aR antagonist, a CSF-1/1R binding agent, a c-MET inhibitor, or a GITR agonist. In some embodiments, the combination is used to treat a pancreatic cancer, a colorectal cancer, a gastric cancer, or a melanoma (e.g., a refractory melanoma). In some embodiments, the IDO inhibitor is chosen from (4E)-4-[(3-chloro-4-fluoroanilino)-nitrosomethylidene]-1,2,5-oxadiazol-3-amine (also known as epacadostat or INCB24360), indoximod (NLG8189), (1-methyl-D-tryptophan), α-cyclohexyl-5H-Imidazo[5,1-a]isoindole-5-ethanol (also known as NLG919), indoximod, BMS-986205 (formerly F001287).

In certain embodiments, a combination described herein comprises a Galectin, e.g., Galectin-1 or Galectin-3, inhibitor. In some embodiments, the combination comprises a Galectin-1 inhibitor and a Galectin-3 inhibitor. In some embodiments, the combination comprises a bispecific inhibitor (e.g., a bispecific antibody molecule) targeting both Galectin-1 and Galectin-3. In some embodiments, the Galectin inhibitor is used in combination with one or more therapeutic agents described herein. In some embodiments, the Galectin inhibitor is chosen from an anti-Galectin antibody molecule, GR-MD-02 (Galectin Therapeutics), Galectin-3C (Mandal Med), Anginex, or OTX-008 (OncoEthix, Merck).

In some embodiments, a combination described herein comprises a MEK inhibitor. In some embodiments, the MEK inhibitor is chosen from Trametinib, selumetinib, AS703026, BIX 02189, BIX 02188, CI-1040, PD0325901, PD98059, U0126, XL-518, G-38963, or G02443714. In some embodiments, the MEK inhibitor is Trametinib.

In one embodiment, a combination described herein includes an interleukin-1 beta (IL-1β) inhibitor. In some embodiments, the IL-1β inhibitor is chosen from canakinumab, gevokizumab, Anakinra, or Rilonacept.

In certain embodiments, a combination described herein comprises an IL-15/IL-15Ra complex. In some embodiments, the IL-15/IL-15Ra complex is chosen from NIZ985 (Novartis), ATL-803 (Altor) or CYP0150 (Cytune).

In certain embodiments, a combination described herein comprises a mouse double minute 2 homolog (MDM2) inhibitor. The human homolog of MDM2 is also known as HDM2. In some embodiments, an MDM2 inhibitor described herein is also known as a HDM2 inhibitor. In some embodiments, the MDM2 inhibitor is chosen from HDM201 or CGM097.

In an embodiment the MDM2 inhibitor comprises (S)-1-(4-chlorophenyl)-7-isopropoxy-6-methoxy-2-(4-(methyl (((1r,4S)-4-(4-methyl-3-oxopiperazin-1-yl)cyclohexyl) methyl)amino)phenyl)-1,2-dihydroisoquinolin-3(4H)-one (also known as CGM097) or a compound disclosed in PCT Publication No. WO 2011/076786 to treat a disorder, e.g., a disorder described herein). In one embodiment, a therapeutic agent disclosed herein is used in combination with CGM097.

In some embodiments, a combination described herein comprises a hypomethylating agent (HMA). In one some embodiments, the HMA is chosen from decitabine or azacitidine.

Pharmaceutical Compositions

To prepare pharmaceutical or sterile compositions including one or more antibodies, antibody fragments (e.g. antigen binding fragments), or antibody drug conjugates described herein, the provided conjugate(s) can be mixed with a pharmaceutically acceptable carrier or excipient.

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., Goodman and Gilman's The Pharmacological Basis of Therapeutics, McGraw-Hill, New York, N.Y., 2001; Gennaro, Remington: The Science and Practice of Pharmacy, Lippincott, Williams, and Wilkins, New York, N.Y., 2000; Avis, et al. (eds.), Pharmaceutical Dosage Forms: Parenteral Medications, Marcel Dekker, NY, 1993; Lieberman, et al. (eds.), Pharmaceutical Dosage Forms: Tablets, Marcel Dekker, NY, 1990; Lieberman, et al. (eds.) Pharmaceutical Dosage Forms: Disperse Systems, Marcel Dekker, NY, 1990; Weiner and Kotkoskie, Excipient Toxicity and Safety, Marcel Dekker, Inc., New York, N.Y., 2000).

In some embodiments, the pharmaceutical composition comprising the antibodies, antibody fragments (e.g. antigen binding fragments), or antibody drug conjugate of the present disclosure is a lyophilisate preparation. In certain embodiments a pharmaceutical composition comprising the antibodies, antibody fragments (e.g. antigen binding fragments), or antibody drug conjugate is a lyophilisate in a vial containing the antibodies, antibody fragments (e.g. antigen binding fragments), or antibody drug conjugate in a buffer solution. The lyophilisate can be reconstituted, e.g., with water, saline, for injection. For intravenous administration, the obtained solution may be further diluted into a carrier solution.

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, Antibody Therapy, Bios Scientific Pub. Ltd, Oxfordshire, U K, 1996; Kresina (ed.), Monoclonal Antibodies, Cytokines and Arthritis, Marcel Dekker, New York, N.Y., 1991; Bach (ed.), Monoclonal Antibodies and Peptide Therapy in Autoimmune Diseases, Marcel Dekker, New York, N.Y., 1993; Baert et al., New Engl. J. Med. 348:601-608, 2003; Milgrom et al., New Engl. J. Med. 341:1966-1973, 1999; Slamon et al., New Engl. J. Med. 344:783-792, 2001; Beniaminovitz et al., New Engl. J. Med. 342:613-619, 2000; Ghosh et al., New Engl. J. Med. 348:24-32, 2003; Lipsky et al., New Engl. J. Med. 343:1594-1602, 2000).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts.

Compositions comprising the antibodies, antibody fragments (e.g. antigen binding fragments), or antibody drug conjugate disclosed herein can be provided by continuous infusion, or by doses at intervals of, e.g., one day, one week, or 1-7 times per week, once every other week, once every three weeks, once every four weeks, once every five weeks, once every six weeks, once every seven weeks, or once every eight weeks. Doses may be provided intravenously, subcutaneously, or intraosseously. A specific dose protocol is one involving the maximal dose or dose frequency that avoids significant undesirable side effects.

For the antibodies, antibody fragments (e.g. antigen binding fragments), or antibody drug conjugates of the present disclosure, the dosage administered to a patient may be 0.0001 mg/kg to 100 mg/kg of the patient's body weight. The dosage may be between 0.001 mg/kg and 50 mg/kg, 0.005 mg/kg and 20 mg/kg, 0.01 mg/kg and 20 mg/kg, 0.02 mg/kg and 10 mg/kg, 0.05 and 5 mg/kg, 0.1 mg/kg and 10 mg/kg, 0.1 mg/kg and 8 mg/kg, 0.1 mg/kg and 5 mg/kg, 0.1 mg/kg and 2 mg/kg, 0.1 mg/kg and 1 mg/kg of the patient's body weight. The dosage of the antibodies, antibody fragments (e.g. antigen binding fragments), or antibody drug conjugate may be calculated using the patient's weight in kilograms (kg) multiplied by the dose to be administered in mg/kg.

Doses of the antibodies, antibody fragments (e.g. antigen binding fragments), or antibody drug conjugates of the present disclosure may be repeated and the administrations may be separated by less than 1 day, at least 1 day, 2 days, 3 days, 5 days, 10 days, 15 days, 30 days, 45 days, 2 months, 75 days, 3 months, 4 months, 5 months, or at least 6 months. In some embodiments, the antibodies, antibody fragments (e.g. antigen binding fragments), or antibody drug conjugates of the present disclosure is administered twice weekly, once weekly, once every two weeks, once every three weeks, once every four weeks, or less frequently.

An effective amount for a particular patient may vary depending on factors such as the condition being treated, the overall health of the patient, the method, route and dose of administration and the severity of side effects (see, e.g., Maynard et al., A Handbook of SOPs for Good Clinical Practice, Interpharm Press, Boca Raton, Fla., 1996; Dent, Good Laboratory and Good Clinical Practice, Urch Publ., London, U K, 2001).

The route of administration may be by, e.g., topical or cutaneous application, injection or infusion by subcutaneous, intravenous, intraperitoneal, intracerebral, intramuscular, intraocular, intraarterial, intracerebrospinal, intralesional administration, or by sustained release systems or an implant (see, e.g., Sidman et al., Biopolymers 22:547-556, 1983; Langer et al., J. Biomed. Mater. Res. 15:167-277, 1981; Langer, Chem. Tech. 12:98-105, 1982; Epstein et al., Proc. Natl. Acad. Sci. USA 82:3688-3692, 1985; Hwang et al., Proc. Natl. Acad. Sci. USA 77:4030-4034, 1980; U.S. Pat. Nos. 6,350,466 and 6,316,024). Where necessary, the composition may also include a solubilizing agent or a local anesthetic such as lidocaine to ease pain at the site of the injection, or both. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

Methods for co-administration or treatment with a second therapeutic agent, e.g., a cytokine, steroid, chemotherapeutic agent, antibiotic, or radiation (such as total body irradiation (TBI)), are known in the art (see, e.g., Hardman et al., (eds.) (2001) Goodman and Gilman's The Pharmacological Basis of Therapeutics, 10.sup.th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies, which can be administered in combination with the antibodies, antibody fragments (e.g. antigen binding fragments), or antibody drug conjugates of the present disclosure may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the antibodies, antibody fragments (e.g. antigen binding fragments), or antibody drug conjugates of the present disclosure. The two or more therapies may be administered within one same patient visit.

The present disclosure provides protocols for the administration of pharmaceutical composition comprising antibodies, antibody fragments (e.g. antigen binding fragments), or antibody drug conjugates alone or in combination with other therapies to a subject in need thereof. The combination therapies disclosed herein can be administered concomitantly or sequentially to a subject. The combination therapies of the present disclosure can also be cyclically administered. Cycling therapy involves the administration of a first therapy for a period of time, followed by the administration of a second therapy for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies of the combination therapies disclosed herein can be administered to a subject concurrently.

The term "concurrently" is not limited to the administration of therapies at exactly the same time, but rather it is meant that a pharmaceutical composition comprising the antibodies, antibody fragments (e.g. antigen binding fragments), and antibody drug conjugates disclosed herein are administered to a subject in a sequence and within a time interval such that the antibodies, antibody fragments (e.g. antigen binding fragments), and antibody drug conjugates can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic effect. Each therapy can be administered to a subject separately, in any appropriate form and by any suitable route. In various embodiments, the therapies are administered to a subject less than 5 minutes apart, less than 15 minutes apart, less than 30 minutes apart, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies are administered within the same patient visit.

The combination therapies can be administered to a subject in the same pharmaceutical composition. Alternatively, the therapeutic agents of the combination therapies can be administered concurrently to a subject in separate pharmaceutical compositions. The therapeutic agents may be administered to a subject by the same or different routes of administration.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1: Generation of Anti-CD48 Antibodies

Generation of Expression Constructs for Human CD48-Mouse IgG1 Fusion Protein as Immunogen Human CD48 was amplified from the commercial vector "Trueclone, CD48 (untagged)-Human CD48 molecule" (Origene, NM_001778.2). The amplified DNA fragment was cloned into appropriate expression vectors.

HEK293T cells were seeded at $1\times10^6$ cells/well in a 6-well cell culture plate in pre-warmed DMEM (Gibco, 32430-027) and 10% FBS (Gibco, 10082-137). The next day, for each well, 3 µg of DNA construct were separately diluted in 150 µL of Opti-MEM (Gibco, 31985070) and 12 µL of Lipofectamine™ 2000 (Thermofischer Scientific, 1051561) in 150 µL of Opti-MEM. Diluted DNA was added to each corresponding tube of diluted Lipofectamine™ 2000 transfection reagent and incubated for 5 min at RT. 250 µL of DNA/Lipofectamine™ 2000 reagent complexes were added per well and incubated for 6 hours in the culture medium at 37° C., 5% $CO_2$. After 6 hours, the culture medium was replaced with pre-warmed DMEM+10% FBS and cells were incubated at 37° C., 5% $CO_2$ for additional 72 hrs.

HumanCD48-mouseIgG recombinant protein was purified using "Serum antibody purification kit—Protein G" (Abcam #ab128751). Following the supplier's recommendations, conditioned media were mixed with binding buffer and incubated for 2 hours at RT with the protein G resin prior to the packing of the columns. The columns were washed to remove unbound proteins and huCD48-mouseIgG protein was eluted at low pH and immediately neutralized. The presence of the protein in the elution fractions was confirmed by A280 OD determination. Elution fractions were pooled desalted and concentrated using Amicon Ultra-15 Centrifugal Filter Device (30K). Quantitation of purified protein was performed by anti-mouse IgG ELISA.

Expression of Recombinant Human and Cynomolgus CD48 Proteins

Human and cynomolgus proteins were gene synthesized (GeneArt, Switzerland) based on amino acid sequences (see Table 5). All synthesized DNA fragments were cloned into appropriate expression vectors with different C-terminal tags (hFc1P, APP6-Avi, His) to allow for purification and labelling.

TABLE 5

CD48 Protein Sequences

| Name | Description | Sequence | SEQ ID NO |
|---|---|---|---|
| Human CD48 | humanCD48 | MCSRGWDSCLALELL LLPLSLLVTSIQGHL VHMTVVSGSNVTLNI SESLPENYKQLTWFY TFDQKIVEWDSRKSK YFESKFKGRVRLDPQ SGALYISKVQKEDNS TYIMRVLKKTGNEQE WKIKLQVLDPVPKPV IKIEKIEDMDDNCYL KLSCVIPGESVNYTW YGDKRPFPKELQNSV LETTLMPHNYSRCYT CQVSNSVSSKNGTVC LSPPCTLARSFGVEW IASWLVVTVPTILGL LLT | 53 |
| Human CD48 | Met-humanCD48 (aa29-130)- APP6-Avi-His for Fab-Complex Crystallization | MHLVHMTVVSGSNVT LNISESLPENKQLTW FYTFDQKIVEWDSRK SKYFESKFKGRVRLD PQSGALYISKVQKED NSTYIMRVLKKTGNE QEWKIKLQVLDPGLN DIFEAQKIEWHEHHH HHH | 68 |
| Cynomolgus Monkey CD48 | CynoCD48 (aa29-217) | MGSRGWNRCLALELL LLSLSLLAISIQGRL VHMTVVSGSNVTLNIS ESLPENYKQLTWFYT FDQKIVEWDSGKSKY FESKFKGRVRLDPQS GALYISKVQKEDNST YVMRVLKDGYEQEWK IKLQVLDPVPKPVIK IEKDVDDNCYLKLSC VIPGESVNYTWYGEL PKEIQNSVLETTLKP HKHSRCYTCQVSVSS KNGTFCFSPPCTAAR SFGVEWIASWLVVTV PIILGLLLI | 69 |

HEK293T cells were seeded at $1\times10^6$ cells/well in a 6-well cell culture plate in pre-warmed DMEM (Gibco, 32430-027) and 10% FBS (Gibco, 10082-137). The next day, for each well, 2 µg of DNA construct were separately diluted in 100 µL of Opti-MEM (Gibco, 31985070) and 7 µL of FuGENE HD (Promega, 104810) added. Mix was incubated for 15 minutes at room temperature and added to cells. Plates were incubated for 72 hours in the culture medium at 37° C., 5% $CO_2$.

Human and cynomolgus CD48-huIgG-Fc and APP tagged recombinant proteins were purified by anti-APP or protein-A columns. The columns were washed and equilibrated to remove unbound proteins with PBS, pH7.4. Bound protein was eluted with 0.1 M Glycine, pH 2.7 and immediately neutralized. Protein concentration was determined by A280 OD measurement.

Human and Cynomolgus Monkey CD48 Protein Overexpressing Cell Lines

CHO and 300.19 cells were engineered to express human CD48 in combination with a GFP marker. HKB11 cell were transfected with either a human or a cynomolgus CD48 expressing vector. For the CHO and 300.19 cell lines, a CD48-EGFP coding expression plasmid was facilitated applying Amaxa 4D Nucleofection. Per sample 2.5×10⁵ cells were suspended in 20 µl 4DNucleofector™ Solution (Lonza, V4XC-9064), DNA added and placed in the cuvette. After electroporation, cuvettes were incubated for 10 minutes at room temperature. Cells were suspended in pre-warmed culture medium (RPMI 1640, (Gibco, 72400-021), 10% FBS (Gibco, 16000044), Penicillin-Streptomycin (Gibco, 15140122) and, 2-Mercaptoethanol (Gibco, 31350010), and incubated in humidified 37° C./5% $CO_2$ incubator. For selection, G418 (Gibco, 10131-027) was added at a final concentration of 1 mg/ml. Cell pools were analyzed by flow cytometry after staining the cells with a fluorescence labelled anti-human CD48 antibody, clone CD48A-PE (PE labeled antibody from Molecular Probes, A15768) applying non-transfected 300.19 or CHO cells acting as CD48-negative control cells. For both cell lines one pool was identified that showed a high and homogeneous expression of the respective target protein. Vials of this pool were frozen; the stability of recombinant CD48 overexpression was confirmed after continued culture of the cells in G418-containing cell culture medium over two weeks.

For the overexpressing HKB11 cell lines human full length CD48 was gene synthesized based on amino acid sequences from the Uniprot database. The sequence encoding cynomolgus monkey full length CD48 was gene synthesized based on amino acid sequence information generated using mRNA isolated from various cyno tissues. All sequences synthesized by GenArt (Switzerland). For engineering the HKB11 cell line the synthesized DNA fragments were cloned into pD2529-CMVa Leap-In transposon vectors (Atum, Newark/CA, USA). HKB11 (ATCC, CRL-12568) cells were transfected in triplicates using the JetMessenger transfection reagent (Polyplus, 150-07). The transposon vectors were co-transfected into the cells together with mRNA encoding the Leap-In transposase enzyme (Atum, Newark/CA, USA). Transfected cells were cultured in the presence of the antibiotic puromycin in the culture medium over 4 weeks to select for stably transfected cells. Cell pools were analyzed by flow cytometry after staining the cells with an anti-CD48 primary antibody (CD48A) and a fluorescently labelled secondary antibody, with non-transfected HKB11 cells acting as CD48-negative control cells. For both human and cyno CD48 one pool was identified that showed a high and homogeneous expression of the respective target protein. Vials of this pool were frozen; the stability of recombinant CD48 overexpression was confirmed after continued culture of the cells in puromycin-containing cell culture medium over two weeks.

All synthesized DNA fragments were cloned into pD2529-CMVa Leap-In transposon vectors (Atum, Newark/CA, USA). HKB11 (ATCC, CRL-12568) cells were transfected in triplicates using the JetMessenger transfection reagent. The transposon vectors were co-transfected into the cells together with mRNA encoding the Leap-In transposase enzyme (Atum, Newark/CA, USA). Transfected cells were cultured in the presence of the antibiotic Puromycin in the culture medium over 4 weeks to select for stably transfected cells. Cell pools were analyzed by flow cytometry after staining the cells with an anti-CD48 primary antibody (MEM-102, PE labeled, Molecular Probes, A15768) and a fluorescently labelled secondary antibody, with non-transfected HKB11 cells acting as CD48-negative control cells. For both human and cyno CD48 one pool was identified that showed a high and homogeneous expression of the respective target protein. Vials of this pool were frozen; the stability of recombinant CD48 overexpression was confirmed after continued culture of the cells in Puromycin-containing cell culture medium over two weeks.

TABLE 6

Constructs applied to engineer overexpressing cell line

| Name (Uniprot ID) | Sequence |
|---|---|
| Human CD48-IRES_EGFP (P09326- n/a) | MCSRGWDSCLALELLLLPLS LLVTSIQGHLVHMTVVSGSN VTLNISESLPENYKQLTWFY TFDQKIVEWDSRKSKYFESK FKGRVRLDPQSGALYISKVQ KEDNSTYIMRVLKKTGNEQE WKIKLQVLDPVPKPVIKIEK IEDMDDNCYLKLSCVIPGES VNYTWYGDKRPFPKELQNSV LETTLMPHNYSRCYTCQVSN SVSSKNGTVCLSPPCTLARS FGVEWIASWLVVTVPTILGL LLT (SEQ ID NO: 53) -IRES- MVSKGEELFTGVVPILVELD GDVNGHKFSVSGEGEGDATY GKLTLKFICTTGKLPVPWPT LVTTLTYGVQCFSRYPDHMK QHDFFKSAMPEGYVQERTIF FKDDGNYKTRAEVKFEGDTL VNRIELKGIDFKEDGNILGH KLEYNYNSHNVYIMADKQKN GIKVNFKIRHNIEDGSVQLA DHYQQNTPIGDGPVLLPDNH YLSTQSALSKDPNEKRDHMV LLEFVTAAGITLGMDELYKS GSDYKDDDDKSGSDYKDDDD KSG (SEQ ID NO: 72) |
| Human CD48 (P09326) | MCSRGWDSCLALELLLLPLS LLVTSIQGHLVHMTVVSGSN VTLNISESLPENYKQLTWFY TFDQKIVEWDSRKSKYFESK FKGRVRLDPQSGALYISKVQ KEDNSTYIMRVLKKTGNEQE WKIKLQVLDPVPKPVIKIEK IEDMDDNCYLKLSCVIPGES VNYTWYGDKRPFPKELQNSV LETTLMPHNYSRCYTCQVSN SVSSKNGTVCLSPPCTLARS FGVEWIASWLVVTVPTILGL LLT (SEQ ID NO: 53) |

Culture of CD48 Expressing Raji and U266 Cell Lines

High CD48 expressing Raji, ATCC® CCL-86™ and U266 ATCC® TIB-196™ were grown in RPMI with Glutamax (Gibco, 11835-063) supplemented with 10% FCS (Gibco,16000-044), 10 mM HEPES (Gibco,15630080) and with Penicillin/Streptomycin (Gibco,15140-122) at 37° C. with 5% $CO_2$ and sufficient humidity. CD48 expression was highly variable on Raji cells. Cells were stained with α-CD48-PE (Invitrogen A-15768) and α-CD45-APC (BD Pharmingen, 555485). CD48 highly expressing cells were sorted on FACS ARIA and subsequently cultured as Raji-CD48high at different seeding concentrations, low and high in above-mentioned medium with addition of ZellShield, Minerva Biolabs 13-0150, at 37° C. with 5% $CO_2$ and sufficient humidity. After expansion, both low and high density seeded Raji CD48high+ cells showed identical high CD48 expression.

Immunization of Mice and Production of Hybridomas

Antigen solutions were prepared in PBS. For recombinant human CD48 (R&D, 3644-CD-050) at 125 µg/ml and cell lines at 200×10⁶ cells/ml. BALB/c and Biozzi ABH/RjiHSD mice, three male and three female each, were primed and boosted two times with antigen with either recombinant human CD48 (R&D, 3644-CD-050), Raji or U266 cells. Four mice were selected for fusions. Spleens not used for fusions were frozen as single cell suspension.

Serum Antibody Determination and Hybridoma Screening by ELISA

For titer determination F96 cent Maxisorp Nunc Immuno plates (Thermo Scientific, 439454) were coated with recombinant human CD48 at 1 µg/ml, 100 µl/well in coating buffer (Biolegend, 421701) and incubated at 4° C. overnight. Murine α-human CD48 antibody, clone MEM-102 (Invitrogen, MA-19119S) (also described herein a "CD48A") and mouse α-human CD48, clone 156-4H9 (eBioscience, 16-0489-85) were applied as calibrator and diluted in assay diluent (PBS with 2% FCS and 0.05% Tween 20) to 1000 ng/ml. Serial 1:3 dilution steps were done down to 1.37 ng/ml. No antibody on coated wells was used as background. In order to exclude unspecific effects, non protein-coated wells with antibody dilution served as negative control. For hybridoma screening the supernatants were diluted 1:10. 100 µl/well were applied in duplicates for each calibrator concentration and mouse serum or hybridoma supernatant dilution. The plates were incubated for 1 h at 37° C. with 300×rpm on an orbital shaker.

After incubation, plates were flicked to remove supernatants and each well washed five times with 300 µl washing buffer. The secondary antibody, goat α-mouse IgG (H+L) HRP (Invitrogen, 31430) was diluted 1:10000 in assay diluent and 100 µl applied per well. The plates were incubated for one hour at RT at 300×rpm on an orbital shaker. Again, plates were flicked to remove supernatant and each well washed for seven times with 300 µl washing buffer. The detection reaction was started by adding 100 µl substrate solution (Life Technology, 002023) per well. The plates were incubated in the dark at RT without agitation for 15-30 min. Depending on the kinetics of color development the assay was stopped by addition of 100 µl/well stop solution (Life Technology, SS04). Absorbance was read at 450 nm and 570 nm within 30 min of stopping the reaction with a SpectraMax.

Serum Antibody Determination and Hybridoma Screening by FACS

All sera were analyzed for their specificity to native CD48 protein by incubation and FACS analysis with the cell lines used for immunization, RajiCD48high+ and U266. The CD48 negative T cell line CEM (ATCC, CCL-119™) served as control. 1 µl of undiluted, 1:10 and 1:100 diluted serum of each mouse was incubated with $0.5 \times 10^6$ cells/well of the corresponding cell lines in FACS buffer (AutoMACS rinsing buffer, Milteny; 130-091-222 and 1:20 diluted BSA stock solution; Milteny; 130-091-376) for 30 min on ice. After incubation, samples were washed twice with FACS buffer, stained with a secondary antibody α-mouse IgG-FITC; BD Pharmingen, 554001 (1:50 dilution in FACS buffer) and incubated for 30 min on ice in the dark. After incubation, cells were washed twice with FACS buffer and the cell pellets suspended in FACS buffer and measured on a FACS CANTO II.

For the hybridoma screening $1.5 \times 10^5$ 300-19 WT and $0.5 \times 10^5$ huCD48 GFP transfectants were applied. Cells were suspended in 100 µl of hybridoma supernatant (pure or 1:10 diluted). As control 0.2 µl/well unlabeled CD48A (MEM-102, Invitrogen, A-15768) was applied and detection was performed with 0.1 µl/well anti-mouse IgG APC (BD Bioscience, 550826).

Generation of Hybridomas

Single cell solutions of CD48 immunized mice spleens were prepared. The fusion was done with PEG Hybrimax solution (Sigma, P7181) and cells plated on 96-well plates, (100 ml/well) in HAT medium (RPMI 1640 with Glutamax and 25 mM HEPES, 50 µM β-Mercaptoethanol, 100 µM Hypoxanthine, 400 nM Aminopterin, 16 µM Thymidine, 10% ultra low IgG FCS and 100 µg/ml Normocin), containing a feeder cell layer of 50 µl mouse peritoneal cells (BALB/c, Request ID107701). The fused cells were seeded at three different concentrations: $10 \times 10^4$, $3 \times 10^4$, and $5 \times 10^3$ cells/well.

Screening started on day 13 after fusion applying ELISA and FACS. On day 15, HAT medium was exchanged with HT medium without aminopterin.

ELISA and FACS positive clones were subcloned in feeder free cloning and expansion medium (RPMI 1640 with Glutamax and 25 mM HEPES, 10% ultra low IgG FCS, 50 µM β-Mercaptoethanol, 100 µg/ml Normocin, HT supplement (Gibco, 41056-012) and conditioned H1 hybridoma cloning supplement; Roche Diagnostics 11088947001) adjusted to a cell concentration of 2.5 cells/ml plated on two 96-well plates for each hybrid.

Cloning of Selected Hybridoma Clones

RNA isolation of pelleted hybridoma cells was performed with the RNeasy Mini Kit according to manufacturer's protocol (Qiagen, 74104). RNA yield was determined using NanoDrop (Thermo Fischer).

RNA was converted into cDNA using the Superscript III First-Strand Synthesis System for RT PCR from LifeTechnologies (180880-051) according to manufacturer's instructions. Amplification of synthesized cDNA was performed applying the Mouse Ig-Primer Set from Novagen (69831-3) and Taq Polymerase from Fermentas (K0171), according to manufacturer's instructions. 25 µl of PCR reactions were analyzed on a 1.2% agarose gel and stained with Ethidium Bromide. Bands were excised using a scalpel and gel extraction of DNA performed using the QIAquick Gel Extraction kit from Qiagen (28704), according to manufacturer's protocol. Extracted DNA was used for PCR Cloning using the PCR Cloning Kit from Qiagen (231122) according to manufacturer's instructions and final plasmid products were used for transformation of TOP10 chemically competent cells (Invitrogen, C-404010). Transformed cells were spread on LB-Kanamycine plates treated with X-gal (Invitrogen, R-0402). Cells transformed by pDrive Cloning Vectors, which do not contain a PCR product, will express LacZ α-peptide, and will form blue colonies when grown in the presence of X-gal. Therefore, only white colonies were picked and cultured for plasmid preparation using the QIAprep Spin Miniprep Kit (Qiagen 27106), according to manufacturer's protocol.

Transfection of HEK cells for antibody expression as well as purification was performed as described for CD48 immunogen generation.

Generation of Humanized Sequences

DNA sequences coding for humanized VL and VH domains were ordered at GeneArt (Life Technologies Inc. Zug, Switzerland) including codon optimization for *Homo sapiens*. Sequences coding for VL and VH domains were subcloned by cut and paste from the GeneArt derived vectors into expression vectors suitable for secretion in mammalian cells. The heavy and light chains were cloned into individual expression vectors to allow co-transfection. Elements of the expression vector include a promoter (Cytomegalovirus (CMV) enhancer-promoter), a signal sequence to facilitate secretion, a polyadenylation signal and transcription terminator (Bovine Growth Hormone (BGH) gene), an element allowing episomal replication and replication in prokaryotes (e.g. SV40 origin and ColE1 or others known in the art) and elements to allow selection (ampicillin resistance gene).

Expression and Purification of Antibodies

CAP-T® cells (human amniocytes; CEVEC Pharmaceuticals GmbH, Cologne, Germany) were transiently transfected with the appropriate heavy and light chain expression plasmid in FreeStyle293™ Expression Medium (Invitrogen, 12338) using 40 kDa linear PEI (PEI Max, Polysciences, VWR, POLS24765-2) as gene delivery vehicle.

Briefly, 30 ug of light and heavy chain plasmid DNA in 1 ml OptiMEM medium (Invitrogen, 51985) were added dropwise to a 250 ml shaking flask containing 1E+8 cells in 18 ml FreeStyle medium, followed by 1 ml Pei Max solution while shaking. The flask was thereafter incubated for 4 hours at 37° C., 6% $CO_2$, 85% humidity at 100 rpm. Subsequently, 20 ml pre-warmed protein expression medium (PEM, Invitrogen, 12661) containing 4 mM L-Glutamine, and 5 ug/ml blasticidin (Invitrogen R21001), as well as valproic acid (Sigma-Aldrich, P4543) to a final concentration of 4 mM were added to the culture. Cell culture continued at 37° C., 6% $CO_2$, 85% humidity, 115 rpm for 7 days.

Supernatants were filtered with Steri-Flip and antibodies purified with Tecan robot MabSelect Sure on 200 µl resin. Briefly, column were washed with 10 volumes of water and PBS (Novartis). Samples loaded and washed again with 10 volumes of water. Antibody elution was performed with three volumes of 50 mM citrate, 70 mM NaCl pH 3.2 followed by neutralization with 140 µl 1 M Tris pH 9.0, and filtering through a 0.22 µm membrane (Millipore Steriflip).

For concentration, determination antibodies were measured at 280 nm in a Spectrophotometer ND-1000 (NanoDrop), and the protein concentration was calculated based on the sequence data. The eluate was tested for aggregation (SEC-MALS).

Antibodies Panned from Novartis Pallas Phage Library

A synthetic human Fab phagemid library (Novartis Institutes for BioMedical Research) was used for the phage display selection. A gene fragment encoding the germline framework combinations IGHV3-23 and IGKV1-39, IGHV3-23 and IGLV3-9, IGHV1-46 and IGKV1-39, IGHV3-15 and IGLV1-47 were synthesized by GeneArt (Life Technologies Inc. Zug, Switzerland) in Fab format and cloned into a phagemid vector serving as the base template. These human germlines were used as the display favorable framework combinations for a phage display library. The phagemid vector consists of ampicillin resistance, CilE1 origin, M13 origin, and a bi-cistronic expression cassette under lac promoter with OmpA-light chain followed by phoA-heavy chain-Flag-6×His (SEQ ID NO: 84)—Amber stop-truncated pIII (amino acids 231-406).

Only HCDR3 was diversified, and primer were designed to incorporate up to 11 amino acids at defined ratios mimicking their natural occurrence: aspartic acid, glutamic acid, arginine, histidine, serine, glycine, alanine, proline, valine, tyrosine, and tryptophan. Leucine and phenylalanine were also allowed at a certain position of HCDR3. Certain residues were omitted on purpose to remove potential post-translational modification sites. Randomized primer synthesis was performed using the Trinucleotide technology (ELLA Biotech) in order to exclude stop codons, methionine, cysteine, and asparagine.

Lengths between 8, 10, 12, 14, 16, and 20 amino acids were allowed, in which the last two amino acids were kept constant with the sequence Asp-Tyr for length 8-16 and Asp-Val for length 20. The design of the final two HCDR3 amino acids reflects human VDJ recombination. Short HCDR3s more often use J-fragment IGHJ4 with "DY" at the end of HCDR3, while longer HCDR3s (here 20 aa) more often use IGHJ6 with "DV" at the end of HCDR3. Library inserts were generated by PCR using Phusion High-Fidelity DNA polymerase (NEB Biolabs). The resulting HCDR3 library inserts were ligated into the base templates, transformed into E. coli TG1F+ DUO (Lucigen) with a minimal library size of 3E+08 transformants per HCDR3 length, and phages were produced using VCSM13 helper phage (Agilent Technologies) using standard protocols.

Whole cell panning was employed for the isolation of antibodies recognizing human CD48. Phage libraries were blocked in 1 ml PBS/5% FBS (Gibco,16000044) for 2 hours at room temperature followed by the addition of 1E+07 CHO wild type cells. The mixture was incubated over night at 4° C., 30 rpm followed by 5 min centrifugation at 300 g, 4° C. Pre-adsorbed phage supernatant was added to the target cells.

CHO wild type and human CD48 overexpressing cells were labelled with different fluorochromes (Vibrant Cell-Labelling Solutions, Invitrogen, #V22885, #V22886, #V22887) and mixed in different ratios. Panning proceeded on a rotator at 4° C. for 4 hours. Cells were washes three times in 5 ml 5% FBS/PBS and centrifuged at 300 g, 4° C. Cells were suspended in FACS buffer (PBS, 0.5% FBS) and filter into FACS tubes. Cells were FACS sorted on a BD Aria II according to color into two tubes—WT CHO and $CD48^+$ CHO cells.

To elute the bound phages, cell pellets were suspended in 1 ml 100 mM Glycine-HCl, 500 mM NaCl pH 2.2 (GE Healthcare, BR-1003-55). Incubated for 10 min at room temperature, centrifuged at 300 g for 2 min and the eluted phages (supernatant) transferred to a new tube containing 110 µl of 1 M Tris pH 8 (Fluka, 93350) for neutralization.

Eluted phages were used to infect exponentially growing Amber suppressor TG1F+ cells (Lubio Science). Infected bacteria were cultured in 2YT (16 g/l bactotryptone; Becton-Dickinson 211699, 10 g/l bactoyeast extract; Becton-Dickinson 212720), 5 g/l NaCl; Merck 6404), 100 µg/ml Ampicillin (Sigma, A0166) and 1% glucose (Sigma, G8270) medium overnight at 37° C., 200 rpm and superinfected with VCSM13 helper phages.

The production of phage particles was then induced by culturing the superinfected bacteria in 2YT/Ampicillin/Kanamycin (Calbiochem, 420411) medium containing 0.25 mM isopropyl b-D-1-thiogalactopyranoside (IPTG, Roche, 11 411 446 001)), overnight at 22° C., 180 rpm. Supernatant containing phages from the overnight culture were purified by PEG/NaCl precipitation, titrated, and selected in the following round.

Recovery of Enriched Antibody Sequences by NGS Screening

After each round of phage selection, polyclonal plasmid DNA of recovered binders to wild type and CD48 expressing CHO cells was prepared using QIAprep Spin Miniprep Kit (Qiagen). In a first PCR the CDR-H3 was amplified over 9 cycles with overhanging primers allowing the annealing of the standard TruSeq primers in a consecutive step. In the second PCR, primers with the TruSeq universal forward adapter and one of the 24 TrueSeq index reverse primer were used over 12 cycles. The resulting fragments were purified using a 1.5% agarose gel and the Wizard SV Gel and PCR Clean-up System (Promega, A9282). DNA concentration was measured using the Qubit DNA High sensitivity kit (Invitrogen, Q32B54). Samples were analyzed on a MiSeq using MiSeq Reagent 5 Kit v3 (Illumina) with 150 forward cycles.

The data analysis of the NGS FastQ output files was performed as described (Liu et al, 2019, BMC Bioinformatics, 20, 401). For each panning output, 100,000 sequences were analyzed using the fixed flanking sequences on the boundary of variable region as template to locate and segment out the HCDR3 sequence. ~40,000 to 70,000 HCDR3 sequences were identified depending on the panning output pools, and included into frequency reports in CSV format. For antibody expression, clones with higher than 2% occurrence were selected.

Affinity Maturation of Phage and Hybridoma Derived/Humanized Antibodies

The Pallas selected antibodies NOV3731 was further engineered in Fab format to improve the affinity by using affinity maturation cassette libraries with diversification in the HCDR1, HCDR2 and all light chain CDRs. The CDRs were diversified according to naturally occurring repertoire of rearranged human CDR sequences. Primers were designed to incorporate the respective heavy and light chain CDR amino acids at defined ratios mimicking their natural occurrences aspartic acid, glutamic acid, arginine, histidine, threonine, serine, glycine, alanine, leucine, valine, and tyrosine. Glutamine, proline and tryptophan were also allowed at certain positions of LCDR3.

For the CDR maturation cassettes, the synthesis of randomized primer was performed using the Trinucleotide technology (ELLA Biotech) in order to exclude stop codons, methionine, cysteine and asparagine. The randomization of the CDRs was performed by two PCR steps using Phusion High-Fidelity DNA polymerase (NEB Biolabs). Firstly, a randomization PCR was performed followed by amplifying the randomized fragments applying primers introducing restriction sites at both ends. This amplification PCR was then ligated into the base templates phagemid vectors using the appropriate restriction sites, transformed into $E.\ coli$ TG1F+ DUO (Lucigen) with a minimal library size of 1E+08 transformants.

The heavy and light chain CDR specific affinity maturation libraries were restricted with the relevant enzymes and cloned individually into the parental antibody replacing the parental CDRs with randomized cassettes of diversified sequences. Libraries were transformed into TG1F+ competent cells (Invitrogen). Phage particles were produced by superinfection with VCSM13 helper phage and then precipitated by PEG/NaCl.

The hybridoma derived and humanized antibody NY258 was further engineered in Fab format, by generating NNK libraries for LCDR1 and LCDR3 as well as HCDR1, HCDR2, and HCDR3. Amplified Libraries were cloned via the appropriate restriction sites into the phagemid vector, transformed into $E.\ coli$ TG1F+ DUO (Lucigen) with a minimal library size of 1E+08 transformants. Phage particles were produced by superinfection with VCSM13 helper phage and then precipitated by PEG/NaCl.

These five affinity maturation libraries for each candidate, NOV3731 and NY258 were subjected to two rounds of solid phase panning on recombinant human (Acrobiosystems, BC1-H5255) and cynomolgus (in house iProt 112617) CD48-hulgG-FC. $5 \times 10^9$ phages per library were blocked in a volume of 500 µL 2.5% milk powder in PBS (PanReac AppliChem, A0830), 0.05% Tween (Sigma, P9416) overnight. 96-well maxisorb plates (Nunc, 442404) were coated with 300 ul of an irrelevant FC protein at 5 ug/ml in PBS. Plates were washed 3 times with 300 µL PBS and blocked phage libraries incubated to pre-adsorb potential human IgG-FC binding phages at 250 µL/well at room temperature for 30 minutes while rocking.

Thereafter, the pre-adsorbed phages were transferred to human or cynomolgus CD48 coated plates and incubated for 2 hours at room temperature while rocking. Plates were coated with 300 µL CD48-IgGFc protein at 5 µL/ml and washed 3 times with PBS. Additionally, phage libraries were incubated with an irrelevant protein and BSA. Phages were also only carried over from round to round, Mock panning.

The washing regimen was intensified during the selection rounds with 2 cycles (3× quick and 2×5 minutes) using PBS with 0.05% Tween20 for the quick washes and PBS for the 5 minute washes, followed by 2 cycles (5× quick and 4×5 minutes) in the second round. Phages were eluted with 10 mM Glycine/HCl pH 2.0. $E.\ coli$ TG1F+ were infected with eluted phages, which were neutralized beforehand using 1M Tris/HCl, pH8.0. Propagation of phages between rounds was performed using VCSM13 helper phage (Agilent). After the second round of panning, DNA minipreps were used for NGS screening. Selected sequences were ordered cloned in individual heavy and light chain expression vectors at GenArt. IgG expression was performed in HEK293 cells and antibodies purified with Tecan robot MabSelect Sure on 200 µl resin.

Analysis of NGS Screened Antibodies—Cross Binding to Human and Cynomolgus CD48

Purified Antibodies tested in ELISA for binding to recombinant human and cynomolgus CD48. Black Maxisorp™ (Nunc) 384 well plates (Thermofischer, 460518) were coated with 20 µl huCD48-huFc, cyCD48-huFc, huCD48-bio, or BSA as control (Sigma, A7906) diluted in PBS at 5 µg/mL overnight at 4° C. The next day, plates were washed three times with 120 µL/well with TBST (TBS-0.05% Tween20). Plates were blocked with 120 µL/well of 5% milk powder/PBS for 3 h at room temperature and washed three times with 120 µL/well with TBST. Antibodies were 1:3 diluted from 100 nM down to 45 µM and 20 µL/well added. After 1 hour incubation at room temperature, plates were washed 3 times with 120 µL/well with TBST. For detection, 20 µl AP conjugated anti-hulgG, Fab fragment specific (Jackson, 109-055-097) in 0.25% milk powder/PBS+0.05% Tween20 at 1:5000 dilution was added per well. After 1 hour incubation at room temperature, plates were washed 3 times with 120 µL/well with TBST. Attophos fluorescence substrate (Roche, 11681982001) was diluted 1:5 in water and 20 µL/well added, incubated for 10 min and the absorbance measured at 405 nm. Utilizing ELISA methodology, specific binding for the candidate antibodies NY920 and NY938 to human and cynomolgus CD48 was detected.

Purified Antibodies tested for binding to cell expressed human and cynomolgus CD48. $5 \times 10^5$ human or cynomolgus CD48 over expressing HKB11 cells as well as wild type cells were applied per staining in one well of 96 well plate (Thermo Fischer, Nunclon Delta Surface 163320). Antibodies were applied in 3 concentrations, 100, 10, and, 1 µg/ml. Antibodies were diluted in 50 µl PBS/1% FCS (FACS buffer) per well and incubate for 30 minutes on ice. Wells were washes 2 times with 250 µl FACS buffer by centrifugation at 300 g for 2 minutes and removing the supernatant by flipping the plate and patting on paper. For detection, 50 µl 1:2000 in FACS buffer diluted mouse anti-human Fab, PE-conjugated (Jackson-109-116-097) was added per well and incubate for 30 minutes on ice in the dark. Cells were washes 2 times with 250 µl FACS buffer and suspend in 200 µl FACS buffer per well for FACS analysis. Cells were analyzed on a BD Calibur. Utilizing cell binding and FACS analysis revealed specific binding for the candidate antibodies NY920 and NY938 to human and cynomolgus CD48.

Example 2: Affinity of Anti-CD48 Antibodies to Human and Cynomolgus CD48 Protein The affinity of various antibodies to human CD48 and its *Macaca fascicularis* orthologue was determined using SPR technology using a Biacore T200 instrument (Cytiva) equipped with a protein A sensor chip (Cytiva, ordering #29-1275-56). HBS-EP+pH 7.4 containing 10 mM HEPES, 150 mM NaCl, 3 mM EDTA and 0.05% (v/v) surfactant P20 (Teknova, ordering #H8022) was used as running buffer as well as for sample dilution.

The anti-CD48 antibodies were diluted at 5 µg/ml and injected on flow cells 2 and 4 for 20 sec at 10 µl/min. Capture level for all antibodies was 370-440 RU. Flow cells 1 and 3 were left blank (no antibody captured) and used as a reference surface. Human and cynomolgus CD48 served as analytes in solution. Kinetic data were acquired by subsequent injections of analyte 1:2 dilution series (human CD48: 100-0.8 nM, cynomolgus CD48: 500-3.9 nM) on all flow cells for 180 s at 50 µl/min followed by a dissociation time of 360 s. After each cycle of antibody capture and analyte injection, the chip surface was regenerated with 10 mM Glycine-HCl pH 1.5 (Cytiva, ordering #BR100354) for 2×30 s at a flow rate of 50 µl/min. Three runs with duplicate measurements and buffer blank injections were performed. Measurements were executed at 25° C. and data collected at a rate of 10 Hz.

Data were evaluated using the Biacore 8K evaluation software. The raw data were double referenced, i.e. the response of the measuring flow cells was corrected for the response of the reference flow cells (no antibody captured), and in a second step the response of a blank injection (buffer) was subtracted. Finally, the sensorgrams were fitted by applying a 1:1 interaction model with a constant fit of RI (0) and a global fit for $R_{max}$. Kinetic rate constants ($k_a$, $k_d$) and equilibrium dissociation constants ($K_D$) were calculated. Data were processed separately for each run. The generated values were used to calculate average values and standard deviations of the respective equilibrium dissociation constants and the kinetic rate constants.

TABLE 7

Affinity estimates of anti-CD48 antibodies obtained against human and cynomolgus CD48

| Anti-CD48 construct | Analyte | $k_a$ [1/MS] | $k_d$ [1/S] | $K_D$ [M] |
|---|---|---|---|---|
| NY920 | cyno CD48 | $1.7E^4$ | $1.6E^{-3}$ | $9.4E^{-8}$ |
| | human CD48 | $7.2E^4$ | $7.4E^{-4}$ | $1.0E^{-8}$ |
| NY938 | cyno CD48 | $2.5E^5$ | $3.7E^{-4}$ | $1.5E^{-9}$ |
| | human CD48 | $2.5E^5$ | $1.3E^{-4}$ | $5.0E^{-10}$ |

Example 3: Epitope Binning with Mutated Human CD48 Protein Constructs

Applying the 3D structure models of the CD48 protein, three exposed loops of the protein were selected and changed by site directed mutagenesis utilizing PCR. Antibody binding epitopes were determined by ELISA. Designated sites were residues 50-55; ENYKQ (SEQ ID NO: 78)-modified into GSSKQ (SEQ ID NO: 79), residues 70-74; DSRK (SEQ ID NO: 80)-modified into AAGK (SEQ ID NO: 81), and residues 103-108; KKTGNE (SEQ ID NO: 82) modified into KKDASG (SEQ ID NO: 83). The template construct, hCD48EC:mouse-Ig originates from the expression plasmid generated to express the human CD48-mouse IgG1 fusion protein for immunization amplified from the commercial vector "Trueclone, CD48 (untagged)-Human CD48 molecule" (Origene, NM_001778.2). Primer for the site directed mutagenesis were synthesized by Microsynth (Switzerland).

ELISA for epitope binning was performed with 1:10 dilutions of HEKT293 culture supernatants and anti-CD48 antibodies NY938, NY920, and humanized CD48A (also known as humanized MEM102 antibody:

```
Heavy Chain sequence
QVQLVQSGSELKKPGASVKVSCKASGYTFTDFGMN

WVRQAPGQGLEWMGWINTFTGEPSYGNVFKGRFVF

SLDTSVSTAYLQISSLKAEDTAVYYCARRHGNGNV

FDSWGQGTLVTVSSATKGPSVFPLAPSSKSTSGGT

AALGCLVKDYFPEPVTVSWNSGALTSGVHTFPAVL

QSSGLYSLSSVVTVPSSSLGTQTYICNVNHKPSNT

KVDKRVEPKSCDKTHTCPPCPAPELLGGPSVFLFP

PKPKDTLMISRTPEVTCVVVDVSHEDPEVKFNWYV

DGVEVHNAKTKPREEQYNSTYRVVSVLTVLHQDWL

NGKEYKCKVSNKALPAPIEKTISKAKGQPREPQVY

TLPPSREEMTKNQVSLTCLVKGFYPSDIAVEWESN

GQPENNYKTTPPVLDSDGSFFLYSKLTVDKSRWQQ

GNVFSCSVMHEALHNHYTQKSLSLSPGK
(SEQ ID NO: 73);

Light Chain sequence
EIVLTQSPDFQSVTPKEKVTITCRASQSIGSNIHW

YQQKPDQSPKLLIKYTSESISGVPSRFSGSGSGTD

FTLTINSLEAEDAATYYCQQSNSWPLTFGGGTKVE

IKRTVAAPSVFIFPPSDEQLKSGTASVVCLLNNFY

PREAKVQWKVDNALQSGNSQESVTEQDSKDSTYSL

SSTLTLSKADYEKHKVYACEVTHQGLSSPVTKSFN

RGEC
(SEQ ID NO:74)) at 500, 250
and 25 ng/ml.
```

Non-mutated CD48-mouse IgG fusion construct served as positive and non-transfected cell supernatant as negative control. Detection was undertaken with goat α-mouse IgG (H+L) HRP (Invitrogen, 31430).

Figure 1B:
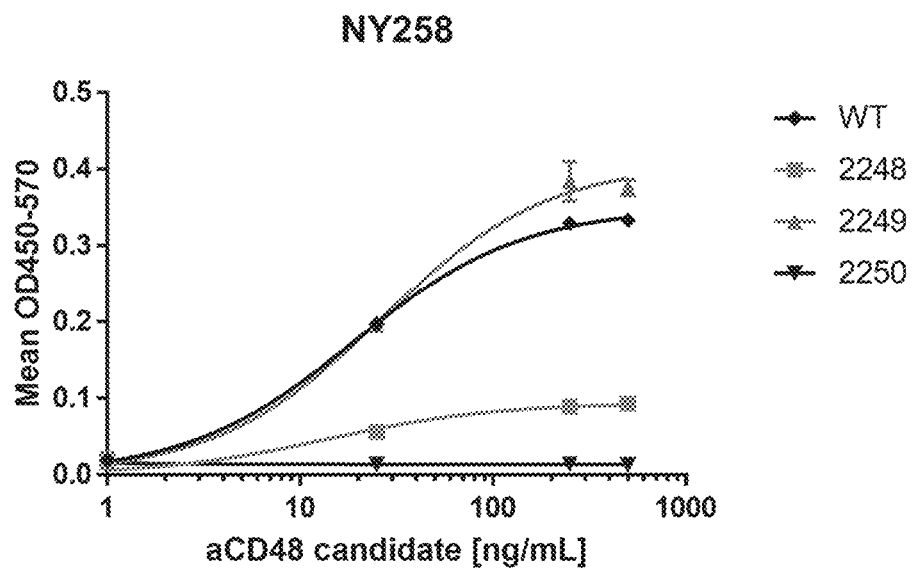
FIG. 1B is a graph depicting binding of anti-CD48 antibody NY254 (parent antibody of NY938) to the constructs.
Figure 1C:
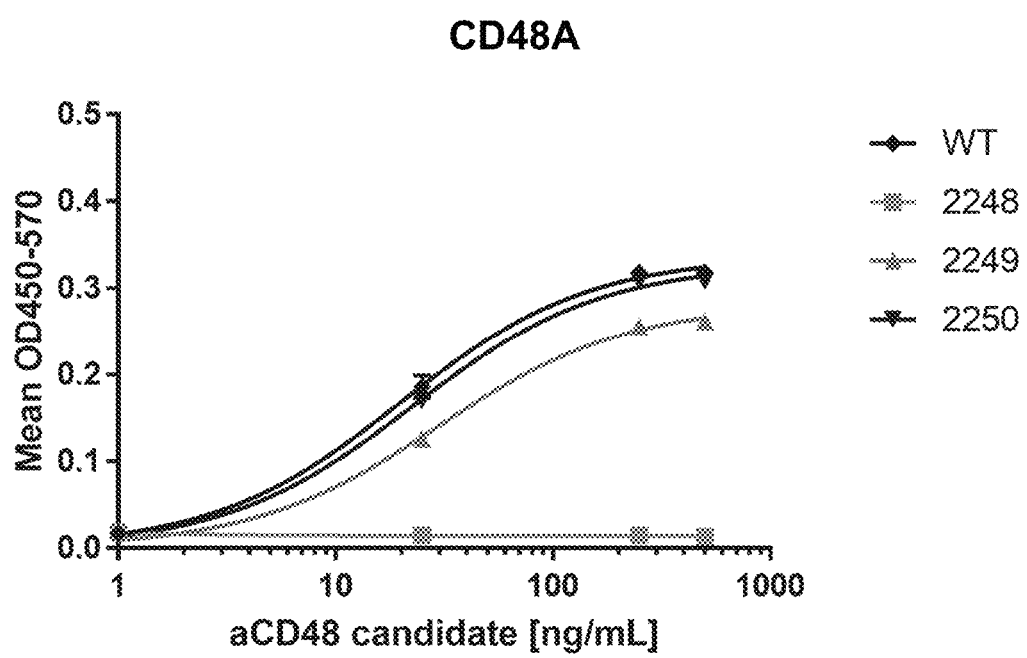

Construct #2248 carries mutated residues at amino acid 50-55, #2249 at amino acids 70-74 and #2250 at amino acids 103-105. The candidate antibodies NOV3731 (FIG. 1A) and NY258 (FIG. 1B) lost binding to construct #2250 and demonstrated reduced binding to construct #2248, whereby NY258 is more affected by the mutation of amino acids 50-55. The control antibody humanized CD48A (FIG. 1C) showed binding to construct #2250 in the same range as to the non-mutated CD48 protein and did not bind to construct #2248. These analyses indicate the antibodies NOV3731 and NY258 bind to a different epitope than CD48A.

Example 4: X-Ray Crystallographic Structure Determination of the Human CD48 EC Domain in Complex with the NY938 IgG The three dimensional structure of human CD48 was hitherto unknown. The crystal structure of a human CD48 extracellular domain fragment in complex with the anti-CD48 NY938-hIgG1_kappa (a-fuc) was determined. As detailed below, human CD48, amino acids 29-130 was expressed, purified and mixed with the anti-CD48-NY938-hIgG1_kappa (a-fuc) to form a complex, which was subsequently crystallized. Protein crystallography was then employed to generate atomic resolution data for human CD48 bound to the NY938 to define the epitope.

TABLE 8

Amino acid sequences of human CD48 ECD and anti-CD48-NY938-hIgG1_kappa (a-fuc) produced for crystallography

| | |
|---|---|
| Met-humanCD48 (aa29-130)- APP6-Avi-His for NY938 Complex formation and Crystallization | MHLVHMTVVSGSNVT LNISESLPENKQLTW FYTFDQKIVEWDSRK SKYFESKFKGRVRLD PQSGALYISKVQKED NSTYIMRVLKKTGNE QEWKIKLQVLDPGLN DIFEAQKIEWHEHHH HHH (SEQ ID NO: 68) |
| Heavy Chain anti-CD48-NY938- hIgG1_kappa (a-fuc) | QVQLVQSGAEVKKPG ASVKVSCKASGYTFT EYTMHWVRQAPGQGL EWMGGINPDTGDTSY NQKFTGRATLTVDKS TSTAYMELSSLRSED TAVYYCARAQFWTTP RFAYWGQGTLVTVSS ASTKGPSVFPLAPSS KSTSGGTAALGCLVK DYFPEPVTVSWNSGA LTSGVHTFPAVLQSS GLYSLSSVVTVPSSS LGTQTYICNVNHKPS NTKVDKRVEPKSCDK THTCPPCPAPELLGG PSVFLFPPKPKDTLM ISRTPEVTCVVVDVS HEDPEVKFNWYVDGV EVHNAKTKPREEQYN STYRVVSVLTVLHQD WLNGKEYKCKVSNKA LPAPIEKTISKAKGQ PREPQVYTLPPSREE MTKNQVSLTCLVKGF YPSDIAVEWESNGQP ENNYKTTPPVLDSDG SFFLYSKLTVDKSRW QQGNVFSCSVMHEAL HNHYTQKSLSLSPGK (SEQ ID NO: 65) |
| Light Chain anti-CD48-NY938- hIgG1_kappa (a-fuc) | DIQMTQSPSSLSASV GDRVTITCKASQDVG TAVAWYQQKPGKVPK LLIYWASTRHTGVPS RFSGSGSGTDFTLTI SSLQPEDVATYYCQQ YSTYPITFGQGTKLE IKRTVAAPSVFIFPP SDEQLKSGTASVVCL LNNFYPREAKVQWKV DNALQSGNSQESVTE |

TABLE 8-continued

Amino acid sequences of human CD48 ECD and anti-CD48-NY938-hIgG1_kappa (a-fuc) produced for crystallography

| |
|---|
| QDSKDSTYSLSSTLT LSKADYEKHKVYACE VTHQGLSSPVTKSFN RGEC (SEQ ID NO: 51) |

Protein Production of Human CD48 Extra Cellular Domain and Anti-CD48-NY938-hIgG1 Kappa (a-Fuc) for Crystallography Generation of NY938-hIgG1 Kappa (a-Fuc)

For NY938-hIgG1 generation, HEK293T cells were transiently transfected with the expression constructs applying PeiMAX (Polyscience, 24765). Briefly, cells were cultivated in M11V3 serum free medium (Bioconcept, CH, Cat: V3K) and adjusted to $2.8 \times 10^6$ cells/ml in 36% of the final volume. The DNA solution (solution 1) was prepared by diluting 0.8 mg/l final volume DNA in 7% final volume M11V3 and gentle mixing. To prevent contamination of the cultures, this solution might be filtered using a 0.22 μm filter (e.g. Millipore Stericup). Then 2.4 mg/l final volume PEI solution was diluted in 7% final volume M11V3 and mixed gently (solution 2). Both solutions were incubated for 5 to 10 min at room temperature. Thereafter, solution 2 is added to solution 1 with gentle mixing and incubated another 5 to 15 minutes at RT. After the incubation, the transfection mix was added to the cells and the culture cultivated for four to six hours. Finally, to adjust for the remaining 50% culture volume ExCell VPRO medium (SigmaAldrich, Cat: 14561C) was added. Cell culture was continued for 7 days. Supernatant was centrifugation 4500 rpm, 20 min, 4° C. (Heraeus, Multifuge 3 SR) and clarification through a sterile filter, 0.22 μm (Stericup filter). 950 ml of cell culture supernatant (2.6 mg/ml) was loaded onto a 25 ml Mab Select SuRe column (stripped with 2 CV of 0.1 M NaOH; equilibrated with PBS, pH 7.4) at 1 ml/min overnight. After baseline washing with PBS, pH 7.4, bound material was eluted with 50 mM Citrate/140 mm NaCl, pH 2.7, pH adjusted to 7.2 with 5 M NaOH and sterile filtered. Theoretical pI: 9.2 Yield: 130.0 mg at 2.6 mg/ml. Analysis demonstrated 14.3% of protein aggregation. Mab Select SuRe Eluate was concentrated to 10 ml using an Amicon stirred cell, MWCO 30 kDa (Millipore; #PLTK04310) and concentrated material injected to a HiLoad XK26/600 Superdex 200 PrepGrade column via a 10 ml sample loop. Running buffer: PBS, pH 7.4; flow rate: 1.0 ml/min; 5 ml fractions were collected. Fractions containing the protein were pooled revealing 34 ml at 2.48 mg/ml.

Generation of the Met-humanCD48 (aa29-130)-APP6-Avi-His Protein

The Met-humanCD48 (aa29-130)-APP6-Avi-His was expressed at 1 liter scale in *E. coli*. First, the plasmid encoding the protein fragment was transformed into chemically competent TG1F⁻ *E. coli* cells. After overnight growth of the bacteria on $L_B$/Agar/1% Glucose/25 g/ml kanamycin plate at 37° C., one colony was used to inoculate a 3 ml pre-culture (2×YT/1.0% Glucose/34 g/ml kanamycin). The culture was incubated at 37° C., shaking at 220 rpm until reaching $OD_{600\,nm}$=2. Pre-culture was then transferred to 100 mL pre culture (2×YT/1.0% Glucose/25 g/ml kanamycin). This culture was incubated at 37° C., shaking at 220 rpm until reaching $OD_{600\,nm}$=2. The next day, 10 mL pre-culture was transferred to 1000 ml expression culture (2×YT/0.1% Glucose/25 g/ml kanamycin). The expression culture was incubated at 37° C., shaking at 200 rpm until an OD$_{600\ nm}$ of 1.0-1.2 was reached. Expression was induced by adding IPTG to a final concentration of 1 mM. The expression was carried on overnight at 20° C. and 200 rpm. Next day, cells were pelleted and frozen at −80° C.

Bacteria pellet was suspended in 10 ml lysis buffer (0.1M Tris/HCl, 0.1 M NaCl, 1 mM EDTA, 3 mM methionine, 0.1% lysozyme) per 1 gram pallet and incubated while gently stirring at 4° C. for 30 minutes. 10 mM MgCl$_2$ and 10 U/ml Benzonase were added and cells again gently stirred at 4° C. for 30 minutes. Lysed cells had two passages at 800 bar through a French press. 0.5 volume of 60 mM EDTA, 1.5 M NaCl, 5% (v/v) Triton X-100 solution was added followed by an incubation at 4° C. for 60 minutes while stirring.

The cell debris was removed by centrifugation at 10,000 g for 30 min. The pallet was washed twice with one volume 50 mM Tris/HCl, 0.8M NaCl, 30 mM EDTA, 3 mM methionine and 3 times with 50 mM Tris/HCl, 0.3M NaCl, 10 mM EDTA, 3 mM methionine.

Inclusion bodies (IBs) were solubilized in 10 ml of 6M Guanidine pH 8.5, 20 mM Tris, 1 mM EDTA, and 5 mM DTT for each gram at room temperature overnight. The solubilized IBs were supplemented with 20 mM DTT and applied to refolding. Refolding was performed in 50 mM Tris pH 8.5, 0.5 M Arg, 5 mM EDTA, 4 mM, GSH, 1.5 mM GSSG at 4° C. and the refold concentrated on a TFF device (cut off, 5 kDA). The concentrated refold was loaded on a 5 mL HisTrap Excel column previously equilibrated with 10 mM Hepes, 100 mM NaCl pH 7. The column was washed to baseline with the same buffer and elution was performed by a linear gradient from 0 to 100% 500 mM Imidazole in 20 mL buffer. The fractions containing the protein were pooled and dialyzed against 10 mM Hepes, 100 mM NaCl pH 7 to remove the imidazole. Protein was frozen at −80° C.

The complex of human CD48 with the NY938-IgG was prepared by mixing the proteins at a 1.5:1.0 molar ratio equilibrate in 25 mM Hepes pH 7, 150 mM NaCl having a total concentration of 1.4 mg/ml. Crystals were grown in Swissci 96-well 2-Drop MRC crystallization plate by sitting drop vapor diffusion method. In detail, 0.2 µl of protein was mixed with 0.2 µl of reservoir solution, and the drop was equilibrated against 80 µl of the same reservoir solution at 20° C. Crystals suitable for X-ray diffraction analysis were obtained within 10 days with a reservoir solution made of 0.1M Sodium Acetate Trihydrate, 40% w/v PEG200.

For data collection, one anti-CD48 (29-130)-Avi-His//anti-CD48 (NY938)-hIgG1_kappa crystal was mounted in a cryo-loop and directly flash cooled in liquid nitrogen. Diffraction data were collected at beamline X10SA (PX-II) of the Swiss Light Source (Paul Scherrer Institute, Switzerland), with a Pilatus pixel detector and X-rays of 0.99984 Å wavelength. In total, 720 images of 0.25 deg oscillation each were recorded at a crystal to detector distance of 430 mm. Data were processed and scaled at 2.38 Å resolution using the autoPROC toolbox (Vonrhein, C., Flensburg, C., Keller, P., Sharff, A., Smart, O., Paciorek, W., Womack, T. & Bricogne, G. Acta Crystallogr D Biol Crystallogr 2011 April; 67(Pt 4):293-302). The crystal was in space group P2$_1$2$_1$2$_1$ with cell dimensions a=60.58 Å, b=85.25 Å, c=246.62 Å, alpha=90°, beta=90.0°, gamma=90°. The human CD48 residues 29-130/NY938 Fab complex structure was solved by molecular replacement using Phaser (McCoy et al., (2007) J. Appl. Cryst. 40:658-674). The final model was built in COOT (Emsley et al., (2010) Acta Crystallogr. Sect. D: Biol. Crystallogr. 66:486-501) and refined with Buster (Global Phasing, LTD) to R$_{work}$ and R$_{free}$ values of 20.1% and 24.8%, respectively, with a rmsd of 0.007 Å and 1.11° for bond lengths and bond angles, respectively. Residues of human CD48 residues 29-130 that contain atoms within 4.0 Å of any atom in NY938 Fab were identified by the program Ncont of the CCP4 program suite (Collaborative Computing Project, Number 4 (1994) Acta Crystallogr. Sect. D: Biol. Crystallogr. 50:760-763) and listed in Table 9 and Table 10.

CD48 Epitope for NY938

The crystal structure of the CD48-NY938 IgG complex was used to identify the CD48 epitope for NY938 IgG. The interaction surface on human CD48 by the NY938 IgG is formed by two discontinuous (i.e., noncontiguous) sequences, encompassing amino acid residues 54 through 64, and residues 105 through 121. Among those, residues 54, 58, 60, 61, 62, 64, 105, 107, 119, 111, 114, 115, 117, 119, and 121 could be mapped contributing to direct intermolecular contacts shorter than 4.0 Å (between non-hydrogen atoms), as detailed in Table 9 and Table 10. These residues form the three-dimensional surface on human CD48 that is recognized by NY938.

TABLE 9

Interactions between human CD48 and the NY938-IgG heavy chain (H). CD48 residues are numbered based upon human CD48 sequence (SEQ ID NO: 53). NY938-IgG heavy chain residues are numbered based upon their linear amino acid sequence SEQ ID NO: 65. CD48 residues shown have at least one atom within 4.0 Å of an atom in the NY938 IgG.

| Human CD48 | | NY938 heavy chain | | |
| --- | --- | --- | --- | --- |
| Amino acid | Number | Amino acid | Number | Chain |
| Phe | 58 | Thr | 103 | H |
| Thr | 60 | Asp | 57 | H |
| Phe | 61 | Thr | 33 | H |
| | | Gly | 50 | H |
| | | Asn | 52 | H |
| | | Asp | 57 | H |
| | | Thr | 103 | H |
| Asp | 62 | Ser | 59 | H |
| Thr | 105 | Trp | 102 | H |
| Ile | 107 | Trp | 102 | H |
| | | Thr | 103 | H |
| Arg | 109 | Thr | 103 | H |
| | | Thr | 104 | H |
| Glu | 117 | Gln | 100 | H |
| | | Phe | 101 | H |
| | | Thr | 104 | H |
| | | Arg | 106 | H |
| Glu | 119 | Phe | 101 | H |
| | | Trp | 102 | H |
| | | Thr | 103 | H |
| Lys | 121 | Trp | 102 | H |

TABLE 10

Interactions between human CD48 and the NY938-IgG light chain (L). CD48 residues are numbered based upon human CD48 (SEQ ID NO: 53). NY938-IgG light chain residues are numbered based upon amino acid sequence of SEQ ID NO: 51. CD48 residues shown have at least one atom within 4.0 Å of an atom in the NY938 IgG.

| Human CD48 | | NY938 light chain | | |
|---|---|---|---|---|
| Residue | Number | Residue | Number | Chain |
| Gln | 54 | Thr | 31 | L |
|  |  | Trp | 50 | L |
| Phe | 61 | Tyr | 94 | L |
| Asp | 62 | Tyr | 94 | L |
| Lys | 64 | Ser | 92 | L |
| Arg | 109 | Trp | 50 | L |
| Leu | 111 | Trp | 50 | L |
| Thr | 114 | Thr | 53 | L |
| Gly | 115 | Tyr | 49 | L |
|  |  | Trp | 50 | L |
|  |  | Thr | 53 | L |
| Glu | 117 | Trp | 50 | L |

NY938 was affinity matured based on the parental antibody NY258. The Epitope binning with mutated human CD48 protein constructs (page 23) showed the main contact of NY258 to CD48 being in the areas of the CD48 protein amino acids 50-55, and 105-108. This result is in line with the crystallization and structure determination of the NY938 IgG-CD48 complex.

Example 5: Anti-CD48 Antibody Conjugation

Synthesis of CD48A-Valcit-MMAE

Expression vectors coding for heavy chain and light chain of CD48A-CysMab antibody

```
(Heavy Chain sequence:
QVQLVQSGSELKKPGASVKVSCKASGYTFTDFGMN

VVVRQAPGQGLEWMGWINTFTGEPSYGNVFKGRFV

FSLDTSVSTAYLQISSLKAEDTAVYYCARRHGNGN

VFDSWGQGTLVTVSSATKGPSVFPLAPSSKSTSGG

TAALGCLVKDYFPCPVTVSWNSGALTSGVHTFPAV

LQSSGLYSLSSVVTVPSSSLGTQTYICNVNHKPSN

TKVDKRVEPKSCDKTHTCPPCPAPELLGGPSVFLF

PPKPKDTLMISRTPEVTCVVVDVSHEDPEVKFNWY

VDGVEVHNAKTKPREEQYNSTYRVVSVLTVLHQDW

LNGKEYKCKVSNKALPAPIEKTISKAKGQPREPQV

YTLPPSREEMTKNQVSLTCLVKGFYPCDIAVEWES

NGQPENNYKTTPPVLDSDGSFFLYSKLTVDKSRWQ

QGNVFSCSVMHEALHNHYTQKSLSLSPGK
(SEQ ID NO: 70);

Light Chain sequence

EIVLTQSPDFQSVTPKEKVTITCRASQSIGSNIHW

YQQKPDQSPKLLIKYTSESISGVPSRFSGSGSGTD

FTLTINSLEAEDAATYYCQQSNSWPLTFGGGTKVE

IKRTVAAPSVFIFPPSDEQLKSGTASVVCLLNNFY

PREAKVQWKVDNALQSGNSQESVTEQDSKDSTYSL

SSTLTLSKADYEKHKVYACEVTHQGLSSPVTKSFN

RGEC
(SEQ ID NO: 74))
``` were transfected into suspension HEK293 cells using polyethylenimine and cultured for 5 days. Culture supernatant was harvested by centrifugation, filtered, and antibodies purified by Protein A affinity chromatography. If needed, aggregates were removed by size exclusion chromatography. Antibody purity after affinity chromatography was determined by analytical size exclusion chromatography and were >98% monomer. Antibodies were buffered in phosphate buffered saline pH 7.2. 10 mg of CD48A antibody (0.068 μmoles, 1.0 equiv.) was incubated with 1 ml of settled RMP Protein A resin (GE Lifesciences, 17513803) and agitated for 15 minutes. Cysteine HCl monohydrate was added to a final concentration of 20 mM and incubated with agitation for 30 min at room temperature to allow the reactive cysteines to be deblocked. The resin was washed rapidly with 50 column volumes PBS on a vacuum manifold. The resin was then resuspended in an equal volume PBS containing 250 nM $CuCl_2$. Reformation of antibody interchain disulfides was monitored by taking time points. At each time point, 25 μL of resin slurry was removed, 1 μL of 20 mM MC-valcit-PAB-MMAE (Levena Biopharm; SET0201) was added, and the tube flicked several times. The resin was spun down, supernatant removed, and then eluted with 50 μL Antibody elution buffer (Thermo Scientific, 21004). The resin was pelleted and the supernatant analyzed by reverse phase chromatography using an Agilent PLRP-S 4000A 5 um, 4.6×50 mm column (Buffer A is water, 0.1% TFA, Buffer B Acetonitrile, 0.1% TFA, column held at 80 C, Flowrate 1.5 ml/min; Gradient 0 minutes—30% B, 5 minutes—45% B, 6.5 min—100% B, 8 minutes—100% B, 10 minutes—30%). At 60 minutes after addition of $CuCl_2$, was removed by washing with 50 column volumes of PBS on a vacuum manifold and then 2 ml of PBS was added to resuspend. To this slurry of resin and antibody MC-valcit-MMAE (27.5 μl of a 20 mM solution in DMSO, 0.544 μmoles, 8 equiv.) was added. The resulting mixture was then incubated at ambient temperature for 3 hours. The resin was then washed with 50 column volumes PBS. The ADC was eluted from the resin with Antibody elution buffer (Thermo Scientific, 21004). The ADC was then buffer exchanged into 1×PBS (20×PBS, Teknova P0191) by dialysis. The material was then concentrated using a centrifugal concentrator using an Amicon Ultra-15, 50 KDa, regenerated cellulose (Millipore, UFC0905024), to 1 mg/ml and filtered sterilely through 0.22 μm sterile PVDF Filter, 25 mm (Millapore, SLGV013SL) and stored at 4° C. The final yield was 1.7 mg (0.011 μmol) The following analyses were performed: analytical size-exclusion chromatography (SEC) to determine percent monomer, mass spectroscopy (MS) to determine DAR, LAL test to determine endotoxin load and protein concentration determined by A280 utilizing extinction coefficient and molecular weight of antibody. HRMS data (protein method) indicated a dominant mass of the heavy chain was 53042 da, giving a DAR of 3.9 was calculated by comparing MS intensities of peaks for DAR1 DAR2 and DAR3 species. SEC indicated 1.3% aggregation, as determined by comparison of the area of the high-molecularweight peak absorbance at 210 and 280 nm with the area of the peak absorbance for monomeric ADC.

General Methodology (1): Drug-to-antibody ratio (DAR) of exemplary ADCs was determined by liquid chromatography-mass spectrometry (LC/MS) according to the following method. For all LC methods, mobile phase A was purified MS grade water (Honeywell, LC015-1), mobile phase B was MS grade 80% Isopropanol (Honeywell LC323-1): 20% acetonitrile (Honeywell, LC015-1), LC323-1), supplemented with 1% of formic acid (FA) (Thermo Scientific, 85178). The column temperature was set at 80° C. A general MS method was optimized for all ADCs synthesized. The column used for analysis was an Agilent PLRP-S 4000 A; 2.1×150 mm, 8 um (Agilent, PL1912-3803). Flowrate used was 0.3 ml/min. The gradient used was 0-0.75 minute 95% A, 0.76-1.9 minute 75% A, 1.91-11.0 minute 50% A, 11.01-11.50 10% A, 11.51-13.50 minute 95% A, 13.51-18 minute 95% A on an Acquitty Bio H-Class Quaternary UPLC (Waters). MS system was Xevo G2-XS QToF ESI mass spectrometer (Waters) and data acquired from 1.5-11 minutes and masses were analyzed between 15000-80000 daltons. DAR was determined from the deconvoluted spectra or UV chromatogram by summing the integrated MS (total ion current) or UV (280 nm) peak area of unconjugated and conjugated given species (mAb or associated fragment), weighted by multiplying each area by the number of drug attached. The summed, weighted areas were divided by the sum of total area and the results produced a final average DAR value for the full ADC.

Size exclusion chromatography (SEC) (1) was performed to determine the quality of the ADCs and aggregation percentage (%) after purification. The analysis was performed on analytical column Superdex200 Increase 5/150 GL (GE Healthcare, 28990945) in isocratic conditions 100% PBS pH 7.2 ((Hyclone SH30028.03)), 150 mM NaCl, 1 mM EDTA, flow 0.45 ml/min for 8 minutes. The % aggregate fraction of the ADC sample was quantified based on the peak area absorbance at 280 nm. Calculation was based on the ratio between the high molecular weight eluent at 280 nm divided by the sum of peak area absorbance at the same wavelength of the high molecular weight and monomeric eluents multiplied by 100%. Data was acquired on an Agilent Bio-Inert 1260 HPLC outfitted with a Wyatt miniDAWN light scattering and Treos refractive index detectors (Wyatt Technologies, Santa Barbara, Calif.).

Synthesis of NY920-Valcit-MMAE

Antibody NY920 is synthesized and expressed generally as described above. 20 mg of antibody NY920 CysMab (0.136 μmoles, 1.0 equiv.) is incubated with 2 ml of settled RMP Protein A resin (GE Lifesciences, 17513803) and agitated for 15 minutes. Cysteine HCl monohydrate is added to a final concentration of 20 mM and incubated with agitation for 30 min at room temperature to allow the reactive cysteines to be deblocked. The resin is washed rapidly with 50 column volumes PBS on a vacuum manifold. The resin is then resuspended in an equal volume PBS containing 250 nM $CuCl_2$. Reformation of antibody interchain disulfides is monitored by taking time points. At each time point, 25 μL of resin slurry is removed, 1 μL of 20 mM MC-valcit-PAB-MMAE is added, and the tube flicked several times. The resin is spun down, supernatant removed, and then eluted with 50 μL Antibody elution buffer (Thermo Scientific, 21004). The resin is pelleted and the supernatant analyzed by reverse phase chromatography using an Agilent PLRP-S 4000A 5 μm, 4.6×50 mm column (Buffer A is water, 0.1% TFA, Buffer B Acetonitrile, 0.1% TFA, column held at 80 C, Flowrate 1.5 ml/min; Gradient 0 minutes—30% B, 5 minutes—45% B, 6.5 min—100% B, 8 minutes—100% B, 10 minutes—30%). At 60 minutes after addition of $CuCl_2$, the $CuCl_2$ is removed by washing with 50 column volumes of PBS on a vacuum manifold and then 2 ml of PBS is added to resuspend. To this slurry of resin and antibody, MC-valcit-MMAE (55 μl of a 20 mM solution in DMSO, 1.088 μmoles, 8 equiv.) is added. The resulting mixture is then incubated at ambient temperature for 3 hours. The resin is then washed with 50 column volumes PBS. The ADC is eluted from the resin with Antibody elution buffer (Thermo Scientific, 21004). The ADC is then buffer exchanged into 1×PBS (20×PBS, TeknovaP0191) by dialysis and preparative size exclusion chromatography eluted in Dulbecco's PBS pH 7.2 (Hyclone SH30028.03) to remove aggregates is performed with a HiLoad 16/600 Superdex 200 μg (GE Healthcare, 28989335). The material is then concentrated using a centrifugal concentrator using an Amicon Ultra-15, 50 KDa, regenerated cellulose (Millipore, UFC0905024), to 4.5 mg/ml and filtered sterilely through 0.22 μm sterile PVDF Filter, 25 mm (Millapore, SLGV013SL) and stored at 4° C. The following analyses are performed: analytical size-exclusion chromatography (SEC) to determine percent monomer, mass spectroscopy (MS) to determine DAR (Drug Antibody Ratio), LAL test to determine endotoxin load, and protein concentration determined by A280 utilizing extinction coefficient and molecular weight of antibody. HRMS data (protein method) can indicate a dominant mass of the heavy chain+2 species, giving a DAR of 4.0, which is calculated by comparing MS intensities of peaks for DAR1, DAR2, and DAR3 species. SEC can indicate aggregation, as determined by comparison of the area of the high-molecular-weight peak absorbance at 210 and 280 nm with the area of the peak absorbance for monomeric ADC.

Additional ADCs with different CD48 antibodies as disclosed herein are made using similar protocols as disclosed above.

Example 6: Internalization and Cell Proliferation Inhibition of CD48 Antibodies

The internalization activity of CD48 antibodies were tested against three endogenous cancer cell lines: KMS-27: JCRB No. JCRB1188 cultured in RPMI-1640+10% FBS; NCI-H929: ATCC No. CRL-9068 cultured in RPMI-1640+10% FBS+0.05 mM 2-mercaptoethanol; and KMS-21-BM: JCRB No. JCRB1185 cultured in RPMI-1640+10% FBS. The ability of the CD48 antibodies NY920, NY938, and humanized CD48A to internalize bound to a secondary anti-human Fc ADC conjugate leading to the inhibition of cell proliferation and survival was assessed using the Promega CellTiter-Glo® proliferation assay.

CD48 antibodies were synthesized and expressed generally as described in Example 5. Cell lines were cultured in media that is optimal for their growth at 5% $CO_2$, 37° C. in a tissue culture incubator. Prior to seeding for the proliferation assay, the cells were split at least 2 days before the assay to ensure optimal growth density. On the day of seeding, cell viability and cell density were determined using a cell counter (Vi-Cell XR Cell Viability Analyzer, Beckman Coulter). Cells with higher than 85% viability were seeded in white clear bottom 384-well TC treated plates (Corning cat. #3765). Cells were seeded at a density of 1,000 cells per well in 40 µL of standard growth media. Plates were incubated at 5% $CO_2$, 37° C. overnight in a tissue culture incubator. The next day free MMAE payload, a CD48A-CysMab-VC-MMAE ADC (synthesis described in Example 5), CD48 antibodies, and a non-targeting isotype antibody were prepared at 10× in standard growth media. The MMAE free payload and CD48A-CysMab-VC-MMAE ADC were added to the cells resulting in final concentrations of 0.007-150 nM and a final volume of 50 µL per well. The prepared antibody treatments, including CD48 IgGs and a non-targeting isotype antibody, were then added to the cells resulting in final concentrations of 0.001-20 nM and a final volume of 45 µL per well. An anti-human Fc-VC-MMAE ADC (DAR2.0) was prepared at 10× in standard growth media. The prepared ADC was then added to the cells resulting in a final concentration of 60 nM and a final volume of 50 µL per well. Each drug concentration was tested in quadruplets. Plates were incubated at 5% $CO_2$, 37° C. for 5 days in a tissue culture incubator, after which cell viability was assessed through the addition of 25 µL of CellTiter Glo® (Promega, cat #G7573), a reagent which lyses cells and measures total adenosine triphosphate (ATP) content. Plates were incubated at room temperature for 10 minutes to stabilize luminescent signals prior to reading using a luminescence reader (EnVision Multilabel Plate Reader, PerkinElmer). To evaluate the effect of the drug treatments, luminescent counts from wells containing untreated cells (100% viability) were used to normalize treated samples. A variable slope model was applied to fit a nonlinear regression curve to the data in GraphPad PRISM version 7.02 software. $IC_{50}$ and $A_{max}$ values were extrapolated from the resultant curves.

Figure 2A:
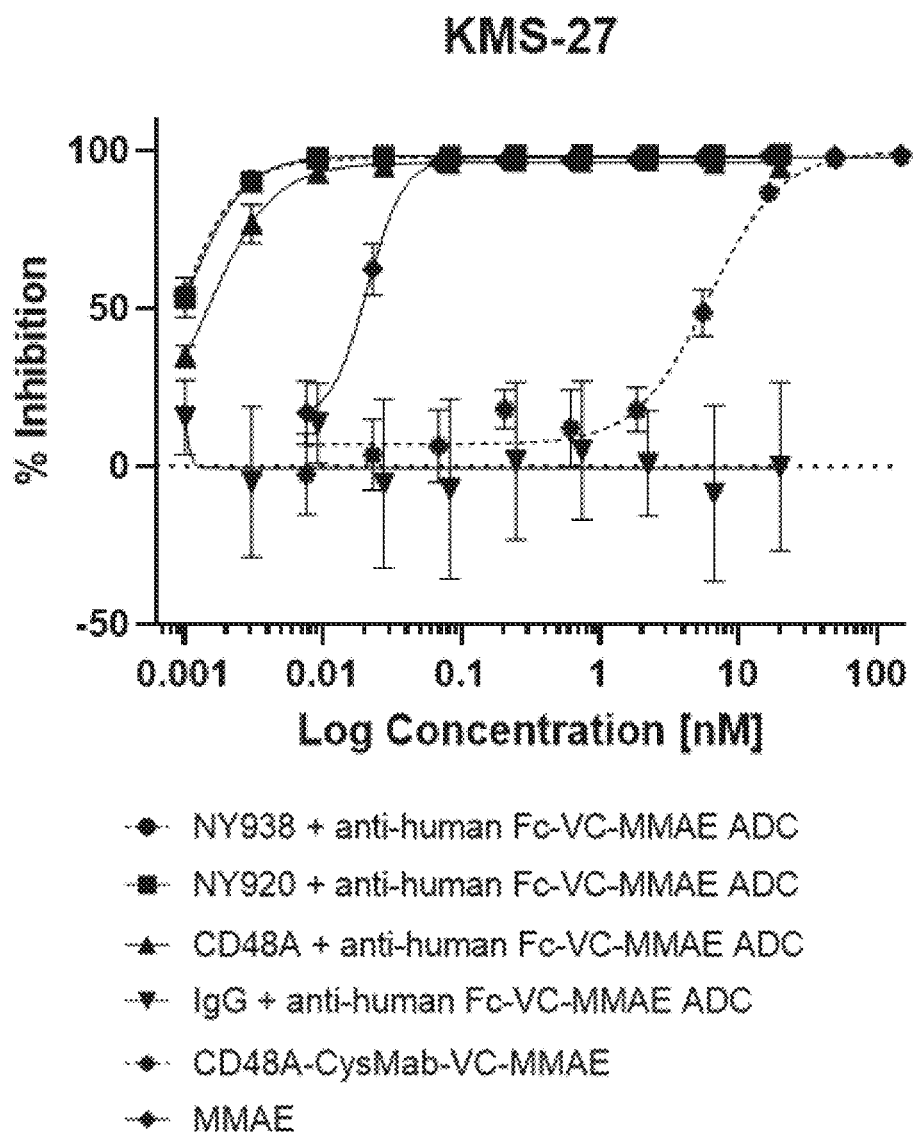
FIG. 2A is a dose response curve of anti-CD48 antibodies in internalization and cell proliferation assays against endogenous cancer cell line KMS-27. NY938 and NY920 anti-CD48 antibodies were more potent than the anti-CD48A antibody in this assay.
Figure 2B:
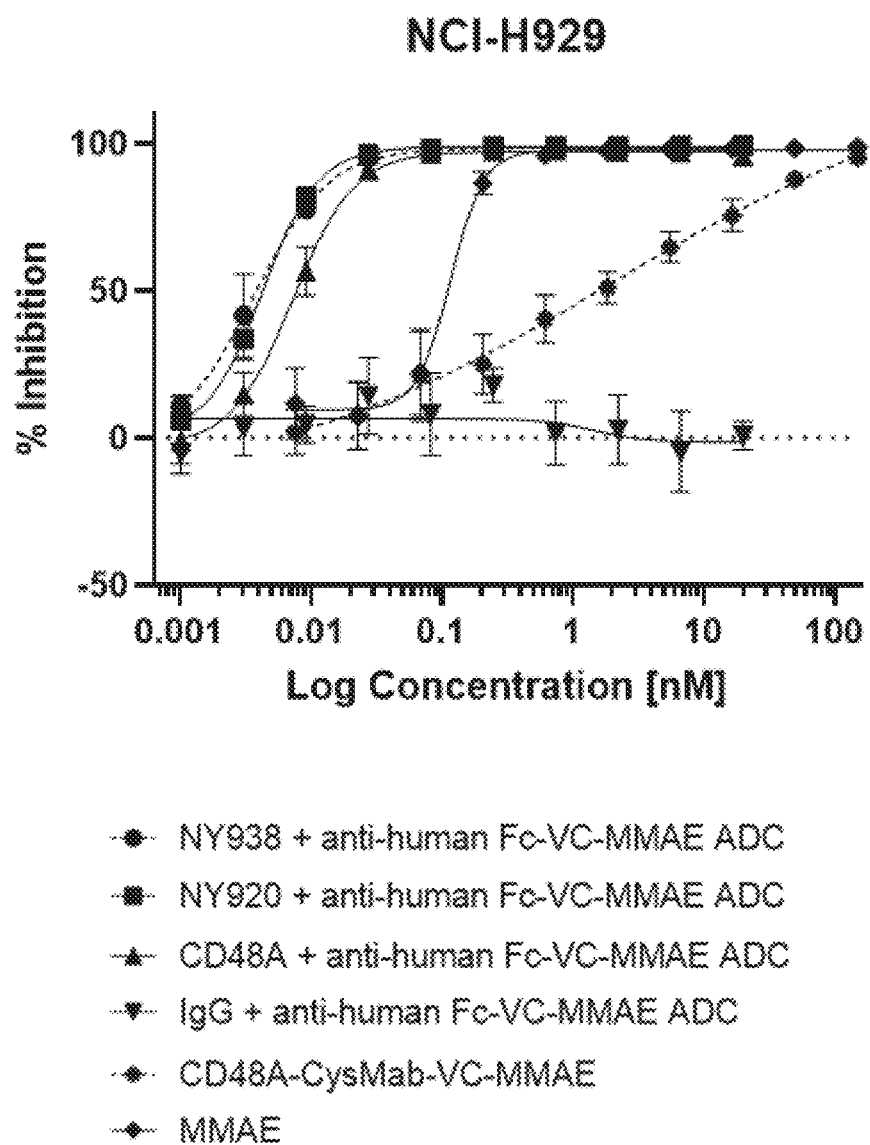
FIG. 2B is a dose response curve of anti-CD48 antibodies in internalization and cell proliferation assays against endogenous cancer cell line NCI-H929. NY938 and NY920 anti-CD48 antibodies were more potent than the anti-CD48A antibody in this assay.
Figure 2C:
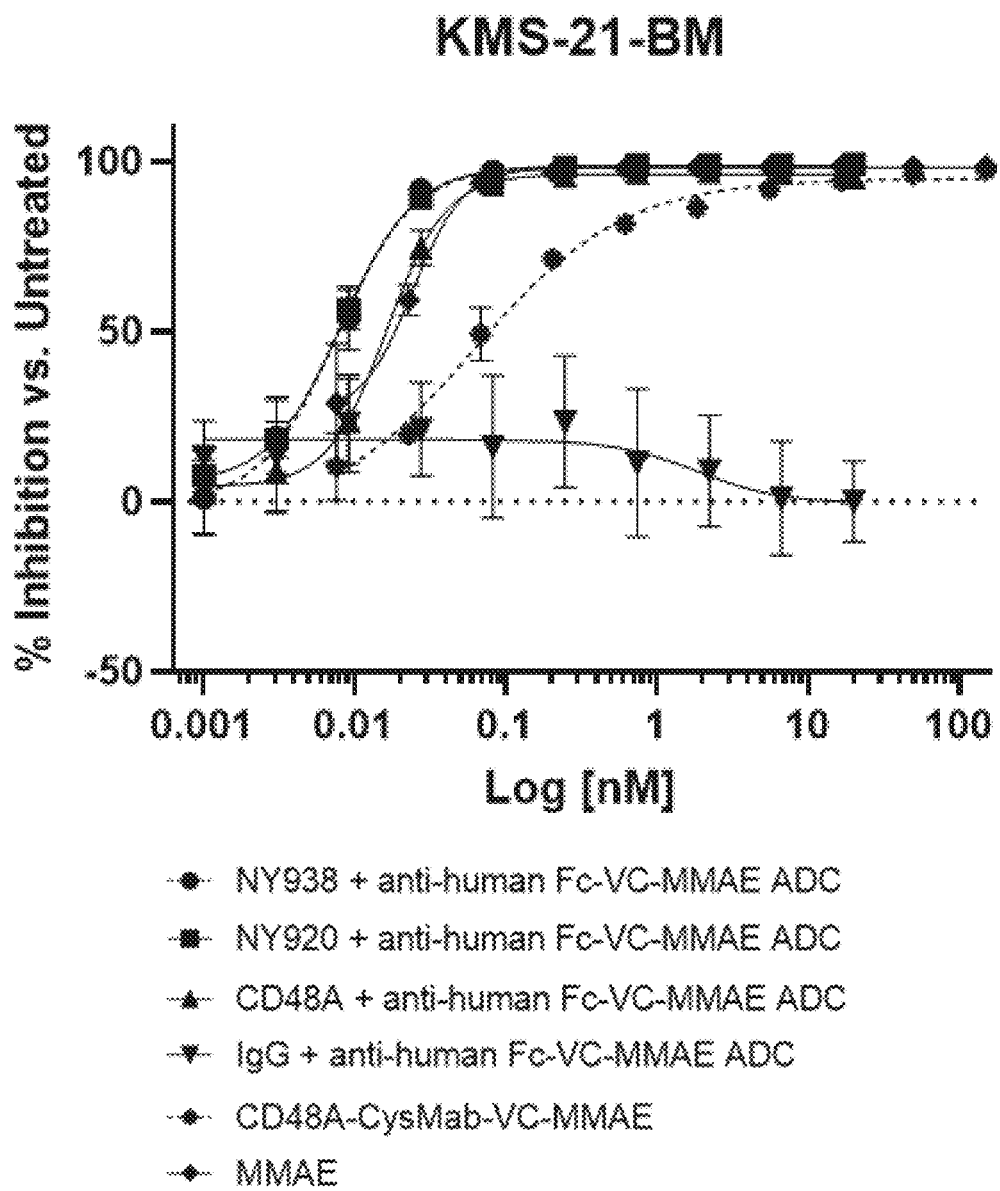
FIG. 2C is a dose response curve of anti-CD48 antibodies in internalization and cell proliferation assays against endogenous cancer cell line KMS-21-BM. NY938 and NY920 anti-CD48 antibodies were more potent than the anti-CD48A antibody in this assay.

The concentrations of mAb treatment required to inhibit 50% of cell growth or survival (IC50) were calculated with representative IC50 values of the cell lines tested summarized in Table 11. The dose response curves of representative cancer cell lines are shown in FIG. 2A (KMS-27), FIG. 2B (NCI-H929), and FIG. 2C (KMS-21-BM).

The representative cancer cell lines were shown to be sensitive to the MMAE payload with $IC_{50}$ values ranging from 0.021-0.116 nM activity. The isotype control IgG dosed in combination with the anti-human Fc-VC-MMAE ADC did not induce off target activity. The representative cancer cell lines were sensitive to the CD48A-CysMab-VC-MMAE ADC with $IC_{50}$ values ranging from 0.062-6.1 nM activity indicating that internalization and cytotoxicity is possible with a CD48 targeting ADC. NY938 and NY920 when dosed in combination with the anti-human Fc ADC induced cell death with activity greater than that of CD48A. The two candidates, NY938 and NY920, were the most potent across the three cancer cell lines.

These studies indicate that CD48 IgG candidates were capable of internalization and ultimately inhibition of cell proliferation on various cancer cell lines expressing CD48. NY938 and NY920 anti-CD48 antibodies were more potent than CD48A. Little cytotoxic activity was demonstrated relative to isotype matched non-targeting IgG control on the cancer cell lines.

TABLE 11

| | CD48 IgG Candidates: IC50 | | | | | |
| --- | --- | --- | --- | --- | --- | --- |
| | KMS-27 | | NCI-H929 | | KMS-21-BM | |
| Treatment | $IC_{50}$ (nM) | Span (Amax) | $IC_{50}$ (nM) | Span (Amax) | $IC_{50}$ (nM) | Span (Amax) |
| NY938 + anti-human Fc-VC-MMAE | <0.001 | >100 | 0.004 | 99.7 | 0.008 | 98.9 |
| NY920 + anti-human Fc-VC-MMAE | <0.001 | 81.5 | 0.004 | 98.1 | 0.008 | 93.3 |
| CD48A + anti-human Fc-VC-MMAE | 0.001 | 93.4 | 0.007 | 100.3 | 0.016 | 92.0 |
| IgG + anti-human Fc-VC-MMAE | — | — | — | — | — | — |
| MMAE | 0.021 | 83.9 | 0.116 | 88.5 | 0.024 | 72.9 |
| CD48A-CysMab-VC-MMAE | 6.10 | 92.9 | 2.10 | 142.4 | 0.062 | 100.4 |

Example 7: $K_D$ Determination of CD48 Antibodies

Binding to human and cyno CD48 for the WT IgG and DAPA (D265A and P329A mutation) variant was assessed for affinity determinations using Biacore. Kinetic rate constants was performed via SPR using the Biacore T200 instrument (Cytiva, formerly GE Healthcare Lifesciences) as described below.

The Protein A capture method was utilized in order to determine kinetics for the antibodies. A commercially available Protein A sensor chip was used (Cytiva, cat #29127556), by which the protein A on the surface captured the WT and DAPA variant, and the soluble human and cyno CD48 flowed over as the analyte. The human CD48 and cyno CD48 concentration started at 50 nM and 200 nM respectively, and were serially diluted at one part to one part for nine concentrations. Regeneration was performed at the end of each concentration washing with the Glycine pH1.5 (Cytiva, cat #BR100354).

Figure 3:
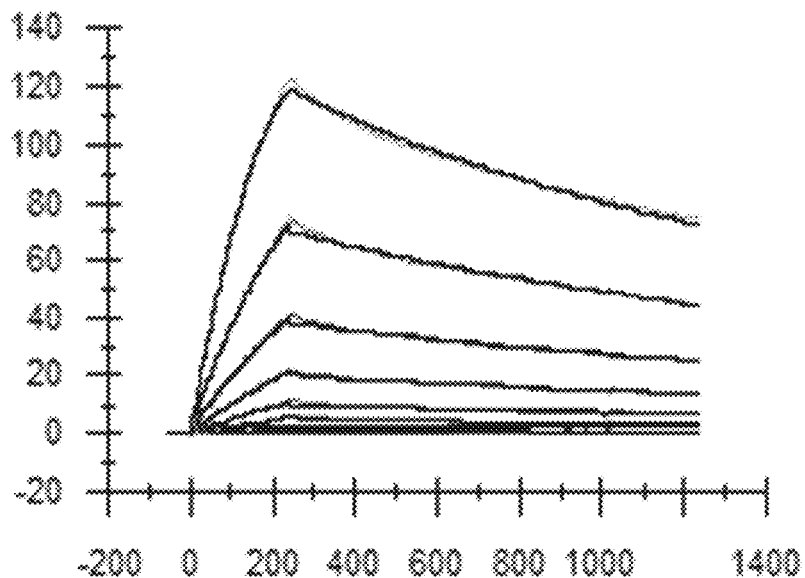
FIG. 3 are graphs depicting the binding kinetics of the NY920 WT antibody to the human CD48 antigen. Two experimental runs (Exp #1 and Exp #2) were conducted.
Figure 3:
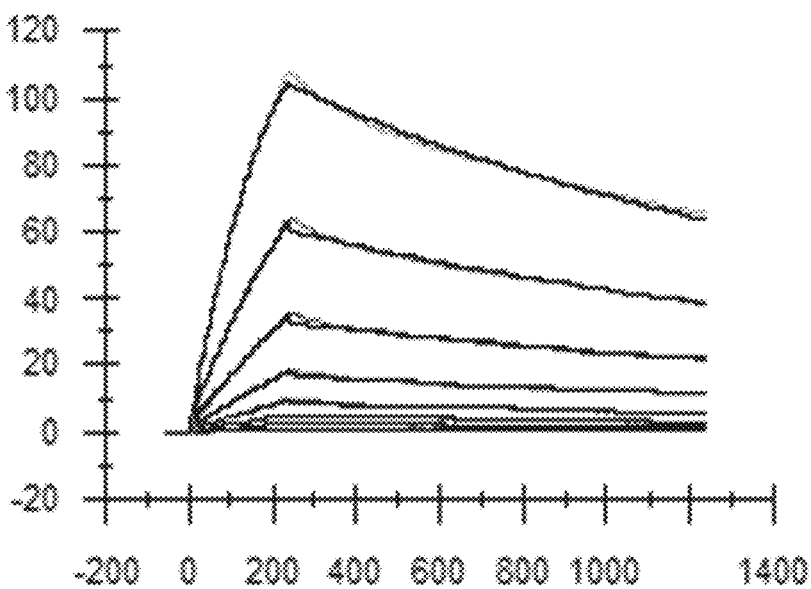
Figure 4:
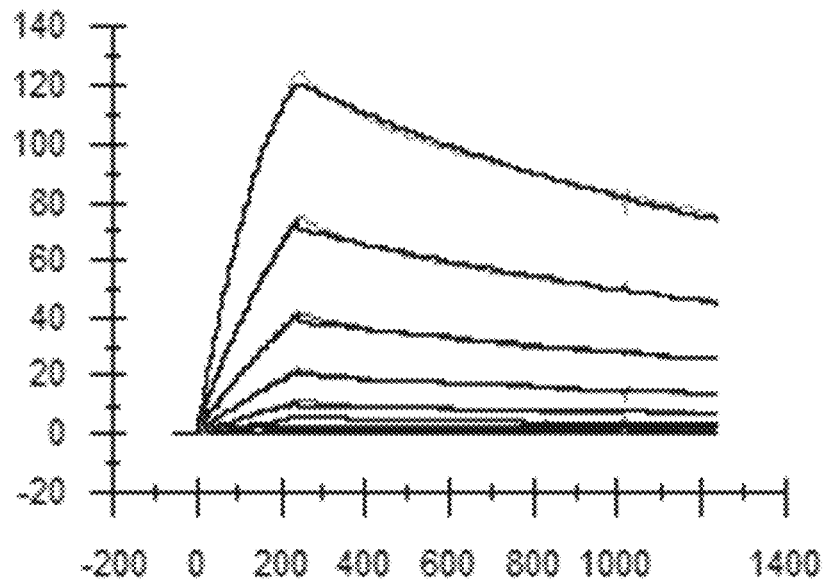
FIG. 4 are graphs depicting the binding kinetics of the NY920 DAPA antibody to the human CD48 antigen. Two experimental runs (Exp #1 and Exp #2) were conducted.
Figure 4:
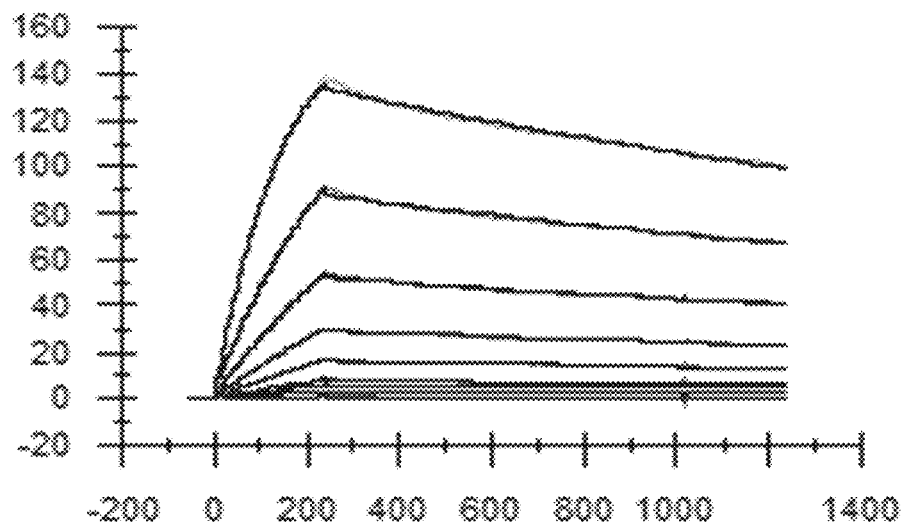
Figure 5:
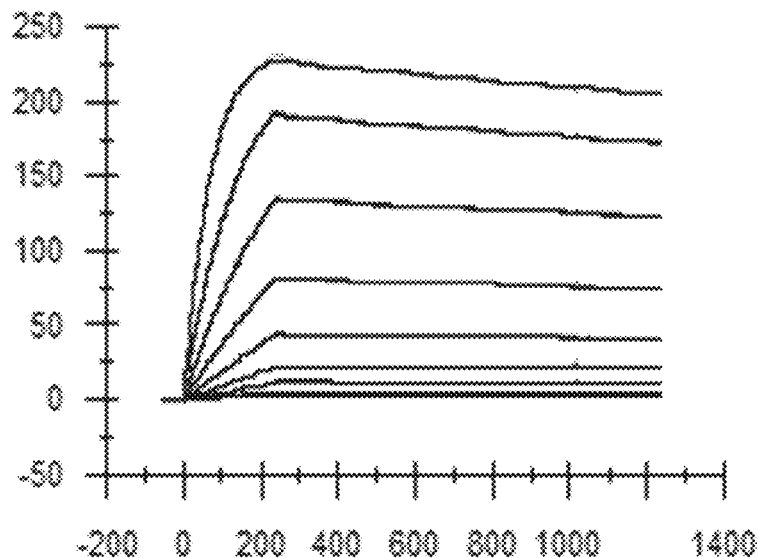
FIG. 5 are graphs depicting the binding kinetics of the NY938 DAPA antibody to the human CD48 antigen. Two experimental runs (Exp #1 and Exp #2) were conducted.
Figure 5:
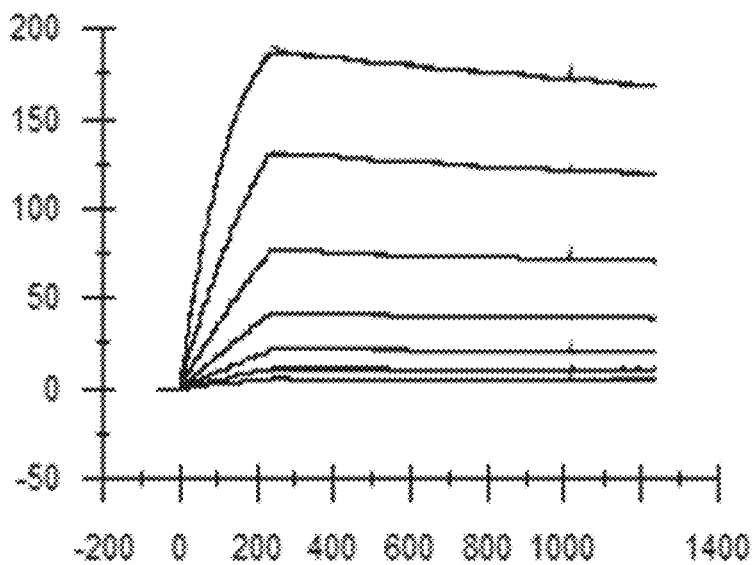
Figure 6:
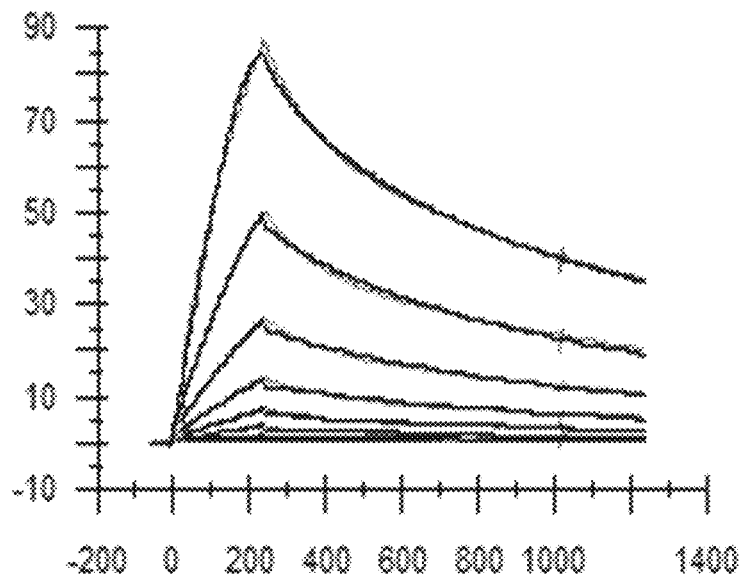
FIG. 6 are graphs depicting the binding kinetics of the NY920 WT antibody to the cyno CD48 antigen. Two experimental runs (Exp #1 and Exp #2) were conducted.
Figure 6:
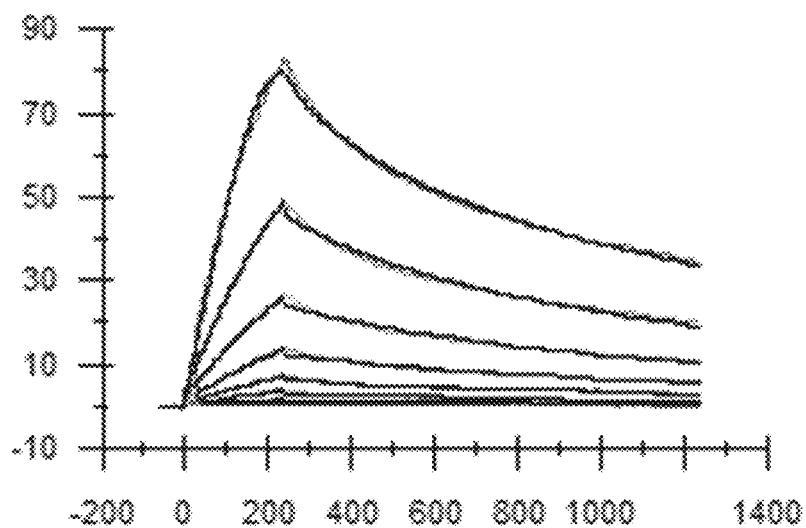
Figure 7:
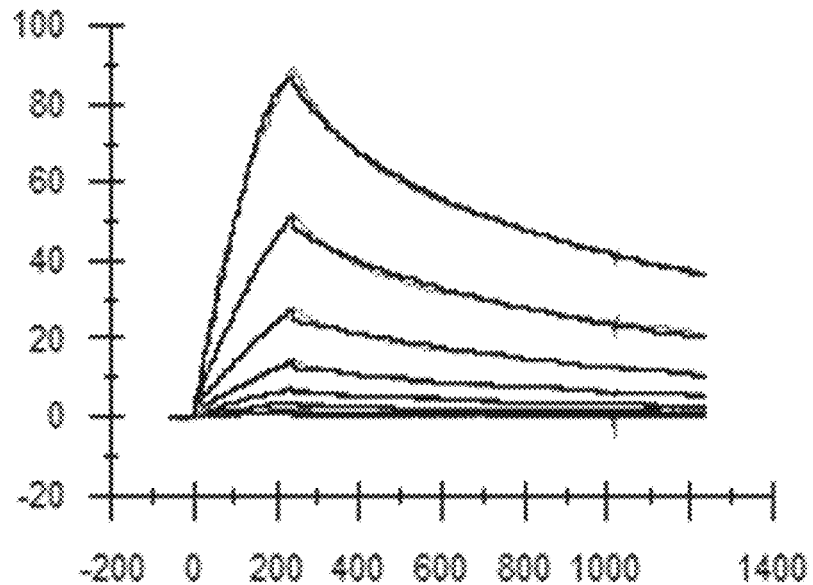
FIG. 7 are graphs depicting the binding kinetics of the NY920 DAPA antibody to the cyno CD48 antigen. Two experimental runs (Exp #1 and Exp #2) were conducted.
Figure 7:
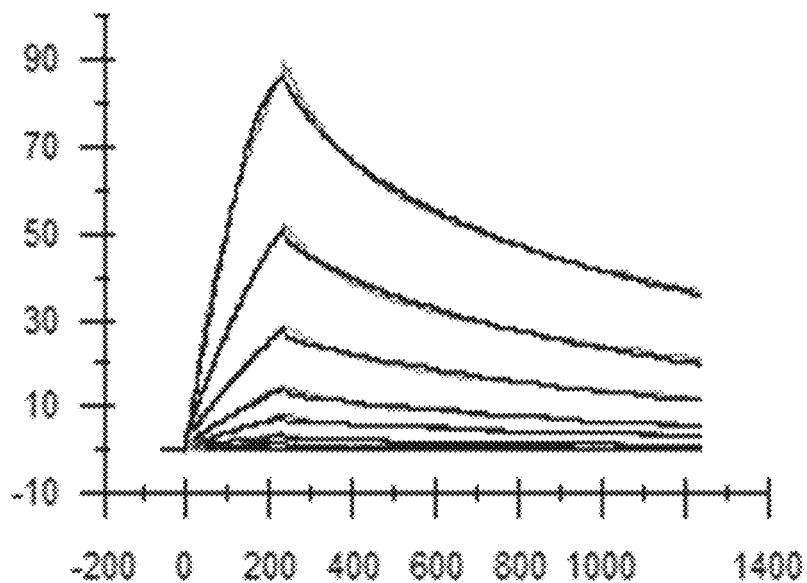
Figure 8:
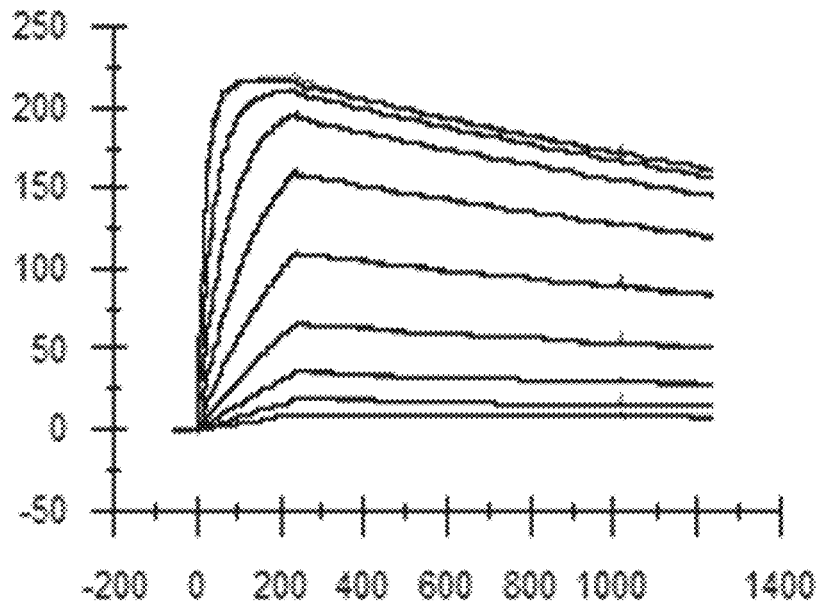
FIG. 8 are graphs depicting the binding kinetics of the NY938 DAPA antibody to the cyno CD48 antigen. Two experimental runs (Exp #1 and Exp #2) were conducted.
Figure 8:
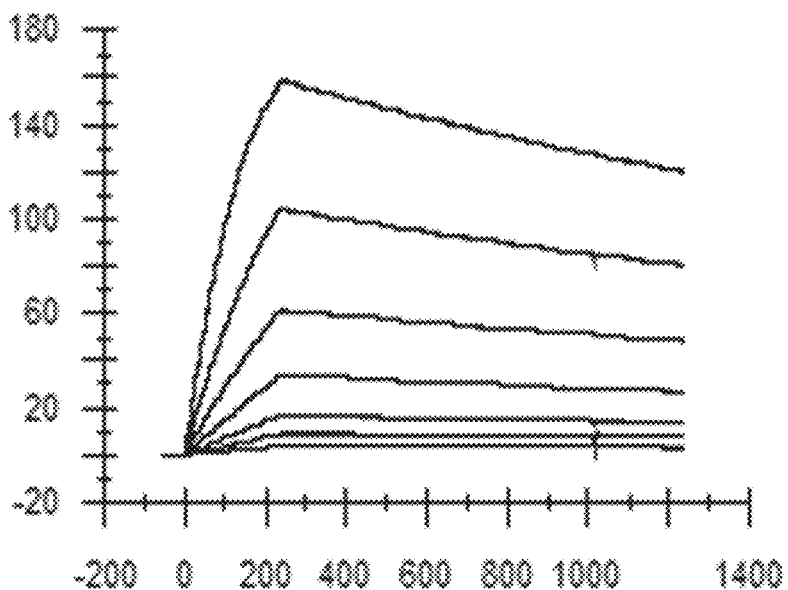
Figure 9A:
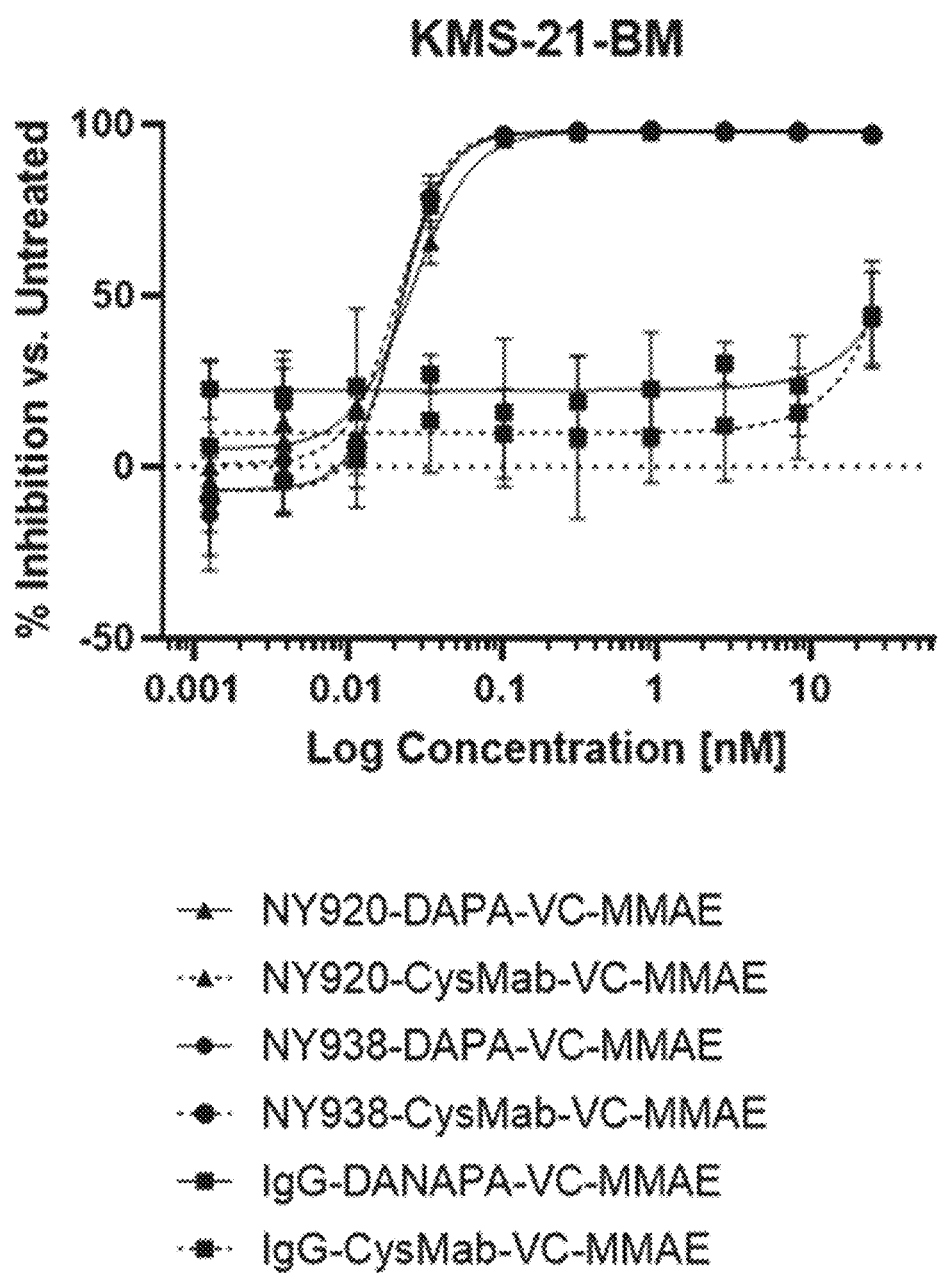
FIG. 9A is a dose response curve of anti-CD48 MMAE ADCs in cell proliferation and survival assays against endogenous cancer cell line KMS-21-BM. Non-targeting IgG-VC-MMAE ADC was used as a negative control.
Figure 9B:
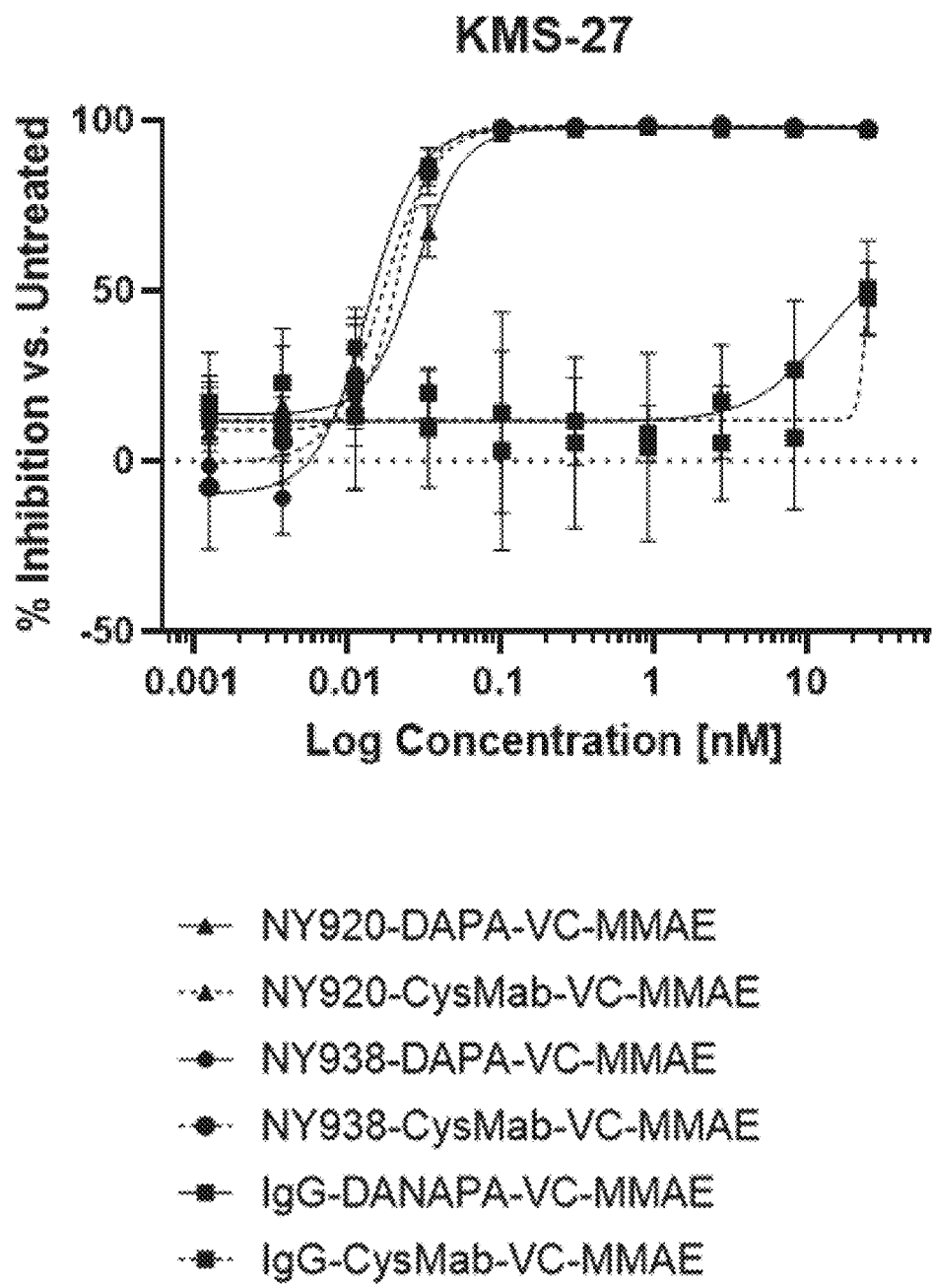
FIG. 9B is a dose response curve of anti-CD48 MMAE ADCs in cell proliferation and survival assays against endogenous cancer cell line KMS-27. Non-targeting IgG-VC-MMAE ADC was used as a negative control.
Figure 9C:
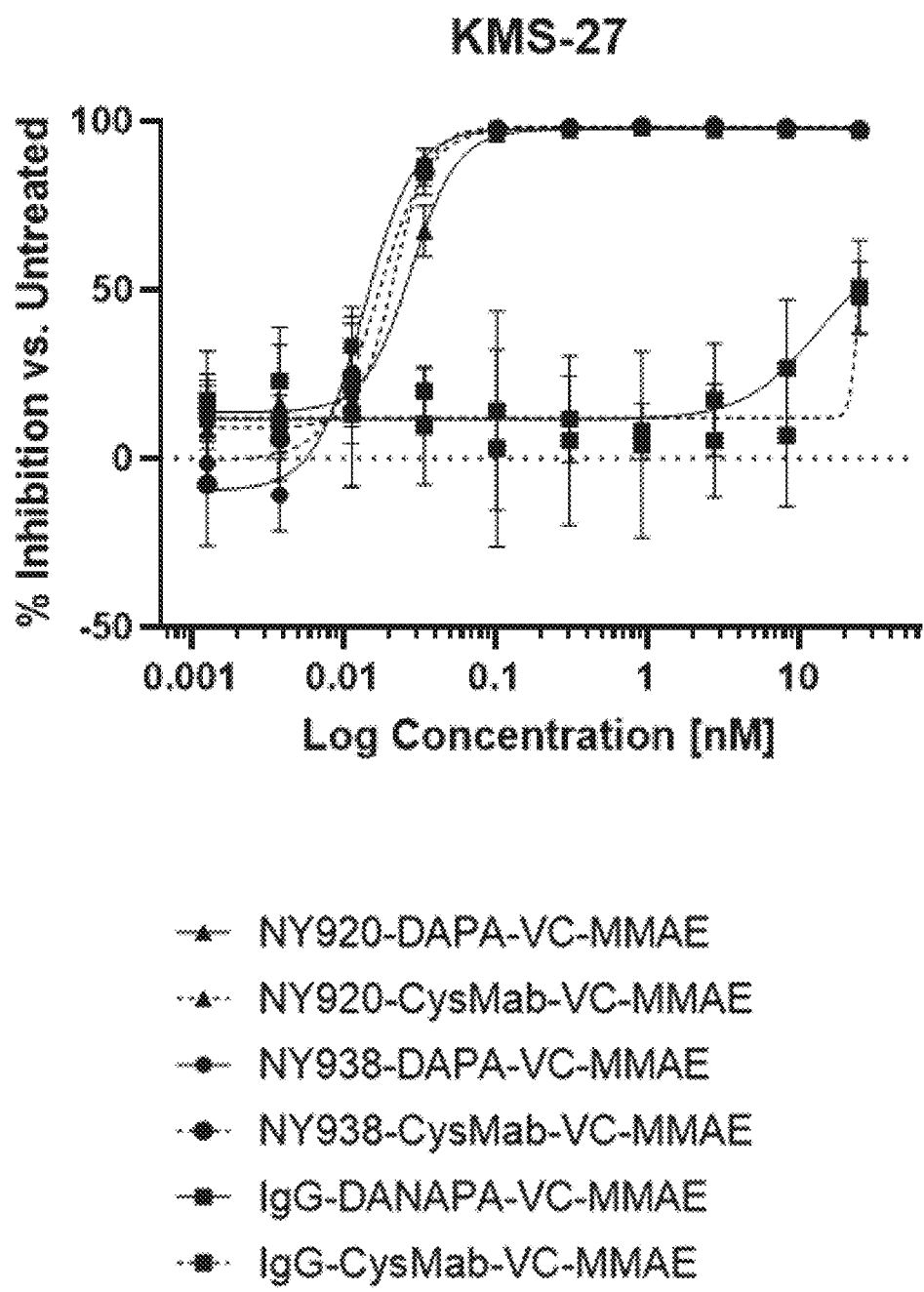
FIG. 9C is a dose response curve of anti-CD48 MMAE ADCs in cell proliferation and survival assays against endogenous cancer cell line NCI-H929. Non-targeting IgG-VC-MMAE ADC was used as a negative control.
Figure 9D:
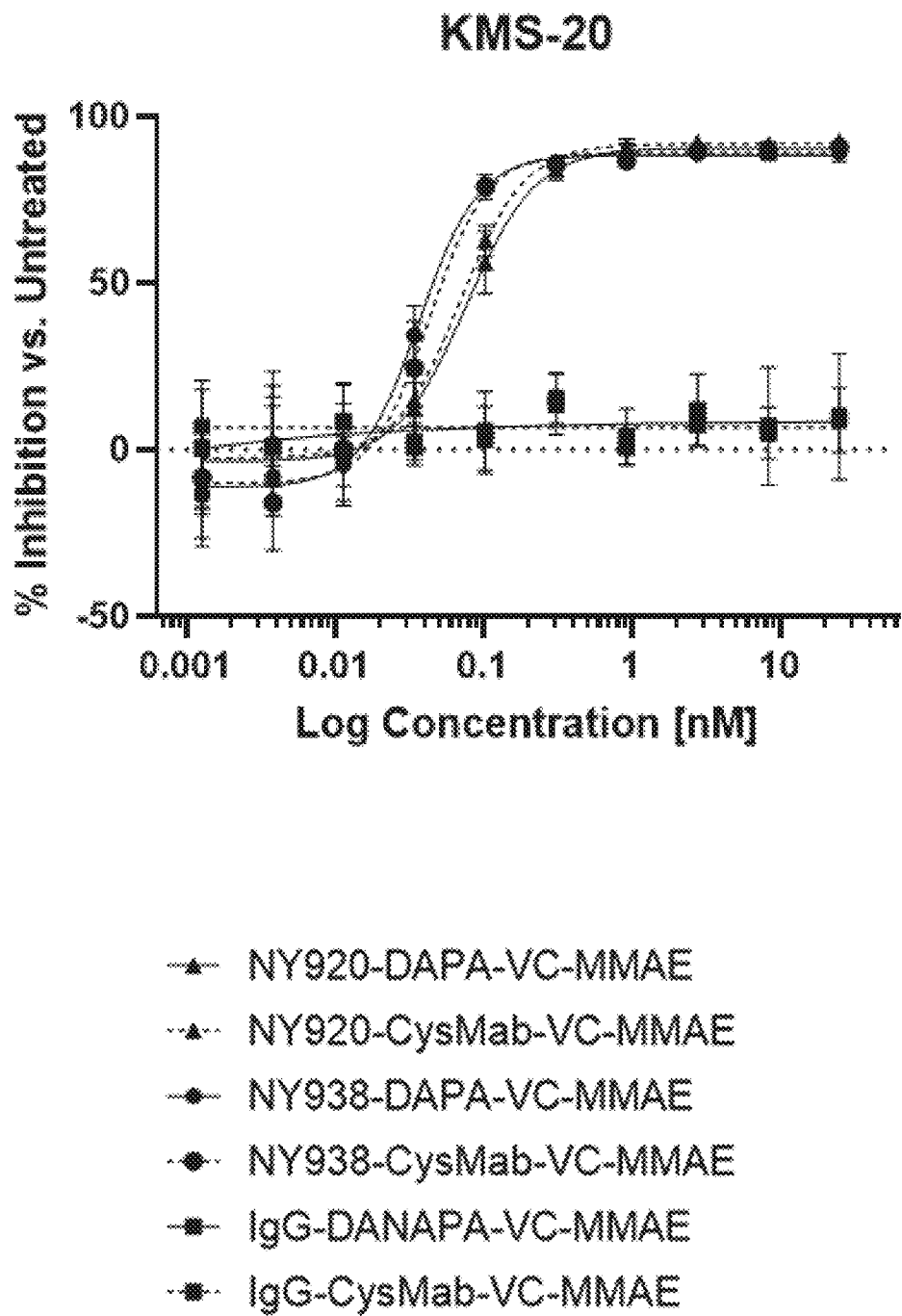
FIG. 9D is a dose response curve of anti-CD48 MMAE ADCs in cell proliferation and survival assays against endogenous cancer cell line KMS-20. Non-targeting IgG-VC-MMAE ADC was used as a negative control.

Double reference subtraction was completed to generate the final data. The raw data was fitted to a 1:1 binding model, with parameter(s) Rmax set to local. The kinetic results for the WT and DAPA IgG variants to the human antigen are shown in FIGS. 3-5 and Table 12. The kinetic results for the WT and DAPA IgG variants to the cyno antigen are shown in FIGS. 6-8 and Table 13.

TABLE 12

Binding Affinity of WT and DAPA IgG Candidates to Human CD48

| Exp# | Sample | Antigen | ka (1/Ms) | kd (1/s) | KD (M) |
|---|---|---|---|---|---|
| 1 | NY920 WT | Human CD48 | 2.57E+05 | 7.21E−04 | 2.81E−09 |
| 2 | NY920 WT | Human CD48 | 2.24E+05 | 6.98E−04 | 3.11E−09 |
| 1 | NY920 DAPA | Human CD48 | 2.74E+05 | 7.26E−04 | 2.65E−09 |
| 2 | NY920 DAPA | Human CD48 | 2.06E+05 | 3.43E−04 | 1.67E−09 |
| 1 | NY938 DAPA | Human CD48 | 3.52E+05 | 1.04E−04 | 2.96E−10 |
| 2 | NY938 DAPA | Human CD48 | 4.56E+05 | 1.15E−04 | 2.52E−10 |

TABLE 13

Binding Affinity of WT and DAPA IgG Candidates to Cyno CD48

| Exp# | Sample | Antigen | ka (1/Ms) | kd (1/s) | KD (M) |
|---|---|---|---|---|---|
| 1 | NY920 WT | Cyno CD48 | 3.25E+05 | 4.47E−03 | 1.38E−08 |
| 2 | NY920 WT | Cyno CD48 | 3.11E+05 | 4.01E−03 | 1.29E−08 |
| 1 | NY920 DAPA | Cyno CD48 | 3.19E+05 | 4.25E−03 | 1.34E−08 |
| 2 | NY920 DAPA | Cyno CD48 | 3.01E+05 | 3.92E−03 | 1.30E−08 |
| 1 | NY938 DAPA | Cyno CD48 | 2.71E+05 | 2.89E−04 | 1.07E−09 |
| 2 | NY938 DAPA | Cyno CD48 | 4.09E+05 | 3.16E−04 | 7.74E−10 |

Example 8: In Vitro Assessment of Anti-CD48 MMAE ADCs

Cell Lines

The CD48 antibody drug conjugates (ADCs) were tested against four endogenous cancer cell lines: NCI-H929: ATCC No. CRL-9068 cultured in RPMI-1640+10% FBS+0.05 mM 2-mercaptoethanol; KMS-21-BM: JCRB No. JCRB1185 cultured in RPMI-1640+10% FBS; KMS-27: JCRB No. JCRB1188 cultured in RPMI-1640+10% FBS; and KMS-20: JCRB No. JCRB1196 cultured in RPMI-1640+10% FBS.

Inhibition of Cell Proliferation and Survival

The ability of the CD48 ADCs to inhibit cell proliferation and survival was assessed using the Promega CellTiter-Glo® proliferation assay. Cell lines were cultured in media that is optimal for their growth at 5% $CO_2$, 37° C. in a tissue culture incubator. Prior to seeding for the proliferation assay, the cells were split at least 2 days before the assay to ensure optimal growth density. On the day of seeding, cell viability and cell density were determined using a cell counter (Vi-Cell XR Cell Viability Analyzer, Beckman Coulter). Cells with higher than 85% viability were seeded in white clear bottom 384-well TC treated plates (Corning cat. #3765). Cells were seeded at a density of 1,000 cells per well in 45 µL of standard growth media. Plates were incubated at 5% $CO_2$, 37° C. overnight in a tissue culture incubator.

The next day, CD48 targeting MMAE ADCs and non-targeting isotype ADCs were prepared at 10× in standard growth media. The prepared CD48 targeting and isotype matched non-targeting control ADC treatments were added to the cells resulting in final concentrations of 0.001-25 nM and a final volume of 50 µL per well. Each drug concentration was tested in quadruplets.

Plates were incubated at 5% $CO_2$, 37° C. for 5 days in a tissue culture incubator, after which cell viability was assessed through the addition of 25 µL of CellTiter Glo® (Promega, cat #G7573), a reagent which lyses cells and measures total adenosine triphosphate (ATP) content. Plates were incubated at room temperature for 10 minutes to stabilize luminescent signals prior to reading using a luminescence reader (EnVision Multilabel Plate Reader, PerkinElmer). To evaluate the effect of the drug treatments, luminescent counts from wells containing untreated cells (100% viability) were used to normalize treated samples. A variable slope model was applied to fit a nonlinear regression curve to the data in GraphPad PRISM version 7.02 software. IC50 and Amax values were extrapolated from the resultant curves.

The dose response curves of representative cancer cell lines are shown in FIGS. 9A-9D. The concentrations of treatment required to inhibit 50% of cell growth or survival (IC50) were calculated with representative IC50 values of the cell lines tested summarized in Table 14.

The representative cancer cell lines were shown to be sensitive to the CD48 targeting MMAE ADCs relative to the isotype matched non-targeting control ADC, IgG-VC-MMAE, with IC50s ranging from 0.014 nM-0.077 nM. The NY920 and NY938 CD48 antibodies were tested as ADCs in an Fc silenced format, DAPA, and a wild type format, CysMab. There was no difference in activity between the various antibody formats when conjugated to VC-MMAE. The NY920 MMAE ADCs and the NY938 MMAE ADCs were equivalent in activity on a given cell line model as demonstrated in the cell proliferation assay. These studies indicate that the CD48 targeting VC-MMAE ADCs were capable of inhibiting cell proliferation on various cancer cell lines expressing CD48.

TABLE 14

CD48 ADC In Vitro Activity

| ADC | KMS-21-BM | | KMS-27 | | NCI-H929 | | KMS-20 | |
|---|---|---|---|---|---|---|---|---|
| | IC$_{50}$ (nM) | Amax (Span) | IC$_{50}$ (nM) | Amax (Span) | IC$_{50}$ (nM) | Amax (Span) | IC$_{50}$ (nM) | Amax (Span) |
| NY920-DAPA-VC-MMAE | 0.026 | 92.9 | 0.028 | 83.9 | 0.027 | 89.7 | 0.077 | 94 |
| NY920-CysMab-VC-MMAE | 0.021 | 97.4 | 0.022 | 89.2 | 0.021 | 92.9 | 0.070 | 94.2 |
| NY938-DAPA-VC-MMAE | 0.021 | 104.6 | 0.014 | 107.5 | 0.016 | 104.8 | 0.037 | 99.8 |
| NY938-CysMab-VC-MMAE | 0.021 | 104.8 | 0.017 | 98.6 | 0.018 | 100.7 | 0.043 | 99.2 |
| IgG-DANAPA-VC-MMAE | — | — | — | — | — | — | — | — |
| IgG-CysMab-VC-MMAE | — | — | — | — | — | — | — | — |

Unless defined otherwise, the technical and scientific terms used herein have the same meaning as that usually understood by a specialist familiar with the field to which the disclosure belongs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein. Unless indicated otherwise, each of the references cited herein is incorporated in its entirety by reference.

Claims to the invention are non-limiting and are provided below.

Although particular aspects and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the disclosure without departing from the spirit and scope of the disclosure as defined by the claims. The choice of nucleic acid starting material, clone of interest, or library type is believed to be a matter of routine for a person of ordinary skill in the art with knowledge of the aspects described herein. Other aspects, advantages, and modifications considered to be within the scope of the following claims. Those skilled in the art will recognize or be able to ascertain, using no more than routine experimentation, many equivalents of the specific aspects of the invention described herein. Such equivalents are intended to be encompassed by the following claims. Redrafting of claim scope in later filed corresponding applications may be due to limitations by the patent laws of various countries and should not be interpreted as giving up subject matter of the claims.

What is claimed is:

1. An anti-CD48 antibody or antigen-binding fragment comprising three heavy chain CDRs and three light chain CDRs selected from one of the following:
   (i) heavy chain CDR1 (HCDR1) consisting of SEQ ID NO:1, heavy chain CDR2 (HCDR2) consisting of SEQ ID NO:2, heavy chain CDR3 (HCDR3) consisting of SEQ ID NO:3; light chain CDR1 (LCDR1) consisting of SEQ ID NO:16, light chain CDR2 (LCDR2) consisting of SEQ ID NO:17, and light chain CDR3 (LCDR3) consisting of SEQ ID NO:18;
   (ii) heavy chain CDR1 (HCDR1) consisting of SEQ ID NO:4, heavy chain CDR2 (HCDR2) consisting of SEQ ID NO:2, heavy chain CDR3 (HCDR3) consisting of SEQ ID NO:3; light chain CDR1 (LCDR1) consisting of SEQ ID NO:16, light chain CDR2 (LCDR2) consisting of SEQ ID NO:17, and light chain CDR3 (LCDR3) consisting of SEQ ID NO:18;
   (iii) heavy chain CDR1 (HCDR1) consisting of SEQ ID NO:5, heavy chain CDR2 (HCDR2) consisting of SEQ ID NO:6, heavy chain CDR3 (HCDR3) consisting of SEQ ID NO:3; light chain CDR1 (LCDR1) consisting of SEQ ID NO:19, light chain CDR2 (LCDR2) consisting of SEQ ID NO:20, and light chain CDR3 (LCDR3) consisting of SEQ ID NO:21;
(iv) heavy chain CDR1 (HCDR1) consisting of SEQ ID NO:7, heavy chain CDR2 (HCDR2) consisting of SEQ ID NO:8, heavy chain CDR3 (HCDR3) consisting of SEQ ID NO:9; light chain CDR1 (LCDR1) consisting of SEQ ID NO:22, light chain CDR2 (LCDR2) consisting of SEQ ID NO:20, and light chain CDR3 (LCDR3) consisting of SEQ ID NO:18;
(v) heavy chain CDR1 (HCDR1) consisting of SEQ ID NO:27, heavy chain CDR2 (HCDR2) consisting of SEQ ID NO:28, heavy chain CDR3 (HCDR3) consisting of SEQ ID NO:29; light chain CDR1 (LCDR1) consisting of SEQ ID NO:42, light chain CDR2 (LCDR2) consisting of SEQ ID NO:43, and light chain CDR3 (LCDR3) consisting of SEQ ID NO:44;
(vi) heavy chain CDR1 (HCDR1) consisting of SEQ ID NO:30, heavy chain CDR2 (HCDR2) consisting of SEQ ID NO:28, heavy chain CDR3 (HCDR3) consisting of SEQ ID NO:29; light chain CDR1 (LCDR1) consisting of SEQ ID NO:42, light chain CDR2 (LCDR2) consisting of SEQ ID NO:43, and light chain CDR3 (LCDR3) consisting of SEQ ID NO:44;
(vii) heavy chain CDR1 (HCDR1) consisting of SEQ ID NO:31, heavy chain CDR2 (HCDR2) consisting of SEQ ID NO:32, heavy chain CDR3 (HCDR3) consisting of SEQ ID NO:29; light chain CDR1 (LCDR1) consisting of SEQ ID NO:45, light chain CDR2 (LCDR2) consisting of SEQ ID NO:46, and light chain CDR3 (LCDR3) consisting of SEQ ID NO:47; or
(viii) heavy chain CDR1 (HCDR1) consisting of SEQ ID NO:33, heavy chain CDR2 (HCDR2) consisting of SEQ ID NO:34, heavy chain CDR3 (HCDR3) consisting of SEQ ID NO:35; light chain CDR1 (LCDR1) consisting of SEQ ID NO:48, light chain CDR2 (LCDR2) consisting of SEQ ID NO:46, and light chain CDR3 (LCDR3) consisting of SEQ ID NO:44.

2. The antibody or antigen-binding fragment thereof of claim 1, wherein the anti-CD48 antibody or antigen-binding fragment thereof comprises:
(i) a heavy chain variable region comprising the amino acid sequence of SEQ ID NO:10, and a light chain variable region comprising the amino acid sequence of SEQ ID NO:23; or
(ii) a heavy chain variable region comprising the amino acid sequence of SEQ ID NO:36, and a light chain variable region comprising the amino acid sequence of SEQ ID NO:49.

3. The antibody or antigen-binding fragment of claim 1, wherein the anti-CD48 antibody comprises:
(a) the heavy chain amino acid sequence of SEQ ID NO:12 and the light chain amino acid sequence of SEQ ID NO:25;
(b) the heavy chain amino acid sequence of SEQ ID NO:14 and the light chain amino acid sequence of SEQ ID NO:25;
(c) The heavy chain amino acid sequence of SEQ ID NO:63 and the light chain amino acid sequence of SEQ ID NO:25;
(e) the heavy chain amino acid sequence of SEQ ID NO:38 and the light chain amino acid sequence of SEQ ID NO:51;
(f) the heavy chain amino acid sequence of SEQ ID NO:40 and the light chain amino acid sequence of SEQ ID NO:51; or
(g) The heavy chain amino acid sequence of SEQ ID NO:65 and the light chain amino acid sequence of SEQ ID NO:51.

4. The antibody or antigen-binding fragment thereof of claim 1, wherein the antibody or antigen-binding fragment thereof comprises a Fab fragment, a Fab' fragment, a F(ab')2 fragment, a single chain Fv (scFv), a disulfide-linked Fv (sdFv), a Fd fragment, a Fv fragment, a maxibody, a minibody, an intrabody, a diabody, a half antibody, a one-arm antibody, a monoclonal antibody, a bispecific antibody, a bispecific T-cell engage antibody, a multispecific antibody, a chimeric antigen receptor T-cell, or a radioimmunconjugate.

5. A nucleic acid encoding the antibody or antigen-binding fragment thereof of claim 1.

6. The nucleic acid of claim 5 comprising the nucleic acid sequence of SEQ ID NO:11, SEQ ID NO:37, SEQ ID NO:24, or SEQ ID NO:50.

7. The nucleic acid of claim 5 comprising the nucleic acid sequence of SEQ ID NOs:13, 15, 39, 41, 75, 77, 26, or 52.

8. A vector comprising the nucleic acid of claim 5.

9. A cell line comprising the vector of claim 8.

10. A method of making an antibody or antigen-binding fragment thereof comprising growing the cell line of claim 9 under suitable conditions to express the antibody or antigen-binding fragment thereof, then purifying and isolating the antibody or antigen-binding fragment thereof.

11. An antibody drug conjugate of Formula (I):

$$A\text{-}(L_B\text{-}(D)_n)_y \qquad (I);$$

wherein:
A is the antibody or antigen-binding fragment thereof of claim 1;
$L_B$ is a linker;
D is a cytotoxic agent, wherein D is not a BCL-2 inhibitor, MCL-1 inhibitor, or BCL-XL inhibitor;
n is an integer from 1 to 10, and
y is an integer from 1 to 10,
wherein the Linker-Drug moiety $(L_B\text{-}(D)_n)$ is covalently attached to the antibody or antigen binding fragment thereof (A).

12. The antibody drug conjugate of claim 11, wherein the cytotoxic agent is an Eg5 inhibitor, a V-ATPase inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alkylating agent, a DNA intercalator, a DNA minor groove binder, an RNA polymerase inhibitor, an amanitin, a spliceosome inhibitor, a topoisomerase inhibitor, a DHFR inhibitor, or a pro-apoptotic agent, but excluding BCL-2 inhibitors, MCL-1 inhibitors, and BCL-XL inhibitors.

13. The antibody drug conjugate of claim 11, wherein the cytotoxic agent is an Eg5 inhibitor, a V-ATPase inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alkylating agent, a DNA intercalator, a DNA minor groove binder, an RNA polymerase inhibitor, an amanitin, a spliceosome inhibitor, a topoisomerase inhibitor, or a DHFR inhibitor, but excluding BCL-2 inhibitors, MCL-1 inhibitors, and BCL-XL inhibitors.

14. The antibody drug conjugate of claim 11, wherein the cytotoxic agent is an auristatin.

15. The antibody drug conjugate of claim 11, wherein:
D is a cytotoxic agent selected from a compound of Formula (A):

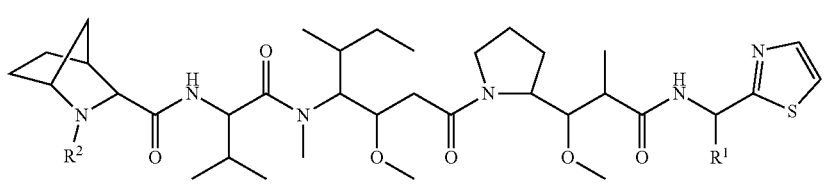

Formula (A)

wherein:
R$^1$ is

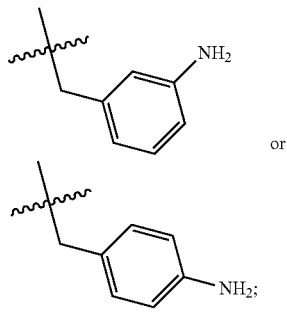

or

R$^2$ is H, C$_1$-C$_6$alkyl, —C(=O)R$^3$, —(CH$_2$)$_m$OH, —C(=O)(CH$_2$)$_m$OH, —C(=O)((CH$_2$)$_m$O)$_n$R$^4$, —((CH$_2$)$_m$O)$_n$R$^4$ or C$_1$-C$_6$alkyl which is optionally substituted with —CN, —C(=O)NH$_2$ or 1 to 5 hydroxyl;

each R$^3$ is independently selected from C$_1$-C$_6$alkyl and C$_1$-C$_6$alkyl, which is optionally substituted with 1 to 5 hydroxyl; m is independently selected from 1, 2, 3, 4, 5, 6, 7, 8, 9 and 10; and each R$^4$ is independently selected from H and C$_1$-C$_6$alkyl;

or D is a cytotoxic agent selected from a compound of Formula (B):

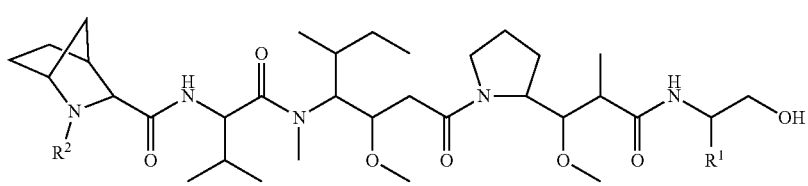

Formula (B)

wherein:

R¹ is

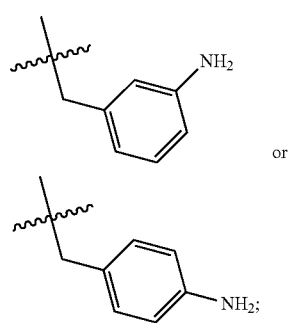 [SMILES: *Cc1cccc(N)c1 ; *Cc1ccc(N)cc1]

or

R² is H, $C_1$-$C_6$alkyl, —C(=O)R³, —$(CH_2)_m$OH, —C(=O)$(CH_2)_m$OH, —C(=O)$((CH_2)_m$O$)_n$R⁴, —$((CH_2)_m$O$)_n$R⁴ or $C_1$-$C_6$alkyl which is optionally substituted with —CN, —C(=O)NH₂ or 1 to 5 hydroxyl;

each R³ is independently selected from $C_1$-$C_6$alkyl and $C_1$-$C_6$alkyl, which is optionally substituted with 1 to 5 hydroxyl; and each R⁴ is independently selected from H and $C_1$-$C_6$alkyl.

16. The antibody drug conjugate of claim 11, wherein n is 1, 2, 3, 4, 5, 6, 7 or 8.

17. The antibody drug conjugate of claim 11, wherein y is 1, 2, 3 or 4.

18. The antibody drug conjugate of claim 11, wherein each $L_B$ is a cleavable linker.

19. The antibody drug conjugate of claim 11, wherein each $L_B$ is a non-cleavable linker.

20. An antibody drug conjugate of claim 11, selected from

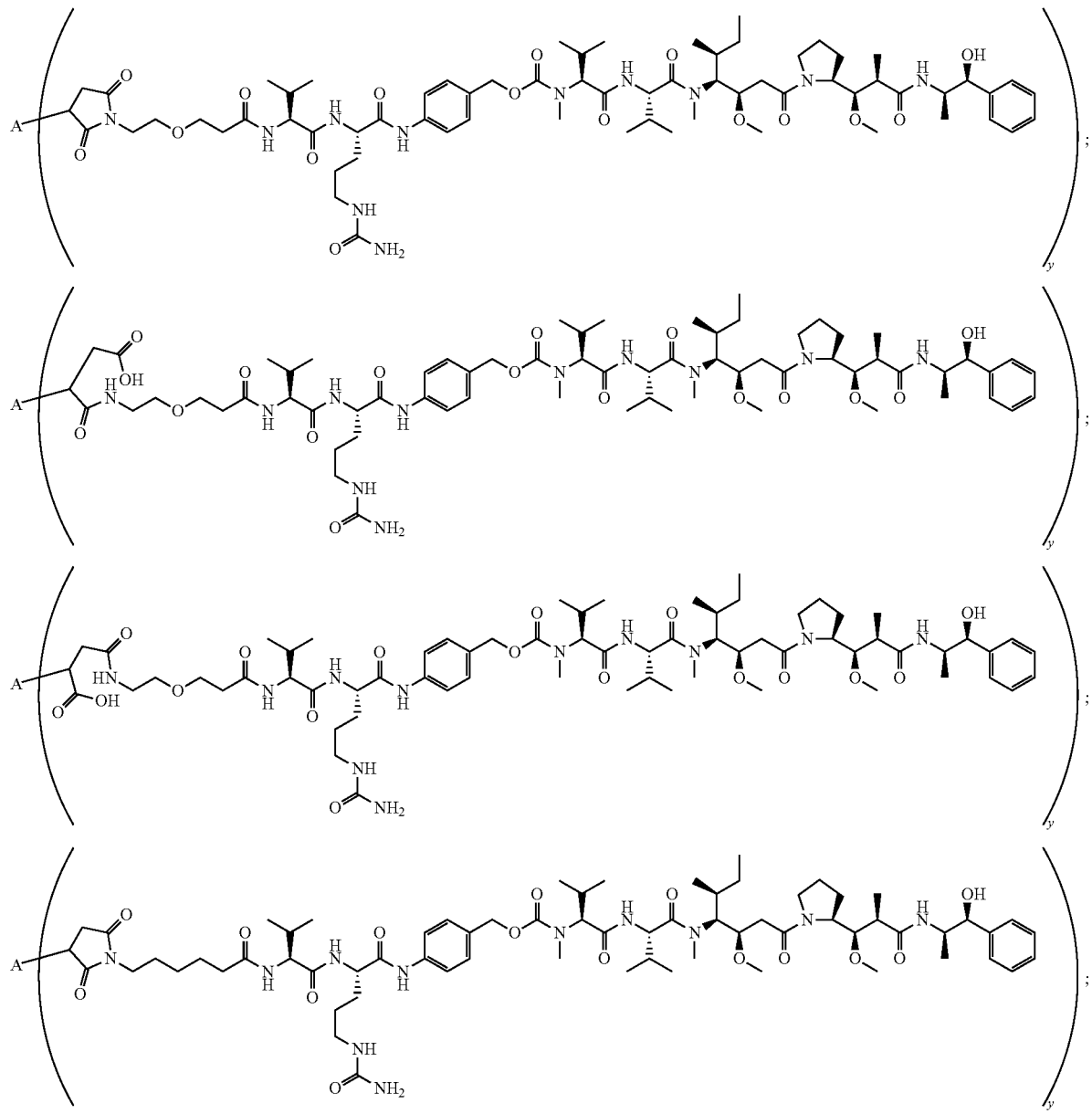

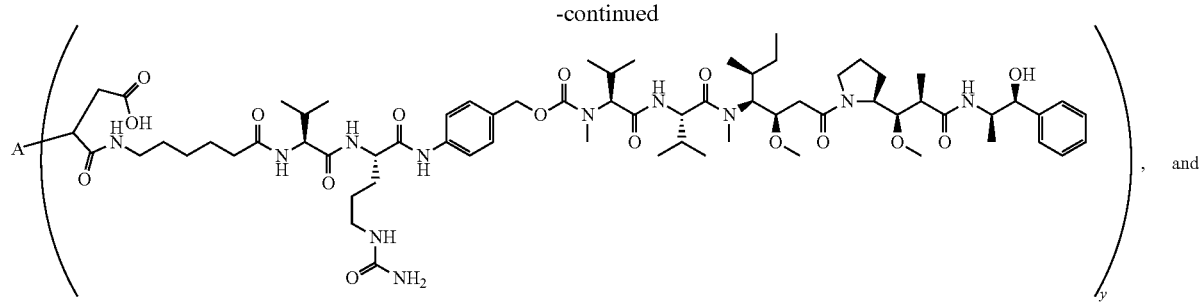

, and

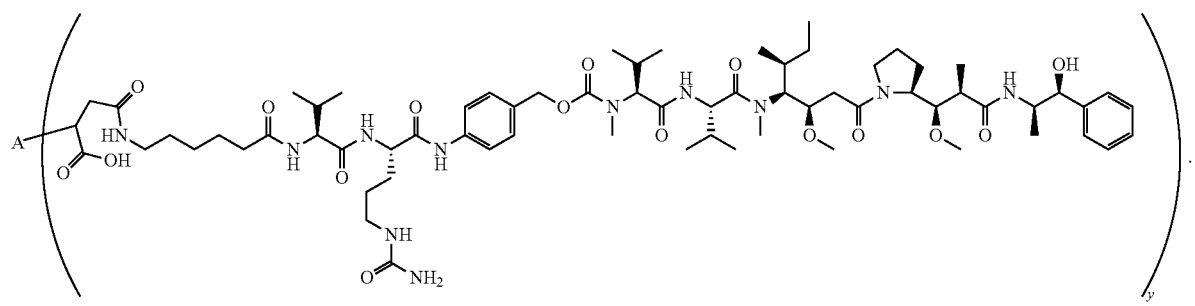

.

21. An antibody drug conjugate comprising the structure of Formula (E):

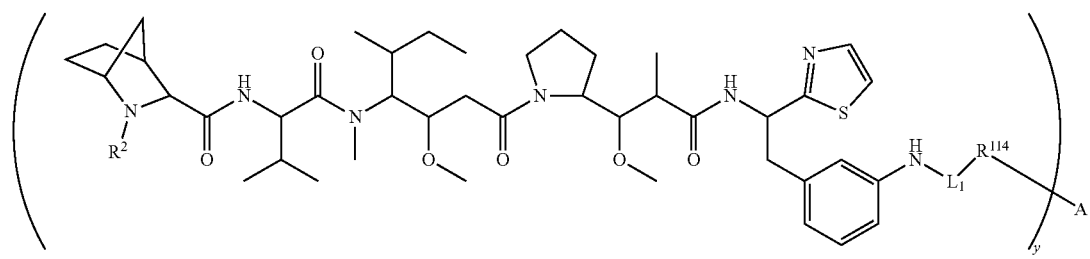

Formula (E)

wherein:
A is the antibody or antigen-binding fragment thereof of claim 1;
y is an integer from 1 to 10; n is independently selected from 1, 2, 3, 4, 5, 6, 7, 8, 9, 10, 11, and 12;
$R^2$ is H, $C_1$-$C_6$alkyl, —C(=O)$R^3$, —(CH$_2$)$_m$OH, —C(=O)(CH$_2$)$_m$OH, —C(=O)((CH$_2$)$_m$O)$_n$$R^4$, —((CH$_2$)$_m$O)$_n$$R^4$ or $C_1$-$C_6$alkyl which is optionally substituted with —CN, —C(=O)NH$_2$ or 1 to 5 hydroxy;
each $R^3$ is independently selected from $C_1$-$C_6$alkyl and $C_1$-$C_6$alkyl, which is optionally substituted with 1 to 5 hydroxyl;
each $R^4$ is independently selected from H and $C_1$-$C_6$alkyl;
$L_1$ is —X$_1$C(=O)((CH$_2$)$_m$O)$_p$(CH$_2$)$_m$—, —X$_1$C(=O)(CH$_2$)$_m$—, —X$_2$X$_1$C(=O)((CH$_2$)$_m$O)$_p$(CH$_2$)$_m$—, —X$_2$X$_1$C(=O)(CH$_2$)$_m$—, —X$_3$C(=O)((CH$_2$)$_m$O)$_p$(CH$_2$)$_m$—, —X$_3$C(=O)(CH$_2$)$_m$—, —X$_3$C(=O)(CH$_2$)$_m$NHC(=O)((CH$_2$)$_m$O)$_p$(CH$_2$)$_m$—, —X$_3$C(=O)(CH$_2$)$_m$NHC(=O)(CH$_2$)$_m$—, —X$_3$C(=O)(CH$_2$)$_m$—, —X$_1$C(=O)((CH$_2$)$_m$O)$_p$(CH$_2$)$_m$X$_4$(CH$_2$)$_m$—, —X$_1$C(=O)(CH$_2$)$_m$X$_4$(CH$_2$)$_m$—, —X$_2$X$_1$C(=O)((CH$_2$)$_m$O)$_p$(CH$_2$)$_m$X$_4$(CH$_2$)$_m$— or —X$_2$X$_1$C(=O)(CH$_2$)$_m$X$_4$(CH$_2$)$_m$—, where  indicates the point of attachment to $R^{114}$;
$X_1$ is

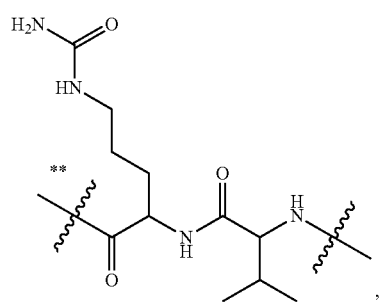

,

341
-continued
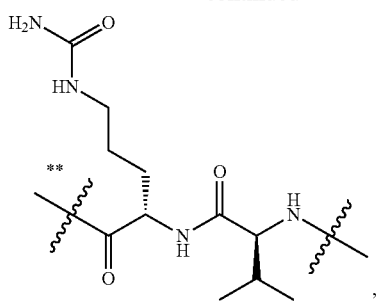
,
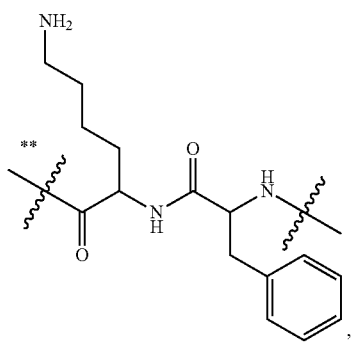
,
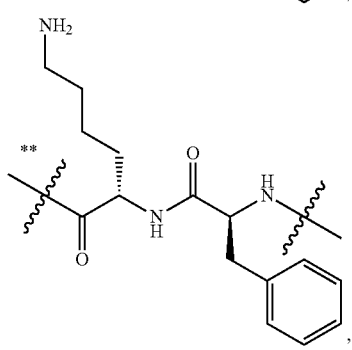
,
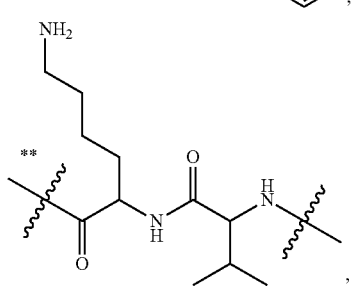
,
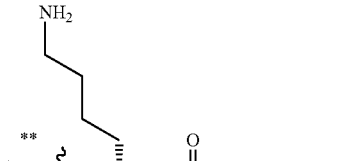
,
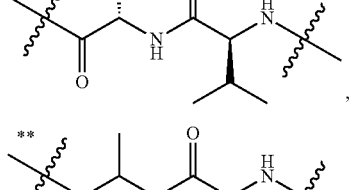
or
342
-continued
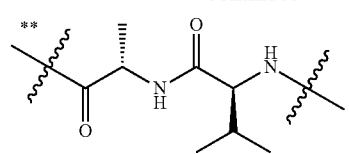
,
where ** indicates the point of attachment to the —NH— or to $X_2$;
$X_2$ is
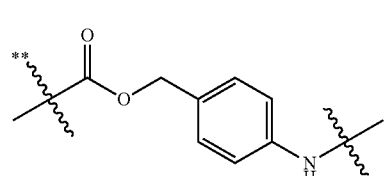
,
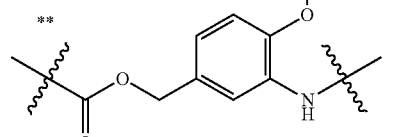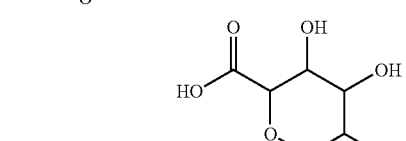
or
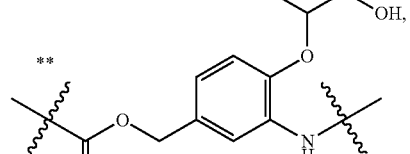
,
where ** indicates the point of attachment to the —NH—;
$X_3$ is
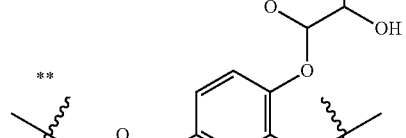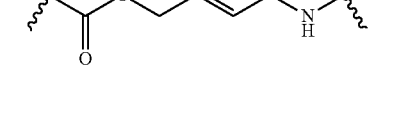
or -continued
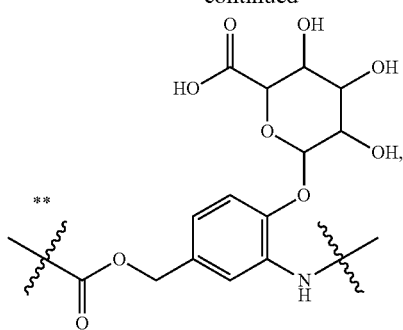
where ** indicates the point of attachment to the —NH—;
X₄ is
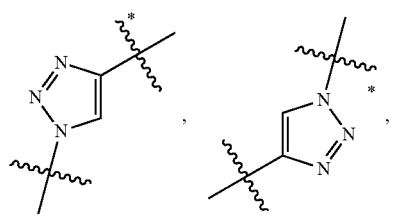
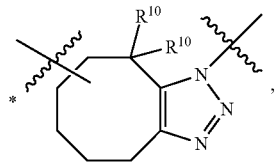
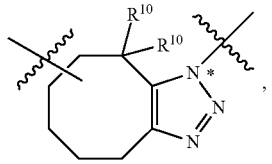
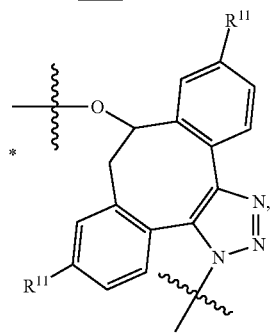
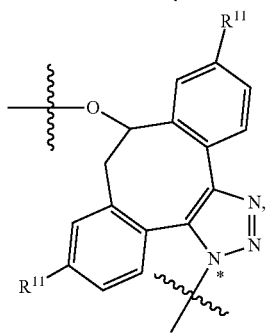
-continued
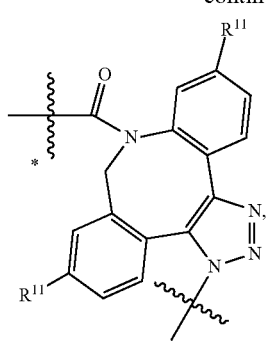
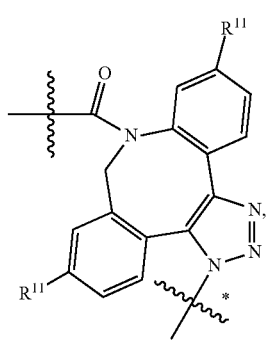
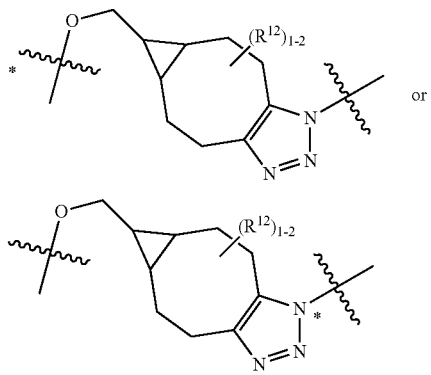
where the * indicates the point of attachment is toward $R^{114}$;
$R^{114}$ is
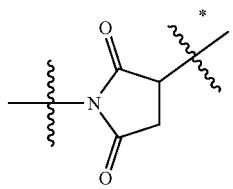 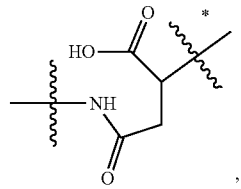
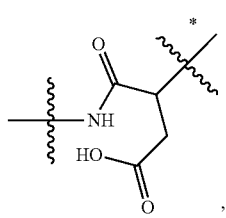 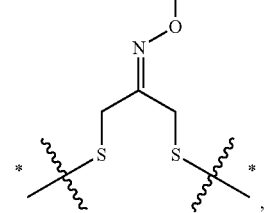

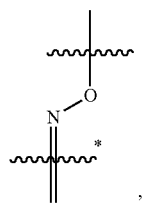
—NR⁶C(=O)CH₂—*,    —NHC(=O)CH₂—*,
—S(=O)₂CH₂CH₂—*,    —(CH₂)₂S(=O)₂CH₂CH₂—*,    —NR⁶S(=O)₂CH₂CH₂—*,
—NR⁶C(=O)CH₂CH₂—*,    —NH—,    —C(=O)—,
—NHC(=O)—*,    —CH₂NHCH₂CH₂—*,
—NHCH₂CH₂—*,    —S—,
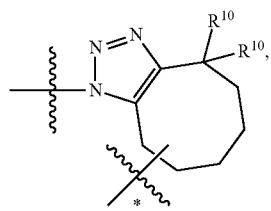
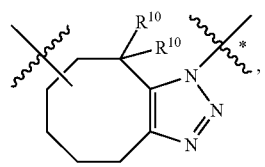
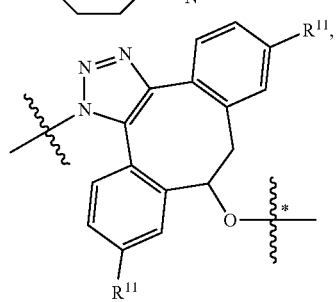
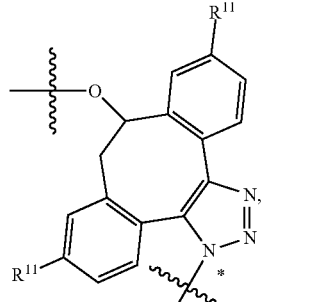
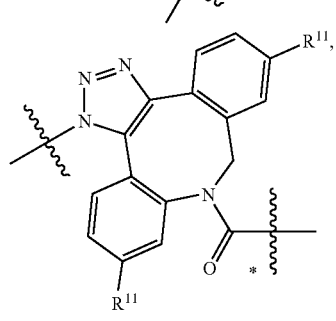
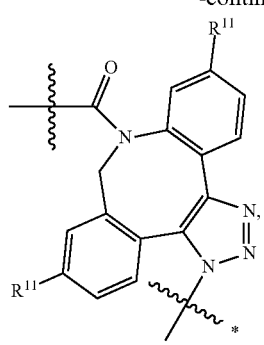
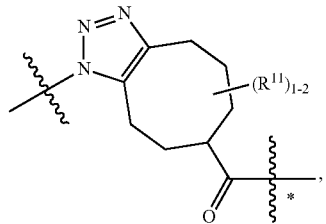
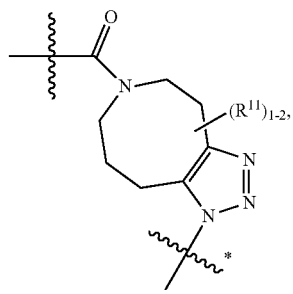
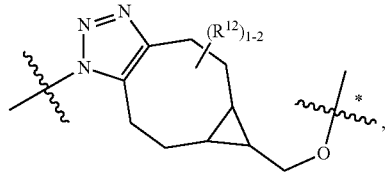
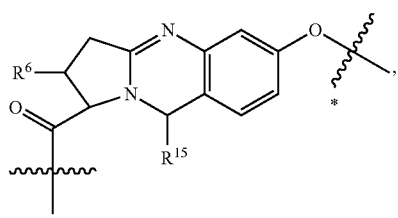
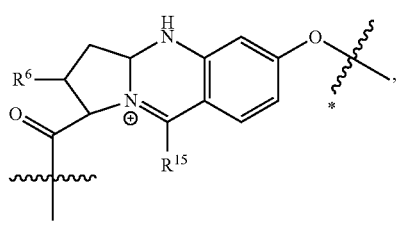
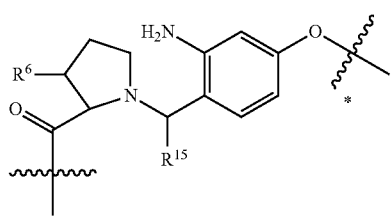

347
-continued

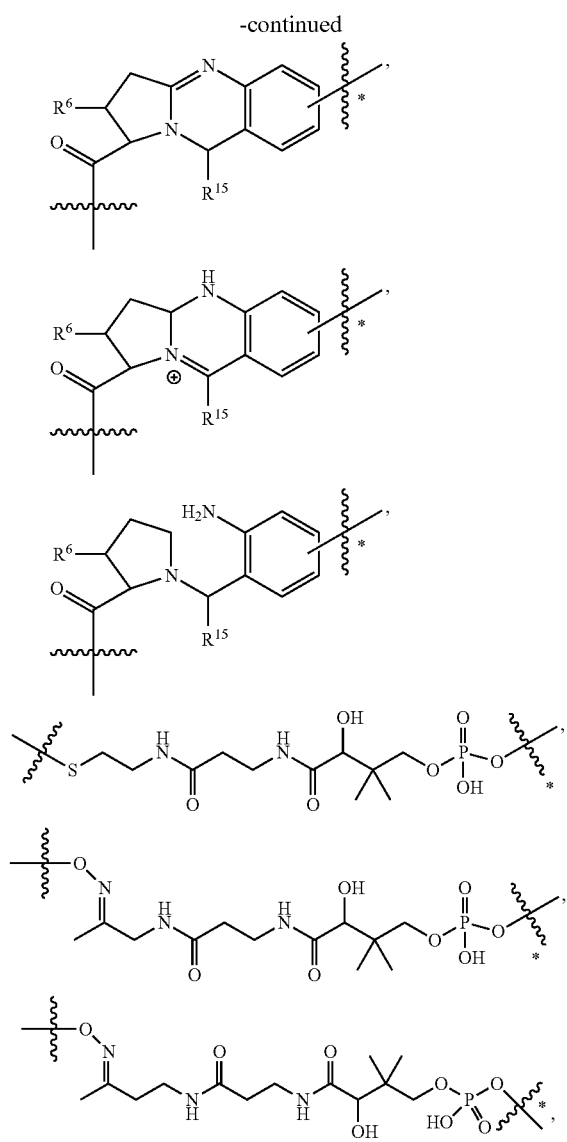

348
-continued

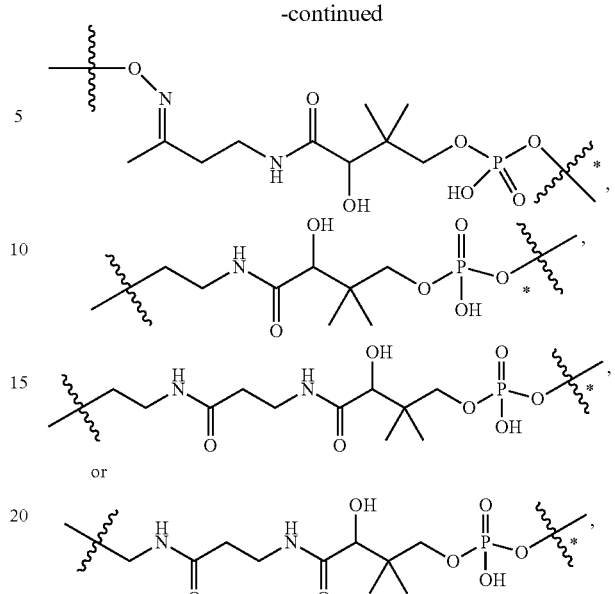

where the * indicates the point of attachment to A;
each $R^6$ is independently selected from H and $C_1$-$C_6$alkyl;
each $R^{10}$ is independently selected from H, $C_1$-$C_6$alkyl, F, Cl, and —OH;
each $R^{11}$ is independently selected from H, $C_1$-$C_6$alkyl, F, Cl, —NH$_2$, —OCH$_3$, —OCH$_2$CH$_3$, —N(CH$_3$)$_2$, —CN, —NO$_2$ and —OH;
each $R^{12}$ is independently selected from H, $C_{1\text{-}6}$alkyl, fluoro, benzyloxy substituted with —C(=O)OH, benzyl substituted with —C(=O)OH, $C_{1\text{-}4}$alkoxy substituted with —C(=O)OH and $C_1$-4alkyl substituted with —C(=O)OH;
each $R^{15}$ is independently selected from H, —CH$_3$ and phenyl;
each m is independently selected from 1, 2, 3, 4, 5, 6, 7, 8, 9 and 10, and
each p is independently selected from 1, 2, 3, 4, 5, 6, 7, 8, 9, 10, 11, 12, 13 and 14.

22. The antibody drug conjugate of claim 21, selected from

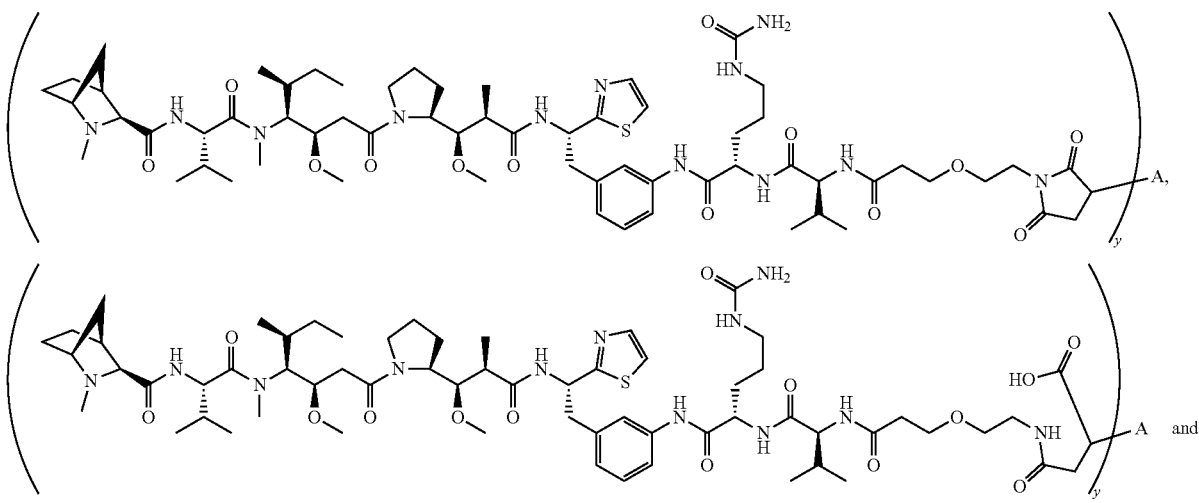

-continued

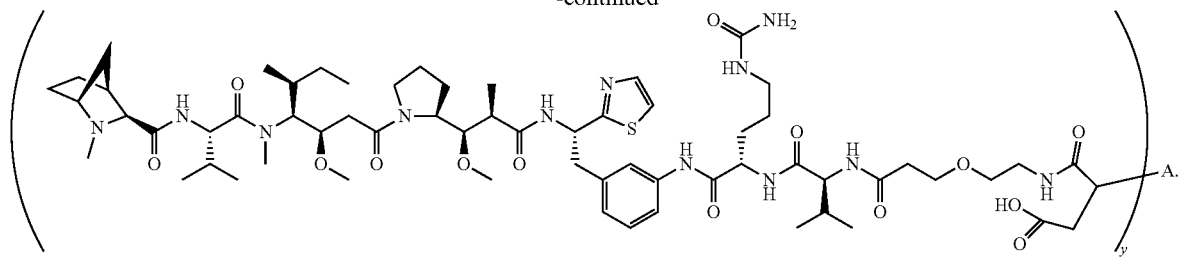

23. An antibody drug conjugate comprising the structure of Formula (G):

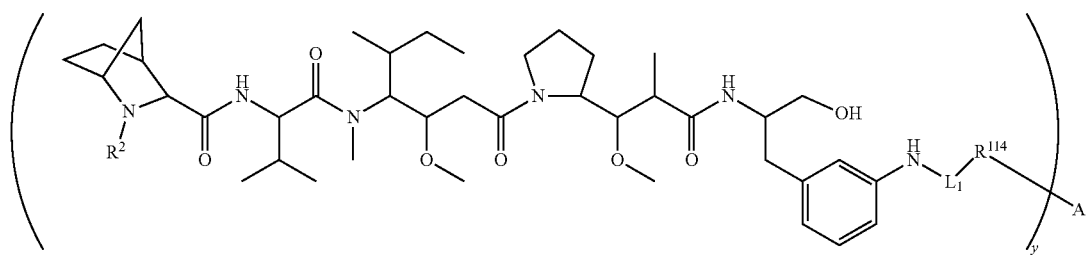

Formula (G)

wherein:

A is the antibody or antigen-binding fragment thereof of claim 1;

y is an integer from 1 to 10;

$R^2$ is H, —C(=O)$R^3$, —(CH$_2$)$_m$OH, —C(=O)(CH$_2$)$_m$OH, —C(=O)((CH$_2$)$_m$O)$_n$$R^4$, —((CH$_2$)$_m$O)$_n$$R^4$ or C$_1$-C$_6$alkyl which is optionally substituted with —CN, —C(=O)NH$_2$ or 1 to 5 hydroxy;

each $R^3$ is independently selected from C$_1$-C$_6$alkyl and C$_1$-C$_6$alkyl, which is optionally substituted with 1 to 5 hydroxyl;

each $R^4$ is independently selected from H and C$_1$-C$_6$alkyl;

$L_1$ is —X$_1$C(=O)((CH$_2$)$_m$O)$_p$(CH$_2$)$_m$—, —X$_1$C(=O)(CH$_2$)$_m$—, —X$_2$X$_1$C(=O)((CH$_2$)$_m$O)$_p$(CH$_2$)$_m$—, —X$_2$X$_1$C(=O)(CH$_2$)$_m$—, —X$_3$C(=O)((CH$_2$)$_m$O)$_p$(CH$_2$)$_m$—, —X$_3$C(=O)(CH$_2$)$_m$—, —X$_3$C(=O)(CH$_2$)$_m$NHC(=O)((CH$_2$)$_m$O)$_p$(CH$_2$)$_m$—, —X$_3$C(=O)(CH$_2$)$_m$NHC(=O)(CH$_2$)$_m$—, —X$_3$C(=O)(CH$_2$)$_m$—, —X$_1$C(=O)((CH$_2$)$_m$O)$_p$(CH$_2$)$_m$X$_4$(CH$_2$)$_m$—, —X$_1$C(=O)(CH$_2$)$_m$X$_4$(CH$_2$)$_m$—, —X$_2$X$_1$C(=O)((CH$_2$)$_m$O)$_p$(CH$_2$)$_m$X$_4$(CH$_2$)$_m$— or —X$_2$X$_1$C(=O)(CH$_2$)$_m$X$_4$(CH$_2$)$_m$—, where  indicates the point of attachment to $R^{114}$;

$X_1$ is

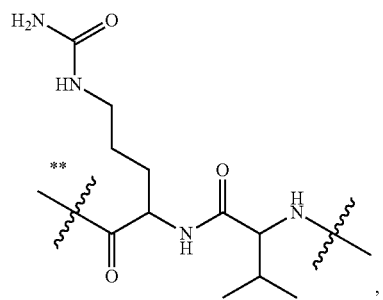

,

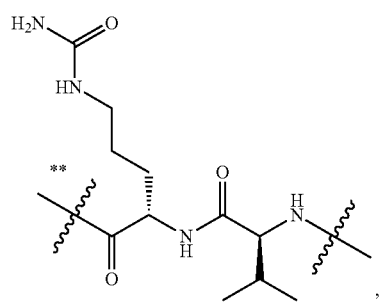

,

-continued
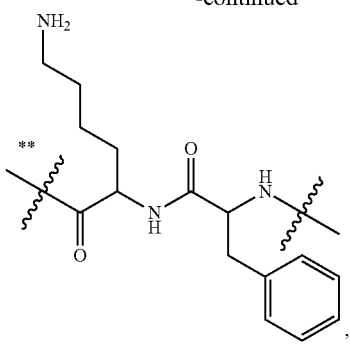
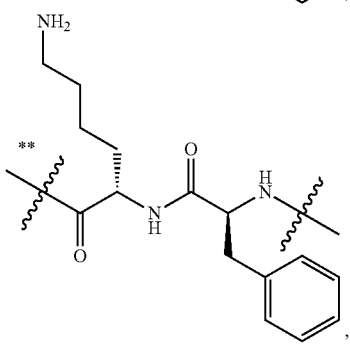
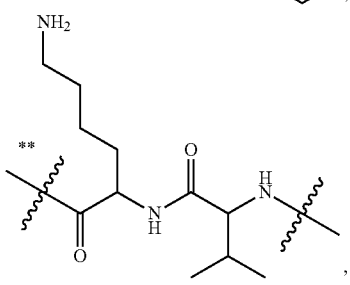
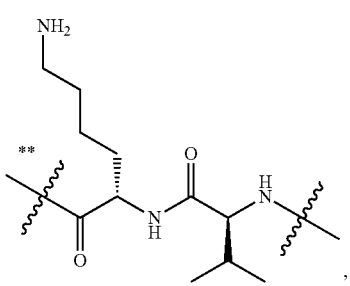
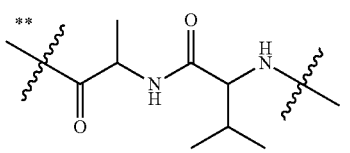
or
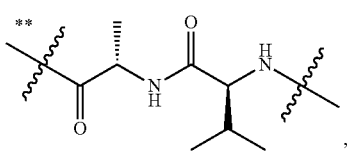
where ** indicates the point of attachment to the —NH— or to $X_2$;
$X_2$ is
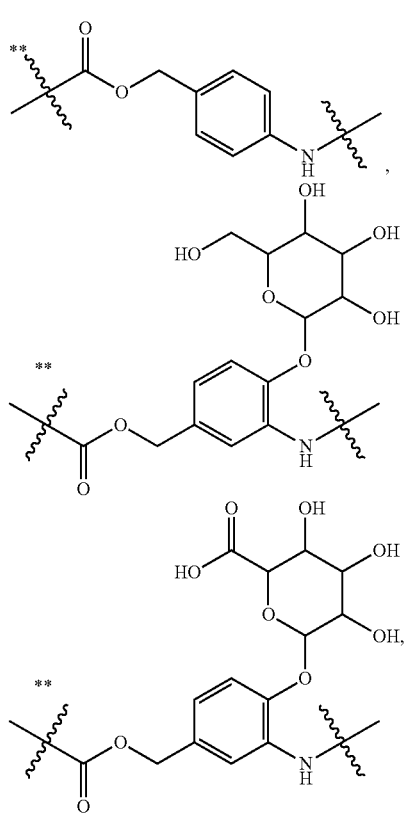
where ** indicates the point of attachment to the —NH—;
$X_3$ is
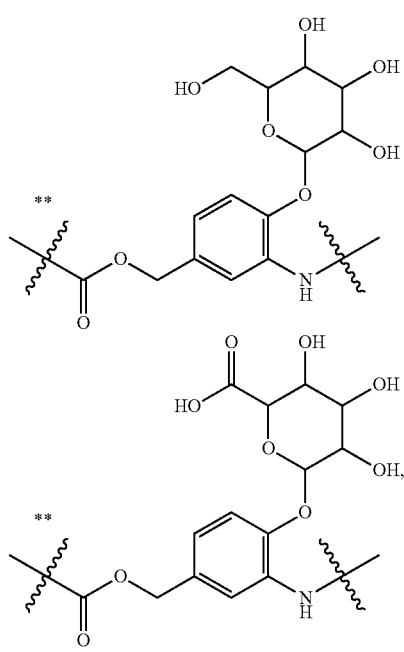

where ** indicates the point of attachment to the —NH—;
$X_4$ is
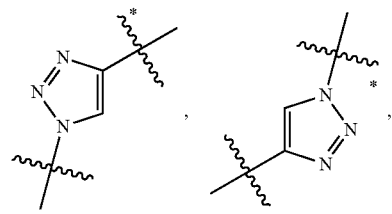,
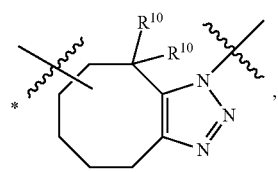,
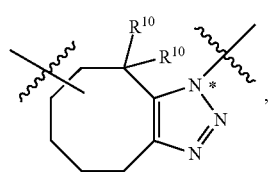,
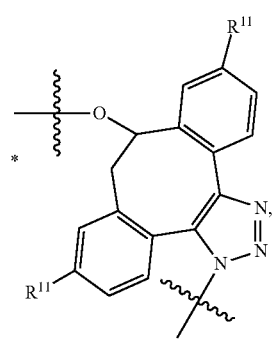,
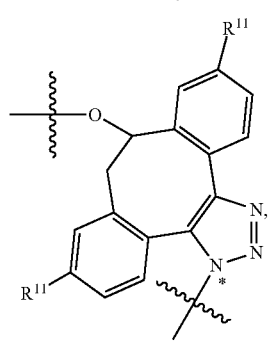,
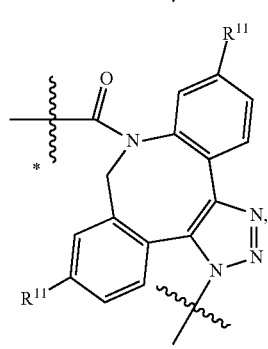,
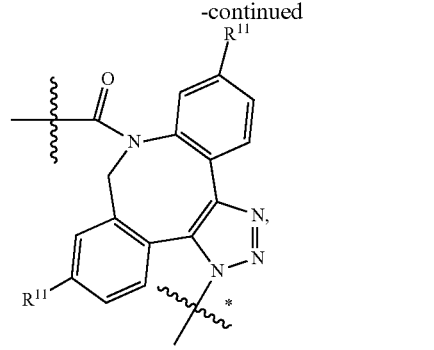,
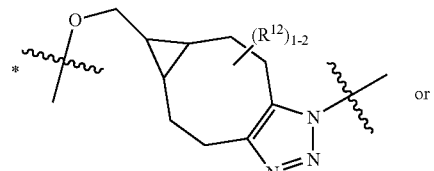,
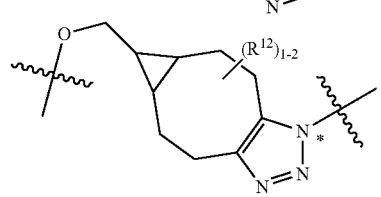
where the * indicates the point of attachment is toward $R^{114}$;
$R^{114}$ is
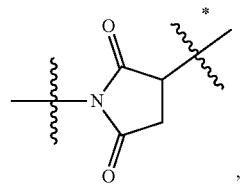, 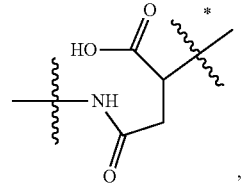,
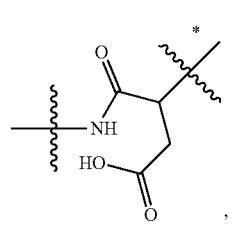, 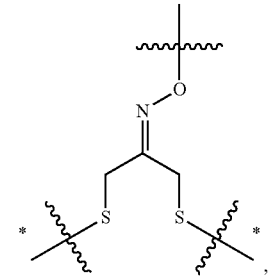,
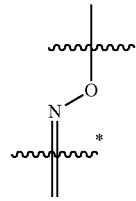,
—NR⁶C(=O)CH₂—*, —NHC(=O)CH₂—*,
—S(=O)₂CH₂CH₂—*, —(CH₂)₂S(=O)₂CH₂CH₂—*, —NR⁶S(=O)₂CH₂CH₂—*,
—NR⁶C(=O)CH₂CH₂—*, —NH—, —C(=O)—,
—NHC(=O)—*, —CH₂NHCH₂CH₂—*,
—NHCH₂CH₂—*, —S—,

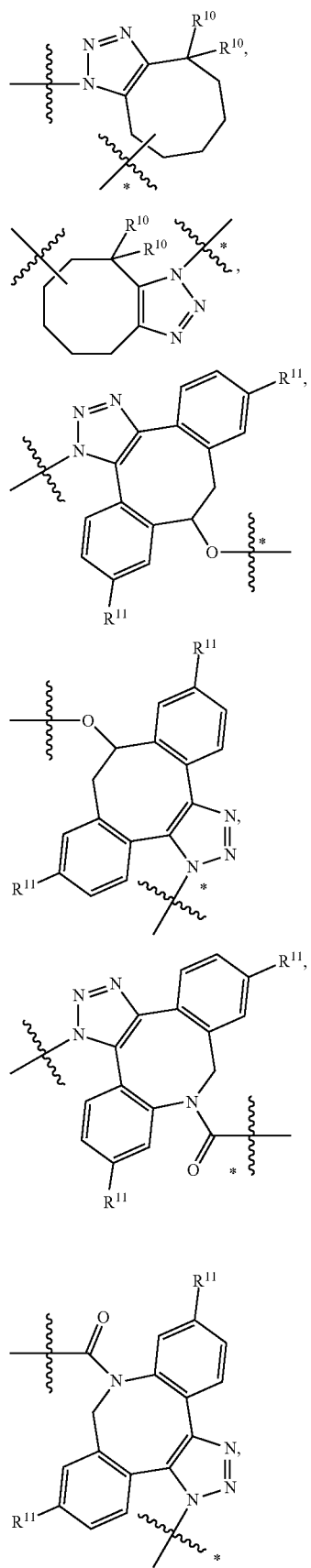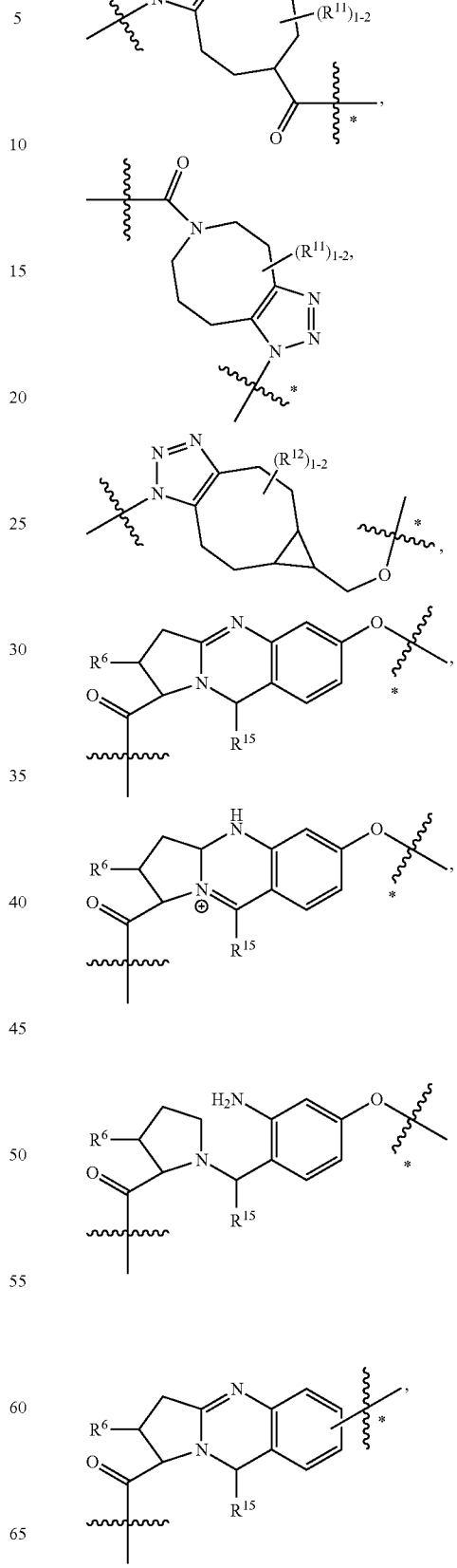

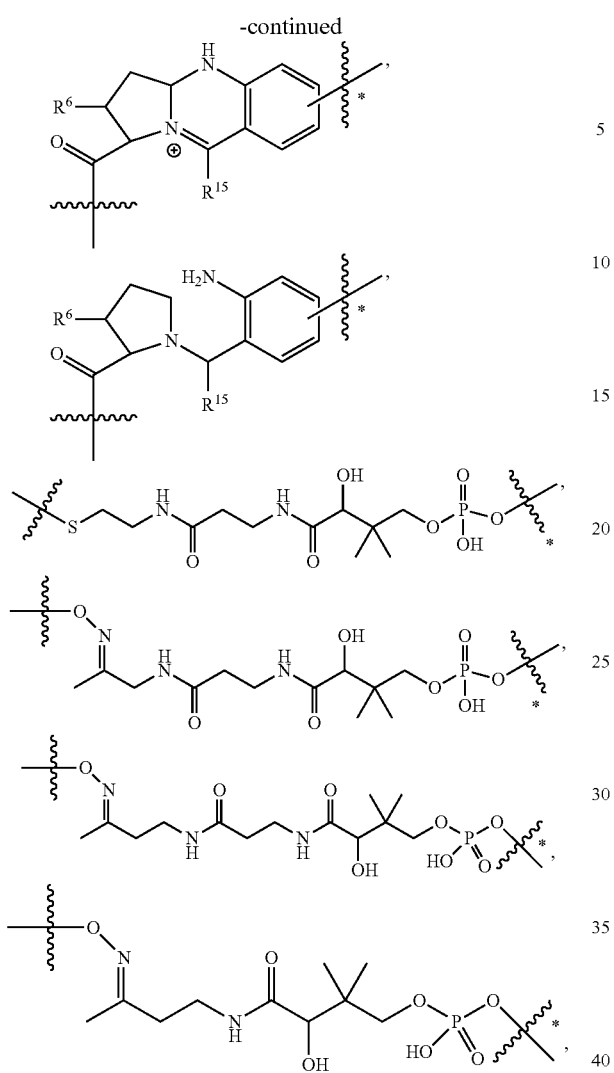

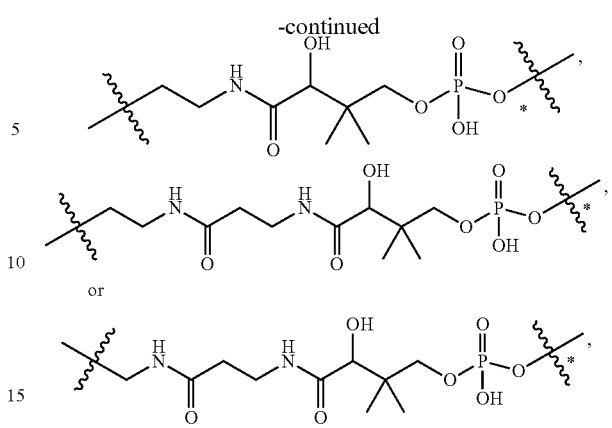

where the * indicates the point of attachment to A;

each $R^6$ is independently selected from H and $C_1$-$C_6$alkyl;

each $R^{10}$ is independently selected from H, $C_1$-$C_6$alkyl, F, Cl, and —OH;

each $R^{11}$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;

each $R^{12}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_1$-4alkyl substituted with —C(=O)OH;

each $R^{15}$ is independently selected from H, —$CH_3$ and phenyl;

each m is independently selected from 1, 2, 3, 4, 5, 6, 7, 8, 9 and 10, each n is independently selected from 1, 2, 3, 4, 5, 6, 7, 8, 9, 10, 11, and 12; and each p is independently selected from 1, 2, 3, 4, 5, 6, 7, 8, 9, 10, 11, 12, 13 and 14.

24. The antibody drug conjugate of claim 23 selected from

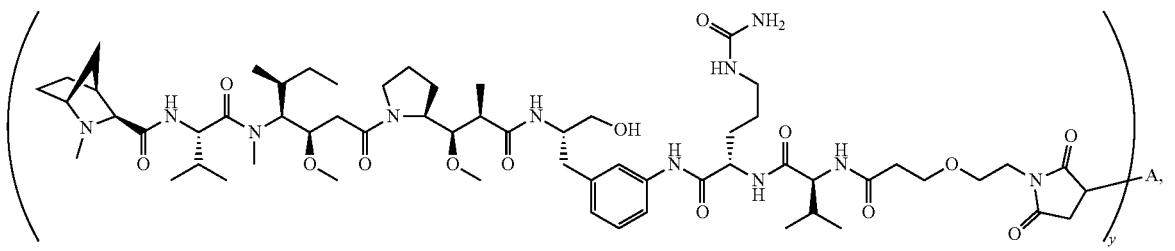

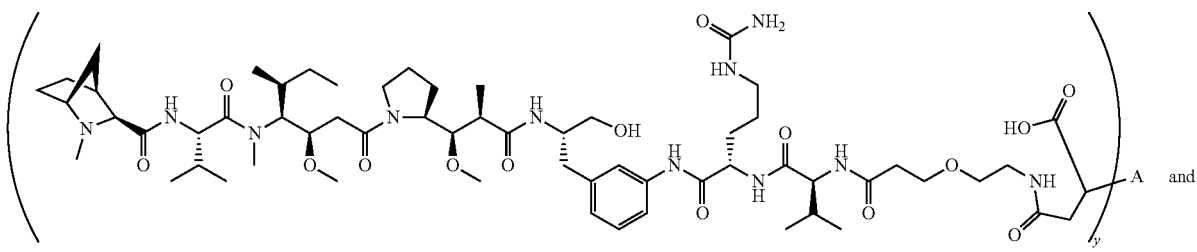

and

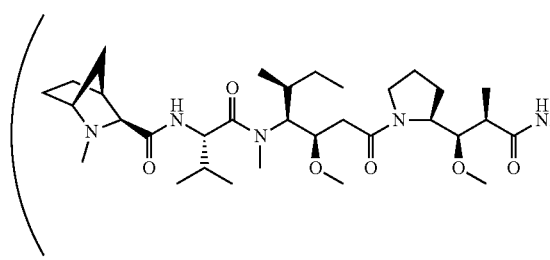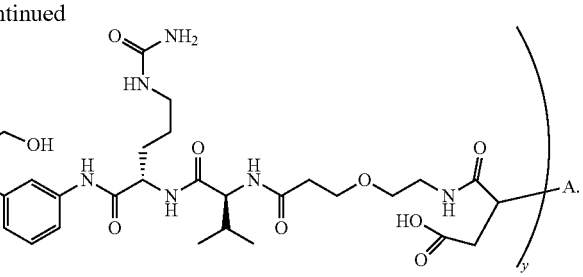

25. A pharmaceutical composition comprising the antibody or antigen-binding fragment thereof of claim 1 and a pharmaceutically acceptable carrier.

26. The pharmaceutical composition of claim 25 further comprising one or more additional therapeutic agents.

27. The pharmaceutical composition of claim 25, wherein the composition is a lyophilisate.

28. A method of treating cancer in a subject, comprising administering to the subject a therapeutically effective amount of the antibody or antigen-binding fragment thereof of claim 1.

29. The method of claim 28, wherein the cancer expresses CD48.

30. The method of claim 28, wherein the cancer is a tumor, a hematological cancer, a breast cancer, multiple myeloma, B-cell lymphoma, plasma cell myeloma, leukemia, lymphoma, gastric cancer, acute myeloid leukemia, bladder cancer, brain cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, prostate cancer, small cell lung cancer, or spleen cancer.

31. The method of claim 28, further comprising administering or using one or more additional therapeutic agents.

32. A method of reducing or inhibiting the growth of a tumor in a subject, comprising administering to the subject a therapeutically effective amount of an antibody or antigen-binding fragment thereof of claim 1.

33. The method of claim 32, wherein the tumor expresses CD48.

34. The method of claim 32, wherein administration of the antibody or antigen-binding fragment thereof reduces or inhibits the growth of the tumor by at least about 10%, at least about 20%, at least about 30%, at least about 40%, at least about 50%, at least about 60%, at least about 70%, at least about 80%, at least about 90%, at least about 95%, or at least about 99%.

35. A method of reducing or slowing the expansion of a cancer cell population in a subject, comprising administering to the subject a therapeutically effective amount of the antibody or antigen-binding fragment thereof of claim 1.

36. The method of claim 35, wherein the cancer cell population expresses CD48.

37. The method of claim 35, wherein the cancer cell population is from a tumor, a hematological cancer, a breast cancer, multiple myeloma, B-cell lymphoma, plasma cell myeloma, leukemia, lymphoma, gastric cancer, acute myeloid leukemia, bladder cancer, brain cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, prostate cancer, small cell lung cancer, or spleen cancer.

38. The method of claim 35, wherein administration of the antibody or antigen-binding fragment thereof reduces the cancer cell population or slows the expansion of the cancer cell population by at least about 10%, at least about 20%, at least about 30%, at least about 40%, at least about 50%, at least about 60%, at least about 70%, at least about 80%, at least about 90%, at least about 95%, or at least about 99%.

39. A diagnostic agent comprising the antibody or antigen-binding fragment thereof of claim 1, wherein the antibody or antigen-binding fragment comprises a label.

40. The diagnostic agent of claim 39, wherein the label is a radiolabel, a fluorophore, a chromophore, an imaging agent, or a metal ion.

41. A method of detecting human CD48 in a tissue or cell comprising contacting the diagnostic agent of claim 39 to the tissue or cell and detecting binding of the diagnostic agent to the tissue or cell.

* * * * *

SEQUENCE LISTING

```
<160> NUMBER OF SEQ ID NOS: 84

<210> SEQ ID NO 1
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Phe Thr Phe Ser Ser Phe Ala Met Ser
1               5                   10

<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ala Ile Ser Gly Phe Gly Gly Ser Thr Tyr Tyr Ala Asp Ser Val Lys
```

```
1               5              10             15
Gly

<210> SEQ ID NO 3
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gln Phe Trp Glu Asp Gln Pro Phe Tyr Phe Asp Tyr
1               5                   10

<210> SEQ ID NO 4
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ser Phe Ala Met Ser
1               5

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Phe Thr Phe Ser Ser Phe
1               5

<210> SEQ ID NO 6
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ser Gly Phe Gly Gly Ser
1               5

<210> SEQ ID NO 7
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Phe Thr Phe Ser Ser Phe Ala
1               5
```

<210> SEQ ID NO 8
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 8

Ile Ser Gly Phe Gly Gly Ser Thr
1               5

<210> SEQ ID NO 9
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 9

Ala Arg Gln Phe Trp Glu Asp Gln Pro Phe Tyr Phe Asp Tyr
1               5                   10

<210> SEQ ID NO 10
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Ala Ile Ser Gly Phe Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Phe Trp Glu Asp Gln Pro Phe Tyr Phe Asp Tyr Trp Gly
            100                 105                 110

Gln Gly Thr Leu Val Thr Val Ser Ser
        115                 120

<210> SEQ ID NO 11
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 11
gaagtgcagc tgctggagtc cggggggtgga ctggtgcagc ccggaggttc cctgcggttg      60

-continued

```
tcttgtgccg cctcgggatt caccttctcg tccttcgcga tgagctgggt ccgccaagct    120
cctggaaaag ggctcgaatg ggtgtccgcg atcagcggat ttggcggctc cacctactac    180
gccgattcag tgaagggccg gttcaccatc tcacgggaca acagcaagaa cacgctgtat    240
ctgcaaatga actccctgcg cgctgaggac accgcagtgt actactgcgc agacagttc    300 tgggaggacc agccgttcta cttcgactac tggggacagg ggaccctcgt gactgtctcc    360
tcc                                                                   363
```

<210> SEQ ID NO 12
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Ala Ile Ser Gly Phe Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Phe Trp Glu Asp Gln Pro Phe Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Cys Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285
```

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Cys Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 13
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13

```
gaagtgcagc tgctggagtc cggggggtgga ctggtgcagc ccggaggttc cctgcggttg      60
tcttgtgccg cctcgggatt caccttctcg tccttcgcga tgagctgggt ccgccaagct     120
cctggaaaag ggctcgaatg ggtgtccgcg atcagcggat ttggcggctc cacctactac     180
gccgattcag tgaagggccg gttcaccatc tcacgggaca acagcaagaa cacgctgtat     240
ctgcaaatga actccctgcg cgctgaggac accgcagtgt actactgcgc gagacagttc     300
tgggaggacc agccgttcta cttcgactac tggggacagg ggaccctcgt gactgtctcc     360
tccgcctcca ctaagggccc atccgtgttc cctctggccc cttccagcaa gtccacctct     420
ggcggcaccg ccgctctggg ctgcctggtc aaggactact cccctgtcc cgtgaccgtg     480 tcctggaact ctggcgccct gacctccggc gtgcacacct ccctgccgt gctgcagtcc     540 tccggcctgt actccctgtc ctccgtcgtg accgtgccct ccagctctct gggcacccag     600
acctacatct gcaacgtgaa ccacaagccc tccaacacca agtggacaa gcgggtggaa     660 cccaagtcct gcgacaagac ccacacctgt cctccctgcc ctgcccctga gctgctgggc     720 ggacccctccg tgttcctgtt ccctccaaag cccaaggaca ccctgatgat ctcccggacc     780
cctgaagtga cctgcgtggt ggtggacgtg tcccacgagg atcccgaagt gaagttcaat     840
tggtacgtgg acggcgtgga agtgcacaac gccaagacca gcccagaga ggaacagtac     900 aactccaccat accgggtggt gtccgtgctg accgtgctgc accaggactg gctgaacggc     960
aaagagtaca gtgcaaagt gtccaacaag gccctgcctg ccccaatcga aaagaccatc    1020
```

-continued

```
tccaaggcca agggccagcc ccgcgagccc aagtgtaca cactgcctcc cagccgggaa    1080
gagatgacca agaaccaagt gtccctgacc tgcctcgtga agggcttcta cccctgcgat    1140
atcgccgtgg agtgggagtc caacggccag cccgagaaca actacaagac caccccctccc  1200 gtgctggact ccgacggctc attcttcctg tactccaagc tgaccgtgga caagtcccgg    1260
tggcagcagg gcaacgtgtt ctcctgctcc gtgatgcacg aggccctgca caaccactac    1320
acccagaagt ccctgtccct gagccccggc aag                                1353
```

<210> SEQ ID NO 14
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 14

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Ala Ile Ser Gly Phe Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Phe Trp Glu Asp Gln Pro Phe Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Cys Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ala Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
```

```
                    290                 295                 300
Arg Val Ser Val Leu Thr Val His Gln Asp Trp Leu Asn Gly
305                     310                 315                 320

Lys Glu Tyr Lys Cys Lys Val Ser Asn Lys Ala Leu Ala Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Cys Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 15
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15
gaagtgcagc tgctggagtc cggggtgga ctggtgcagc ccggaggttc cctgcggttg      60
tcttgtgccg cctcgggatt caccttctcg tccttcgcga tgagctgggt ccgccaagct    120
cctggaaaag ggctcgaatg ggtgtccgcg atcagcggat ttggcggctc cacctactac    180
gccgattcag tgaagggccg gttcaccatc tcacgggaca cagcaagaa cacgctgtat    240 ctgcaaatga actccctgcg cgctgaggac accgcagtgt actactgcgc gagacagttc    300
tgggaggacc agccgttcta cttcgactac tggggacagg ggaccctcgt gactgtctcc    360
tccgcctcca ctaagggccc tagcgtgttc ccactggcgc cttcctcgaa atcgactagc    420
gggggtaccg ccgctctggg atgcttggtg aaagactact tccgtgtcc ggtgaccgtg     480 agctggaact ccggggcact cacctccggt gtgcatactt ccctgctgt cttgcagtcc     540 tcgggcctgt acagcctgtc ctccgtggtg accgtgcctt cgtcgtccct gggaacccag    600
acgtacatct gcaacgtgaa ccacaagccg agcaacacca agtcgataa agagtcgag      660 cccaagagct gcgataagac ccacacttgt ccgccttgtc ctgcccctga gcttctgggt    720
ggcccatcgg tgtttctgtt tccccgaag cccaagaca ccctgatgat ctcgcgcact      780
ccggaggtca cttgcgtggt cgtggcggtg tcccacgagg acccagaagt gaagtttaac    840
tggtacgtgg acggagtgga agtccacaac gcgaaaacta gccccggga ggaacaatac     900 aactccacct accgcgtcgt gtccgtgctc actgtgctgc accaggattg gctgaacggt    960
aaagagtaca agtgtaaggt gtcgaacaaa gccctcgccg cccctatcga aaagactatt   1020
tcgaaagcta agggccagcc gcgagaaccc caagtgtata ccctgccccc ttcacgggaa   1080
```

```
gagatgacta agaatcaggt gtcgctcacc tgtctggtga agggatttta tccctgcgac    1140
attgccgtgg agtgggaatc gaacggccag cctgagaaca actacaagac cactccgccg    1200
gtgcttgaca gcgacggttc gttcttcctc tactctaagc tcaccgtgga caagtcacgg    1260
tggcaacagg gcaacgtgtt ctcgtgctct gtgatgcacg aagctctcca caaccattac    1320
acccagaagt ccctcagcct cagcccgggg aag                                 1353
```

<210> SEQ ID NO 16
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 16

Arg Ala Ser Gln Ser Ile Ser Ser Tyr Leu Asn
1               5                   10

<210> SEQ ID NO 17
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 17

Ala Ala Ser Ser Leu Gln Ser
1               5

<210> SEQ ID NO 18
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 18

Gln Gln Ser Tyr Ser Thr Pro Leu Thr
1               5

<210> SEQ ID NO 19
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 19

Ser Gln Ser Ile Ser Ser Tyr
1               5

<210> SEQ ID NO 20
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 20

Ala Ala Ser
1

<210> SEQ ID NO 21
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ser Tyr Ser Thr Pro Leu
1               5

<210> SEQ ID NO 22
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gln Ser Ile Ser Ser Tyr
1               5

<210> SEQ ID NO 23
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 24
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24

```
gatattcaga tgacccagtc cccgtcgtcg ctgagcgcca gcgtgggaga cagagtgacc      60
attacctgtc gggccagcca gtcgatctcc tcctacctta actggtatca gcagaagcca     120
ggaaaggcac cgaaactgct gatctacgcc gcgtcctcct tgcaatccgg agtgccctca     180
aggttctccg gtcgggttc tggcactgac tttaccctga ccatcagcag cctccagccc     240
gaggacttcg ccacctacta ctgccagcag tcatactcca cccctctgac attcggccaa     300
gggaccaagg tcgaaatcaa g                                               321
```

<210> SEQ ID NO 25
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 26
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

```
<400> SEQUENCE: 26
gatattcaga tgacccagtc cccgtcgtcg ctgagcgcca gcgtgggaga cagagtgacc      60
attacctgtc gggccagcca gtcgatctcc tcctaccta actggtatca gcagaagcca     120
ggaaaggcac cgaaactgct gatctacgcc gcgtcctcct tgcaatccgg agtgccctca     180
aggttctccg ggtcgggttc tggcactgac tttaccctga ccatcagcag cctccagccc     240
gaggacttcg ccacctacta ctgccagcag tcatactcca ccctctgac attcggccaa      300 gggaccaagg tcgaaatcaa gcgtacggtg gccgctccca gcgtgttcat cttcccccc      360 agcgacgagc agctgaagag cggcaccgcc agcgtggtgt gcctgctgaa caacttctac     420
ccccgggagg ccaaggtgca gtggaaggtg acaacgccc tgcagagcgg caacagccag     480
gagagcgtca ccgagcagga cagcaaggac tccacctaca gcctgagcag caccctgacc     540
ctgagcaagg ccgactacga aagcataag gtgtacgcct gcgaggtgac ccaccagggc     600
ctgtccagcc ccgtgaccaa gagcttcaac aggggcgagt gc                       642
```

```
<210> SEQ ID NO 27
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Gly Tyr Thr Phe Thr Glu Tyr Thr Met His
1               5                   10
```

```
<210> SEQ ID NO 28
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gly Ile Asn Pro Asp Thr Gly Asp Thr Ser Tyr Asn Gln Lys Phe Thr
1               5                   10                  15

Gly
```

```
<210> SEQ ID NO 29
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ala Gln Phe Trp Thr Thr Pro Arg Phe Ala Tyr
1               5                   10
```

```
<210> SEQ ID NO 30
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 30

Glu Tyr Thr Met His
1               5

<210> SEQ ID NO 31
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Gly Tyr Thr Phe Thr Glu Tyr
1               5

<210> SEQ ID NO 32
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Asn Pro Asp Thr Gly Asp
1               5

<210> SEQ ID NO 33
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Gly Tyr Thr Phe Thr Glu Tyr Thr
1               5

<210> SEQ ID NO 34
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ile Asn Pro Asp Thr Gly Asp Thr
1               5

<210> SEQ ID NO 35
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Ala Arg Ala Gln Phe Trp Thr Thr Pro Arg Phe Ala Tyr
1               5                   10

<210> SEQ ID NO 36
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Met His Trp Val Arg Gln Ala Pro Gly Gln Gly Leu Glu Trp Met
            35                  40                  45

Gly Gly Ile Asn Pro Asp Thr Gly Asp Thr Ser Tyr Asn Gln Lys Phe
        50                  55                  60

Thr Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Gln Phe Trp Thr Thr Pro Arg Phe Ala Tyr Trp Gly Gln
                100                 105                 110

Gly Thr Leu Val Thr Val Ser Ser
        115                 120

<210> SEQ ID NO 37
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37
caagtgcagc tcgtgcagtc cggagcggaa gtgaaaaagc ccggagcctc agtgaaagtg     60
tcctgcaaag cctcggggta caccttcacc gagtacacta tgcattgggt ccgccaagct    120
cctggtcaag gcctcgaatg gatgggcggc atcaatcccg acaccggcga caccagctat    180
aaccagaagt tcaccggacg cgccactctg actgtcgata agagcacaag caccgcctac    240
atggaactgt cgtccttgcg gtccgaggat accgccgtgt actactgcgc gagagcgcag    300
ttttggacta ccccgcggtt cgcctactgg ggacagggca ctctcgtgac tgtgtcatcg    360

<210> SEQ ID NO 38
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr

```
                    20                  25                  30
Thr Met His Trp Val Arg Gln Ala Pro Gly Gln Gly Leu Glu Trp Met
            35                  40                  45
Gly Gly Ile Asn Pro Asp Thr Gly Asp Thr Ser Tyr Asn Gln Lys Phe
        50                  55                  60
Thr Gly Arg Ala Thr Leu Thr Val Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ala Gln Phe Trp Thr Thr Pro Arg Phe Ala Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Cys Pro Val Thr Val Ser
145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
            195                 200                 205
Pro Ser Asn Thr Lys Val Asp Lys Arg Val Glu Pro Lys Ser Cys Asp
        210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Cys Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
            435                 440                 445
```

Gly Lys
    450

<210> SEQ ID NO 39
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 39

```
caagtgcagc tcgtgcagtc cggagcggaa gtgaaaaagc ccggagcctc agtgaaagtg      60
tcctgcaaag cctcggggta caccttcacc gagtacacta tgcattgggt ccgccaagct     120
cctggtcaag gcctcgaatg gatgggcggc atcaatcccg acaccggcga caccagctat     180
aaccagaagt tcaccggacg cgccactctg actgtcgata gagcacaag caccgcctac      240 atggaactgt cgtccttgcg gtccgaggat accgccgtgt actactgcgc gagagcgcag     300
ttttggacta ccccgcggtt cgcctactgg ggacagggca ctctcgtgac tgtgtcatcg     360
gcgtccacca agggcccatc cgtgttccct ctggccccctt ccagcaagtc cacctctggc    420
ggcaccgccg ctctgggctg cctggtcaag gactacttcc cctgtcccgt gaccgtgtcc    480
tggaactctg gcgccctgac ctccggcgtg cacaccttcc ctgccgtgct gcagtcctcc    540
ggcctgtact ccctgtcctc cgtcgtgacc gtgccctcca gctctctggg cacccagacc    600
tacatctgca acgtgaacca caagccctcc aacaccaaag tggacaagcg ggtggaaccc    660
aagtcctgcg acaagaccca cacctgtcct cctgccctg cccctgagct gctgggcgga     720
cccctcgtgt tcctgttccc tccaaagccc aaggacaccc tgatgatctc ccggacccct    780
gaagtgacct gcgtggtggt ggacgtgtcc cacgaggatc ccgaagtgaa gttcaattgg    840
tacgtggacg gcgtggaagt gcacaacgcc aagaccaagc cagagagga acagtacaac     900 tccacctacc gggtggtgtc cgtgctgacc gtgctgcacc aggactggct gaacggcaaa    960
gagtacaagt gcaaagtgtc caacaaggcc ctgcctgccc aatcgaaaa gaccatctcc    1020 aaggccaagg gccagccccg cgagcccaa gtgtacacac tgcctcccag ccgggaagag   1080
atgaccaaga accaagtgtc cctgacctgc ctcgtgaagg gcttctaccc ctgcgatatc    1140
gccgtggagt gggagtccaa cggccagccc gagaacaact acaagaccac ccctcccgtg    1200
ctggactccg acggctcatt cttcctgtac tccaagctga ccgtggacaa gtcccggtgg    1260
cagcagggca acgtgttctc ctgctccgtg atgcacgagg ccctgcacaa ccactacacc    1320
cagaagtccc tgtccctgag ccccggcaag                                     1350
```

<210> SEQ ID NO 40
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

-continued

```
Thr Met His Trp Val Arg Gln Ala Pro Gly Gln Gly Leu Glu Trp Met
        35                  40                  45
Gly Gly Ile Asn Pro Asp Thr Gly Asp Thr Ser Tyr Asn Gln Lys Phe
 50                  55                  60
Thr Gly Arg Ala Thr Leu Thr Val Asp Lys Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Ala Gln Phe Trp Thr Thr Pro Arg Phe Ala Tyr Trp Gly Gln
                100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Cys Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Ala Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Ala Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Cys Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
```

Gly Lys
   450

<210> SEQ ID NO 41
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 41

```
caagtgcagc tcgtgcagtc cggagcggaa gtgaaaaagc ccggagcctc agtgaaagtg      60
tcctgcaaag cctcggggta caccttcacc gagtacacta tgcattgggt ccgccaagct     120
cctggtcaag gcctcgaatg gatgggcggc atcaatcccg acaccggcga caccagctat     180
aaccagaagt tcaccggacg cgccactctg actgtcgata gagcacaag caccgcctac     240
atggaactgt cgtccttgcg gtccgaggat accgccgtgt actactgcgc gagagcgcag     300
ttttggacta ccccgcggtt cgcctactgg ggacagggca ctctcgtgac tgtgtcatcg     360
gcgtccacca agggccctag cgtgttccca ctggcgcctt cctcgaaatc gactagcggg     420
ggtaccgccg ctctgggatg cttggtgaaa gactactttc cgtgtccggt gaccgtgagc     480
tggaactccg gggcactcac ctccggtgtg catactttcc ctgctgtctt gcagtcctcg     540
ggcctgtaca gcctgtcctc cgtggtgacc gtgccttcgt cgtccctggg aacccagacg     600
tacatctgca acgtgaacca caagccgagc aacaccaaag tcgataagag agtcgagccc     660
aagagctgcg ataagaccca cacttgtccg ccttgtcctg ccctgagct tctgggtggc      720
ccatcggtgt ttctgttttcc cccgaagccc aaagacaccc tgatgatctc gcgcactccg     780
gaggtcactt gcgtggtcgt ggcggtgtcc cacgaggacc cagaagtgaa gtttaactgg     840
tacgtggacg gagtggaagt ccacaacgcg aaaactaagc cccgggagga acaatacaac     900
tccacctacc gcgtcgtgtc cgtgctcact gtgctgcacc aggattggct gaacggtaaa     960
gagtacaagt gtaaggtgtc gaacaaagcc ctcgccgccc ctatcgaaaa gactatttcg    1020
aaagctaagg gccagccgcg agaacccaa gtgtataccc tgccccctt acgggaagag     1080
atgactaaga atcaggtgtc gctcacctgt ctggtgaagg gatttatcc ctgcgacatt     1140
gccgtggagt gggaatcgaa cggccagcct gagaacaact acaagaccac tccgccggtg    1200
cttgacagcg acggttcgtt cttcctctac tctaagctca ccgtggacaa gtcacggtgg    1260
caacagggca acgtgttctc gtgctctgtg atgcacgaag ctctccacaa ccattacacc    1320
cagaagtccc tcagcctcag cccggggaag                                     1350
```

<210> SEQ ID NO 42
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Lys Ala Ser Gln Asp Val Gly Thr Ala Val Ala
1               5                   10

<210> SEQ ID NO 43
<211> LENGTH: 7

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Trp Ala Ser Thr Arg His Thr
1               5

<210> SEQ ID NO 44
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gln Gln Tyr Ser Thr Tyr Pro Ile Thr
1               5

<210> SEQ ID NO 45
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Ser Gln Asp Val Gly Thr Ala
1               5

<210> SEQ ID NO 46
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Trp Ala Ser
1

<210> SEQ ID NO 47
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Tyr Ser Thr Tyr Pro Ile
1               5

<210> SEQ ID NO 48
<211> LENGTH: 6
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 48

Gln Asp Val Gly Thr Ala
1               5

<210> SEQ ID NO 49
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Thr Tyr Pro Ile
                85                  90                  95

Thr Phe Gly Gln Gly Thr Lys Leu Glu Ile Lys
            100                 105

<210> SEQ ID NO 50
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 50
gacatccaaa tgacccagag cccttcgagc ctgtcagcct ccgtgggcga cagagtgacc      60
attacttgca aagccagcca ggacgtggga actgcagtcg cctggtatca gcagaagcca     120
ggaaaggtcc ccaagctcct gatctactgg gcttccaccc ggcacactgg cgtgccgtca     180
aggttttcgg gatcgggttc cgggactgat ttcaccctga ccatttcctc cctccaaccc     240
gaggatgtgg ccacctacta ctgccagcag tactccacct acccgatcac attcggacag     300
ggcaccaagc tcgaaatcaa g                                               321

<210> SEQ ID NO 51
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Thr Tyr Pro Ile
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 52
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 52
gacatccaaa tgacccagag cccttcgagc ctgtcagcct ccgtgggcga cagagtgacc      60
attacttgca aagccagcca ggacgtggga actgcagtcg cctggtatca gcagaagcca     120
ggaaaggtcc ccaagctcct gatctactgg gcttccaccc ggcacactgg cgtgccgtca    180
aggttttcgg gatcgggttc cgggactgat ttcaccctga ccatttcctc cctccaaccc    240
gaggatgtgg ccacctacta ctgccagcag tactccacct acccgatcac attcggacag    300
ggcaccaagc tcgaaatcaa gcgtacggtg gccgctccca gcgtgttcat cttccccccc    360
agcgacgagc agctgaagag cggcaccgcc agcgtggtgt gcctgctgaa caacttctac    420
ccccgggagg ccaaggtgca gtggaaggtg gacaacgccc tgcagagcgg caacagccag    480
gagagcgtca ccgagcagga cagcaaggac tccacctaca gcctgagcag caccctgacc    540
ctgagcaagg ccgactacga gaagcataag gtgtacgcct gcgaggtgac ccaccagggc    600
ctgtccagcc ccgtgaccaa gagcttcaac agggcgagt gc                        642

<210> SEQ ID NO 53
<211> LENGTH: 243
<212> TYPE: PRT
<213> ORGANISM: Homo sapiens

<400> SEQUENCE: 53

```
Met Cys Ser Arg Gly Trp Asp Ser Cys Leu Ala Leu Glu Leu Leu Leu
1               5                   10                  15

Leu Pro Leu Ser Leu Leu Val Thr Ser Ile Gln Gly His Leu Val His
            20                  25                  30

Met Thr Val Val Ser Gly Ser Asn Val Thr Leu Asn Ile Ser Glu Ser
        35                  40                  45

Leu Pro Glu Asn Tyr Lys Gln Leu Thr Trp Phe Tyr Thr Phe Asp Gln
    50                  55                  60

Lys Ile Val Glu Trp Asp Ser Arg Lys Ser Lys Tyr Phe Glu Ser Lys
65                  70                  75                  80

Phe Lys Gly Arg Val Arg Leu Asp Pro Gln Ser Gly Ala Leu Tyr Ile
                85                  90                  95

Ser Lys Val Gln Lys Glu Asp Asn Ser Thr Tyr Ile Met Arg Val Leu
            100                 105                 110

Lys Lys Thr Gly Asn Glu Gln Glu Trp Lys Ile Lys Leu Gln Val Leu
        115                 120                 125

Asp Pro Val Pro Lys Pro Val Ile Lys Ile Glu Lys Ile Glu Asp Met
130                 135                 140

Asp Asp Asn Cys Tyr Leu Lys Leu Ser Cys Val Ile Pro Gly Glu Ser
145                 150                 155                 160

Val Asn Tyr Thr Trp Tyr Gly Asp Lys Arg Pro Phe Pro Lys Glu Leu
                165                 170                 175

Gln Asn Ser Val Leu Glu Thr Thr Leu Met Pro His Asn Tyr Ser Arg
            180                 185                 190

Cys Tyr Thr Cys Gln Val Ser Asn Ser Val Ser Ser Lys Asn Gly Thr
        195                 200                 205

Val Cys Leu Ser Pro Pro Cys Thr Leu Ala Arg Ser Phe Gly Val Glu
210                 215                 220

Trp Ile Ala Ser Trp Leu Val Val Thr Val Pro Thr Ile Leu Gly Leu
225                 230                 235                 240

Leu Leu Thr
```

<210> SEQ ID NO 54
<211> LENGTH: 252
<212> TYPE: PRT
<213> ORGANISM: Homo sapiens

<400> SEQUENCE: 54

```
Met Cys Ser Arg Gly Trp Asp Ser Cys Leu Ala Leu Glu Leu Leu Leu
1               5                   10                  15

Leu Pro Leu Ser Leu Leu Val Thr Ser Ile Gln Gly His Leu Val His
            20                  25                  30

Met Thr Val Val Ser Gly Ser Asn Val Thr Leu Asn Ile Ser Glu Ser
        35                  40                  45

Leu Pro Glu Asn Tyr Lys Gln Leu Thr Trp Phe Tyr Thr Phe Asp Gln
    50                  55                  60

Lys Ile Val Glu Trp Asp Ser Arg Lys Ser Lys Tyr Phe Glu Ser Lys
65                  70                  75                  80

Phe Lys Gly Arg Val Arg Leu Asp Pro Gln Ser Gly Ala Leu Tyr Ile
                85                  90                  95

Ser Lys Val Gln Lys Glu Asp Asn Ser Thr Tyr Ile Met Arg Val Leu
            100                 105                 110
```

```
Lys Lys Thr Gly Asn Glu Gln Glu Trp Lys Ile Lys Leu Gln Val Leu
            115                 120                 125
Asp Pro Val Pro Lys Pro Val Ile Lys Ile Glu Lys Ile Glu Asp Met
130                 135                 140
Asp Asp Asn Cys Tyr Leu Lys Leu Ser Cys Val Ile Pro Gly Glu Ser
145                 150                 155                 160
Val Asn Tyr Thr Trp Tyr Gly Asp Lys Arg Pro Phe Pro Lys Glu Leu
            165                 170                 175
Gln Asn Ser Val Leu Glu Thr Thr Leu Met Pro His Asn Tyr Ser Arg
            180                 185                 190
Cys Tyr Thr Cys Gln Val Ser Asn Ser Val Ser Ser Lys Asn Gly Thr
            195                 200                 205
Val Cys Leu Ser Pro Pro Cys Thr Leu Gly Lys Lys Asp Pro Trp Glu
210                 215                 220
Leu Arg Gly Ala Gln Gly Asn Trp Ser Cys Phe Glu Gln Arg Lys Ala
225                 230                 235                 240
Gly Gly Pro Ile Gln Pro Pro Cys Thr Val Trp Trp
            245                 250
```

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 63

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Ala Ile Ser Gly Phe Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Phe Trp Glu Asp Gln Pro Phe Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335
```

-continued

```
Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
        450

<210> SEQ ID NO 64

<400> SEQUENCE: 64

000

<210> SEQ ID NO 65
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Gly Ile Asn Pro Asp Thr Gly Asp Thr Ser Tyr Asn Gln Lys Phe
    50                  55                  60

Thr Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Gln Phe Trp Thr Thr Pro Arg Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 66

<400> SEQUENCE: 66

000

<210> SEQ ID NO 67

<400> SEQUENCE: 67

000

<210> SEQ ID NO 68
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Met His Leu Val His Met Thr Val Val Ser Gly Ser Asn Val Thr Leu
1               5                   10                  15

-continued

Asn Ile Ser Glu Ser Leu Pro Glu Asn Lys Gln Leu Thr Trp Phe Tyr
           20                  25                  30

Thr Phe Asp Gln Lys Ile Val Glu Trp Asp Ser Arg Lys Ser Lys Tyr
       35                  40                  45

Phe Glu Ser Lys Phe Lys Gly Arg Val Arg Leu Asp Pro Gln Ser Gly
   50                  55                  60

Ala Leu Tyr Ile Ser Lys Val Gln Lys Glu Asp Asn Ser Thr Tyr Ile
65                  70                  75                  80

Met Arg Val Leu Lys Lys Thr Gly Asn Glu Gln Glu Trp Lys Ile Lys
               85                  90                  95

Leu Gln Val Leu Asp Pro Gly Leu Asn Asp Ile Phe Glu Ala Gln Lys
           100                 105                 110

Ile Glu Trp His Glu His His His His His His
       115                 120

<210> SEQ ID NO 69
<211> LENGTH: 235
<212> TYPE: PRT
<213> ORGANISM: Macaca fascicularis

<400> SEQUENCE: 69

Met Gly Ser Arg Gly Trp Asn Arg Cys Leu Ala Leu Glu Leu Leu Leu
1               5                   10                  15

Leu Ser Leu Ser Leu Leu Ala Ile Ser Ile Gln Gly Arg Leu Val His
               20                  25                  30

Met Thr Val Val Ser Gly Ser Asn Val Thr Leu Asn Ile Ser Glu Ser
           35                  40                  45

Leu Pro Glu Asn Tyr Lys Gln Leu Thr Trp Phe Tyr Thr Phe Asp Gln
   50                  55                  60

Lys Ile Val Glu Trp Asp Ser Gly Lys Ser Lys Tyr Phe Glu Ser Lys
65                  70                  75                  80

Phe Lys Gly Arg Val Arg Leu Asp Pro Gln Ser Gly Ala Leu Tyr Ile
               85                  90                  95

Ser Lys Val Gln Lys Glu Asp Asn Ser Thr Tyr Val Met Arg Val Leu
           100                 105                 110

Lys Asp Gly Tyr Glu Gln Glu Trp Lys Ile Lys Leu Gln Val Leu Asp
       115                 120                 125

Pro Val Pro Lys Pro Val Ile Lys Ile Glu Lys Asp Val Asp Asp Asn
   130                 135                 140

Cys Tyr Leu Lys Leu Ser Cys Val Ile Pro Gly Glu Ser Val Asn Tyr
145                 150                 155                 160

Thr Trp Tyr Gly Glu Leu Pro Lys Glu Ile Gln Asn Ser Val Leu Glu
               165                 170                 175

Thr Thr Leu Lys Pro His Lys His Ser Arg Cys Tyr Thr Cys Gln Val
           180                 185                 190

Ser Val Ser Ser Lys Asn Gly Thr Phe Cys Phe Ser Pro Pro Cys Thr
       195                 200                 205

Ala Ala Arg Ser Phe Gly Val Glu Trp Ile Ala Ser Trp Leu Val Val
   210                 215                 220

Thr Val Pro Ile Ile Leu Gly Leu Leu Leu Ile
225                 230                 235

<210> SEQ ID NO 70
<211> LENGTH: 448
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 70

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Phe
            20                  25                  30

Gly Met Asn Trp Val Arg Gln Ala Pro Gly Gln Gly Leu Glu Trp Met
        35                  40                  45

Gly Trp Ile Asn Thr Phe Thr Gly Glu Pro Ser Tyr Gly Asn Val Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Arg His Gly Asn Gly Asn Val Phe Asp Ser Trp Gly Gln Gly
            100                 105                 110

Thr Leu Val Thr Val Ser Ser Ala Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Cys Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Cys Asp Ile Ala Val Glu Trp Glu Ser
    370                 375                 380

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 71

<400> SEQUENCE: 71

000

<210> SEQ ID NO 72
<211> LENGTH: 263
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Ser Asp Tyr Lys Asp Asp Asp Lys Ser Gly Ser Asp Tyr Lys
                245                 250                 255
```

Asp Asp Asp Asp Lys Ser Gly
            260

<210> SEQ ID NO 73
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Phe
            20                  25                  30

Gly Met Asn Trp Val Arg Gln Ala Pro Gly Gln Gly Leu Glu Trp Met
        35                  40                  45

Gly Trp Ile Asn Thr Phe Thr Gly Glu Pro Ser Tyr Gly Asn Val Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Arg His Gly Asn Gly Asn Val Phe Asp Ser Trp Gly Gln Gly
            100                 105                 110

Thr Leu Val Thr Val Ser Ser Ala Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 74
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Asn
            20                  25                  30

Ile His Trp Tyr Gln Gln Lys Pro Asp Gln Ser Pro Lys Leu Leu Ile
        35                  40                  45

Lys Tyr Thr Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Ser Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 75
<211> LENGTH: 1353
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 75

```
gaggtccaat tgctggaatc tggcggagga ctggttcagc ctggtggctc tctgagactg      60
tcttgtgccg ccagcggctt caccttcagc agctttgcca tgtcctgggt tcgacaggcc     120
cctggaaaag gactcgagtg ggtgtccgct atctctggct ttggcggcag cacatattac     180
gccgatagcg tgaagggcag attcaccatc agccggaca acagcaagaa cacccctgtac    240
ctgcagatga acagcctgag agccgaggac acagccgtgt attactgcgc gcgtcagttc     300
tgggaagatc agcccttcta cttcgactac tggggccagg gcacactggt cacagttagc     360
tcagctagca ccaagggccc cagcgtgttc cccctggccc ccagcagcaa gagcaccagc     420
ggcggcacag ccgccctggg ctgcctggtg aaggactact ccccgagcc cgtgaccgtg     480
tcctggaaca gcggagccct gacctccggc gtgcacacct tccccgccgt gctgcagagc     540
agcggcctgt acagcctgtc cagcgtggtg acagtgccca gcagcagcct gggcacccag     600
acctacatct gcaacgtgaa ccacaagccc agcaacacca aggtggacaa gagagtggag     660
cccaagagct gcgacaagac ccacacatgc cccccctgcc cggcgccaga gctgctgggc     720
ggaccctccg tgttcctgtt cccccccaag cccaaggaca cctgatgat cagcaggacc     780
cccgaggtga cctgcgtggt ggtggacgtg agccacgagg acccagaggt gaagttcaac     840
tggtacgtgg acggcgtgga ggtgcacaac gccaagacca gcccagaga ggagcagtac    900
aacagcacct acagggtggt gtccgtgctg accgtgctgc accaggactg gctgaacggc     960
aaggaataca gtgcaaggt ctccaacaag gccctgccag cccccatcga aaagaccatc    1020
agcaaggcca agggccagcc acgggagccc caggtgtaca ccctgccccc ctcccgggag    1080
gagatgacca gaaccaggt gtccctgacc tgtctggtga agggcttcta ccccagcgac    1140
atcgccgtgg agtgggagag caacggccag ccgagaaca actacaagac caccccccca   1200
gtgctggaca cgacggcag cttcttcctg tacagcaagc tgaccgtgga caagtccagg    1260
tggcagcagg gcaacgtgtt cagctgcagc gtgatgcacg aggccctgca caaccactac    1320
acccagaaga gcctgagctt aagccccggc aag                                 1353
```

<210> SEQ ID NO 76

<400> SEQUENCE: 76

000

<210> SEQ ID NO 77
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 77

```
caggtccaat tggtgcagtc tggcgccgaa gtgaagaaac caggcgccag cgtgaaggtg      60
tcctgtaaag ccagcggcta caccttacc gagtacacca tgcactgggt ccgacaggct     120
ccaggacaag gactcgagtg gatgggcggc atcaatcctg ataccggcga caccagctac     180
```

```
aaccagaagt tcacaggcag agccacactg accgtggaca agagcacaag caccgcctac    240
atggaactga gcagcctgag aagcgaggac accgccgtgt attattgcgc gcgtgcccag    300
ttttggacca cacctagatt tgcctactgg ggccagggca ccctggtcac agttagctca    360
gctagcacca agggcccag cgtgttcccc ctggccccca gcagcaagag caccagcggc     420
ggcacagccg ccctgggctg cctggtgaag gactacttcc ccgagcccgt gaccgtgtcc    480
tggaacagcg gagccctgac ctccggcgtg cacaccttcc ccgccgtgct gcagagcagc    540
ggcctgtaca gcctgtccag cgtggtgaca gtgcccagca gcagcctggg cacccagacc    600
tacatctgca cgtgaacca caagcccagc aacaccaagg tggacaagag agtggagccc     660
aagagctgcg acaagaccca cacatgcccc cctgcccgg cgccagagct gctgggcgga    720
ccctccgtgt tcctgttccc ccccaagccc aaggacaccc tgatgatcag caggaccccc    780
gaggtgacct gcgtggtggt ggacgtgagc cacgaggacc cagaggtgaa gttcaactgg    840
tacgtggacg gcgtggaggt gcacaacgcc aagaccaagc cagagagga gcagtacaac    900 agcacctaca gggtggtgtc cgtgctgacc gtgctgcacc aggactggct gaacggcaag    960
gaatacaagt gcaaggtctc caacaaggcc ctgccagccc ccatcgaaaa gaccatcagc    1020
aaggccaagg gccagccacg ggagcccag gtgtacaccc tgccccctc ccgggaggag     1080 atgaccaaga accaggtgtc cctgacctgt ctggtgaagg gcttctaccc cagcgacatc    1140
gccgtggagt gggagagcaa cggccagccc gagaacaact acaagaccac cccccagtg    1200 ctggacagcg acggcagctt cttcctgtac agcaagctga ccgtggacaa gtccaggtgg    1260
cagcagggca cgtgttcag ctgcagcgtg atgcacgagg ccctgcacaa ccactacacc      1320
cagaagagcc tgagcttaag ccccggcaag                                    1350

<210> SEQ ID NO 78
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Glu Asn Tyr Lys Gln
1               5

<210> SEQ ID NO 79
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Gly Ser Ser Lys Gln
1               5

<210> SEQ ID NO 80
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 80

Asp Ser Arg Lys
1

<210> SEQ ID NO 81
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Ala Ala Gly Lys
1

<210> SEQ ID NO 82
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Lys Lys Thr Gly Asn Glu
1               5

<210> SEQ ID NO 83
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Lys Lys Asp Ala Ser Gly
1               5

<210> SEQ ID NO 84
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 84

His His His His His His
1               5
```